(12) United States Patent
Bradner et al.

(10) Patent No.: US 10,239,888 B2
(45) Date of Patent: Mar. 26, 2019

(54) TARGETED PROTEIN DEGRADATION USING A MUTANT E3 UBIQUITIN LIGASE

(71) Applicant: Dana-Farber Cancer Institute, Inc., Boston, MA (US)

(72) Inventors: James Bradner, Weston, MA (US); Mette Ishoey, Boston, MA (US); Dennis Buckley, Jamaica Plains, MA (US); Joshiawa Paulk, Boston, MA (US); Marc Andrew Cohen, McLean, VA (US); Rhamy Zeid, Arlington, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/045,346

(22) Filed: Jul. 25, 2018

(65) Prior Publication Data
US 2018/0327419 A1     Nov. 15, 2018

Related U.S. Application Data

(63) Continuation of application No. PCT/US2017/054522, filed on Sep. 29, 2017.

(60) Provisional application No. 62/401,303, filed on Sep. 29, 2016.

(51) Int. Cl.
| | |
|---|---|
| *C07D 495/14* | (2006.01) |
| *A61P 35/02* | (2006.01) |

(52) U.S. Cl.
CPC ........... *C07D 495/14* (2013.01); *A61P 35/02* (2018.01)

(58) Field of Classification Search
None
See application file for complete search history.

(56) References Cited

U.S. PATENT DOCUMENTS

| | | | |
|---|---|---|---|
| 6,306,663 B1 | 10/2001 | Kenten et al. | |
| 6,559,280 B2 | 5/2003 | Kenten et al. | |
| 7,041,298 B2 | 5/2006 | Deshaies et al. | |
| 7,074,620 B2 | 7/2006 | Kenten et al. | |
| 7,208,157 B2 | 4/2007 | Deshaies et al. | |
| 7,273,920 B2 | 9/2007 | Kenten et al. | |
| 9,125,915 B2 | 9/2015 | Miyoshi et al. | |
| 9,249,161 B2 | 2/2016 | Albrecht et al. | |
| 9,494,084 B2* | 11/2016 | Kohlenberg | F04D 29/522 |
| 9,750,816 B2* | 9/2017 | Bradner | C07J 43/003 |
| 9,821,068 B2* | 11/2017 | Bradner | C07J 43/003 |
| 2010/0286127 A1* | 11/2010 | Miyoshi | C07D 495/14 514/220 |
| 2013/0190340 A1 | 7/2013 | Hedstrom et al. | |
| 2014/0302523 A1 | 10/2014 | Crews et al. | |
| 2014/0356322 A1 | 12/2014 | Crews et al. | |
| 2015/0119435 A1 | 4/2015 | Crews et al. | |
| 2015/0274738 A1 | 10/2015 | Gray et al. | |
| 2015/0291562 A1 | 10/2015 | Crew et al. | |
| 2016/0016966 A1 | 1/2016 | Amans et al. | |
| 2016/0022642 A1 | 1/2016 | Crews et al. | |
| 2016/0045607 A1 | 2/2016 | Crew et al. | |

(Continued)

FOREIGN PATENT DOCUMENTS

| | | |
|---|---|---|
| WO | WO 1998/011111 A1 | 3/1998 |
| WO | WO 2006/102557 A2 | 9/2006 |

(Continued)

OTHER PUBLICATIONS

Anand P. et al., "BET bromodomains mediate transcriptional pause release in heart failure," *Cell* 154, 569-582 (2013).

(Continued)

*Primary Examiner* — Nyeemah A Grazier
(74) *Attorney, Agent, or Firm* — Knowles Intellectual Property Strategies, LLC

(57) ABSTRACT

The present application provides bifunctional compounds of Formula I or II:

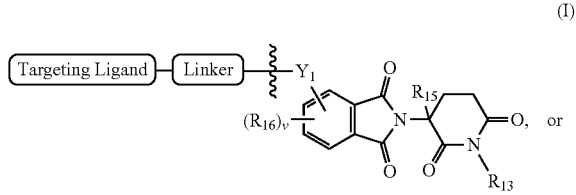

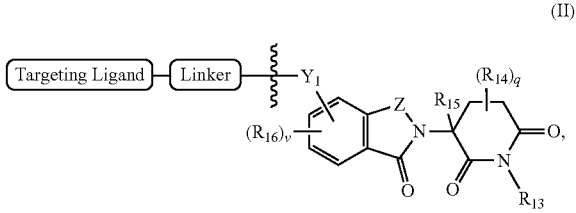

or an enantiomer, diastereomer, or stereoisomer, or a pharmaceutically acceptable salt thereof, which act as protein degradation inducing moieties. The present application also relates to methods for the targeted degradation of endogenous proteins through the use of the bifunctional compounds of Formula (I) or (II) that link a mutant cereblon-binding moiety to a ligand that is capable of binding to a targeted protein which can be utilized in the treatment of proliferative disorders. The present application also provides methods for making compounds of the application and intermediates thereof. The present application also relates to polynucleotides or polypeptides of a mutant cereblon and methods of use thereof.

2 Claims, 7 Drawing Sheets

Specification includes a Sequence Listing.

(56) References Cited

U.S. PATENT DOCUMENTS

| | | |
|---|---|---|
| 2016/0046661 A1 | 2/2016 | Gray et al. |
| 2016/0058872 A1 | 3/2016 | Crew et al. |
| 2016/0176916 A1* | 6/2016 | Bradner ............... C07J 43/003 540/560 |
| 2017/0327469 A1 | 11/2017 | Crew et al. |
| 2018/0009779 A1 | 1/2018 | Bradner et al. |
| 2018/0134684 A1 | 5/2018 | Bradner et al. |
| 2018/0147202 A1 | 5/2018 | Crew et al. |
| 2018/0228907 A1 | 8/2018 | Crew et al. |

FOREIGN PATENT DOCUMENTS

| | | |
|---|---|---|
| WO | WO 2008/122038 A1 | 10/2008 |
| WO | WO 2011/143669 A2 | 11/2011 |
| WO | WO 2012/003281 A2 | 1/2012 |
| WO | WO 2012/079022 A1 | 6/2012 |
| WO | WO 2012/178208 A2 | 12/2012 |
| WO | WO 2013/106643 A2 | 7/2013 |
| WO | WO 2013/106646 A2 | 7/2013 |
| WO | WO 2015/160845 A2 | 10/2015 |
| WO | WO 2016/065139 A1 | 4/2016 |
| WO | WO 2016/105518 A1 | 6/2016 |
| WO | WO 2017/007612 A1 | 1/2017 |
| WO | WO 2017/024317 A2 | 2/2017 |
| WO | WO 2017/024318 A1 | 2/2017 |
| WO | WO 2017/024319 A1 | 2/2017 |
| WO | WO 2017/117474 A1 | 7/2017 |
| WO | WO 2017/185036 A1 | 10/2017 |
| WO | WO 2017/197036 A1 | 11/2017 |
| WO | WO 2017/197046 A1 | 11/2017 |
| WO | WO 2017/197051 A1 | 11/2017 |
| WO | WO 2017/197055 A1 | 11/2017 |
| WO | WO 2017/197056 A1 | 11/2017 |

OTHER PUBLICATIONS

Anders L. et al., "Genome-wide determination of drug localization," Nature Biotechnology 32, 92-96 (2013).

Banaszynski, L. A., et al. (2006). "A rapid, reversible, and tunable method to regulate protein function in living cells using synthetic small molecules." Cell 126(5): 995-1004.

Banaszynski, L. A., et al. (2008). "Chemical control of protein stability and function in living mice." Nat Med 14(10): 1123-1127.

Bartlett, J. B., et al. (2004). "The evolution of thalidomide and its IMiD derivatives as anticancer agents." Nat Rev Cancer 4(4): 314-322.

Brown J.D. et al., "NF-κB directs dynamic super enhancer formation in inflammation and atherogenesis," Mol. Cell 56, 219-231 (2014).

Buckley et al., HaloPROTACS: Use of Small Molecule PROTACs to Induce Degradation of HaloTag Fusion Proteins, ACS Chemical Biology, 2015, 10; 1831-1837.

Buckley et al., Small-Molecule Control of Intracellular Protein Levels through Modulation of the Ubiquitin Proteasome System, Angewandte Reviews, 2014, 53; 2312-2330.

Buckley et al., Small-Molecule Inhibitors of the Interaction between the E3 Ligase VHL and HIF1α, Angewandte Chemie, 2012, 51; 11463-11467.

Budin G. et al., "Bioorthogonal Probes for Polo-like Kinase 1 Imaging and Quantification," Angewandte Chemie International Ed. 50, 9378-9381 (2011).

Burkhard, J. A. et al (2013) "Synthesis and Stability of Oxetane Analogs of Thalidomide and Lenalidomide" Org Lett 15(7): 4312-4315.

Chang X. and Stewart K. A., "What is the functional role of the thalidomide binding protein cereblon?" Int J Biochem Mol Biol. 2(3), 287-294 (2011).

Chapuy B. et al., "Discovery and characterization of super-enhancer-associated dependencies in diffuse large B cell lymphoma.," Cancer Cell 24, 777-790 (2013).

Chung et al., Discovery and Characterization of Small Molecule Inhibitors of the BET-O97Family Bromodomains, Journal of Medical Chemistry, 2011, 54; 3827-3838.

Corson et al, Design and applications of bifunctional small molecules: Why two heads are better than one, ACS Chemical Biology, 2008, 3(11); 677-692.

Crews C.M., "Targeting the undruggable proteome: the small molecules of my dreams.," Chem. Biol. 17(6), 551-555 (2010).

Dawson et al., Inhibition of BET recruitment to chromatin as an effective treatment for MLL-fusion leukaemia, Nature, 2011, 478; 529-533.

Delmore J.E. et al., "BET bromodomain inhibition as a therapeutic strategy to target c-Myc," Cell 146, 904-917 (2011).

Faden et al., Generic tools for conditionally altering protein abundance and phenotypes on demand, Biol.Chem., 2014, 395(7-8); 737-762.

Filippakopoulos P. et al., "Selective inhibition of BET bromodomains," Nature 468, 1067-1073 (2010).

Filippakopoulos, P. and S. Knapp (2014). "Targeting bromodomains: epigenetic readers of lysine acetylation." Nat Rev Drug Discov 13(5): 337-356.

Fischer E.S. et al., "Structure of the DDB1-CRBN E3 ubiquitin ligase in complex with thalidomide," Nature 512, 49-53 (2014).

Fischer E.S. et al., "The Molecular Basis of CRL4$^{DDB2/CSA}$ Ubiquitin Ligase Architecture, Targeting, and Activation," Cell 147, 1024-1039 (2011).

Giancotti, Deregulation of cell signaling in cancer, FEBS Letters, 2014, 588; 2558-2570.

Gosink et al., Redirecting the specificity of ubiquitination by modifying ubiquitin-conjugating enzymes, PNAS, 1995, 92; 9117-9121.

Gustafson et al., Small-Molecule-Mediated Degradation of the Androgen Receptor through Hydrophobic Tagging, Angewandte Chemie, 2015, 54; 9659-962.

Hewings et al., 3,5-Dimethylisoxazoles Act As Acetyl-lysine-mimetic Bromodomain2011nds, Journal of Medical Chemistry, 2011, 54; 6761-6770.

Hines, J., et al. (2013). "Posttranslational protein knockdown coupled to receptor tyrosine kinase activation with phosphoPROTACs." Proc Natl Acad Sci U S A 110(22): 8942-8947.

Holt D.A. et al., "Design, synthesis, and kinetic evaluation of high-affinity FKBP ligands and the X-ray crystal structures of their complexes with FKBP12," J. Am. Chem. Soc. 115, 9925-9938 (1993).

Huttlin, E. L., et al. (2010). "A tissue-specific atlas of mouse protein phosphorylation and expression." Cell 143(7): 1174-1189.

International Search Report and Written Opinion for PCT/US2015/000274 dated Mar. 18, 2016.

International Search Report and Written Opinion for PCT/US2016/39048 dated Jan. 1, 2017.

Ito, T., et al. (2010). "Identification of a Primary Target of Thalidomide Teratogenicity." Science 327(5971): 1345-1350.

Itoh, Y., et al. (2010). "Protein knockdown using methyl bestatin-ligand hybrid molecules: design and synthesis of inducers of ubiquitination-mediated degradation of cellular retinoic acid-binding proteins." J Am Chem Soc 132(16): 5820-5826.

Jacques et al., Differentiation of antiinflamatory and antitumorigenic properties of stabilized enantiomers of thalidomide analogs, PNAS, 2015, 112; E1471-E1479.

Jan Kronke et al.: "Lenalidomide induces ubiquitination and degradation of CK1[alpha] in del(5q) MDS", Nature, vol. 523, No. 7559, Jul. 9, 2015 (Jul. 9, 2015), pp. 183-188.

Krönke, J., et al. (2014). "Lenalidomide Causes Selective Degradation of IKZF1 and IKZF3 in Multiple Myeloma Cells." Science 343(6168): 301-305.

Lallemand-Breitenbach et al., Role of Promyelocytic Leukemia (PML) Sumolation in Nuclear Body Formation, 11S Proteasome Recruitment, and As2O3-induced PML or PML/Retinoic Acid Receptor α Degradation, j. Exp. Med.. 2001, 193; 1361-1371.

Lee et al., Targeted Degradation of the Aryl Hydrocarbon Receptor by the PROTAC Approach: A Useful Chemical Genetic Tool, ChemBioChem, 2007, 8: 2058-2062.

(56) References Cited

OTHER PUBLICATIONS

Liu J. et al., "Calcineurin is a common target of cyclophilin-cyclosporin A and FKBP-FK506 complexes," *Cell* 66, 807-15 (1991).
Liu, K. et al. (2013) "Design and biological characterization of hybrid compounds of curcumin and thalidomide for multiple myeloma." Org. Biomol. Chem., 2013, 11, 4757.
Lou et al. "Hijacking the E3 Ubiquitin Ligase Cereblon to Efficiently Target BRD4" Chemistry & Biology 22, 755-763, Jun. 18, 2015.
Loven J. et al., "Selective inhibition of tumor oncogenes by disruption of super-enhancers," *Cell* 153, 320-334 (2013).
Lu G. et al., "The myeloma drug lenalidomide promotes the cereblon-dependent destruction of Ikaros proteins," *Science* 343, 305-309 (2014).
M. Sekiguchi et al. "An evaluation tool for FKBP12-dependent and independent mTOR inhibitors using a combination of FKBP-mTOR fusion protein, DSC and NMR", Protein Engineering, Design and Selection, vol. 24, No. 11, Sep. 6, 2011, pp. 811-817.
Mayer D. A. et al., "Multicenter randomized trial comparing tacrolimus (FK506) and cyclosporine in the prevention of renal allograft rejection: a report of the European Tacrolimus Multicenter Renal Study Group," *Transplantation* 64(3), 436-43 (1997).
McKeown M. R. et al., "Biased multicomponent reactions to develop novel bromodomain inhibitors," *J. Med. Chem.* 57, 9019-9027 (2014).
Mertz, J. A., et al. (2011). "Targeting MYC dependence in cancer by inhibiting BET bromodomains." Proceedings of the National Academy of Sciences 108(40): 16669-16674.
Nawaz et al., Proteasome-dependent degradation of the human estrogen receptor, PNAS, 1999, 96; 1758-1862.
Neklesa, T. K., et al. (2011). "Small-molecule hydrophobic tagging-induced degradation of HaloTag fusion proteins." Nat Chem Biol 7(8): 538-543.
Nicodeme E. et al., "Suppression of inflammation by a synthetic histone mimic," *Nature* 468, 1119-1123 (2010).
Petroski M.E. and Deshaies R. J., "Function and regulation of cullin-ring ubiquitin ligases," *Nat. Rev. Mol. Cell. Biol.* 6, 9-20 (2005).
Philip P. Chamberlain et al: "Structure of the human Cereblon-DDB1-lenalidomide complex reveals basis for responsiveness to thaliadomide analogs", Nature Structural and Molecular Biology, vol. 21, No. 9, Aug. 10, 2014 (Aug. 10, 2014, pp. 803-809
Pratt, M. R., et al. (2007). "Small-molecule-mediated rescue of protein function by an inducible proteolytic shunt." Proceedings of the National Academy of Sciences 104(27): 11209-11214.
Raina et al., Chemical Inducers of Targeted Protein Degradation, Journal of Biological Chemistry, 2010, 285; 11057-11060.
Robers Matt et al. "Flourescent labeling of proteins in living cells using the FKBP12 (F36V) tag", Cytometry. Part A: The Journal of the International Society for Analytical Cytology, vol. 75, No. 3, Mar. 2009.
Rodriguez-Gonzalez et al., Targeting steroid hormone receptors for ubiquitination and degradation in breast and prostate cancer, Oncogene, 2008, 27; 7201-7211.
Ruchelman et al.,Isosteric analogs of lenalidomide and pomalidomide: Synthesis and biological activity, Bioorganic & Medical Chemistry Letters. 2012, 23; 360-365.
Sakamoto et al., Development of Protacs to Target Cancer-promoting Proteins for Ubiquitination and Degradation, Molecular & Cellular Proteomics, 2003, 2.12; 1350-1357.
Sakamoto, K. M., et al. (2001). "Protacs: chimeric molecules that target proteins to the Skp1-Cullin-F box complex for ubiquitination and degradation." Proc Natl Acad Sci U S A 98(15): 8554-8559.
Schneekloth et al., Targeted Intracellular protein degradation induced by a small molecule: En route to chemical proteomics, Bioorganic & Medicinal Chemistry Letters, 2008, 18; 5904-5908.
Schneekloth J.S. Jr. and Crews C. M., "Chemical approaches to controlling intracellular protein degradation," *Chembiochem* 6(1), 40-46 (2005).
Schneekloth, J. S., et al. (2004). "Chemical Genetic Control of Protein Levels: Selective in Vivo Targeted Degradation." J Am Chem Soc 126(12): 3748-3754.
Siekierka J. J. et al., "A cytosolic binding protein for the immuno-suppressant FK506 has peptidyl-prolyl isomerase activity but is distinct from cyclophilin," *Nature* 341, 755-7 (1989).
Smith et al., Targeted Intracellular Protein Degradation Induced by a Small Molecule: En Route to Chemical Proteomics, Bioorg.Med. Chem. Lett., 2008, 18(22); 5904-5908.
Soucy, T. A., et al. (2009). "An inhibitor of NEDD8-activating enzyme as a new approach to treat cancer." Nature 458(7239): 732-736.
Sufan R.I., and Ohh M., "Role of the NEDD8 modification of Cul2 in the sequential activation of ECV complex," *Neoplasia* 8, 956-963 (2006).
Wang T. et al., "Specific interaction of type I receptors of the TGF-beta family with the immunophilin FKBP-12," *Science* 265, 674-6 (1994).
Winter, G. E., et al. (2015). "Phthalimide conjugation as a strategy for in vivo target protein degradation." Science 348(6241): 1376-1381.
Wu, Y. L., et al. (2005). "Structural basis for an unexpected mode of SERM-mediated ER antagonism." Mol Cell 18(4): 413-424.
Zengerle et al. "Selective Small Molecule Induced Degradation of the BET Bromodomain Protein BRD4" ACS Chem. Biol. 2015, vol. 10, pp. 1770-1777.
Zhou et al., Harnessing the Ubiquitination Machinery to Target the Degradation of Specific Cellular Proteins, Molecular Cell, 2000, 6; 751-756.
Zuber J. et al., "RNAi screen identifies Brd4 as a therapeutic target in acute myeloid leukaemia," *Nature* 478, 524-528 (2011).

* cited by examiner

SEQUENCE LISTING

<160> NUMBER OF SEQ ID NOS: 10

<210> SEQ ID NO 1
<211> LENGTH: 442
<212> TYPE: PRT
<213> ORGANISM: Homo sapiens

<400> SEQUENCE: 1

Met Ala Gly Glu Gly Asp Gln Gln Asp Ala His Asn Met Gly Asn
1               5                   10                  15

His Leu Pro Leu Pro Ala Glu Ser Glu Glu Asp Glu Met Glu
            20                  25                  30

Val Glu Asp Gln Asp Ser Lys Glu Ala Lys Lys Pro Asn Ile Ile Asn
                35                  40                  45

Phe Asp Thr Ser Leu Pro Thr Ser His Thr Tyr Leu Gly Ala Asp Met
    50                  55                  60

Glu Glu Phe His Gly Arg Thr Leu His Asp Asp Ser Cys Gln Val
65              70                  75                  80

Ile Pro Val Leu Pro Gln Val Met Met Ile Leu Ile Pro Gly Gln Thr
                85                  90                  95

Leu Pro Leu Gln Leu Phe His Pro Gln Glu Val Ser Met Val Arg Asn
            100                 105                 110

Leu Ile Gln Lys Asp Arg Thr Phe Ala Val Leu Ala Tyr Ser Asn Val
        115                 120                 125

Gln Glu Arg Glu Ala Gln Phe Gly Thr Thr Ala Glu Ile Tyr Ala Tyr
130                 135                 140

Arg Glu Glu Gln Asp Phe Gly Ile Glu Ile Val Lys Val Lys Ala Ile
145                 150                 155                 160

Gly Arg Gln Arg Phe Lys Val Leu Glu Leu Arg Thr Gln Ser Asp Gly
                165                 170                 175

Ile Gln Gln Ala Lys Val Gln Ile Leu Pro Glu Cys Val Leu Pro Ser
            180                 185                 190

Thr Met Ser Ala Val Gln Leu Glu Ser Leu Asn Lys Cys Gln Ile Phe
        195                 200                 205

Pro Ser Lys Pro Val Ser Arg Glu Asp Gln Cys Ser Tyr Lys Trp Trp
210                 215                 220

Gln Lys Tyr Gln Lys Arg Lys Phe His Cys Ala Asn Leu Thr Ser Trp
225                 230                 235                 240

Pro Arg Trp Leu Tyr Ser Leu Tyr Asp Ala Glu Thr Leu Met Asp Arg
                245                 250                 255

Ile Lys Lys Gln Leu Arg Glu Trp Asp Glu Asn Leu Lys Asp Asp Ser
            260                 265                 270

Leu Pro Ser Asn Pro Ile Asp Phe Ser Tyr Arg Val Ala Ala Cys Leu
        275                 280                 285

Pro Ile Asp Asp Val Leu Arg Ile Gln Leu Leu Lys Ile Gly Ser Ala
290                 295                 300

Ile Gln Arg Leu Arg Cys Glu Leu Asp Ile Met Asn Lys Cys Thr Ser
305                 310                 315                 320

Leu Cys Cys Lys Gln Cys Gln Glu Thr Glu Ile Thr Thr Lys Asn Glu
                325                 330                 335

Ile Phe Ser Leu Ser Leu Cys Gly Pro Met Ala Ala Tyr Val Asn Pro
            340                 345                 350

His Gly Tyr Val His Glu Thr Leu Thr Val Tyr Lys Ala Cys Asn Leu
        355                 360                 365

Asn Leu Ile Gly Arg Pro Ser Thr Glu His Ser Trp Phe Pro Gly Tyr
370                 375                 380

Ala Trp Thr Val Ala Gln Cys Lys Ile Cys Ala Ser His Ile Gly Trp
385                 390                 395                 400

Lys Phe Thr Ala Thr Lys Lys Asp Met Ser Pro Gln Lys Phe Trp Gly

```
                    405                 410                 415
Leu Thr Arg Ser Ala Leu Leu Pro Thr Ile Pro Asp Thr Glu Asp Glu
                420                 425                 430

Ile Ser Pro Asp Lys Val Ile Leu Cys Leu
                435                 440

<210> SEQ ID NO 2
<211> LENGTH: 441
<212> TYPE: PRT
<213> ORGANISM: Homo sapiens

<400> SEQUENCE: 2

Met Ala Gly Glu Gly Asp Gln Gln Asp Ala Ala His Asn Met Gly Asn
1               5                   10                  15

His Leu Pro Leu Leu Pro Glu Ser Glu Glu Glu Asp Glu Met Glu Val
                20                  25                  30

Glu Asp Gln Asp Ser Lys Glu Ala Lys Lys Pro Asn Ile Ile Asn Phe
            35                  40                  45

Asp Thr Ser Leu Pro Thr Ser His Thr Tyr Leu Gly Ala Asp Met Glu
        50                  55                  60

Glu Phe His Gly Arg Thr Leu His Asp Asp Asp Ser Cys Gln Val Ile
65                  70                  75                  80

Pro Val Leu Pro Gln Val Met Met Ile Leu Ile Pro Gly Gln Thr Leu
                85                  90                  95

Pro Leu Gln Leu Phe His Pro Gln Glu Val Ser Met Val Arg Asn Leu
                100                 105                 110

Ile Gln Lys Asp Arg Thr Phe Ala Val Leu Ala Tyr Ser Asn Val Gln
            115                 120                 125

Glu Arg Glu Ala Gln Phe Gly Thr Thr Ala Glu Ile Tyr Ala Tyr Arg
        130                 135                 140

Glu Glu Gln Asp Phe Gly Ile Glu Ile Val Lys Val Lys Ala Ile Gly
145                 150                 155                 160

Arg Gln Arg Phe Lys Val Leu Glu Leu Arg Thr Gln Ser Asp Gly Ile
                165                 170                 175

Gln Gln Ala Lys Val Gln Ile Leu Pro Glu Cys Val Leu Pro Ser Thr
                180                 185                 190

Met Ser Ala Val Gln Leu Glu Ser Leu Asn Lys Cys Gln Ile Phe Pro
            195                 200                 205

Ser Lys Pro Val Ser Arg Glu Asp Gln Cys Ser Tyr Lys Trp Trp Gln
        210                 215                 220

Lys Tyr Gln Lys Arg Lys Phe His Cys Ala Asn Leu Thr Ser Trp Pro
225                 230                 235                 240

Arg Trp Leu Tyr Ser Leu Tyr Asp Ala Glu Thr Leu Met Asp Arg Ile
                245                 250                 255

Lys Lys Gln Leu Arg Glu Trp Asp Glu Asn Leu Lys Asp Asp Ser Leu
                260                 265                 270

Pro Ser Asn Pro Ile Asp Phe Ser Tyr Arg Val Ala Ala Cys Leu Pro
            275                 280                 285

Ile Asp Asp Val Leu Arg Ile Gln Leu Leu Lys Ile Gly Ser Ala Ile
        290                 295                 300

Gln Arg Leu Arg Cys Glu Leu Asp Ile Met Asn Lys Cys Thr Ser Leu
305                 310                 315                 320

Cys Cys Lys Gln Cys Gln Glu Thr Glu Ile Thr Thr Lys Asn Glu Ile
                325                 330                 335
```

```
Phe Ser Leu Ser Leu Cys Gly Pro Met Ala Ala Tyr Val Asn Pro His
            340                 345                 350

Gly Tyr Val His Glu Thr Leu Thr Val Tyr Lys Ala Cys Asn Leu Asn
        355                 360                 365

Leu Ile Gly Arg Pro Ser Thr Glu His Ser Trp Phe Pro Gly Tyr Ala
    370                 375                 380

Trp Thr Val Ala Gln Cys Lys Ile Cys Ala Ser His Ile Gly Trp Lys
385                 390                 395                 400

Phe Thr Ala Thr Lys Lys Asp Met Ser Pro Gln Lys Phe Trp Gly Leu
                405                 410                 415

Thr Arg Ser Ala Leu Leu Pro Thr Ile Pro Asp Thr Glu Asp Glu Ile
            420                 425                 430

Ser Pro Asp Lys Val Ile Leu Cys Leu
            435                 440

<210> SEQ ID NO 3
<211> LENGTH: 444
<212> TYPE: PRT
<213> ORGANISM: Mus musculus

<400> SEQUENCE: 3

Met Ala Gly Glu Gly Asp Gln Gln Asp Ala Ala His Asn Met Gly Asn
1               5                   10                  15

His Leu Pro Leu Leu Pro Asp Ser Glu Asp Glu Asp Asp Glu Ile Glu
            20                  25                  30

Met Glu Val Glu Asp Gln Asp Ser Lys Glu Ala Arg Lys Pro Asn Ile
        35                  40                  45

Ile Asn Phe Asp Thr Ser Leu Pro Thr Ser His Thr Tyr Leu Gly Ala
    50                  55                  60

Asp Met Glu Glu Phe His Gly Arg Thr Leu His Asp Asp Ser Cys
65                  70                  75                  80

Gln Val Ile Pro Val Leu Pro Glu Val Leu Met Ile Leu Ile Pro Gly
                85                  90                  95

Gln Thr Leu Pro Leu Gln Leu Ser His Pro Gln Glu Val Ser Met Val
            100                 105                 110

Arg Asn Leu Ile Gln Lys Asp Arg Thr Phe Ala Val Leu Ala Tyr Ser
        115                 120                 125

Asn Val Gln Glu Arg Glu Ala Gln Phe Gly Thr Thr Ala Glu Ile Tyr
    130                 135                 140

Ala Tyr Arg Glu Glu Gln Glu Phe Gly Ile Glu Val Val Lys Val Lys
145                 150                 155                 160

Ala Ile Gly Arg Gln Arg Phe Lys Val Leu Glu Leu Arg Thr Gln Ser
                165                 170                 175

Asp Gly Ile Gln Gln Ala Lys Val Gln Ile Leu Pro Glu Cys Val Leu
            180                 185                 190

Pro Ser Thr Met Ser Ala Val Gln Leu Glu Ser Leu Asn Lys Cys Gln
        195                 200                 205

Val Phe Pro Ser Lys Pro Ile Ser Trp Glu Asp Gln Tyr Ser Cys Lys
    210                 215                 220

Trp Trp Gln Lys Tyr Gln Lys Arg Lys Phe His Cys Ala Asn Leu Thr
225                 230                 235                 240

Ser Trp Pro Arg Trp Leu Tyr Ser Leu Tyr Asp Ala Glu Thr Leu Met
                245                 250                 255

Asp Arg Ile Lys Lys Gln Leu Arg Glu Trp Asp Glu Asn Leu Lys Asp
            260                 265                 270
```

Asp Ser Leu Pro Glu Asn Pro Ile Asp Phe Ser Tyr Arg Val Ala Ala
            275                 280                 285

Cys Leu Pro Ile Asp Asp Val Leu Arg Ile Gln Leu Leu Lys Ile Gly
            290                 295                 300

Ser Ala Ile Gln Arg Leu Arg Cys Glu Leu Asp Ile Met Asn Lys Cys
305                 310                 315                 320

Thr Ser Leu Cys Cys Lys Gln Cys Gln Glu Thr Glu Ile Thr Thr Lys
            325                 330                 335

Asn Glu Ile Phe Ser Leu Ser Leu Cys Gly Pro Met Ala Ala Tyr Val
            340                 345                 350

Asn Pro His Gly Tyr Val His Glu Thr Leu Thr Val Tyr Lys Ala Ser
            355                 360                 365

Asn Leu Asn Leu Ile Gly Arg Pro Ser Thr Val His Ser Trp Phe Pro
            370                 375                 380

Gly Tyr Ala Trp Thr Ile Ala Gln Cys Lys Ile Cys Ala Ser His Ile
385                 390                 395                 400

Gly Trp Lys Phe Thr Ala Thr Lys Lys Asp Met Ser Pro Gln Lys Phe
            405                 410                 415

Trp Gly Leu Thr Arg Ser Ala Leu Leu Pro Thr Ile Pro Glu Thr Glu
            420                 425                 430

Asp Glu Ile Ser Pro Asp Lys Val Ile Leu Cys Leu
            435                 440

<210> SEQ ID NO 4
<211> LENGTH: 445
<212> TYPE: PRT
<213> ORGANISM: Mus musculus

<400> SEQUENCE: 4

Met Ala Gly Glu Gly Asp Gln Gln Asp Ala Ala His Asn Met Gly Asn
1               5                   10                  15

His Leu Pro Leu Leu Pro Ala Asp Ser Glu Asp Glu Asp Asp Glu Ile
            20                  25                  30

Glu Met Glu Val Glu Asp Gln Asp Ser Lys Glu Ala Arg Lys Pro Asn
        35                  40                  45

Ile Ile Asn Phe Asp Thr Ser Leu Pro Thr Ser His Thr Tyr Leu Gly
    50                  55                  60

Ala Asp Met Glu Glu Phe His Gly Arg Thr Leu His Asp Asp Asp Ser
65                  70                  75                  80

Cys Gln Val Ile Pro Val Leu Pro Glu Val Leu Met Ile Leu Ile Pro
                85                  90                  95

Gly Gln Thr Leu Pro Leu Gln Leu Ser His Pro Gln Glu Val Ser Met
            100                 105                 110

Val Arg Asn Leu Ile Gln Lys Asp Arg Thr Phe Ala Val Leu Ala Tyr
        115                 120                 125

Ser Asn Val Gln Glu Arg Glu Ala Gln Phe Gly Thr Thr Ala Glu Ile
    130                 135                 140

Tyr Ala Tyr Arg Glu Glu Gln Glu Phe Gly Ile Glu Val Val Lys Val
145                 150                 155                 160

Lys Ala Ile Gly Arg Gln Arg Phe Lys Val Leu Glu Leu Arg Thr Gln
                165                 170                 175

Ser Asp Gly Ile Gln Gln Ala Lys Val Gln Ile Leu Pro Glu Cys Val
            180                 185                 190

Leu Pro Ser Thr Met Ser Ala Val Gln Leu Glu Ser Leu Asn Lys Cys

```
                195                 200                 205
Gln Val Phe Pro Ser Lys Pro Ile Ser Trp Glu Asp Gln Tyr Ser Cys
    210                 215                 220

Lys Trp Trp Gln Lys Tyr Gln Lys Arg Lys Phe His Cys Ala Asn Leu
225                 230                 235                 240

Thr Ser Trp Pro Arg Trp Leu Tyr Ser Leu Tyr Asp Ala Glu Thr Leu
                245                 250                 255

Met Asp Arg Ile Lys Lys Gln Leu Arg Glu Trp Asp Glu Asn Leu Lys
            260                 265                 270

Asp Asp Ser Leu Pro Glu Asn Pro Ile Asp Phe Ser Tyr Arg Val Ala
        275                 280                 285

Ala Cys Leu Pro Ile Asp Asp Val Leu Arg Ile Gln Leu Leu Lys Ile
    290                 295                 300

Gly Ser Ala Ile Gln Arg Leu Arg Cys Glu Leu Asp Ile Met Asn Lys
305                 310                 315                 320

Cys Thr Ser Leu Cys Cys Lys Gln Cys Gln Glu Thr Glu Ile Thr Thr
                325                 330                 335

Lys Asn Glu Ile Phe Ser Leu Ser Leu Cys Gly Pro Met Ala Ala Tyr
            340                 345                 350

Val Asn Pro His Gly Tyr Val His Glu Thr Leu Thr Val Tyr Lys Ala
        355                 360                 365

Ser Asn Leu Asn Leu Ile Gly Arg Pro Ser Thr Val His Ser Trp Phe
    370                 375                 380

Pro Gly Tyr Ala Trp Thr Ile Ala Gln Cys Lys Ile Cys Ala Ser His
385                 390                 395                 400

Ile Gly Trp Lys Phe Thr Ala Thr Lys Lys Asp Met Ser Pro Gln Lys
                405                 410                 415

Phe Trp Gly Leu Thr Arg Ser Ala Leu Leu Pro Thr Ile Pro Glu Thr
            420                 425                 430

Glu Asp Glu Ile Ser Pro Asp Lys Val Ile Leu Cys Leu
        435                 440                 445

<210> SEQ ID NO 5
<211> LENGTH: 445
<212> TYPE: PRT
<213> ORGANISM: Rattus norvegicus

<400> SEQUENCE: 5

Met Ala Gly Glu Gly Asp His Gln Asp Ala His Asn Met Gly Asn
1               5                   10                  15

His Leu Pro Leu Leu Pro Ala Asp Ser Glu Asp Glu Asp Glu Ile
                20                  25                  30

Glu Met Glu Val Glu Asp Gln Asp Ser Lys Glu Ala Arg Lys Pro Asn
            35                  40                  45

Ile Ile Asn Phe Asp Thr Ser Leu Pro Thr Ser His Thr Tyr Leu Gly
        50                  55                  60

Ala Asp Met Glu Glu Phe His Gly Arg Thr Leu His Asp Asp Ser
65                  70                  75                  80

Cys Gln Val Ile Pro Val Leu Pro Glu Val Met Met Ile Leu Ile Pro
                85                  90                  95

Gly Gln Thr Leu Pro Leu Gln Leu Ser His Pro Gln Glu Val Ser Met
            100                 105                 110

Val Arg Asn Leu Ile Gln Lys Asp Arg Thr Phe Ala Val Leu Ala Tyr
        115                 120                 125
```

```
Ser Asn Val Gln Glu Arg Glu Ala Gln Phe Gly Thr Thr Ala Glu Ile
    130                 135                 140

Tyr Ala Tyr Arg Glu Glu Gln Glu Phe Gly Ile Glu Val Val Lys Val
145                 150                 155                 160

Lys Ala Ile Gly Arg Gln Arg Phe Lys Val Leu Glu Leu Arg Thr Gln
                165                 170                 175

Ser Asp Gly Ile Gln Gln Ala Lys Val Gln Ile Leu Pro Glu Cys Val
            180                 185                 190

Leu Pro Ser Thr Met Ser Ala Val Gln Leu Glu Ser Leu Asn Lys Cys
        195                 200                 205

Gln Ile Phe Pro Ser Lys Pro Ile Ser Trp Glu Asp Gln Tyr Ser Cys
    210                 215                 220

Lys Trp Trp Gln Lys Tyr Gln Lys Arg Lys Phe His Cys Ala Asn Leu
225                 230                 235                 240

Thr Ser Trp Pro Arg Trp Leu Tyr Ser Leu Tyr Asp Ala Glu Thr Leu
                245                 250                 255

Met Asp Arg Ile Lys Lys Gln Leu Arg Glu Trp Asp Glu Asn Leu Lys
            260                 265                 270

Glu Asp Ser Leu Pro Ala Asn Pro Ile Asp Phe Ser Tyr Arg Val Ala
        275                 280                 285

Ala Cys Leu Pro Ile Asp Asp Val Leu Arg Ile Gln Leu Leu Lys Ile
    290                 295                 300

Gly Ser Ala Ile Gln Arg Leu Arg Cys Glu Leu Asp Ile Met Asn Lys
305                 310                 315                 320

Cys Thr Ser Leu Cys Cys Lys Gln Cys Gln Glu Thr Glu Ile Thr Thr
                325                 330                 335

Lys Asn Glu Ile Phe Ser Leu Ser Leu Cys Gly Pro Met Ala Ala Tyr
            340                 345                 350

Val Asn Pro His Gly Tyr Val His Glu Thr Leu Thr Val Tyr Lys Ala
        355                 360                 365

Ser Asn Leu Asn Leu Ile Gly Arg Pro Ser Thr Val His Ser Trp Phe
    370                 375                 380

Pro Gly Tyr Ala Trp Thr Ile Ala Gln Cys Lys Ile Cys Ala Ser His
385                 390                 395                 400

Ile Gly Trp Lys Phe Thr Ala Thr Lys Lys Asp Met Ser Pro Gln Lys
                405                 410                 415

Phe Trp Gly Leu Thr Arg Ser Ala Leu Leu Pro Thr Ile Pro Glu Thr
            420                 425                 430

Glu Asp Glu Ile Ser Pro Asp Lys Val Ile Leu Cys Leu
        435                 440                 445

<210> SEQ ID NO 6
<211> LENGTH: 444
<212> TYPE: PRT
<213> ORGANISM: Bos taurus

<400> SEQUENCE: 6

Met Ala Gly Glu Gly Asp Pro Glu Asp Ala Ala His Asn Met Gly Asn
1               5                   10                  15

His Leu Pro Leu Leu Pro Ala Glu Glu Glu Glu Asp Glu Ile Glu
            20                  25                  30

Met Glu Val Glu Asp Gln Asp Asn Lys Glu Pro Lys Lys Pro Asn Ile
        35                  40                  45

Ile Asn Phe Asp Thr Ser Leu Pro Thr Ser His Thr Tyr Leu Gly Ser
    50                  55                  60
```

Asp Met Glu Glu Phe His Gly Arg Thr Leu His Asp Asp Ser Cys
65                  70                  75                  80

Pro Val Ile Pro Val Leu Pro Gln Val Val Met Thr Leu Ile Pro Gly
                85                  90                  95

Gln Thr Leu Pro Leu Gln Leu Phe Ser Pro Gln Glu Val Ser Met Val
            100                 105                 110

Arg Asn Leu Ile Gln Lys Asp Arg Thr Phe Ala Val Leu Ala Tyr Ser
        115                 120                 125

Asn Val Gln Glu Arg Glu Ala Gln Phe Gly Thr Thr Ala Glu Ile Tyr
    130                 135                 140

Ala Tyr Arg Glu Glu Gln Asp Phe Gly Ile Glu Val Val Lys Val Lys
145                 150                 155                 160

Ala Ile Gly Arg Gln Arg Phe Lys Val Leu Glu Ile Arg Thr Gln Ser
                165                 170                 175

Asp Gly Ile Gln Gln Ala Lys Val Gln Ile Leu Pro Glu Cys Val Leu
            180                 185                 190

Pro Ser Thr Met Ser Ala Val Gln Leu Glu Ser Leu Asn Lys Cys Arg
        195                 200                 205

Ile Phe Pro Ser Lys Pro Val Ser Trp Glu Asp Gln Cys Ser Tyr Lys
    210                 215                 220

Trp Trp Gln Lys Tyr Gln Lys Arg Lys Phe His Cys Ala Asn Leu Thr
225                 230                 235                 240

Ser Trp Pro Arg Trp Leu Tyr Ser Leu Tyr Asp Ala Glu Thr Leu Met
                245                 250                 255

Asp Arg Ile Lys Lys Gln Leu Arg Glu Trp Asp Glu Asn Leu Lys Glu
            260                 265                 270

Asp Ser Leu Pro Ser Asn Pro Ile Asp Phe Ser Tyr Arg Val Ala Ala
        275                 280                 285

Cys Leu Pro Ile Asp Asp Val Leu Arg Ile Gln Leu Leu Lys Ile Gly
    290                 295                 300

Ser Ala Ile Gln Arg Leu Arg Cys Glu Leu Asp Ile Met Asn Lys Cys
305                 310                 315                 320

Thr Ser Leu Cys Cys Lys Gln Cys Gln Glu Thr Glu Ile Thr Thr Lys
                325                 330                 335

Asn Glu Ile Phe Ser Leu Ser Leu Cys Gly Pro Met Ala Ala Tyr Val
            340                 345                 350

Asn Pro His Gly Tyr Val His Glu Thr Leu Thr Val Tyr Lys Ala Ser
        355                 360                 365

Asn Leu Asn Leu Ile Gly Arg Pro Ser Thr Asp His Ser Trp Phe Pro
    370                 375                 380

Gly Tyr Ala Trp Thr Ile Ala Gln Cys Arg Ile Cys Ala Ser His Ile
385                 390                 395                 400

Gly Trp Lys Phe Thr Ala Thr Lys Lys Asp Met Ser Pro Gln Lys Phe
                405                 410                 415

Trp Gly Leu Thr Arg Ser Ala Leu Leu Pro Thr Ile Pro Asp Thr Glu
            420                 425                 430

Asp Asp Ile Ser Pro Asp Lys Val Ile Leu Cys Leu
        435                 440

<210> SEQ ID NO 7
<211> LENGTH: 431
<212> TYPE: PRT
<213> ORGANISM: Danio rerio

<400> SEQUENCE: 7

Met Gly Asn Gln Leu Gln Leu Leu Pro Glu Asn Glu Glu Glu Glu
1               5                   10                  15

Asp Asp Met Glu Thr Glu Asp Arg Asp Gly Glu Asp Val Glu Lys Pro
            20                  25                  30

Ser Ile Ile Asn Phe Asp Thr Ser Leu Pro Thr Ser His Ala Tyr Leu
        35                  40                  45

Gly Ser Asp Met Glu Glu Phe His Gly Arg Thr Leu His Asp Glu Asp
    50                  55                  60

Ser Val Gln Asn Leu Pro Val Leu Pro His Val Ala Leu Ile Leu Ile
65                  70                  75                  80

Pro Gly Gln Thr Leu Pro Leu Gln Leu Phe Arg Pro Gln Glu Val Ser
            85                  90                  95

Met Phe Arg Asn Leu Val Ser Gln Asp Arg Thr Phe Ala Val Leu Ala
            100                 105                 110

His Ser Pro Asp Pro Ser Gly Thr Glu Thr Lys Ala Glu Phe Gly Thr
        115                 120                 125

Thr Ala Glu Ile Tyr Ala Phe Arg Glu Glu Gln Tyr Gly Ile Glu
    130                 135                 140

Thr Val Lys Ile Lys Ala Val Gly Arg Gln Arg Phe Arg Val His Asp
145                 150                 155                 160

Ile Arg Thr Gln Ala Asp Gly Ile Arg Gln Ala Lys Val Gln Ile Leu
            165                 170                 175

Pro Glu Arg Ile Leu Pro Asp Pro Leu Cys Ala Leu Gln Phe Leu Pro
            180                 185                 190

Arg Leu His Thr His Ser Pro Gln Thr Lys His Thr Gln Thr Thr Pro
            195                 200                 205

Pro Gln Lys Arg Cys Ser Gln Asn Tyr Arg Gln Lys Lys Leu His Cys
            210                 215                 220

Ala Ser Met Thr Ser Trp Pro Pro Trp Val Tyr Ser Leu Tyr Asp Ser
225                 230                 235                 240

Lys Thr Leu Met Ser Arg Val Lys Lys Gln Leu His Glu Trp Asp Glu
            245                 250                 255

Asn Leu Lys Asp Glu Ser Leu Pro Thr Asn Pro Thr Asp Phe Ser Tyr
            260                 265                 270

Arg Val Ala Ala Cys Leu Pro Ile Asp Asp Ala Leu Arg Leu Gln Leu
            275                 280                 285

Leu Lys Ile Gly Ser Ala Ile Gln Arg Leu Arg Cys Glu Leu Asp Ile
    290                 295                 300

Met Asp Arg Cys Thr Ser Leu Cys Cys Lys Gln Cys Gln Asp Thr Glu
305                 310                 315                 320

Ile Thr Ser Lys Asn Glu Ile Phe Ser Leu Ser Leu Tyr Gly Pro Met
            325                 330                 335

Ala Ala Tyr Val Asn Pro His Gly Tyr Val His Glu Thr Leu Thr Val
            340                 345                 350

Tyr Lys Ala Ser Asn Leu Asn Leu Ile Gly Arg Pro Ser Thr Leu His
    355                 360                 365

Ser Trp Phe Pro Gly Tyr Ala Trp Thr Ile Ala Gln Cys Arg Thr Cys
    370                 375                 380

Ser Ser His Met Gly Trp Lys Phe Ser Ala Val Lys Lys Asp Leu Ser
385                 390                 395                 400

Pro Pro Arg Phe Trp Gly Leu Thr Arg Ser Ala Leu Leu Pro Thr Ile
            405                 410                 415

```
Pro Gln Gly Glu Glu Gly Val Glu Gly Ser Arg Leu Leu Cys Leu
            420                 425                 430
```

<210> SEQ ID NO 8
<211> LENGTH: 1368
<212> TYPE: PRT
<213> ORGANISM: Streptococcus pyogenes

<400> SEQUENCE: 8

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
```

```
                355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
            690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
            770                 775                 780
```

-continued

```
Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
        820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
    915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
        980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140
```

| | | | | | | | | | | |
|---|---|---|---|---|---|---|---|---|---|---|
| Leu | Val | Val | Ala | Lys | Val | Glu | Lys | Gly | Lys | Ser Lys Leu Lys |
| | 1145 | | | | 1150 | | | | 1155 | |

Leu Val Val Ala Lys Val Glu Lys Gly Lys Ser Lys Leu Lys
    1145                1150               1155

Ser Val Lys Glu Leu Leu Gly Ile Thr Ile Met Glu Arg Ser Ser
    1160                1165               1170

Phe Glu Lys Asn Pro Ile Asp Phe Leu Glu Ala Lys Gly Tyr Lys
    1175                1180               1185

Glu Val Lys Lys Asp Leu Ile Ile Lys Leu Pro Lys Tyr Ser Leu
    1190                1195               1200

Phe Glu Leu Glu Asn Gly Arg Lys Arg Met Leu Ala Ser Ala Gly
    1205                1210               1215

Glu Leu Gln Lys Gly Asn Glu Leu Ala Leu Pro Ser Lys Tyr Val
    1220                1225               1230

Asn Phe Leu Tyr Leu Ala Ser His Tyr Glu Lys Leu Lys Gly Ser
    1235                1240               1245

Pro Glu Asp Asn Glu Gln Lys Gln Leu Phe Val Glu Gln His Lys
    1250                1255               1260

His Tyr Leu Asp Glu Ile Ile Glu Gln Ile Ser Glu Phe Ser Lys
    1265                1270               1275

Arg Val Ile Leu Ala Asp Ala Asn Leu Asp Lys Val Leu Ser Ala
    1280                1285               1290

Tyr Asn Lys His Arg Asp Lys Pro Ile Arg Glu Gln Ala Glu Asn
    1295                1300               1305

Ile Ile His Leu Phe Thr Leu Thr Asn Leu Gly Ala Pro Ala Ala
    1310                1315               1320

Phe Lys Tyr Phe Asp Thr Thr Ile Asp Arg Lys Arg Tyr Thr Ser
    1325                1330               1335

Thr Lys Glu Val Leu Asp Ala Thr Leu Ile His Gln Ser Ile Thr
    1340                1345               1350

Gly Leu Tyr Glu Thr Arg Ile Asp Leu Ser Gln Leu Gly Gly Asp
    1355                1360               1365

<210> SEQ ID NO 9
<211> LENGTH: 200
<212> TYPE: DNA
<213> ORGANISM: Artificial Sequence
<220> FEATURE:
<223> OTHER INFORMATION: Synthetic

<400> SEQUENCE: 9
tacagaaatg tttccttagc tgatatcttt ccttaatttc ttaggtatgc ctggactgtt      60
gcccagtgta agatctgtgc aagccatatt ggatggaagg ctactgccac caaaaaagac     120
atgtcacctc aaaatttttg gggcttaacg cgatctgctc tgttgcccac gatcccagac     180
actgaagatg aaataagtcc                                                  200

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ccatattgga tggaagttta                                                   20

TARGETED PROTEIN DEGRADATION USING A MUTANT E3 UBIQUITIN LIGASE

CROSS-REFERENCE TO RELATED APPLICATIONS

This application is a continuation of International Application No. PCT/US2017/054522, filed Sep. 29, 2017, which claims the benefit of U.S. Provisional Application 62/401,303 filed Sep. 29, 2016. The entirety of each of these applications is hereby incorporated by reference.

INCORPORATION BY REFERENCE

The contents of the text file named "16010-020WO1US1_sequence_listing_ST25.txt" which was created on Jul. 25, 2018 and is 38.7 KB in size, are hereby incorporated by reference in their entirety.

BACKGROUND

Protein degradation is a highly regulated and essential process that maintains cellular homeostasis. The selective identification and removal of damaged, misfolded, or excess proteins is achieved via the ubiquitin-proteasome pathway (UPP). The UPP in fact is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (*PLOS One*, 2008, 3, 1487) titled "Genome-wide and functional annotation of human E3 ubiquitin ligases identifies MULAN, a mitochondrial E3 that regulates the organelle's dynamics and signaling."; Berndsen et al. (*Nat. Struct. Mol. Biol.*, 2014, 21, 301-307) titled "New insights into ubiquitin E3 ligase mechanism"; Deshaies et al. (*Ann. Rev. Biochem.*, 2009, 78, 399-434) titled "RING domain E3 ubiquitin ligases."; Spratt et al. (*Biochem.* 2014, 458, 421-437) titled "RBR E3 ubiquitin ligases: new structures, new insights, new questions."; and Wang et al. (*Nat. Rev. Cancer.*, 2014, 14, 233-347) titled "Roles of F-box proteins in cancer.".

In 1995, Gosink et al. (*Proc. Natl. Acad. Sci. USA* 1995, 92, 9117-9121) in a publication titled "Redirecting the Specificity of Ubiquitination by Modifying Ubiquitin-Conjugating Enzymes", provided proof of concept in vitro that engineered peptides can selectively direct ubiquitination of intracellular proteins. The publication by Nawaz et al. (*Proc. Natl. Acad. Sci. U.S.A.* 1999, 96, 1858-1862) titled "Proteasome-Dependent Degradation of the Human Estrogen Receptor" describes ER degradation which takes advantage of the ubiquitin-proteasome pathway.

Proteinex, Inc. filed a patent application in February 1999 that issued as U.S. Pat. No. 6,306,663 claiming a method of generating a compound for activating the ubiquitination of a Target Protein which comprises covalently linking a Target Protein binding element able to bind specifically to the Target Protein via a ubiquitination recognition element. Proteinex described that the invention can be used to control protein levels in eukaryotes. While the '663 patent may have been based on the first patent application to describe the high-level concept of how to manipulate the UPP system to degrade selected proteins in vivo, the patent did not provide sufficient detail to allow persons of skill to easily construct the range of proposed compounds. For example, for the ubiquitination recognition elements, the skilled person was told among other things to use standard methods for drug discovery and screen for appropriate small molecules that would bind to the ligase. Proteinex also emphasized the use of peptides as ubiquitination recognition elements, which can pose significant difficulties for oral drug administration.

Since then, harnessing the ubiquitin-proteasome pathway for therapeutic intervention has received significant interest from the scientific community. The publication by Zhou et al. from Harvard Medical School (*Mol. Cell* 2000, 6, 751-756) titled "Harnessing the Ubiquitination Machinery to Target the Degradation of Specific Cellular Proteins" described an engineered receptor capable of directing ubiquitination in mammalian and yeast cells.

Following from these early publications and others in the mid to late 1990s, it was also recognized by Craig Crews and coworkers (Yale University) that a molecule that is capable of binding a Target Protein and a ubiquitin ligase may cause the Target Protein to be degraded. Their first description of such compounds was provided in U.S. Pat. No. 7,041,298 filed in September 2000 by Deshaies et al. and granted in May 2006 titled "Proteolysis Targeting Chimeric Pharmaceutical", which described a "PROTAC" consisting of a small molecule binder of MAP-AP-2 linked to a peptide capable of binding the F-box protein β-TRCP. Information in the '298 patent is also presented in the corresponding publication by Sakamoto et al. (*Proc. Natl. Acad. Sci. USA* 2001, 98, 8554-8559) titled "Protacs: Chimeric Molecules That Target Proteins to the Skp1-Cullin-F Box Complex for Ubiquitination and Degradation". The publication by Sakamoto et al. (*Mol. Cell. Proteomics* 2003, 2, 1350-1358) titled "Development of Protacs to Target Cancer-Promoting Proteins for Ubiquitination and Degradation" describes an analogous PROTAC (PROTAC2) that instead of degrading MAP-AP-2 degrades estrogen and androgen receptors.

The first E3 ligase successfully targeted with a small molecule was MDM2, which ubiquitinates the tumor suppressor p53. The targeting ligand was an HDM2/MDM2 inhibitor identified in Vassilev et al. (*Science* 2004, 303, 844-848) titled "In Vivo Activation of the P53 Pathway by Small-Molecule Antagonists of MDM2".

Other examples of direct small molecule-induced recruitment of Target Proteins to the proteasome for degradation on addition to cultured cells were described in 2004 (Schneekloth et al. (*J. Am. Chem. Soc.* 2004, 126, 3748-3754) titled "Chemical Genetic Control of Protein Levels: Selective in Vivo Targeted Degradation"). Schneekloth et al. describe a degradation agent (PROTAC3) that targets the FK506 binding protein (FKBP12) and shows that both PROTAC2 and PROTAC3 hit their respective targets with green fluorescent protein (GFP) imaging. The publication by Schneekloth et al. (*ChemBioChem* 2005, 6, 40-46) titled "Chemical Approaches to Controlling Intracellular Protein Degradation" described the state of the field at the time.

The publication by Schneekloth et al. (*Bioorg. Med. Chem. Lett.* 2008, 18, 5904-5908) titled "Targeted Intracellular Protein Degradation Induced by a Small Molecule: En Route to Chemical Proteomics" describes a degradation agent that consists of two small molecules linked by PEG that in vivo degrades the androgen receptor by concurrently binding the androgen receptor and ubiquitin E3 ligase.

WO 2013/170147 filed by Crews et al. titled "Compounds Useful for Promoting Protein Degradation and Methods of Using Same" describes compounds comprising a protein degradation moiety covalently bound to a linker, wherein the C log P of the compound is equal to or higher than 1.5. In particular, the specification discloses protein degrading compounds that incorporate certain small molecules that can bind to an E3 ubiquitin ligase.

In unrelated parallel research, scientists were investigating thalidomide toxicity. Ito et al. (*Science* 2010, 327, 1345-1350) titled "Identification of a Primary Target of Thalidomide Teratogenicity", described that cereblon is a thalidomide binding protein. Cereblon forms part of an E3 ubiquitin ligase protein complex which interacts with damaged DNA binding protein 1, forming an E3 ubiquitin ligase complex with Cullin 4 and the E2-binding protein ROC1 (also known as RBX1) where it functions as a substrate receptor to select proteins for ubiquitination. The study revealed that thalidomide-cereblon binding in vivo may be responsible for thalidomide teratogenicity. After the discovery that thalidomide causes teratogenicity in the mid-1960's, the compound and related structures were notwithstanding found to be useful as anti-inflammatory, anti-angiogenic and anti-cancer agents (see Bartlett et al. (*Nat. Rev. Cancer* 2004, 4, 314-322) titled "The Evolution of Thalidomide and Its Imid Derivatives as Anticancer Agents").

The disclosure that thalidomide binds to the cereblon E3 ubiquitin ligase led to research to investigate incorporating thalidomide and certain derivatives into compounds for the targeted destruction of proteins. Two seminal papers were published in *Science* in 2014: G. Lu et al., The Myeloma Drug Lenalidomide Promotes the Cereblon-Dependent Destruction of Ikaros Proteins, *Science,* 343, 305-309 (2014); and J. Kronke et al., Lenalidomide Causes Selective Degradation of IKZF1 and IKZF3 in Multiple Myeloma Cells, *Science,* 343, 301-305 (2014).

U.S. 2014/0356322 assigned to Yale University, GlaxoSmithKline, and Cambridge Enterprise Limited University of Cambridge titled "Compounds and Methods for the Enhanced Degradation of Target Proteins & Other Polypeptides by an E3 Ubiquitin Ligase" describes protein degrading compounds that bind to the VHL E3 Ubiquitin Ligase. See also Buckley et al. (*J. Am. Chem. Soc.* 2012, 134, 4465-4468) titled "Targeting the Von Hippel-Lindau E3 Ubiquitin Ligase Using Small Molecules to Disrupt the Vhl/Hif-1alpha Interaction".

Additional publications in this area include the following: Lu et al. (*Chem. Biol.* 2015, 22, 755-763) titled "Hijacking the E3 Ubiquitin Ligase Cereblon to Efficiently Target Brd4"; Bondeson et al. (*Nat. Chem. Biol.* 2015, 11, 611-617) titled "Catalytic in Vivo Protein Knockdown by Small-Molecule Protacs"; Gustafson et al. (*Angewandite Chemie, International Edition in English* 2015, 54, 9659-9662) titled "Small-Molecule-Mediated Degradation of the Androgen Receptor through Hydrophobic Tagging"; Lai et al. (*Angewamdte Chemie, International Edition in English* 2016, 55, 807-810) titled "Modular Protac Design for the Degradation of Oncogenic Bcr-Abl"; Toure et al. (*Angew. Chem. Int. Ed.* 2016, 55, 1966-1973) titled "Small-Molecule Protacs: New Approaches to Protein Degradation"; and Winter et al. (*Science* 2015, 348, 1376-1381) titled "Drug Development. Phthalimide Conjugation as a Strategy for in Vivo Target Protein Degradation" describes thalidomide based Target Protein degradation technology.

WO 2015/160845 assigned to Arvinas Inc. titled "Imide Based Modulators of Proteolysis and Associated Methods of Use" describes protein degradation compounds that incorporate thalidomide and certain derivatives which bind to a cereblon E3 ligase. Additional patent applications filed by Arvinas Inc. directed towards the degradation of a Target Protein using known E3 ligase ligands to direct the Target Protein to the proteasome for degradation include U.S. 2016/0058872 titled "Imide Based Modulators of Proteolysis and Associated Methods of Use"; U.S. 2016/0045607 titled "Estrogen-related Receptor Alpha Based PROTAC Compounds and Associated Methods of Use"; U.S. 2016/0214972 titled "Compounds and Methods for the Targeted Degradation of Androgen Receptor"; U.S. 2016/0272639 titled "Compounds and Methods for the Enhanced Degradation of Target Proteins"; U.S. 2017/0008904 titled "MDM2-Based Modulators of Proteolysis and Associated Methods of Use"; U.S. 2017/0037004 titled "Alanine-Based Modulators of Proteolysis and Associated Methods of Use", U.S. 2017/0065719 titled "Compounds and Methods for the Targeted Degradation of Bromodomain containing proteins"; WO 2016/036036 titled "Tank Binding Kinase-1 PROTACS and Associated Methods of Use"; and WO 2016/197032 "Imide-Based Modulators and Proteolysis and Associated Methods of Use".

Dana-Farber Cancer Institute has also filed several patent applications directed towards the degradation of a Target Protein using known E3 ligase ligands to direct the Target Protein to the proteasome for degradation. These filings include US 2016/0176916 titled "Methods to Induce Target Protein Degradation through Bifunctional Molecules; WO 2017/024318 titled "Target Protein Degradation to Attenuate Adoptive T-Cell Therapy Associated Adverse Inflammatory Responses"; WO 2017/024317 titled "Methods to Induce Target Protein Degradation through Bifunctional Molecules"; WO 2017/024319 titled "Tunable Endogenous Protein Degradation"; WO 2017/117474 titled "Bifunctional Compounds for HER3 Degradation and Methods of Use"; and WO 2017/117473 titled "Bifunctional Molecules for HER3 Degradation and Methods of Use".

There is a need for the development of new strategies for targeted protein degradation in a selective manner.

SUMMARY

The present invention describes new strategies for targeted protein degradation via the ubiquitin proteasome pathway (UPP) in a tissue specific manner using bifunctional compounds that function to recruit targeted proteins to a functional, mutant E3 ubiquitin ligase, for example a functional, mutant cereblon, resulting in the ubiquitination of the targeted protein and subsequent proteasomal degradation. The use of bifunctional compounds that recruit targeted proteins to a mutant E3 ubiquitin ligase allows for the specific and targeted degradation of proteins in cells expressing the mutant E3 ubiquitin ligase, providing a powerful tool for controlling protein expression in select cells. Because of the selectivity afforded through the utilization of mutant E3 ubiquitin ligase for protein degradation, the bifunctional compounds can be deployed in a wide range of protein degradation strategies that require or benefit from confined protein degradation within a specific cell or tissue, for example but not limited to anti-cancer strategies, engineered T-cell downregulation strategies, therapies targeting tissue specific overexpression, toxic accumulation, or gain of function of expressed proteins, or tissue specific protein functional studies. By using bifunctional compounds that primarily recruit targeted proteins to a mutant E3 ubiquitin ligase, an increased therapeutic index is provided. Furthermore, by limiting protein degradation to cells that express mutant E3 ubiquitin ligase, toxicity is reduced due to the confined nature of degradation and reduction in off-targeting effects.

In one aspect of the present invention, tissue specific protein degradation is accomplished by using a bump-and-hole strategy wherein the mutant E3 ubiquitin ligase has been engineered to have an additional pocket ("hole") which accommodates a substituent on the bifunctional compound ("bump"). The "hole" on the mutant E3 ubiquitin ligase preserves the ubiquitination functionality of the E3 ubiquitin ligase while providing a specific target for the E3 ubiquitin ligase-binding moiety of the bifunctional compound. Conversely, the "bump" on the E3 ubiquitin ligase-binding moiety of the bifunctional compound allows it to bind to mutant E3 ubiquitin ligase, but renders it incapable of binding wild-type E3 ubiquitin ligase, thus allowing for protein degradation to occur in the presence of the mutant E3 ubiquitin ligase. The selectivity of mutant E3 ubiquitin ligase over wild-type E3 ubiquitin ligase allows for the targeted degradation of the protein of interest and decreases side effects as compared to nonselective strategies. The mutant E3 ubiquitin ligase can be selected from E3A, mdm2, Anaphase-promoting complex, UBR5, SOCS/BC-box/eloBC/cul5/RING complex, LNXp80, CBX4, CBLL1, HACE1, HECTD1, HECTD2, HECTD3, HECTD4, HECW1, HECW2, HERC1, HERC2, HERC3, HERC4, HERC5, HERC6, HUWE1, ITCH, NEDD4, NEDD4L, PPIL2, PRPF19, PIAS1, PIAS2, PIAS3, PIAS4, RANBP2, RNF4, PBX1, SMURF1, SMURF2, STUB1, TOPORS, TRIP12, UBE3A, UBE3B, UBE3C, UBE3D, UBE4A, UBE4B, UBOX5, UBR5, VHL, WWP1, WWP2, and Parkin. In one embodiment, the mutant E3 ubiquitin ligase is cereblon.

In one aspect, provided herein are amino acid sequences directed to mutant E3 ubiquitin ligase cereblon, nucleic acid sequences encoding mutant cereblon, and cells expressing mutant cereblon, wherein the mutant cereblon maintains ubiquitination activity and is capable of being bound by a bifunctional compound comprising a mutant cereblon-binding moiety. In one embodiment, the mutant cereblon is derived from a human wild-type cereblon amino acid sequence (UniProtKB-Q96SW2 (CRBN_HUMAN)) (SEQ. ID. No. 1) comprising one or more amino acid substitutions at amino acids N351, H353, W380, and F402. In one embodiment, the mutation is selected from N351C, H353C, W380A, and F402A. In one embodiment, the mutant cereblon is derived from a human wild-type cereblon amino acid sequence (UniProtKB-Q96SW2-2 (CRBN_HUMAN)) (SEQ. ID. No. 2) comprising one or more amino acid substitutions selected from N350, H352, W379, and F401. In one embodiment, the mutation is selected from N350C, H352C, W379A, and F401A. In one embodiment, the mutant cereblon is derived from a mouse wild-type cereblon amino acid sequence (UniProtKB-Q8C7D2-2) (CRBN_MOUSE)) (SEQ. ID. No. 3) comprising one or more amino acid substitutions selected from N353, H355, W382, and F404. In one embodiment, the mutation is selected from N353C, H355C, W382A, and F404A. In one embodiment, the mutant cereblon is derived from a mouse wild-type cereblon amino acid sequence (UniProtKB-Q8C7D2-1 (CRBN_MOUSE)) (SEQ. ID. No. 4) comprising one or more amino acid substitutions selected from N354, H350, W383, and F405. In one embodiment, the mutation is selected from N354C, H350C, W383A, and F405A. In one embodiment, the mutant cereblon is derived from a rat wild-type cereblon amino acid sequence (UniProtKB-Q56AP7 (CRBN_RAT)) (SEQ. ID. No. 5) comprising one or more amino acid substitutions selected from N353, H355, W382, and F404. In one embodiment, the mutation is selected from N353C, H355C, W382A, and F404A. In one embodiment, the mutant cereblon is derived from a bovine wild-type cereblon amino acid sequence (UniProtKB-Q0P564 (CRBN_BOVIN)) (SEQ. ID. No. 6) comprising one or more amino acid substitutions selected from N353, H355, W382, and F404. In one embodiment, the mutation is selected from N353C, H355C, W382A, and F404A. In one embodiment, the mutant cereblon is derived from a zebrafish wild-type cereblon amino acid sequence (UniProtKB-Q68EH9 (CRBN_DANRE)) (SEQ. ID. No. 7) comprising one or more amino acid substitutions selected from N341, H343, W370A, and F392A. In one embodiment, the mutation is selected from N341C, H343C, W370A, and F392A. In one embodiment, the polynucleotide encoding mutant cereblon further includes a tissue-specific promoter sequence operably linked to the nucleic acid sequence encoding mutant cereblon. By utilizing a tissue specific promoter sequence, targeted protein degradation can be limited to select tissues, for example in a transgenic animal.

In one aspect, provided herein is a cell or a transgenic animal comprising a cell having a nucleic acid sequence encoding a mutant E3 ubiquitin ligase, wherein the mutant E3 ubiquitin ligase maintains ubiquitination activity and is capable of being bound by a bifunctional compound comprising a mutant E3 ubiquitin ligase-binding moiety. In one embodiment, the nucleic acid sequence encoding a mutant E3 ubiquitin ligase is operably linked to a nucleic acid sequence comprising a tissue specific promoter sequence which, upon expression, expresses the mutant E3 ubiquitin ligase in a tissue specific manner. In one embodiment, the cell has inserted into its genome a polynucleotide encoding a mutant E3 ubiquitin ligase in-frame with a tissue specific promoter polynucleotide sequence which, upon expression, expresses the mutant cereblon in a tissue specific manner. In on embodiment, the cell has artificially undergone induced mutagenesis to express a mutant E3 ubiquitin ligase. In one embodiment, the mutant E3 ubiquitin ligase cereblon. In one embodiment, the mutant cereblon is derived from SEQ. ID. No. 1 comprising one or more amino acid substitutions selected from N351, H353, W380, and F402, for example N351C, H353C, W380A, and F402A, SEQ. ID. No. 2 comprising one or more amino acid substitutions selected from N350, H352, W379, and F401, for example N350C, H352C, W379A, and F401A, SEQ. ID. No. 3 comprising one or more amino acid substitutions selected from N353C, H355C, W382A, and F404A, for example N353, H355, W382, and F404, SEQ. ID. No. 4 comprising one or more amino acid substitutions selected from N354, H350, W383, and F405, for example N354C, H350C, W383A, and F405A, SEQ. ID. No. 5 comprising one or more amino acid substitutions selected from N353, H355, W382, and F404, for example, N353C, H355C, W382A, and F404A SEQ. ID. No. 6 comprising one or more amino acid substitutions selected from N353C, H355C, W382A, and F404A, for example N353, H355, W382, and F404, or SEQ. ID. No. 7 comprising one or more amino acid substitutions selected from N341, H343, W370, and F392, for example N341C, H343C, W370A, and F392A In one embodiment, the cell is a mammalian cell. In one embodiment, the mammalian cell is a human cell. In one embodiment, the mammalian cell is a cancer cell. In one embodiment, the cell is an immune effector cell, for example a T-cell. In one embodiment, the immune effector cell further expresses a chimeric antigen receptor (CAR) or an engineered T-cell receptor (TCR).

Further provided herein are bifunctional compounds comprising a E3 ubiquitin ligase-binding moiety which selectively binds to a mutant E3 ubiquitin ligase. The E3 ubiquitin ligase-binding moieties of the bifunctional compounds of the invention preferentially do not bind to endogenous E3 ubiquitin ligase, rendering the bifunctional compounds non-functional in a cell that does not express its concomitant mutant E3 ubiquitin ligase partner. In one embodiment, the E3 ubiquitin ligase-binding moiety binds to a mutant cereblon derived from the sequence of a wild-type cereblon with one or more amino acid substitutions, for example as described herein. In one embodiment, the cereblon-binding moiety binds to an exogenous cereblon, for example, an interspecies wild-type cereblon, while not binding to endogenous cereblon.

In one aspect, provided herein is a method for targeting a protein for degradation in a cancer cell that expresses a mutant E3 ubiquitin ligase, comprising exposing the cell to a bifunctional compound comprising a mutant E3 ubiquitin ligase-binding moiety. In one embodiment, the cancer cell has a decreased or downregulated level of endogenous E3 ubiquitin ligase, for example cereblon. In one embodiment, the cancer cell is resistant to treatment with thalidomide or a thalidomide derivative, for example lenalidomide and/or pomalidomide. In one embodiment, the cancer cell is a multiple myeloma cell.

In one aspect, provided herein is a method of regulating chimeric antigen receptor (CAR) or engineered T-cell receptor (TCR) expression in a T-cell, wherein the T-cell expresses a mutant E3 ubiquitin ligase, comprising introducing a bifunctional compound comprising a mutant E3 ubiquitin ligase-binding moiety and a CAR or TCR binding moiety capable of degrading the CAR or TCR. The use of a bifunctional compound to target CAR or TCR ubiquitination and degradation within the CAR or TCR T-cell allows for reversible control of the CAR or TCR expression and in turn the T-cell response, while sparing the CAR or TCR T-cell itself. The bifunctional compound can be used as a rheostat of CAR or TCR expression and, thus, CAR or TCR T-cell stimulation, affording the ability to regulate the expression of the CAR or TCR and degree of CAR or TCR T-cell responses by administration of the bifunctional compound, and regeneration of the CAR or TCR upon clearance of the bifunctional compound. Furthermore, by incorporating a bifunctional compound which is primarily active in a T-cell expressing a mutant E3 ubiquitin ligase, adverse side effects associated with current CAR or TCR T-cell therapies such as inflammatory responses, including CRS, and metabolic responses, such as TIL, may be controlled through the administration of a bifunctional compound that controls CAR or TCR expression, all while allowing the CAR or TCR T-cell to retain its ability to reactivate upon re-expression of the CAR or TCR and clearance of the bifunctional compound, while sparing the degradation of T-cell receptors in T-cells not expressing the mutant E3 ubiquitin ligase.

Therefore, in one embodiment, a method is provided that includes:

(i) removing immune effector cells, for example T-cells, from a patient with a disorder of diseased cells that can be treated by increasing the ability of the patient's T-cells to recognize and bind to the diseased cells;

(ii) transforming the T-cells ex vivo by inserting a nucleic acid encoding a CAR or TCR having at least a sequence targeting a diseased cell surface antigen and an intracellular signaling domain amino acid sequence that can be recognized by and bound to a bifunctional compound to form a CAR or TCR T-cell;

(iii) transforming the T-cells ex vivo by inserting a nucleic acid encoding a functional, mutant E3 ubiquitin ligase or introducing a genetic mutation into an endogenous E3 ubiquitin ligase gene, wherein, upon expression, produces a mutant E3 ubiquitin ligase that can be recognized by and bound to a bifunctional compound;

(iii) administering to the patient the CAR or TCR T-cells; and then (iv) administering to the patient, as needed, a bifunctional compound which binds to a) the intracellular signaling domain of the CAR or TCR and b) the mutant E3 ubiquitin ligase in a manner that brings the CAR or TCR into proximity of the mutant E3 ubiquitin ligase, such that the CAR or TCR, or a portion thereof, is ubiquitinated, and then degraded by a proteasome. In one embodiment, the nucleic acid encoding the CAR or TCR also encodes the mutant E3 ubiquitin ligase. In one embodiment, the nucleic acid sequence encoding the mutant E3 ubiquitin ligase is operably linked to a tissue specific promoter, for example a T-cell specific promoter. In one embodiment, the mutant E3 ubiquitin ligase is mutant cereblon.

By degrading at least a portion of the intracellular signaling domain of the CAR or TCR, the ability of the CAR or TCR to activate the immune effector cell, for example a CAR T-cell, is diminished. As contemplated herein, sufficient degradation of the CAR or TCR occurs wherein the CAR's or TCR's signaling functionality is disrupted.

In one aspect, provided herein is a method of treating a subject suffering from a disorder associated with the overexpression, toxic accumulation, or gain of function of a protein of interest comprising:

(i) transforming an affected cell by inserting a nucleic acid encoding a functional, mutant E3 ubiquitin ligase or introducing a genetic mutation into an endogenous E3 ubiquitin ligase gene, wherein upon expression a mutant E3 ubiquitin ligase that can be recognized by and bound to a bifunctional compound is expressed; and (ii) administering to the patient, as needed, a bifunctional compound, wherein the bifunctional compound binds to a) the protein of interest and b) the mutant E3 ubiquitin ligase in a manner that brings the protein of interest into proximity of the mutant E3 ubiquitin ligase, such that the protein of interest is ubiquitinated, and then degraded by a proteasome. Accordingly, by regulating expression of endogenous proteins in this manner, downstream effects of modulating protein expression can be examined across a wide variety of proteins and cell types, and in various physiological conditions. Because the bifunctional compound concentration within the cell can be titrated, protein concentrations within the cell can be finely tuned, allowing for the conditional alteration of protein abundance within the cell and the ability to alter phenotype within the cell on demand. In one embodiment, the nucleic acid encoding a mutant E3 ubiquitin ligase is operably linked to a tissue specific promoter. In one embodiment, the protein of interest to be targeted for degradation includes, but is not limited to, alpha-1 antitrypsin (A1AT), β-catenin (CTNNB1), apolipoprotein B (APOB), angiopoietin-like protein 3 (ANGPTL3), proprotein convertase subtilisin/kexin type 9 (PCSK9), apolipoprotein C3 (APOC3), low density lipoprotein receptor (LDLR), C-reactive protein (CRP), apolipoprotein a (Apo (a)), Factor VII, Factor XI, antithrombin III (SERPINC1), phosphatidylinositol glycan class A (PIG-A), C5, alpha-1 antitrypsin (SERPINA1), hepcidin regulation (TMPRSS6), (delta-aminolevulinate synthase 1 (ALAS-1), acylCaA:diacylglycerol acyltransferase (DGAT), miR-122, miR-21, miR-155, miR-34a, prekallikrein (KLKB1), connective tissue growth factor (CCN2), intercellular adhesion molecule 1 (ICAM-1), glucagon receptor (GCGR), glucorticoid receptor (GCCR), protein tyrosine phosphatase (PTP-1B), c-Raf kinase (RAF1), fibroblast growth factor receptor 4 (FGFR4), vascular adhesion molecule-1 (VCAM-1), very late antigen-4 (VLA-4), transthyretin (TTR), survival motor neuron 2 (SMN2), growth hormone receptor (GHR), dystophia myotonic protein kinase (DMPK), cellular nucleic acid-binding protein (CNBP or ZNF9), clusterin (CLU), eukaryotic translation initiation factor 4E (eIF-4e), MDM2, MDM4, heat shock protein 27 (HSP 27), signal transduction and activator of transcription 3 protein (STAT3), vascular endothelial growth factor (VEGF), kinesin spindle protein (KIF11), hepatitis B genome, the androgen receptor (AR), Atonal homolog 1 (ATOH1), vascular endothelial growth factor receptor 1 (FLT1), retinoschism 1 (RS1), retinal pigment epithelium-specific 65 kDa protein (RPE65), Rab escort protein 1 (CHM), and the sodium channel, voltage gated, type X, alpha subunit (PN3 or SCN10A).

Selectivity for mutant E3 ubiquitin ligase over endogenous E3 ubiquitin ligase can be achieved by designing a bifunctional molecule with Degrons (cereblon-binding moieties) that cannot sterically fit in the endogenous E3 ubiquitin ligase binding pocket (bumped Degrons) and designing mutant E3 ubiquitin ligase (hole E3 ubiquitin ligase) that can accommodate the sterically modified Degron. Typically, substitution of a moiety on the nitrogen of a glutarimide is expected to prevent the ability of the molecule to bind to, for example, endogenous cereblon. As exemplified in the Examples, it has been surprisingly discovered that cereblon binding can be rescued by mutating the cereblon to facilitate the substitution. In one embodiment, the Degron is bumped at the $R_{13}$ position in the chemical compound provided below.

In one embodiment, a compound of Formula I or Formula II comprising a mutant cereblon-binding moiety is provided:

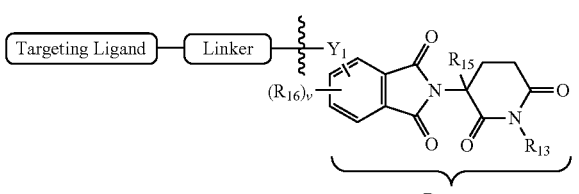

(I)

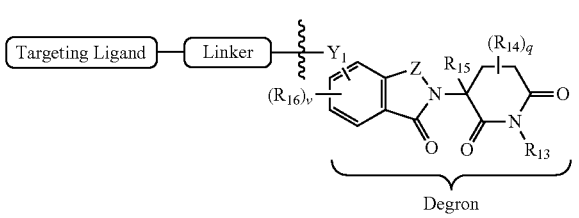

(II)

or an enantiomer, diastereomer, or stereoisomer, or a pharmaceutically acceptable salt thereof, wherein:

$Y_1$ is a bond, $(CH_2)_{1-6}$, $(CH_2)_{0-6}$—O, $(CH_2)_{0-6}$—C(O)NR$_{11}$, $(CH_2)_{0-6}$—NR$_{11}$C(O), $(CH_2)_{0-6}$—NH, or $(CH_2)_{0-6}$—NR$_{12}$;

$R_{11}$ is H or $C_1$-$C_6$ alkyl;

$R_{12}$ is $C_1$-$C_6$ alkyl or C(O)—$C_1$-$C_6$ alkyl;

$R_{13}$ is —(CH$_2$)$_n$—(C$_6$-C$_{10}$) aryl, —(CH$_2$)$_n$-heteroaryl, —(CH$_2$)$_n$—(C$_3$-C$_7$) cycloalkyl, or —(CH$_2$)$_n$-heterocycloalkyl, wherein the aryl, heteroaryl, cycloalkyl, or heterocycloalkyl is optionally substituted with one or more $R_{17}$;

each $R_{14}$ is independently $C_1$-$C_3$ alkyl;

q is 0, 1, or 2; and $R_{15}$ is H, deuterium, $C_1$-$C_3$ alkyl, F, or Cl;

each $R_{16}$ is independently halogen, OH, $C_1$-$C_6$ alkyl, or $C_1$-$C_6$ alkoxy;

each $R_{17}$ is independently $C_1$-$C_6$ alkyl, $C_1$-$C_6$ haloalkyl, $C_1$-$C_6$ alkoxy, $C_1$-$C_6$ haloalkoxy, halogen, NH$_2$, CN, NO$_2$, OH, or C(O)OH; and n and v are each independently 0, 1, 2, or 3;

Z is C(O) or C(R$_{18}$)$_2$;

$R_{18}$ is H or $C_1$-$C_3$ alkyl;

the Linker is a group that covalently binds to the Target Ligand and $Y_1$;

the Degron is capable of binding to a mutant ubiquitin ligase, such as a mutant E3 ubiquitin ligase (e.g., a mutant cereblon); and the Targeting Ligand is capable of binding to a targeted protein.

In an additional embodiment $R_{13}$ is —(CH$_2$)$_2$—(C$_6$-C$_{10}$) aryl, —(C$_6$-C$_{10}$) aryl, —(CH$_2$)$_n$-heteroaryl, —(CH$_2$)$_n$—(C$_3$-C$_7$) cycloalkyl, —(CH$_2$)$_2$-heterocycloalkyl, or heterocycloalkyl, each of which is optionally substituted with one or more $R_{17}$.

In another embodiment $R_{13}$ is —(CH$_2$)$_2$—(C$_6$-C$_{10}$) aryl.

In another embodiment $R_{13}$ is (C$_6$-C$_{10}$) aryl.

In another embodiment $R_{13}$ is —(CH$_2$)$_n$-heteroaryl.

In another embodiment $R_{13}$ is —(CH$_2$)$_n$—(C$_3$-C$_7$) cycloalkyl.

In another embodiment $R_{13}$ is —(CH$_2$)$_2$-heterocycloalkyl.

In another embodiment $R_{13}$ is heterocycloalkyl.

Selectivity for mutant E3 ubiquitin ligase over endogenous E3 ubiquitin ligase can be achieved by designing a bifunctional molecule with Degrons (cereblon-binding moieties) that cannot sterically fit in the endogenous E3 ubiquitin ligase binding pocket (bumped Degrons) and designing mutant E3 ubiquitin ligase (hole E3 ubiquitin ligase) that can accommodate the sterically modified Degron. Additional selectivity can be obtained by modifying the E3 ubiquitin ligase to also contain cysteine for covalent binding and designing Degrons that have can form a covalent bond with cysteine.

In one embodiment, a compound of Formula (III) comprising a mutant cereblon-binding moiety is provided:

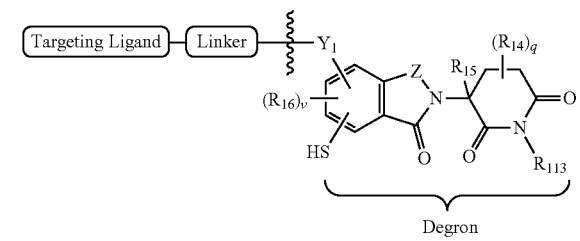

(III)

or an enantiomer, diastereomer, or stereoisomer, or a pharmaceutically acceptable salt thereof, wherein:

$Y_1$ is a bond, $(CH_2)_{1-6}$, $(CH_2)_{0-6}$—O, $(CH_2)_{0-6}$—C(O)$NR_{11}$, $(CH_2)_{0-6}$—$NR_{11}$C(O), $(CH_2)_{0-6}$—NH, or $(CH_2)_{0-6}$—$NR_{12}$;

$R_{11}$ is H or $C_1$-$C_6$ alkyl, $R_{12}$ is $C_1$-$C_6$ alkyl or C(O)—$C_1$-$C_6$ alkyl;

$R_{113}$ is hydrogen, —$(CH_2)_n$—$(C_6$-$C_{10})$ aryl, —$(CH_2)_n$-heteroaryl, —$(CH_2)_n$—$(C_3$-$C_7)$ cycloalkyl, or —$(CH_2)_n$-heterocycloalkyl, wherein the aryl, heteroaryl, cycloalkyl, or heterocycloalkyl is optionally substituted with one or more $R_{17}$;

each $R_{14}$ is independently $C_1$-$C_3$ alkyl;

q is 0, 1, or 2;

$R_{15}$ is H, deuterium, $C_1$-$C_3$ alkyl, F, or Cl;

each $R_{16}$ is independently halogen, OH, $C_1$-$C_6$ alkyl, or $C_1$-$C_6$ alkoxy;

v1 is 0, 1, or 2;

Z is C(O) or $C(R_{18})_2$;

each $R_{17}$ is independently $C_1$-$C_6$ alkyl, $C_1$-$C_6$ haloalkyl, $C_1$-$C_6$ alkoxy, $C_1$-$C_6$ haloalkoxy, halogen, $NH_2$, CN, $NO_2$, OH, or C(O)OH; and $R_{18}$ is H or $C_1$-$C_3$ alkyl;

the Linker is a group that covalently binds to the Target Ligand and $Y_1$;

the Degron is capable of binding to a mutant ubiquitin ligase, such as a mutant E3 ubiquitin ligase (e.g., a mutant cereblon); and the Targeting Ligand is capable of binding to a targeted protein.

In an additional embodiment $R_{113}$ is —$(CH_2)_2$—$(C_6$-$C_{10})$ aryl, —$(C_6$-$C_{10})$ aryl, —$(CH_2)_n$-heteroaryl, —$(CH_2)_n$—$(C_3$-$C_7)$ cycloalkyl, —$(CH_2)_2$-heterocycloalkyl, or heterocycloalkyl, each of which is optionally substituted with one or more $R_{17}$.

In another embodiment $R_{113}$ is —$(CH_2)_2$—$(C_6$-$C_{10})$ aryl.

In another embodiment $R_{113}$ is $(C_6$-$C_{10})$ aryl.

In another embodiment $R_{113}$ is —$(CH_2)_n$-heteroaryl.

In another embodiment $R_{113}$ is —$(CH_2)_n$—$(C_3$-$C_7)$ cycloalkyl.

In another embodiment $R_{113}$ is —$(CH_2)_2$-heterocycloalkyl.

In another embodiment $R_{113}$ is heterocycloalkyl.

In another embodiment $R_{113}$ is hydrogen.

In one embodiment selectivity for mutant E3 ubiquitin ligase over endogenous E3 ubiquitin ligase can be achieved by modifying the E3 ubiquitin ligase to contain cysteine for covalent binding and designing Degrons that have can form a covalent bond with cysteine. In one embodiment the compound of Formula (III) does not have a bump (i.e. $R_{113}$ is H).

In another embodiment the bifunctional compound is of Formula A:

(A)

wherein:

$R^{101}$ is selected from:

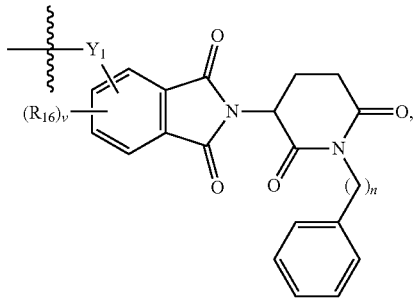

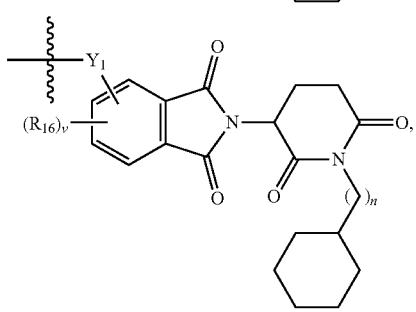

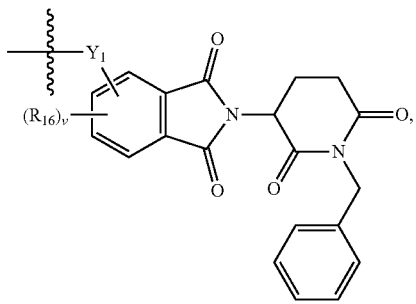

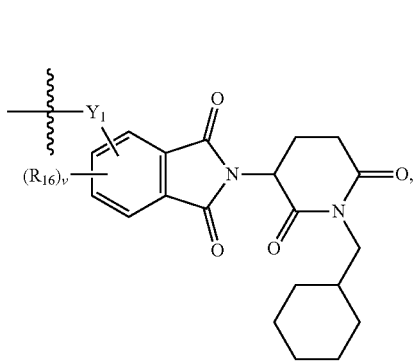

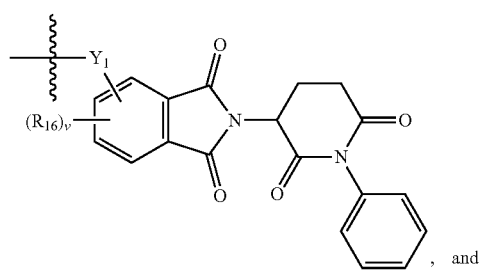

, and

-continued

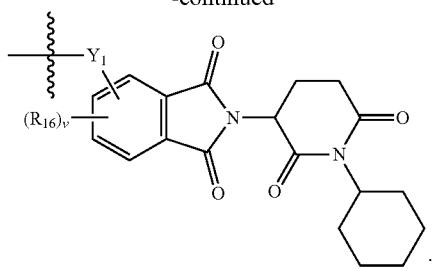

In one embodiment $R^{101}$ is selected from:

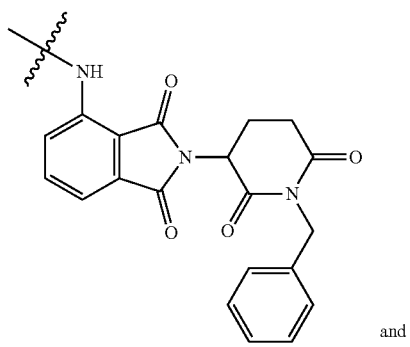

and

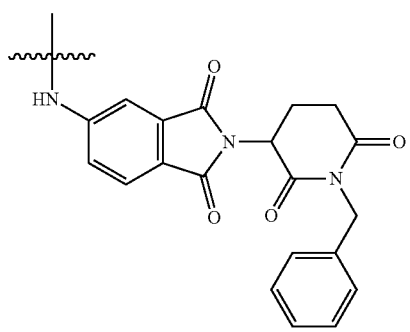

The present application also relates to a bifunctional compound having the following structure:

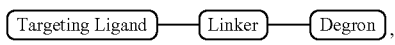

wherein the Linker is covalently bound to at least one Degron and at least one Targeting Ligand, the Degron is capable of binding to a mutant ubiquitin ligase such as a mutant E3 ubiquitin ligase (e.g., a mutant cereblon), and the Targeting Ligand is capable of binding to the targeted protein(s).

The present application also relates to a degradation inducing moiety, or Degron, which is small in size and highly effective in recruiting targeted proteins for degradation.

The present application further relates to a Degron of Formula D1 or D2:

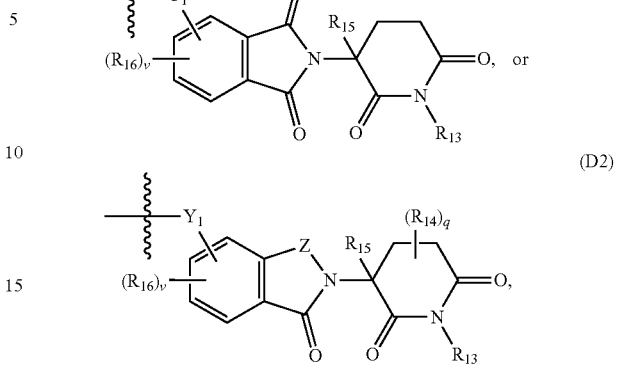

or an enantiomer, diastereomer, or stereoisomer thereof, wherein $Y_1$, Z, $R_{13}$, $R_{14}$, $R_{15}$, $R_{16}$, v, and q are each as defined herein.

The present application further relates to a Linker of Formula L0:

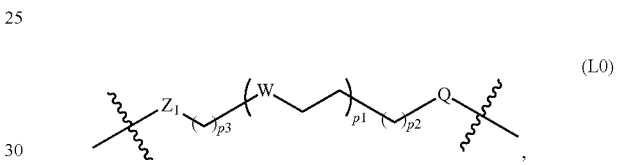

or an enantiomer, diastereomer, or stereoisomer thereof, wherein p1 is an integer selected from 0 to 12;
p2 is an integer selected from 0 to 12;
p3 is an integer selected from 1 to 6;
each W is independently absent, $CH_2$, O, S, NH, or $NR_{19}$;
$Z_1$ is absent, $CH_2C(O)NH$, $OCH_2C(O)NH$, $OCH_2C(O)NR_{19}$, $C(O)NH$, $C(O)NR_{19}$, $NHC(O)$, $NR_{19}C(O)$, $CH_2$, O, NH, or $NR_{19}$;
each $R_{19}$ is independently $C_1$-$C_3$ alkyl;
Q is absent or $NHC(O)CH_2$;
wherein the Linker is covalently bonded to a Degron via the

next to Q, and covalently bonded to a Targeting Ligand via the

next to $Z_1$.

The present application also relates to a pharmaceutical composition comprising a therapeutically effective amount of a compound Formula (I), Formula (II), or Formula (III), or an enantiomer, diastereomer, or stereoisomer, or a pharmaceutically acceptable salt thereof, and a pharmaceutically acceptable carrier.

Another aspect of the present application relates to a method for treating a disease or condition which is modulated by a targeted protein. The method comprises administering to a subject in need thereof an effective amount of a pharmaceutical composition comprising a bifunctional compound of Formula (I), Formula (II), or Formula (III), or an enantiomer, diastereomer, or stereoisomer, or a pharmaceutically acceptable salt thereof, and a pharmaceutically acceptable carrier.

Another aspect of the present application relates to use of a compound of Formula (I), Formula (II), or Formula (III), or an enantiomer, diastereomer, or stereoisomer, or a pharmaceutically acceptable salt thereof, for treating a disease or condition which is modulated by a targeted protein.

Another aspect of the present application relates to use of a pharmaceutical composition comprising a compound of Formula (I), Formula (II), or Formula (III), or an enantiomer, diastereomer, or stereoisomer, or a pharmaceutically acceptable salt thereof, and a pharmaceutically acceptable carrier, for treating a disease or condition which is modulated by a targeted protein.

The present application also relates to use of a compound of Formula (I), Formula (II), or Formula (III), or an enantiomer, diastereomer, or stereoisomer, or a pharmaceutically acceptable salt thereof, in the manufacture of a medicament for treating a disease or condition which is modulated by a targeted protein.

Another aspect of the present application relates to a method for treating cancer (e.g., a cancer modulated by a targeted protein), comprising administering a therapeutically effective amount of a compound of Formula (I), Formula (II), or Formula (III), or an enantiomer, diastereomer, or stereoisomer, or a pharmaceutically acceptable salt thereof, to a subject in need thereof.

In certain embodiments, the disease or condition (e.g., cancer) is resistant to treatment with the Targeting Ligand.

In certain embodiments, a bifunctional compound of Formula (II) is a bifunctional compound of Formula (I).

The details of the application are set forth in the accompanying description below. Although methods and materials similar or equivalent to those described herein can be used in the practice or testing of the present application, illustrative methods and materials are now described. In the case of conflict, the present specification, including definitions, will control. In addition, the materials, methods, and examples are illustrative only and are not intended to be limiting. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs.

The contents of all references (including literature references, issued patents, published patent applications, and co-pending patent applications) cited throughout this application are hereby expressly incorporated herein in their entireties by reference. The references cited herein are not admitted to be prior art to the application.

BRIEF DESCRIPTION OF THE DRAWINGS

FIG. 1A is an immunoblot showing levels of N350C mutant CRBN at the indicated time points after incubation with 0.2 µg/mL of doxycycline. FIG. 1B is an immunoblot showing levels of H352C mutant CRBN at the indicated time points after incubation with 0.2 µg/mL of doxycyclin. FIG. 1C is an immunoblot showing levels of W379A mutant CRBN at the indicated time points after incubation with 0.2 µg/mL of doxycycline. FIG. 1D is an immunoblot showing levels of F401A mutant CRBN at the indicated time points after incubation with 0.2 µg/mL of doxycycline. FIG. 1E is an immunoblot showing levels of WT CRBN at the indicated time points after incubation with 0.2 µg/mL of doxycycline.

FIG. 2A is an immunoblot showing levels of BRD4 in cells (N350C mutant CRBN) treated with DMSO or the indicated concentrations of dBET6. FIG. 2B is an immunoblot showing levels of BRD4 in cells (H352C mutant CRBN) treated with DMSO or the indicated concentrations of dBET6. FIG. 2C is an immunoblot showing levels of BRD4 in cells (W379A mutant CRBN) treated with DMSO or the indicated concentrations of dBET6. FIG. 2D is an immunoblot showing levels of BRD4 in cells (F401A mutant CRBN) treated with DMSO or the indicated concentrations of dBET6. FIG. 2E is an immunoblot showing levels of BRD4 in cells (WT CRBN) treated with DMSO or the indicated concentrations of dBET6.

DEFINITIONS

Figure 1A:
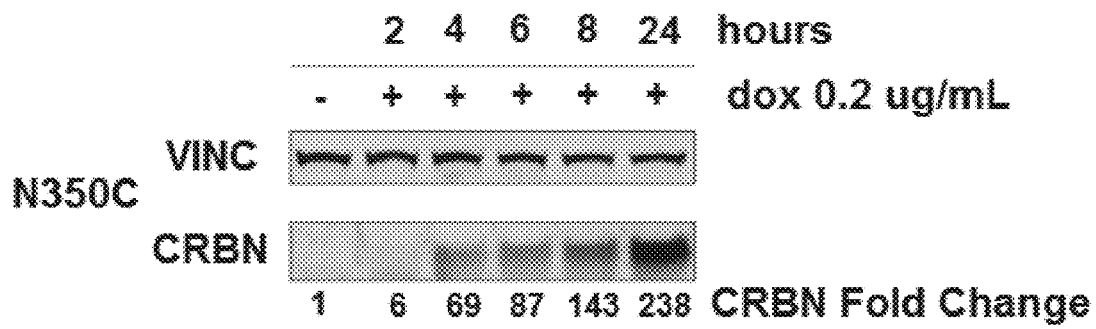
FIG. 1A-1E: Immunoblots of protein levels of mutant or WT CRBN in cells treated with PBS or doxycycline at the time points shown.

Listed below are definitions of various terms used in this application. These definitions apply to the terms as they are used throughout this specification and claims, unless otherwise limited in specific instances, either individually or as part of a larger group.

The term "alkyl," as used herein, refers to saturated, straight or branched-chain hydrocarbon radicals containing, in certain embodiments, between one and six carbon atoms. Examples of $C_1$-$C_6$ alkyl radicals include, but are not limited to, methyl, ethyl, propyl, isopropyl, n-butyl, tert-butyl, neopentyl, and n-hexyl radicals.

The term "alkoxy" refers to an —O-alkyl radical.

The terms "hal," "halo," and "halogen," as used herein, refer to an atom selected from fluorine, chlorine, bromine, and iodine.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "cycloalkyl," as used herein, denotes a monovalent group derived from a monocyclic or polycyclic saturated or partially unsaturated carbocyclic ring compound. Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The term "heterocyclyl," or "heterocycloalkyl," as used herein, refers to a non-aromatic 3-4-, 5-, 6- or 7-membered saturated or unsaturated nonaromatic ring, a 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, and the like.

The term "alkylamino" refers to a group having the structure —NH($C_1$-$C_{12}$ alkyl), e.g., —NH($C_1$-$C_6$ alkyl), where $C_1$-$C_{12}$ alkyl is as previously defined.

The term "dialkylamino" refers to a group having the structure —N($C_1$-$C_{12}$ alkyl)$_2$, e.g., —NH($C_1$-$C_6$ alkyl), where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the application, any of the aryls, substituted aryls, heteroaryls and substituted heteroaryls described herein, can be any aromatic group. Aromatic groups can be substituted or unsubstituted.

The terms "hal," "halo," and "halogen," as used herein, refer to an atom selected from fluorine, chlorine, bromine and iodine.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to: —F, —Cl, —Br, —I, —OH, protected hydroxy, —NO$_2$, —CN, —NH$_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—C3-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkenyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, NHC(O)NH-heterocycloalkyl, —NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NHheterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, C(NH)NH—C$_3$-C$_{12}$-cycloalkyl, —C(NH)NH-aryl, —C(NH)NH-heteroaryl, —C(NH)NHheterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

It is understood that the aryls, heteroaryls, alkyls, and the like can be substituted.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the application encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "Linker", "linker", "Linker group" or "linker group" as used herein, refers to a chemical moiety utilized to attach one part of a compound of interest to another compound of interest. These binding moieties of the present application are linked to the ubiquitin ligase binding moiety preferably through a Linker in order to present a target protein (to which the protein target moiety is bound) in proximity to the ubiquitin ligase for ubiquitination and degradation. Exemplary Linkers are described herein.

As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 2000 g/mol, preferably less than 1500 g/mol, although this characterization is not intended to be limiting for the purposes of the present application. In certain other preferred embodiments, synthetic small molecules are utilized.

The term "independently" is used herein to indicate that the variable, such as atom or functional group, which is independently applied, varies independently from application to application. For example, where more than one substituent or atom (carbon or heteroatom, such as oxygen (O), sulfur (S), or nitrogen (N)) occurs, each substituent or atom is independent of another substituent or atom and such substituents or atom can also alternate.

In chemistry, a "derivative" is a compound that is derived from a similar compound by some chemical or physical process. It is also used to mean that a compound can arise from another compound, if one atom is replaced with another atom or group of atoms. A term "structural analogue" can be also used for this meaning.

The term "structural analogue" or term "analogue" has always been used to describe structural and functional similarity. Extended to drugs, this definition implies that the analogue of an existing drug molecule shares structural and pharmacological similarities with the original compound. Formally, this definition allows the establishment of three categories of drug analogues: analogues possessing chemical and pharmacological similarities (direct analogues); analogues possessing structural similarities only (structural analogues); and chemically different compounds displaying similar pharmacological properties (functional analogues). For example, lenalidomide and pomalidomide are among thalidomide analogs, and are believed to act in a similar fashion.

The term "mutant E3 ubiquitin ligase" or "mutant ubiquitin Ligase" (UL) is used herein to describe a target enzyme(s) which comprises a binding site(s) for the mutant ubiquitin ligase moieties in the bifunctional compounds according to the present application. E3 UL is a protein that in combination with an E2 ubiquitin-conjugating enzyme causes the attachment of ubiquitin to a lysine on a target protein; the E3 ubiquitin ligase targets specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first, a third is attached to the second, and so forth. Polyubiquitination marks proteins for degradation by the proteasome. However, there are some ubiquitination events that are limited to monoubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "protein target moiety" or "target protein ligand" is used herein to describe a small molecule, which is capable of binding to or binds to a target protein or other protein or polypeptide of interest and places/presents that protein or polypeptide in proximity to an ubiquitin ligase such that degradation of the protein or polypeptide by ubiquitin ligase may occur. Any protein, which can bind to a protein target moiety and acted on or degraded by an ubiquitin ligase is a target protein according to the present application. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes including humans as targets for drug therapy, other animals, including domesticated animals, microbials for the determination of targets for antibiotics and other antimicrobials and plants, and even viruses, among numerous others. Non-limiting examples of small molecule target protein binding moieties include Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these small molecule target protein.

As used herein, the term "BRD4" or "Brd4" relates to Bromodomain-containing protein 4 is a protein that in humans is encoded by the BRD4 gene. BDR4 is a member of the BET (bromodomain and extra terminal domain) family, along with BRD2, BRD3, and BRDT. BRD4, similar to its BET family members, contains two bromodomains that recognize acetylated lysine residues. An increase in Brd4 expression led to increased P-TEFb-dependent phosphorylation of RNA polymerase II (RNAPII) CTD and stimulation of transcription from promoters in vivo. Conversely, a reduction in Brd4 expression by siRNA reduced CTD phosphorylation and transcription, revealing that Brd4 is a positive regulatory component of P-TEFb. In chromatin immunoprecipitation (ChIP) assays, the recruitment of P-TEFb to a promoter was dependent on Brd4 and was enhanced by an increase in chromatin acetylation. Together, P-TEFb alternately interacts with Brd4 and the inhibitory subunit to maintain functional equilibrium in the cell.

BRD4 is an exemplary, non-enzymatic protein target. BRD4 is a transcriptional co-activator involved in dynamic transcriptional activation and elongation. BRD4 binds to enhancer and promoter regions adjacent to target genes, via recognition of side-chain acetylated lysine on histone proteins and transcription factors (TFs) by twin acetyl-lysine binding modules or bromodomains. Recently, a first direct-acting inhibitor of BET bromodomains (JQ1) was developed (P. Filippakopoulos et al., *Nature* 468, 1067-1073 (2010)), that displaces BRD4 from chromatin leading to impaired signal transduction from master regulatory TFs to RNA Polymerase II (B. Chapuy et al., *Cancer Cell* 24, 777-790 (2013); J. E. Delmore et al., *Cell* 146, 904-917 (2011); J. Loven et al., *Cell* 153, 320-334 (2013).). Molecular recognition of the BRD4 bromodomains by JQ1 is stereo-specific, and only the (+)-JQ1 enantiomer (JQ1S; from here forward JQ1) is active; the (−)-JQ1 enantiomer (JQ1R) is inactive. Silencing of BRD4 expression by RNA interference in murine and human models of MM and acute myeloid leukemia (AML) elicited rapid transcriptional downregulation of the MYC oncogene and a potent anti-proliferative response (J. E. Delmore et al., *Cell* 146, 904-917 (2011); J. Zuber et al., *Nature* 478, 524-528 (2011)). These and other studies in cancer, inflammation (E. Nicodeme et al., *Nature* 468, 1119-1123 (2010)) and heart disease (P. Anand et al., *Cell* 154, 569-582 (2013); J. D. Brown et al., *Mol. Cell* 56, 219-231 (2014)), establish a desirable mechanistic and translational purpose to target BRD4 for selective degradation.

As used herein, the term "FKBP" relates to a family of proteins that have prolyl isomerase activity and are related to the cyclophilins in function, though not in amino acid sequence (Siekierka et al. *Nature* 341 (6244): 755-7 (1989)). FKBPs have been identified in many eukaryotes from yeast to humans and function as protein folding chaperones for proteins containing proline residues. Along with cyclophilin, FKBPs belong to the immunophilin family (Balbach et al. *Mechanisms of protein folding* (2nd ed.). Oxford: Oxford University Press. pp. 212-237 (2000)). Cytosolic signaling protein FKBP12 is notable in humans for binding the immunosuppressant molecule tacrolimus (originally designated FK506), which is used in treating patients after organ transplant and patients suffering from autoimmune disorders (Wang et al. *Science* 265 (5172): 674-6 (1994)). Tacrolimus has been found to reduce episodes of organ rejection over a related treatment, the drug ciclosporin, which binds cyclophilin (Mayer et al. *Transplantation* 64 (3): 436-43 (1997)). Both the FKBP-tacrolimus complex and the ciclosporin-cyclophilin complex inhibit a phosphatase called calcineurin, thus blocking signal transduction in the T-lymphocytetransduction pathway (Liu et al. *Cell* 66 (4): 807-15 (1991)). This therapeutic role is not related to prolyl isomerase activity. AP1497 is a synthetic pipecolyl α-ketoamide designed to be recognized by FKBP12 (Holt et al., *J. Am. Chem. Soc.* 115, 9925 (1993)).

As used herein the term "CREBBP" relates to CREB binding protein. This gene is ubiquitously expressed and is involved in the transcriptional coactivation of many different transcription factors. First isolated as a nuclear protein that binds to cAMP-response element binding protein (CREB), this gene is now known to play critical roles in embryonic development, growth control, and homeostasis by coupling chromatin remodeling to transcription factor recognition. Chromosomal translocations involving this gene have been associated with acute myeloid leukemia.

As used herein the term "SMARCA4" relates to transcription activator BRG1 also known as ATP-dependent helicase SMARCA4 is a protein that in humans is encoded by the SMARCA4 gene. Mutations in this gene were first recognized in human lung cancer cell lines. It has been demonstrated that BRG1 plays a role in the control of retinoic acid and glucocorticoid-induced cell differentiation in lung cancer and in other tumor types.

As used herein the term "nuclear receptor" relates to a class of proteins found within cells that are responsible for sensing steroid and thyroid hormones and certain other molecules. In response, these receptors work with other proteins to regulate the expression of specific genes, thereby controlling the development, homeostasis, and metabolism of the organism. Since the expression of a large number of genes is regulated by nuclear receptors, ligands that activate these receptors can have profound effects on the organism.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, "treating" or "treat" describes the management and care of a patient for the purpose of combating a disease, condition, or disorder and includes the administration of a bifunctional compound of the present application, or a pharmaceutically acceptable salt, prodrug, metabolite, polymorph or solvate thereof, to alleviate the symptoms or complications of a disease, condition or disorder, or to eliminate the disease, condition or disorder.

A bifunctional compound of the present application, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of bifunctional compounds or pharmaceutical compositions of the application leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

The compounds described herein (e.g., the bifunctional compounds), once produced, can be characterized using a variety of assays known to those skilled in the art to determine whether the compounds have the desired biological activity. For example, the molecules can be characterized by conventional assays, including but not limited to those assays described below (e.g., treating cells of interest, such as MV4-11 cells, human cell line MM1S, or a human cell line MM1S that is deficient in cereblon, with a test compound and then performing immunoblotting against the indicated proteins such as BRD2, BRD3, and BRD4, or treating certain cells of interest with a test compound and then measuring BRD4 transcript levels via qRT-PCR), to determine whether they have a predicted activity, binding activity and/or binding specificity.

The term "targeted protein(s)" is used interchangeably with "target protein(s)", unless the context clearly dictates otherwise.

The terms "disease(s)", "disorder(s)", and "condition(s)" are used interchangeably, unless the context clearly dictates otherwise.

The term "therapeutically effective amount" of a bifunctional compound or pharmaceutical composition of the application, as used herein, means a sufficient amount of the bifunctional compound or pharmaceutical composition so as to decrease the symptoms of a disorder in a subject. As is well understood in the medical arts a therapeutically effective amount of a bifunctional compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, /7-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the bifunctional compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrug", as used herein, refers to those prodrugs of the bifunctional compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein, means a compound which is convertible in vivo by metabolic means (e.g., by hydrolysis) to afford any compound delineated by the formulae of the present application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of bifunctional compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews,* 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

The application also provides for a pharmaceutical composition comprising a therapeutically effective amount of a bifunctional compound of the application, or an enantiomer, diastereomer, stereoisomer, or pharmaceutically acceptable salt thereof, and a pharmaceutically acceptable carrier.

In another aspect, the application provides a method of synthesizing a bifunctional compound disclosed herein.

The synthesis of the bifunctional compounds of the application can be found herein and in the Examples below.

Other embodiments are a method of making a bifunctional compound of any of the formulae herein using any one, or combination of, reactions delineated herein. The method can include the use of one or more intermediates or chemical reagents delineated herein.

Another aspect is an isotopically labeled bifunctional compound of any of the formulae delineated herein. Such compounds have one or more isotope atoms which may or may not be radioactive (e.g., $^3$H, $^2$H, $^{14}$C, $^{13}$C, $^{18}$F, $^{35}$S, $^{32}$P, $^{125}$I, and $^{131}$I) introduced into the bifunctional compound. Such compounds are useful for drug metabolism studies and diagnostics, as well as therapeutic applications.

A bifunctional compound of the application can be prepared as a pharmaceutically acceptable acid addition salt by reacting the free base form of the compound with a pharmaceutically acceptable inorganic or organic acid. Alternatively, a pharmaceutically acceptable base addition salt of a bifunctional compound of the application can be prepared by reacting the free acid form of the bifunctional compound with a pharmaceutically acceptable inorganic or organic base.

Alternatively, the salt forms of the bifunctional compounds of the application can be prepared using salts of the starting materials or intermediates.

The free acid or free base forms of the bifunctional compounds of the application can be prepared from the corresponding base addition salt or acid addition salt from, respectively. For example, a bifunctional compound of the application in an acid addition salt form can be converted to the corresponding free base by treating with a suitable base (e.g., ammonium hydroxide solution, sodium hydroxide, and the like). A bifunctional compound of the application in a base addition salt form can be converted to the corresponding free acid by treating with a suitable acid (e.g., hydrochloric acid, etc.).

Prodrugs of the bifunctional compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized bifunctional compound of the application with a suitable carbamylating agent (e.g., 1,1-acyloxyalkylcarbanochloridate, para-nitrophenyl carbonate, or the like).

Protected derivatives of the bifunctional compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present application can be conveniently prepared or formed during the process of the application, as solvates (e.g., hydrates). Hydrates of bifunctional compounds of the present application can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

When any variable (e.g., $R_{14}$) occurs more than one time in any constituent or formula for a compound, its definition at each occurrence is independent of its definition at every other occurrence. Thus, for example, if a group is shown to be substituted with one or more $R_{14}$ moieties, then $R_{14}$ at each occurrence is selected independently from the definition of $R_{14}$. Also, combinations of substituents and/or variables are permissible, but only if such combinations result in stable compounds within a designated atom's normal valency.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration unless the text so states, thus a carbon-carbon double bond depicted arbitrarily herein as trains may be cis, trans, or a mixture of the two in any proportion. All such isomeric forms of such compounds are expressly included in the present application.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981).

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

In the present application, the structural formula of the bifunctional compound represents a certain isomer for convenience in some cases, but the present application includes all isomers, such as geometrical isomers, optical isomers based on an asymmetrical carbon, stereoisomers, tautomers, and the like. In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, the compounds of the present application, for example, the salts of the bifunctional compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, and if the solvent is alcohol, the solvate formed is an alcoholate. Hydrates are formed by the combination of one or more molecules of water with one molecule of the substance in which the water retains its molecular state as $H_2O$.

The synthesized bifunctional compounds can be separated from a reaction mixture and further purified by a method such as column chromatography, high pressure liquid chromatography, or recrystallization. As can be appreciated by the skilled artisan, further methods of synthesizing the bifunctional compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

As used herein, a "chimeric antigen receptor (CAR)" means a fused protein comprising an extracellular domain capable of binding to an antigen, a transmembrane domain, and at least one intracellular signaling domain. The "chimeric antigen receptor (CAR)" is sometimes called a "chimeric receptor", a "T-body", or a "chimeric immune receptor (CIR)." The "extracellular ligand binding domain" means any oligopeptide or polypeptide that can bind to another protein. The "intracellular signaling domain" or "cytoplasmic signaling domain" means any oligopeptide or polypeptide known to function as a domain that transmits a signal to cause activation or inhibition of a biological process in a cell.

As used herein, a "tumor antigen" means a biological molecule having antigenicity, expression of which is associated with a neoplastic cell. The tumor antigens targeted in the present invention include a tumor specific antigen (an antigen which is present only in tumor cells and is not found in other normal cells), and a tumor-associated antigen (an antigen which is also present in other organs and tissues or heterogeneous and allogeneic normal cells, or an antigen which is expressed on the way of development and differentiation).

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for preparing a scFv are known, and include methods described in U.S. Pat. No. 4,694,778, Science, 242 (1988):423-442, Nature 334 (1989):54454, and Science 240 (1988): 1038-1041.

As used herein, a "domain" means one region in a polypeptide which is folded into a particular structure independently of other regions.

"Activation", as used herein, refers to the state of a T-cell that has been sufficiently stimulated to induce detectable cellular proliferation. Activation can also be associated with induced cytokine production, and detectable effector functions. The term "activated T-cells" refers to, among other things, T-cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies (Harlow et al., "Using Antibodies: A Laboratory Manual", Cold Spring Harbor Laboratory Press, NY (1999); Harlow et al., "Antibodies: A Laboratory Manual", Cold Spring Harbor, N.Y. (1989); Houston et al., Proc. Natl. Acad. Sci. 85 (1988):5879-5883; and Bird et al., Science 242 (1988):423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

The term "antigen" or "Ag" as used herein is defined as a molecule that can be targeted by an antibody or antibody fragment thereof.

As used herein, the term "autologous" is meant to refer to any material derived from the same individual to which it is later to be re-introduced into the individual.

"Co-stimulatory ligand," as the term is used herein, includes a molecule on an antigen presenting cell (e.g., an APC, dendritic cell, B cell, and the like) that specifically binds a cognate co-stimulatory molecule on a T-cell, thereby providing a signal which, in addition to the primary signal provided by, for instance, binding of a TCR/CD3 complex with an MHC molecule loaded with peptide, mediates a T-cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T-cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue, or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host T-cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

A "co-stimulatory molecule" refers to the cognate binding partner on a T-cell that specifically binds with a co-stimulatory ligand, thereby mediating a co-stimulatory response by the T-cell, such as, but not limited to, proliferation. Co-stimulatory molecules include, but are not limited to an MHC class I molecule, BTLA and a Toll ligand receptor.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host T-cell, so they are one of the most efficient methods of a gene delivery vector. HIV, SIV, and FIV are all examples of lentiviruses. Vectors derived from lentiviruses offer the means to achieve significant levels of gene transfer in vivo.

A "co-stimulatory signal", as used herein, refers to a signal, which in combination with a primary signal, such as TCR/CD3 ligation, leads to T-cell proliferation, activation, and/or upregulation or downregulation of key molecules.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "stimulation," is meant a primary response induced by binding of a stimulatory molecule (e.g., a TCR/CD3 complex or CAR) with its cognate ligand thereby mediating a signal transduction event, such as, but not limited to, signal transduction via, for example, the TCR/CD3 or CD3ζ complex. Stimulation can mediate T-cell proliferation, activation, and/or upregulation or downregulation of key molecules, and the like.

The term "transfected" or "transformed" or "transduced" as used herein refers to a process by which exogenous nucleic acid is transferred or introduced into, for example, the host T-cell. A "transfected" or "transformed" or "transduced" cell is one which has been transfected, transformed or transduced with exogenous nucleic acid. The cell includes the primary subject T-cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

DETAILED DESCRIPTION

The present application relates to bifunctional compounds having utility as modulators of ubiquitination and proteasomal degradation of targeted proteins, especially compounds comprising a moiety capable of binding to a polypeptide or a protein that is degraded and/or otherwise inhibited by the bifunctional compounds of the present application. In particular, the present application is directed to compounds which contain a moiety, e.g., a small molecule moiety (i.e., having a molecular weight of below 2,000, 1,000, 500, or 200 Daltons), such as a thalidomide-like moiety, which is capable of binding to a mutant E3 ubiquitin ligase, such as a mutant cereblon, and a ligand that is capable of binding to a target protein, in such a way that the target protein is placed in proximity to the mutant ubiquitin ligase to effect degradation (and/or inhibition) of that protein. The moiety capable of binding to a mutant E3 ubiquitin ligase is sterically incapable of engaging the wild-type E3 ubiquitin ligase.

The present application provides compounds useful for the treatment of cancer and other proliferative conditions.

The present application relates to small molecule E3 ligase ligands (Degrons) which are covalently linked to a targeted protein ligand through a Linker of varying length and functionality, which can be used as therapeutics for treating various diseases including cancer. The present application also relates to a technology platform of bringing targeted proteins to mutant E3 ligases, for example a mutant cereblon, for ubiquitination and subsequent proteasomal degradation using the bifunctional small molecules comprising a thalidomide-like Degron and a Targeting Ligand connected to each other via a Linker.

Compounds of the present application may offer important clinical benefits to patients, in particular for the treatment of the disease states and conditions modulated by the proteins of interest.

Formulas of the Present Invention

In certain embodiments, the present application provides a bifunctional compound of Formula (I):

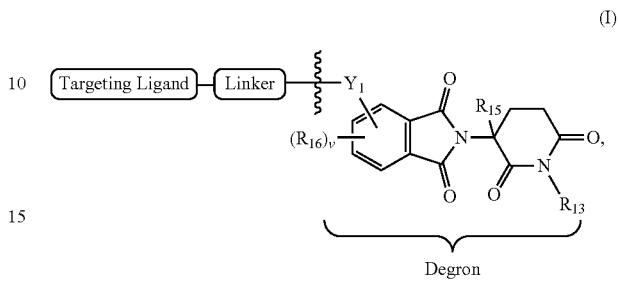

(I)

or an enantiomer, diastereomer, or stereoisomer, or a pharmaceutically acceptable salt thereof, wherein $Y_1$, $R_{13}$, $R_{15}$, $R_{16}$, and v are each as defined herein. In one embodiment, when v is 0 and $Y_1$ is NH and attached to the carbon atom adjacent to the 5-membered ring, $R_{13}$ is not —$(CH_2)$phenyl.

In one embodiment, the bifunctional compounds of Formula (I) have the structure of Formula (Ia):

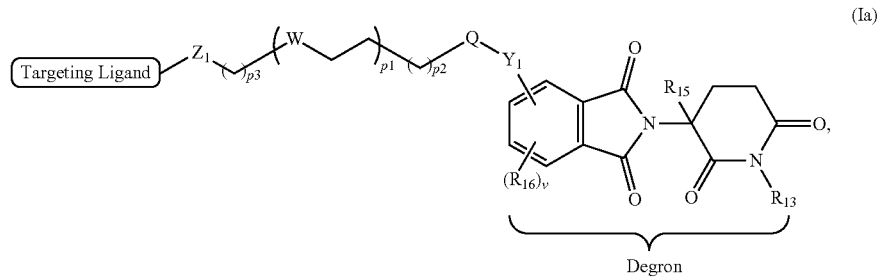

(Ia)

or an enantiomer, diastereomer, or stereoisomer, or a pharmaceutically acceptable salt thereof, wherein Q, W, $Y_1$, $Z_1$, $R_{13}$, $R_{15}$, $R_{16}$, p1, p2, p3, and v are each as defined herein. In one embodiment, when v is 0 and $Y_1$ is NH and attached to the carbon atom adjacent to the 5-membered ring, $R_{13}$ is not —$(CH_2)$phenyl.

In another embodiment, the bifunctional compounds of Formula (I) have the structure of Formula (Ib):

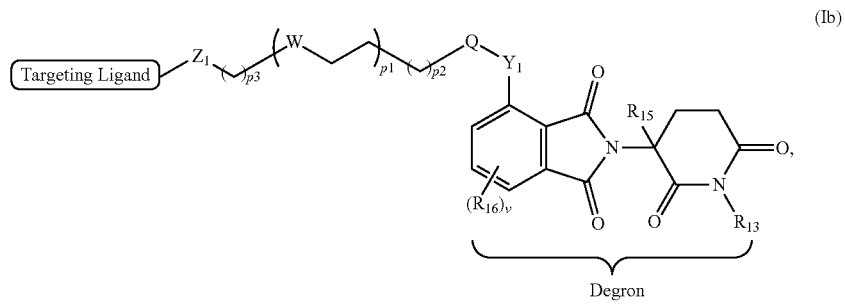

(Ib)

or an enantiomer, diastereomer, or stereoisomer, or a pharmaceutically acceptable salt thereof, wherein Q, W, $Y_1$, $Z_1$, $R_{13}$, $R_{15}$, $R_{16}$, p1, p2, p3, and v are each as defined herein. In one embodiment, when v is 0 and $Y_1$ is NH, $R_{13}$ is not —($CH_2$)phenyl.

In another embodiment, the bifunctional compounds of Formula (I) have the structure of Formula (Ic):

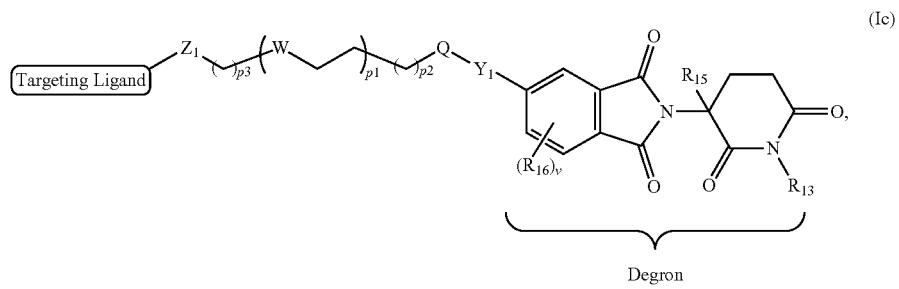

(Ic)

or an enantiomer, diastereomer, or stereoisomer, or a pharmaceutically acceptable salt thereof, wherein Q, W, $Y_1$, $Z_1$, $R_{13}$, $R_{15}$, $R_{16}$, p1, p2, p3, and v are each as defined herein.

In certain embodiments, the present application provides a bifunctional compound of Formula (II):

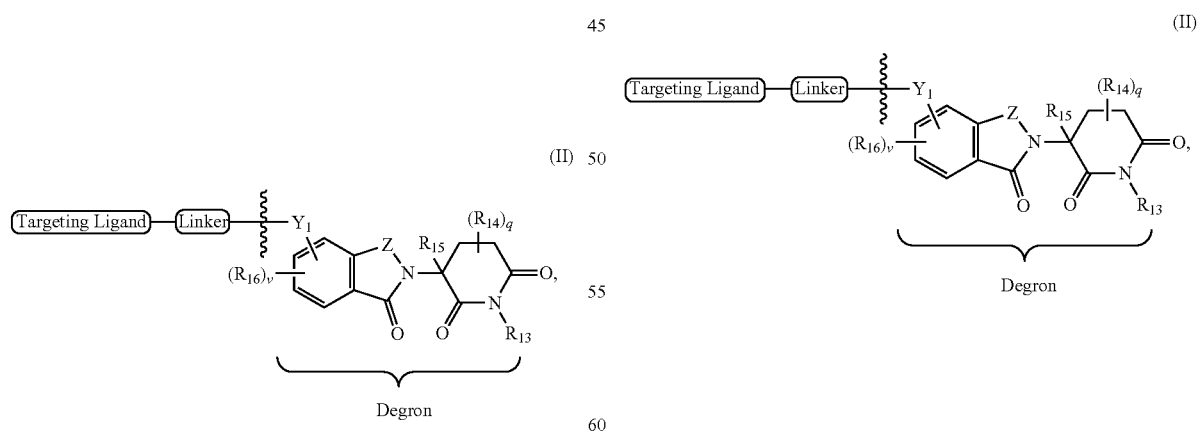

or an enantiomer, diastereomer, or stereoisomer, or a pharmaceutically acceptable salt thereof, wherein $Y_1$, Z, $R_{13}$, $R_{14}$, $R_{15}$, $R_{16}$, q, and v are each as defined herein, for use in treating a disease or condition which is modulated by a targeted protein (e.g., cancer), or for use in the manufacture of a medicament for treating a disease or condition which is modulated by a targeted protein (e.g., cancer).

In certain embodiments, the present application provides a method for treating a disease or condition which is modulated by a targeted protein (e.g., cancer), comprising administering a therapeutically effective amount of a bifunctional compound of Formula (II):

or an enantiomer, diastereomer, or stereoisomer, or a pharmaceutically acceptable salt thereof, wherein $Y_1$, Z, $R_{13}$, $R_{14}$, $R_{15}$, $R_{16}$, q, and v are each as defined herein.

In one embodiment, the bifunctional compounds of Formula (II) have the structure of Formula (IIa):

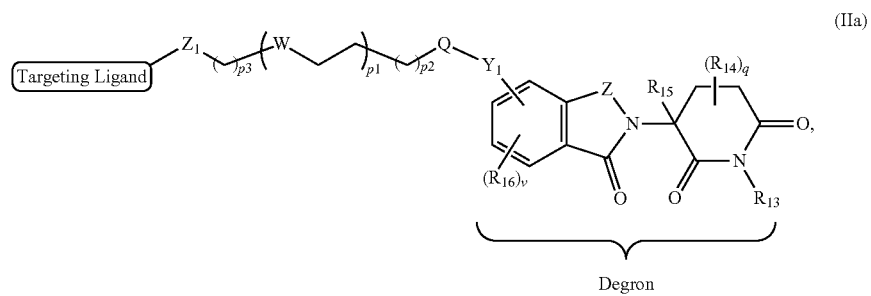

(IIa)

or an enantiomer, diastereomer, or stereoisomer, or a pharmaceutically acceptable salt thereof, wherein Q, W, $Y_1$, $Z_1$, Z, $R_{13}$, $R_{14}$, $R_{15}$, $R_{16}$, p1, p2, p3, q, and v are each as defined herein.

In another embodiment, the bifunctional compounds of Formula (II) have the structure of Formula (IIb):

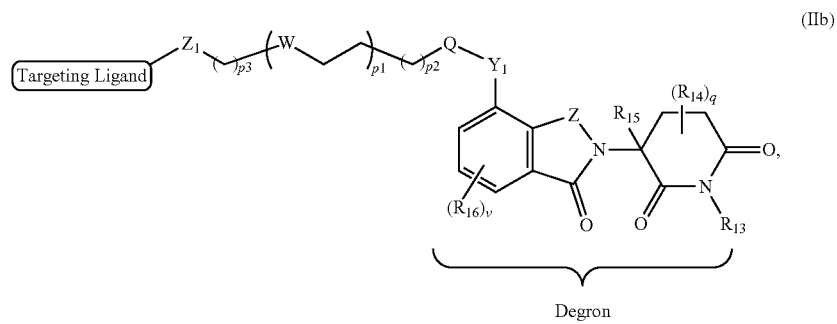

(IIb)

or an enantiomer, diastereomer, or stereoisomer, or a pharmaceutically acceptable salt thereof, wherein Q, W, $Y_1$, $Z_1$, Z, $R_{13}$, $R_{14}$, $R_{15}$, $R_{16}$, p1, p2, p3, q, and v are each as defined herein.

In another embodiment, the bifunctional compounds of Formula (II) have the structure of Formula (IIc):

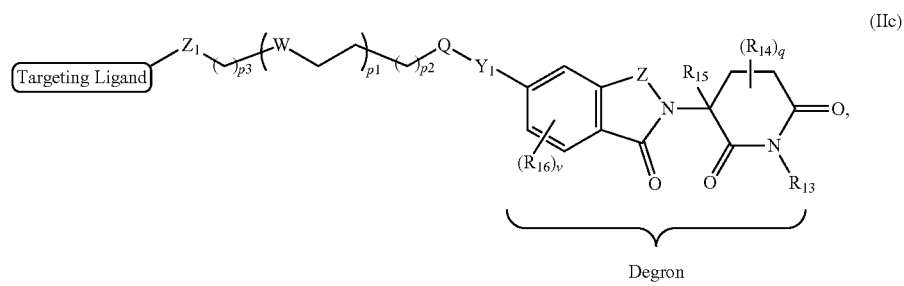

(IIc)

or an enantiomer, diastereomer, or stereoisomer, or a pharmaceutically acceptable salt thereof, wherein Q, W, $Y_1$, $Z_1$, Z, $R_{13}$, $R_{14}$, $R_{15}$, $R_{16}$, p1, p2, p3, q, and v are each as defined herein. In one embodiment, the bifunctional compounds of Formula (III) have the structure of Formula (IIIa):

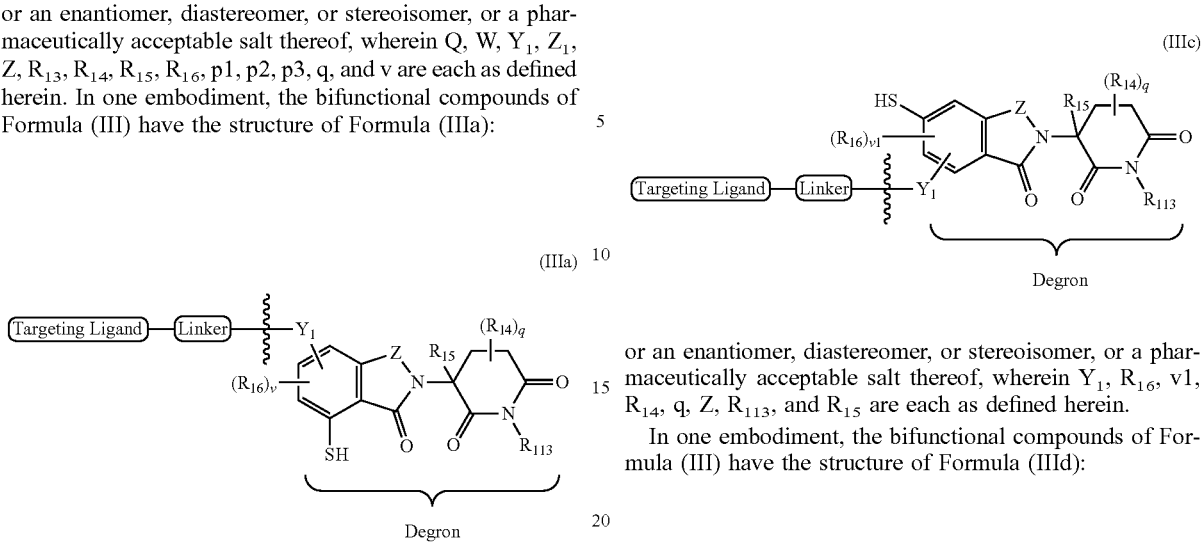

(IIIa)

or an enantiomer, diastereomer, or stereoisomer, or a pharmaceutically acceptable salt thereof, wherein $Y_1$, $R_{16}$, v1, $R_{14}$, q, Z, $R_{113}$, and $R_{15}$ are each as defined herein.

In one embodiment, the bifunctional compounds of Formula (IV) have the structure of Formula (IIIb):

(IIIb)

or an enantiomer, diastereomer, or stereoisomer, or a pharmaceutically acceptable salt thereof, wherein $Y_1$, $R_{16}$, v1, $R_{14}$, q, Z, $R_{113}$, and $R_{15}$ are each as defined herein.

In one embodiment, the bifunctional compounds of Formula (III) have the structure of Formula (IIIc):

(IIIc)

or an enantiomer, diastereomer, or stereoisomer, or a pharmaceutically acceptable salt thereof, wherein $Y_1$, $R_{16}$, v1, $R_{14}$, q, Z, $R_{113}$, and $R_{15}$ are each as defined herein.

In one embodiment, the bifunctional compounds of Formula (III) have the structure of Formula (IIId):

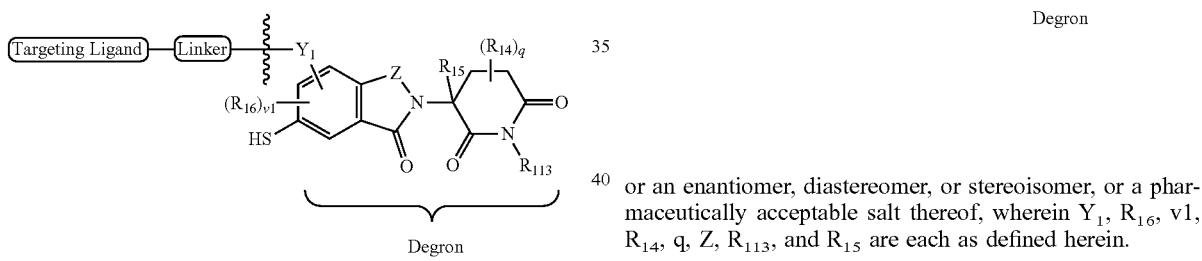

(IIId)

or an enantiomer, diastereomer, or stereoisomer, or a pharmaceutically acceptable salt thereof, wherein $Y_1$, $R_{16}$, v1, $R_{14}$, q, Z, $R_{113}$, and $R_{15}$ are each as defined herein.

In one embodiment, the bifunctional compounds of Formula (III) have the structure:

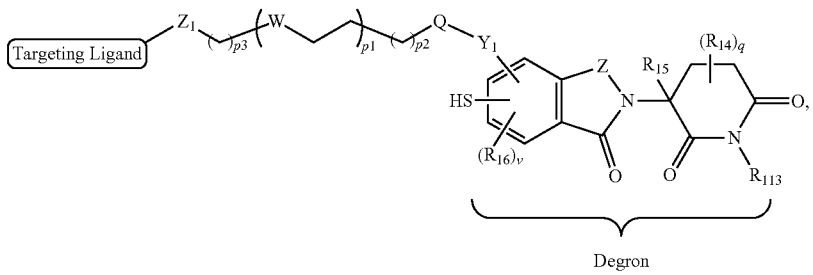

or an enantiomer, diastereomer, or stereoisomer, or a pharmaceutically acceptable salt thereof, wherein $Z_1$, p3, W, p1, p2, Q, $Y_1$, $R_{16}$, v1, $R_{14}$, q, Z, $R_{113}$, and $R_{15}$ are each as defined herein.

Degrons

The Degron serves to link a targeted protein, through a Linker and a Targeting Ligand, to a mutant ubiquitin ligase for proteosomal degradation. In one embodiment, the Degron is capable of binding to a mutant ubiquitin ligase, such as a mutant E3 ubiquitin ligase. In one embodiment, the Degron is capable of binding to a mutant cereblon.

The present application further relates to a Degron of Formula D1 or D2:

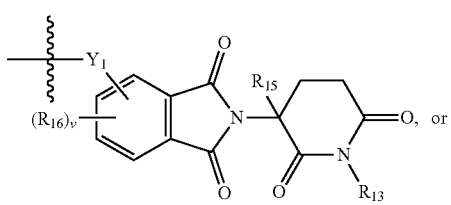
(D1)

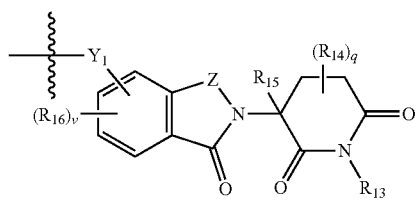
(D2)

or an enantiomer, diastereomer, or stereoisomer thereof, wherein $Y_1$, $Z$, $R_{13}$, $R_{14}$, $R_{15}$, $R_{16}$, q, and v are each as defined herein.

In certain embodiments, the Degron is of Formula D1:

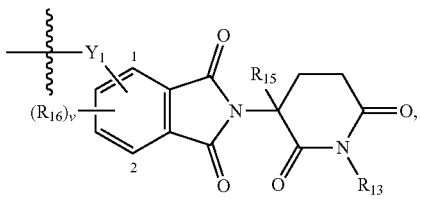
(D1)

or an enantiomer, diastereomer, or stereoisomer thereof, wherein:

$Y_1$ is a bond, $(CH_2)_{1-6}$, $(CH_2)_{0-6}$—O, $(CH_2)_{0-6}$—C(O)NR$_{11}$, $(CH_2)_{0-6}$—NR$_{11}$C(O), $(CH_2)_{0-6}$—NH, or $(CH_2)_{0-6}$—NR$_{12}$;

$R_{11}$ is H or $C_1$-$C_6$ alkyl;

$R_{12}$ is $C_1$-$C_6$ alkyl or C(O)—$C_1$-$C_6$ alkyl;

$R_{13}$ is —(CH$_2$)$_n$—(C$_6$-C$_{10}$) aryl, —(CH$_2$)$_n$-heteroaryl, —(CH$_2$)$_n$—(C$_3$-C$_7$) cycloalkyl, or —(CH$_2$)$_n$-heterocycloalkyl, wherein the aryl, heteroaryl, cycloalkyl, or heterocycloalkyl is optionally substituted with one or more $R_{17}$;

$R_{15}$ is H, deuterium, $C_1$-$C_3$ alkyl, F, or Cl;

each $R_{16}$ is independently halogen, OH, $C_1$-$C_6$ alkyl, or $C_1$-$C_6$ alkoxy;

each $R_{17}$ is independently $C_1$-$C_6$ alkyl, $C_1$-$C_6$ haloalkyl, $C_1$-$C_6$ alkoxy, $C_1$-$C_6$ haloalkoxy, halogen, NH$_2$, CN, NO$_2$, OH, or C(O)OH; and n and v are each independently 0, 1, 2, or 3;

wherein the Degron is covalently bonded to a Linker via

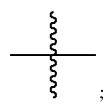

and provided that when v is 0, $R_{15}$ is H, and $Y_1$ is NH and attached to the carbon atom adjacent to the 5-membered ring in Formula D1 (i.e., position 1 or 2 shown above in Formula D1), then $R_{13}$ is not —(CH$_2$)phenyl.

In one embodiment, $Y_1$ is a bond, O, or NH.

In one embodiment, $Y_1$ is a bond.

In one embodiment, $Y_1$ is NH. In one embodiment, $Y_1$ is NH and is attached to a carbon atom which is not at position 1 or 2 shown above in Formula D1.

In one embodiment, $Y_1$ is $(CH_2)_1$, $(CH_2)_2$, $(CH_2)_3$, $(CH_2)_4$, $(CH_2)_5$, or $(CH_2)_6$. In one embodiment, $Y_1$ is $(CH_2)_1$, $(CH_2)_2$, or $(CH_2)_3$. In one embodiment, $Y_1$ is $(CH_2)_1$ or $(CH_2)_2$.

In one embodiment, $Y_1$ is O, CH$_2$—O, (CH$_2$)$_2$—O, (CH$_2$)$_3$—O, (CH$_2$)$_4$—O, (CH$_2$)$_5$—O, or (CH$_2$)$_6$—O. In one embodiment, $Y_1$ is O, CH$_2$—O, (CH$_2$)$_2$—O, or (CH$_2$)$_3$—O. In one embodiment, $Y_1$ is O or CH$_2$—O. In one embodiment, $Y_1$ is O.

In one embodiment, $Y_1$ is C(O)NR$_{11}$, CH$_2$—C(O)NR$_{11}$, (CH$_2$)$_2$—C(O)NR$_{11}$, (CH$_2$)$_3$—C(O)NR$_{11}$, (CH$_2$)$_4$—C(O)NR$_{11}$, (CH$_2$)$_5$—C(O)NR$_{11}$, or (CH$_2$)$_6$—C(O)NR$_{11}$. In one embodiment, $Y_1$ is C(O)NR$_{11}$, CH$_2$—C(O)NR$_{11}$, (CH$_2$)$_2$—C(O)NR$_{11}$, or (CH$_2$)$_3$—C(O)NR$_{11}$. In one embodiment, $Y_1$ is C(O)NR$_{11}$ or CH$_2$—C(O)NR$_{11}$. In one embodiment, $Y_1$ is C(O)NR$_{11}$.

In one embodiment, $Y_1$ is NR$_{11}$C(O), CH$_2$—NR$_{11}$C(O), (CH$_2$)$_2$—NR$_{11}$C(O), (CH$_2$)$_3$—NR$_{11}$C(O), (CH$_2$)$_4$—NR$_{11}$C(O), (CH$_2$)$_5$—NR$_{11}$C(O), or (CH$_2$)$_6$—NR$_{11}$C(O). In one embodiment, $Y_1$ is NR$_{11}$C(O), CH$_2$—NR$_{11}$C(O), (CH$_2$)$_2$—NR$_{11}$C(O), or (CH$_2$)$_3$—NR$_{11}$C(O). In one embodiment, $Y_1$ is NR$_{11}$C(O) or CH$_2$—NR$_{11}$C(O). In one embodiment, $Y_1$ is NR$_{11}$C(O).

In one embodiment, $R_{11}$ is H. In one embodiment, $R_{11}$ is selected from methyl, ethyl, propyl, butyl, i-butyl, t-butyl, pentyl, i-pentyl, and hexyl. In one embodiment, $R_{11}$ is $C_1$-$C_3$ alkyl selected from methyl, ethyl, and propyl.

In one embodiment, $Y_1$ is NH, CH$_2$—NH, (CH$_2$)$_2$—NH, (CH$_2$)$_3$—NH, (CH$_2$)$_4$—NH, (CH$_2$)$_5$—NH, or (CH$_2$)$_6$—NH. In one embodiment, $Y_1$ is NH, CH$_2$—NH, (CH$_2$)$_2$—NH, or (CH$_2$)$_3$—NH. In one embodiment, $Y_1$ is NH or CH$_2$—NH. In one embodiment, $Y_1$ is NH. In one embodiment, $Y_1$ is NH and is attached to a carbon atom which is not at position 1 or 2 shown above in Formula D1.

In one embodiment, $Y_1$ is NR$_{12}$, CH$_2$—NR$_{12}$, (CH$_2$)$_2$—NR$_{12}$, (CH$_2$)$_3$—NR$_{12}$, (CH$_2$)$_4$—NR$_{12}$, (CH$_2$)$_5$—NR$_{12}$, or (CH$_2$)$_6$—NR$_{12}$. In one embodiment, $Y_1$ is NR$_{12}$, CH$_2$—NR$_{12}$, (CH$_2$)$_2$—NR$_{12}$, or (CH$_2$)$_3$—NR$_{12}$. In one embodiment, $Y_1$ is NR$_{12}$ or CH$_2$—NR$_{12}$. In one embodiment, $Y_1$ is NR$_{12}$.

In one embodiment, $R_{12}$ is selected from methyl, ethyl, propyl, butyl, i-butyl, t-butyl, pentyl, i-pentyl, and hexyl. In one embodiment, $R_{12}$ is $C_1$-$C_3$ alkyl selected from methyl, ethyl, and propyl.

In one embodiment, $R_{12}$ is selected from C(O)-methyl, C(O)-ethyl, C(O)-propyl, C(O)-butyl, C(O)-i-butyl, C(O)-t-butyl, C(O)-pentyl, C(O)-i-pentyl, and C(O)-hexyl. In one embodiment, $R_{12}$ is C(O)—$C_1$-$C_3$ alkyl selected from C(O)-methyl, C(O)-ethyl, and C(O)-propyl.

In one embodiment, $R_{13}$ is —(CH$_2$)$_n$—(C$_6$-C$_{10}$) aryl optionally substituted with one or more $R_{17}$. In another embodiment, $R_{13}$ is —(CH$_2$)$_3$—(C$_6$-C$_{10}$) aryl optionally substituted with one or more $R_{17}$. In another embodiment, $R_{13}$ is —(CH$_2$)$_2$—(C$_6$-C$_{10}$) aryl optionally substituted with one or more $R_{17}$. In another embodiment, $R_{13}$ is —(CH$_2$)—(C$_6$-C$_{10}$) aryl optionally substituted with one or more $R_{17}$. In another embodiment, $R_{13}$ is —(C$_6$-C$_{10}$) aryl optionally substituted with one or more $R_{17}$. In another embodiment, $R_{13}$ is —$(CH_2)_3$-phenyl optionally substituted with one or more $R_{17}$. In another embodiment, $R_{13}$ is —$(CH_2)_2$-phenyl optionally substituted with one or more $R_{17}$. In another embodiment, $R_{13}$ is —$(CH_2)$-phenyl optionally substituted with one or more $R_{17}$. In another embodiment, $R_{13}$ is -phenyl optionally substituted with one or more $R_{17}$. In another embodiment, $R_{13}$ is -phenyl.

In one embodiment, $R_{13}$ is —$(CH_2)_n$-heteroaryl optionally substituted with one or more $R_{17}$.

In another embodiment, $R_{13}$ is —$(CH_2)_3$-heteroaryl optionally substituted with one or more $R_{17}$. In another embodiment, $R_{13}$ is —$(CH_2)_2$-heteroaryl optionally substituted with one or more $R_{17}$. In another embodiment, $R_{13}$ is —$(CH_2)$-heteroaryl optionally substituted with one or more $R_{17}$. In another embodiment, $R_{13}$ is -heteroaryl optionally substituted with one or more $R_{17}$. In one embodiment, the heteroaryl is a heteroaryl comprising one or two 5- or 6-membered rings and 1-4 heteroatoms selected from N, O, and S. In one embodiment, the heteroaryl is selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzoimidazolyl, benzothiophenyl, quinolinyl, isoquinolinyl, indolyl, and benzofuranyl. In one embodiment, the heteroaryl is a heteroaryl comprising one 5- or 6-membered ring and 1-3 heteroatoms selected from N, O, and S. In one embodiment, the heteroaryl is selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, and pyrimidinyl.

In one embodiment, $R_{13}$ is —$(CH_2)_n$—$(C_3$-$C_7)$ cycloalkyl optionally substituted with one or more $R_{17}$. In one embodiment, $R_{13}$ is —$(CH_2)_3$—$(C_3$-$C_7)$ cycloalkyl optionally substituted with one or more $R_{17}$. In one embodiment, $R_{13}$ is —$(CH_2)_2$—$(C_3$-$C_7)$ cycloalkyl optionally substituted with one or more $R_{17}$. In one embodiment, $R_{13}$ is —$(CH_2)$—$(C_3$-$C_7)$ cycloalkyl optionally substituted with one or more $R_{17}$. In one embodiment, $R_{13}$ is —$(C_3$-$C_7)$ cycloalkyl optionally substituted with one or more $R_{17}$. In one embodiment, the $(C_3$-$C_7)$ cycloalkyl is selected from cyclopropyl, cyclobutyl, cyclopentyl, cyclohexyl, and cycloheptyl.

In one embodiment, $R_{13}$ is —$(CH_2)_n$-heterocycloalkyl optionally substituted with one or more $R_{17}$. In one embodiment, $R_{13}$ is —$(CH_2)_3$-heterocycloalkyl optionally substituted with one or more $R_{17}$. In one embodiment, $R_{13}$ is —$(CH_2)_2$-heterocycloalkyl optionally substituted with one or more $R_{17}$. In one embodiment, $R_{13}$ is —$(CH_2)$-heterocycloalkyl optionally substituted with one or more $R_{17}$. In one embodiment, $R_{13}$ is -heterocycloalkyl optionally substituted with one or more $R_{17}$. In one embodiment, the heterocycloalkyl is a heterocycloalkyl comprising one or two 5- or 6-membered rings and 1-4 heteroatoms selected from N, O, and S. In one embodiment, the heterocycloalkyl is selected from piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahydrofuranyl, morpholinyl, oxiranyl, azetidinyl, oxetanyl, thietanyl, 2-oxa-5-azabicyclo[2.2.1]heptanyl, 2,5-diazabicyclo[2.2.1]heptanyl, 2-oxa-6-azaspiro[3.3]heptanyl, and 2,6-diazaspiro[3.3]heptanyl. In one embodiment, the heterocycloalkyl is a heterocycloalkyl comprising one 5- or 6-membered ring and 1-3 heteroatoms selected from N, O, and S. In one embodiment, the heterocycloalkyl is selected from piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahydrofuranyl, morpholinyl, oxiranyl, azetidinyl, oxetanyl, and thietanyl.

In one embodiment, at least one $R_{17}$ is $C_1$-$C_6$ alkyl, $C_1$-$C_6$ haloalkyl, $C_1$-$C_6$ alkoxy, $C_1$-$C_6$ haloalkoxy, or halogen. In another embodiment, at least one $R_{17}$ is $NH_2$, CN, $NO_2$, OH, or C(O)OH. In yet another embodiment, at least one $R_{17}$ is $C_1$-$C_6$ alkyl, $C_1$-$C_6$ alkoxy, or halogen. In another embodiment, at least one $R_{17}$ is $C_1$-$C_6$ haloalkyl, $C_1$-$C_6$ haloalkoxy, or halogen. In yet another embodiment, at least one $R_{17}$ is $NH_2$, CN, OH, or C(O)OH. In another embodiment, at least one $R_{17}$ is halogen, $NH_2$, CN, OH, or C(O)OH. In yet another embodiment, at least one $R_{17}$ is $C_1$-$C_6$ alkyl, halogen, $NH_2$, CN, OH, or C(O)OH. In yet another embodiment, at least one $R_{17}$ is $C_1$-$C_6$ alkyl, $C_1$-$C_6$ haloalkyl, halogen, $NH_2$, CN, OH, or C(O)OH.

In one embodiment, n is 0.
In one embodiment, n is 1.
In one embodiment, n is 2.
In one embodiment, n is 3.
In one embodiment, v is 0.
In one embodiment, v is 1.
In one embodiment, v is 2.
In one embodiment, v is 3.

In one embodiment, each $R_{16}$ is independently selected from halogen (e.g., F, Cl, Br, and I), OH, $C_1$-$C_6$ alkyl (e.g., methyl, ethyl, propyl, butyl, i-butyl, t-butyl, pentyl, i-pentyl, and hexyl), and $C_1$-$C_6$ alkoxy (e.g., methoxy, ethoxy, propoxy, butoxy, i-butoxy, t-butoxy, and pentoxy). In a further embodiment, each $R_{16}$ is independently selected from F, Cl, OH, methyl, ethyl, propyl, butyl, i-butyl, t-butyl, methoxy, and ethoxy.

In one embodiment, $R_{15}$ is H, deuterium, or $C_1$-$C_3$ alkyl. In another embodiment, $R_{15}$ is H or $C_1$-$C_3$ alkyl. In a further embodiment, $R_{15}$ is in the (S) or (R) configuration. In a further embodiment, $R_{15}$ is in the (S) configuration. In one embodiment, the compound comprises a racemic mixture of (S)—$R_{15}$ and (R)—$R_{15}$.

In one embodiment, $R_{15}$ is H.
In one embodiment, $R_{15}$ is deuterium.
In one embodiment, $R_{15}$ is $C_1$-$C_3$ alkyl selected from methyl, ethyl, and propyl. In one embodiment, $R_{15}$ is methyl.

In one embodiment, $R_{15}$ is F or Cl. In a further embodiment, $R_{15}$ is in the (S) or (R) configuration. In a further embodiment, $R_{15}$ is in the (R) configuration. In one embodiment, the compound comprises a racemic mixture of (S)—$R_{15}$ and (R)—$R_{15}$. In one embodiment, $R_{15}$ is F.

In one embodiment, when v is 0, and $Y_1$ is NH and attached to the carbon atom adjacent to the 5-membered ring in Formula D1, then $R_{13}$ is not —$(CH_2)$phenyl.

In one embodiment, when $R_{15}$ is H, and $Y_1$ is NH and attached to the carbon atom adjacent to the 5-membered ring in Formula D1, then $R_{13}$ is not —$(CH_2)$phenyl.

In one embodiment, when $Y_1$ is NH and attached to the carbon atom adjacent to the 5-membered ring in Formula D1, then $R_{13}$ is not —$(CH_2)$phenyl.

In one embodiment, $R_{13}$ is —$(CH_2)$phenyl; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, $(CH_2)_{1-6}$—NH, or $(CH_2)_{1-6}$—$NR_{12}$.
In one embodiment, $R_{13}$ is —$(CH_2)$phenyl; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, or $(CH_2)_{1-6}$—$NR_{12}$. In one embodiment, $R_{13}$ is —$(CH_2)$phenyl; and $Y_1$ is a bond, $(CH_2)_{1-6}$, $(CH_2)_{0-6}$—O, $(CH_2)_{0-6}$—$C(O)NR_{11}$, or $(CH_2)_{0-6}$—$NR_{11}C(O)$.

In one embodiment, $R_{13}$ is —$(CH_2)$phenyl substituted with one or more $R_{17}$; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, $(CH_2)_{0-6}$ —NH, or $(CH_2)_{0-6}$—$NR_{12}$. In one embodiment, $R_{13}$ is —$(CH_2)$phenyl substituted with one or more $R_{17}$; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, or $(CH_2)_{0-6}$—$NR_{12}$. In one embodiment, $R_{11}$ is —$(CH_2)$phenyl substituted with one or more $R_{17}$; and $Y_1$ is a bond, $(CH_2)_{1-6}$, $(CH_2)_{0-6}$—O, $(CH_2)_{0-6}$—$C(O)NR_{11}$, or $(CH_2)_{0-6}$—$NR_{11}C(O)$.

In one embodiment, $R_{13}$ is —$(CH_2)$phenyl, v is 1, 2 or 3; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, $(CH_2)_{0-6}$—NH, or $(CH_2)_{0-6}$—$NR_{12}$. In one embodiment, $R_{13}$ is —$(CH_2)$phenyl, v is 1, 2 or 3; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, or $(CH_2)_{0-6}$—$NR_{12}$. In one embodiment, $R_{13}$ is —$(CH_2)$phenyl, v is 1, 2 or 3; and $Y_1$ is a bond, $(CH_2)_{1-6}$, $(CH_2)_{0-6}$—O, $(CH_2)_{0-6}$—$C(O)NR_{11}$, or $(CH_2)_{0-6}$—$NR_{11}C(O)$.

In one embodiment, $R_{13}$ is —$(CH_2)$phenyl, $R_{15}$ is deuterium, $C_1$-$C_3$ alkyl, F, or Cl; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_1C(O)$, $(CH_2)_{0-6}$—NH, or $(CH_2)_{0-6}$—$NR_{12}$. In one embodiment, $R_{13}$ is —$(CH_2)$phenyl, $R_{15}$ is deuterium, $C_1$-$C_3$ alkyl, F, or Cl; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, or $(CH_2)_{0-6}$—$NR_{12}$. In one embodiment, $R_{13}$ is —$(CH_2)$phenyl, $R_{15}$ is deuterium, $C_1$-$C_3$ alkyl, F, or Cl; and $Y_1$ is a bond. $(CH_2)_{1-6}$, $(CH_2)_{0-6}$—O, $(CH_2)_{0-6}$—$C(O)NR_{11}$, or $(CH_2)_{0-6}$—$NR_{11}C(O)$.

In one embodiment, $R_{13}$ is —$(CH_2)$phenyl, $R_{15}$ is $C_1$-$C_3$ alkyl, F, or Cl; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, $(CH_2)_{0-6}$—NH, or $(CH_2)_{0-6}$—$NR_{12}$. In one embodiment, $R_{13}$ is —$(CH_2)$phenyl, $R_{15}$ is $C_1$-$C_3$ alkyl, F, or Cl; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, or $(CH_2)_{0-6}$—$NR_{12}$. In one embodiment, $R_{13}$ is —$(CH_2)$phenyl, $R_{15}$ is $C_1$-$C_3$ alkyl, F, or Cl; and $Y_1$ is a bond, $(CH_2)_{1-6}$, $(CH_2)_{0-6}$—O, $(CH_2)_{0-6}$—$C(O)NR_{11}$, or $(CH_2)_{0-6}$—$NR_{11}C(O)$.

In one embodiment, $Y_1$ is NH; v is 1, 2, or 3; and $R_{13}$ is —$(CH_2)$-phenyl.

In one embodiment, $Y_1$ is NH; $R_{15}$ is deuterium, $C_1$-$C_3$ alkyl, F, or $C_1$; and $R_{13}$ is —$(CH_2)$-phenyl. In one embodiment, $Y_1$ is NH; $R_{15}$ is $C_1$-$C_3$ alkyl, F, or Cl; and $R_{13}$ is —$(CH_2)$-phenyl.

In one embodiment, $Y_1$ is NH; v is 0, 1, 2, or 3; and $R_{13}$ is —$(CH_2)$-phenyl substituted with one or more $R_{17}$. In one embodiment, $Y_1$ is NH; v is 1, 2, or 3; and $R_{13}$ is —$(CH_2)$-phenyl substituted with one or more $R_{17}$.

In one embodiment, $R_{15}$ is H; $R_{13}$ is —$(CH_2)$phenyl; and $Y_1$ is a bond. $(CH_2)_{1-6}$, $(CH_2)_{0-6}$—O, $(CH_2)_{0-6}$—$C(O)NR_{11}$, $(CH_2)_{0-6}$—$NR_{11}C(O)$, $(CH_2)_{1-6}$—NH, or $(CH_2)_{1-6}$—$NR_{12}$. In one embodiment, $R_{15}$ is H; $R_{13}$ is —$(CH_2)$phenyl; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, or $(CH_2)_{1-6}$—$NR_{12}$. In one embodiment, $R_{15}$ is H; $R_{13}$ is —$(CH_2)$phenyl; and $Y_1$ is a bond, $(CH_2)_{1-6}$, $(CH_2)_{0-6}$—O, $(CH_2)_{0-6}$—$C(O)NR_{11}$, or $(CH_2)_{0-6}$—$NR_{11}C(O)$.

In one embodiment, $R_{15}$ is H; $R_{13}$ is —$(CH_2)$phenyl substituted with one or more $R_{17}$; and $Y_1$ is a bond, $(CH_2)_{1-6}$, $(CH_2)_{0-6}$—O, $(CH_2)_{0-6}$—$C(O)NR$, $(CH_2)_{0-6}$—$NR_{11}C(O)$, $(CH_2)_{0-6}$—NH, or $(CH_2)_{0-6}$—$NR_{12}$. In one embodiment, $R_{15}$ is H; $R_{13}$ is —$(CH_2)$phenyl substituted with one or more $R_{17}$; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, or $(CH_2)_{0-6}$—$NR_{12}$. In one embodiment, $R_{15}$ is H; $R_{13}$ is —$(CH_2)$phenyl substituted with one or more $R_{17}$; and $Y_1$ is a bond, $(CH_2)_{1-6}$, $(CH_2)_{0-6}$—O, $(CH_2)_{0-6}$—$C(O)NR_{11}$, or $(CH_2)_{0-6}$—$NR_{11}C(O)$.

In one embodiment, $R_{15}$ is H; $R_{13}$ is —$(CH_2)$phenyl, v is 1, 2 or 3; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, $(CH_2)_{0-6}$—NH, or $(CH_2)_{0-6}$—$NR_{12}$. In one embodiment, $R_{15}$ is H; $R_{13}$ is —$(CH_2)$phenyl, v is 1, 2 or 3; and $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, or $(CH_2)_{0-6}$—$NR_{12}$. In one embodiment, $R_{15}$ is H; $R_{13}$ is —$(CH_2)$phenyl, v is 1, 2 or 3; and $Y_1$ is a bond, $(CH_2)_{1-6}$, $(CH_2)_{0-6}$—O, $(CH_2)_{0-6}$—$C(O)NR_{11}$, or $(CH_2)_{0-6}$—$NR_{11}C(O)$.

Any of the groups described herein for any of $Y_1$, $R_{11}$, $R_{12}$, $R_{13}$, $R_{15}$, $R_{16}$, $R_{17}$, n, and v can be combined with any of the groups described herein for one or more of the remainder of $Y_1$, $R_{11}$, $R_{12}$, $R_{13}$, $R_{15}$, $R_{16}$, $R_{17}$, n, and v, and may further be combined with any of the groups described herein for the Linker.

For a Degron of Formula D1:

(1) In one embodiment, $Y_1$ is a bond; and v is 0.
(2) In one embodiment, $Y_1$ is NH; and v is 0.
(3) In one embodiment, $Y_1$ is $(CH_2)_{0-6}$—O; and v is 0. In a further embodiment, $Y_1$ is O.
(4) In one embodiment, $Y_1$ is a bond; and $R_{13}$ is —$(CH_2)_n$-phenyl optionally substituted with one or more $R_{17}$.
(5) In one embodiment, $Y_1$ is a bond; and $R_{13}$ is —$(CH_2)$-phenyl optionally substituted with one or more $R_{17}$.
(6) In one embodiment, $Y_1$ is a bond; and $R_{13}$ is —$(CH_2)$-phenyl.
(7) In one embodiment, $Y_1$ is a bond; and $R_{15}$ is H.
(8) In one embodiment, $Y_1$ is a bond; $R_{15}$ is H; and $R_{13}$ is —$(CH_2)_n$-phenyl optionally substituted with one or more $R_{17}$.
(9) In one embodiment, $Y_1$ is a bond; $R_{15}$ is H; and $R_{13}$ is —$(CH_2)$-phenyl optionally substituted with one or more $R_{17}$.
(10) In one embodiment, $Y_1$ is a bond; $R_{15}$ is H; and $R_{13}$ is —$(CH_2)$-phenyl.
(11) In one embodiment, $Y_1$ is NH; and $R_{15}$ is H.
(12) In one embodiment, $Y_1$ is NH; $R_{15}$ is H; and $R_{13}$ is —$(CH_2)_n$-phenyl optionally substituted with one or more $R_{17}$.
(13) In one embodiment, $Y_1$ is NH; $R_{15}$ is H; and $R_{13}$ is —$(CH_2)$-phenyl optionally substituted with one or more $R_{17}$.
(14) In one embodiment, $Y_1$ is NH; $R_{15}$ is H; and $R_{13}$ is —$(CH_2)$-phenyl.
(15) In one embodiment, $Y_1$ is $(CH_2)_{0-6}$—O; and $R_{15}$ is H. In a further embodiment, $Y_1$ is O.
(16) In one embodiment, $Y_1$ is $(CH_2)_{0-6}$—O; $R_{15}$ is H; and $R_{13}$ is —$(CH_2)_n$-phenyl optionally substituted with one or more $R_{17}$. In a further embodiment, $Y_1$ is O.
(17) In one embodiment, $Y_1$ is $(CH_2)_{0-6}$—O; $R_{15}$ is H; and $R_{13}$ is —$(CH_2)$-phenyl optionally substituted with one or more $R_{17}$. In a further embodiment, $Y_1$ is O.
(18) In one embodiment, $Y_1$ is $(CH_2)_{0-6}$—O; $R_{15}$ is H; and $R_{13}$ is —$(CH_2)$-phenyl. In a further embodiment, $Y_1$ is O.
(19) In one embodiment, v is 0; and $Y_1$, $R_{13}$, and $R_{15}$ are each as defined, where applicable, in any of (4)-(18).

In one embodiment, $R_{13}$ is —$(CH_2)$phenyl, $R_{15}$ is deuterium, $C_1$-$C_3$ alkyl, F, or Cl, $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, $(CH_2)_{0-6}$—NH, or $(CH_2)_{0-6}$—$NR_{12}$.

In one embodiment, $R_{13}$ is —$(CH_2)$phenyl, $R_{15}$ is $C_1$-$C_3$ alkyl, F, or Cl, $Y_1$ is a bond, $(CH_2)_{1-6}$, $(CH_2)_{0-6}$—O, $(CH_2)_{0-6}$—$C(O)NR_{11}$, $(CH_2)_{0-6}$—$NR_{11}C(O)$, $(CH_2)_{0-6}$—NH, or $(CH_2)_{0-6}$—$NR_{12}$.

In one embodiment, the Degron is of Formula D1a or D1b:

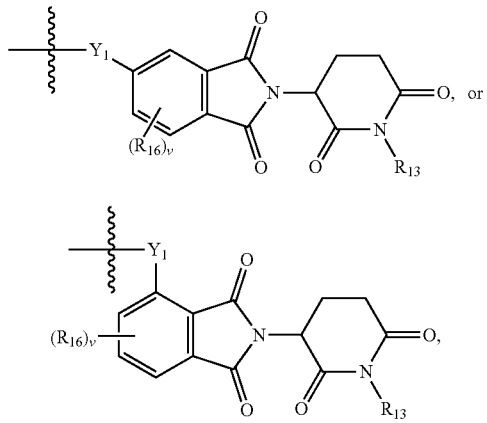

(D1a)

(D1b)

or an enantiomer, diastereomer, or stereoisomer thereof, wherein $Y_1$, $R_{13}$, $R_{16}$, and v are each as defined above in Formula D1, and can be selected from any moieties or combinations thereof described above.

For a Degron of Formula D1a and D1b:

(1) In one embodiment, $Y_1$ is a bond, O, or NH. In one embodiment, $Y_1$ is a bond. In one embodiment, $Y_1$ is O. In one embodiment, $Y_1$ is NH (2) In one embodiment, $Y_1$ is a bond and $R_{13}$ is —(CH$_2$)$_n$-phenyl optionally substituted with one or more $R_{17}$.

(3) In one embodiment, $Y_1$ is a bond and $R_{13}$ is —(CH$_2$)-phenyl optionally substituted with one or more $R_{17}$.

(4) In one embodiment, $Y_1$ is a bond and $R_{13}$ is —(CH$_2$)-phenyl.

(5) In one embodiment, $Y_1$ is NH and $R_{13}$ is —(CH$_2$)$_n$-phenyl optionally substituted with one or more $R_{17}$.

(6) In one embodiment, $Y_1$ is NH and $R_{13}$ is —(CH$_2$)-phenyl optionally substituted with one or more $R_{17}$.

(7) In one embodiment, $Y_1$ is NH and $R_{13}$ is —(CH$_2$)-phenyl substituted with one or more $R_{17}$.

(8) In one embodiment, $Y_1$ is NH and $R_{13}$ is —(CH$_2$)-phenyl.

(9) In one embodiment, $Y_1$ is (CH$_2$)$_{0-6}$—O and $R_{13}$ is —(CH$_2$)$_n$-phenyl optionally substituted with one or more $R_{17}$. In a further embodiment, $Y_1$ is O.

(10) In one embodiment, $Y_1$ is (CH$_2$)$_{0-6}$—O and $R_{13}$ is —(CH$_2$)-phenyl optionally substituted with one or more $R_{17}$. In a further embodiment, $Y_1$ is O.

(11) In one embodiment, $Y_1$ is (CH$_2$)$_{0-6}$—O and $R_{13}$ is —(CH$_2$)-phenyl. In a further embodiment, $Y_1$ is O.

(12) In one embodiment, v is 0; and $Y_1$ and $R_{13}$ are each as defined, where applicable, in any of (1)-(11).

In one embodiment of Formula D1b, when v is 0, then $R_{13}$ cannot be —(CH$_2$)-phenyl.

In one embodiment of Formula D1b, v is 1, 2, or 3 and $R_{13}$ is —(CH$_2$)-phenyl.

In one embodiment of Formula D1b, $R_{13}$ is —(CH$_2$)-phenyl substituted with one or more $R_{17}$.

In one embodiment of Formula D1b, v is 0 and $R_{13}$ is —(CH$_2$)-phenyl substituted with one or more $R_{17}$.

In certain embodiments, the Degron is of Formula D2:

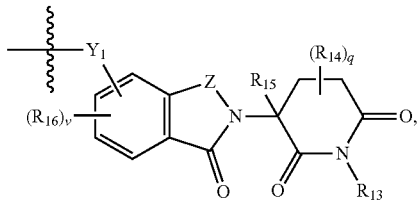

(D2)

or an enantiomer, diastereomer, or stereoisomer thereof, wherein:

$Y_1$ is a bond, (CH$_2$)$_{1-6}$, (CH$_2$)$_{0-6}$—O, (CH$_2$)$_{0-6}$—C(O)NR$_{11}$, (CH$_2$)$_{0-6}$—NR$_{11}$C(O), (CH$_2$)$_{0-6}$—NH, or (CH$_2$)$_{0-6}$—NR$_{12}$;

Z is C(O) or C(R$_{18}$)$_2$;

$R_{11}$ is H or C$_1$-C$_6$ alkyl;

$R_{12}$ is C$_1$-C$_6$ alkyl or C(O)—C$_1$-C$_6$ alkyl;

$R_{13}$ is —(CH$_2$)$_n$—(C$_6$-C$_{10}$) aryl, —(CH$_2$)$_n$-heteroaryl, —(CH$_2$)$_n$—(C$_3$-C$_7$) cycloalkyl, or —(CH$_2$)$_n$-heterocycloalkyl, wherein the aryl, heteroaryl, cycloalkyl, or heterocycloalkyl is optionally substituted with one or more $R_{17}$;

each $R_{14}$ is independently C$_1$-C$_3$ alkyl;

$R_{15}$ is H, deuterium, C$_1$-C$_3$ alkyl, F, or Cl;

each $R_{16}$ is independently halogen, OH, C$_1$-C$_6$ alkyl, or C$_1$-C$_6$ alkoxy;

each $R_{17}$ is independently C$_1$-C$_6$ alkyl, C$_1$-C$_6$ haloalkyl, C$_1$-C$_6$ alkoxy, C$_1$-C$_6$ haloalkoxy, halogen, NH$_2$, CN, NO$_2$, OH, or C(O)OH;

$R_{18}$ is H or C$_1$-C$_3$ alkyl;

q is 0, 1, or 2; and n and v are each independently 0, 1, 2, or 3, wherein the Degron is covalently bonded to the Linker via

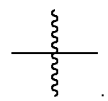

In one embodiment, Z is C(O).

In one embodiment, Z is C(R$_{18}$)$_2$; and each $R_{18}$ is H. In one embodiment, Z is C(R$_{18}$)$_2$; and one of $R_{18}$ is H, and the other $R_{18}$ is C$_1$-C$_3$ alkyl selected from methyl, ethyl, and propyl. In one embodiment, Z is C(R$_{18}$)$_2$; and each $R_{18}$ is independently selected from methyl, ethyl, and propyl.

In one embodiment, $Y_1$ is a bond, O, or NH.

In one embodiment, $Y_1$ is a bond.

In one embodiment, $Y_1$ is (CH$_2$)$_1$, (CH$_2$)$_2$, (CH$_2$)$_3$, (CH$_2$)$_4$, (CH$_2$)$_5$, or (CH$_2$)$_6$. In one embodiment, $Y_1$ is (CH$_2$)$_1$, (CH$_2$)$_2$, or (CH$_2$)$_3$. In one embodiment, $Y_1$ is (CH$_2$)$_1$ or (CH$_2$)$_2$.

In one embodiment, $Y_1$ is O, CH$_2$—O, (CH$_2$)$_2$—O, (CH$_2$)$_3$—O, (CH$_2$)$_4$—O, (CH$_2$)$_5$—O, or (CH$_2$)$_6$—O. In one embodiment, $Y_1$ is O, CH$_2$—O, (CH$_2$)$_2$—O, or (CH$_2$)$_3$—O. In one embodiment, $Y_1$ is O or CH$_2$—O. In one embodiment, $Y_1$ is O.

In one embodiment, $Y_1$ is C(O)NR$_{11}$, CH$_2$—C(O)NR$_{11}$, (CH$_2$)$_2$—C(O)NR$_{11}$, (CH$_2$)$_3$—C(O)NR$_{11}$, (CH$_2$)$_4$—C(O)NR$_{11}$, (CH$_2$)$_5$—C(O)NR$_{11}$, or (CH$_2$)$_6$—C(O)NR$_{11}$. In one embodiment, $Y_1$ is C(O)NR$_{11}$, CH$_2$—C(O)NR$_{11}$, (CH$_2$)$_2$—C(O)NR$_{11}$, or (CH$_2$)$_3$—C(O)NR$_{11}$. In one embodiment, $Y_1$ is C(O)NR$_{11}$ or CH$_2$—C(O)NR$_{11}$. In one embodiment, $Y_1$ is C(O)NR$_{11}$.

In one embodiment, $Y_1$ is $NR_{11}C(O)$, $CH_2$—$NR_{11}C(O)$, $(CH_2)_2$—$NR_{11}C(O)$, $(CH_2)_3$—$NR_{11}C(O)$, $(CH_2)_4$—$NR_{11}C(O)$, $(CH_2)_5$—$NR_{11}C(O)$, or $(CH_2)_6$—$NR_{11}C(O)$. In one embodiment, $Y_1$ is $NR_{11}C(O)$, $CH_2$—$NR_{11}C(O)$, $(CH_2)_2$—$NR_{11}C(O)$, or $(CH_2)_3$—$NR_{11}C(O)$. In one embodiment, $Y_1$ is $NR_{11}C(O)$ or $CH_2$—$NR_{11}C(O)$. In one embodiment, $Y_1$ is $NR_{11}C(O)$.

In one embodiment, $R_{11}$ is H. In one embodiment, $R_{11}$ is selected from methyl, ethyl, propyl, butyl, i-butyl, t-butyl, pentyl, i-pentyl, and hexyl. In one embodiment, $R_{11}$ is $C_1$-$C_3$ alkyl selected from methyl, ethyl, and propyl.

In one embodiment, $Y_1$ is NH, $CH_2$—NH, $(CH_2)_2$—NH, $(CH_2)_3$—NH, $(CH_2)_4$—NH, $(CH_2)_5$—NH, or $(CH_2)_6$—NH. In one embodiment, $Y_1$ is NH, $CH_2$—NH, $(CH_2)_2$—NH, or $(CH_2)_3$—NH. In one embodiment, $Y_1$ is NH or $CH_2$—NH. In one embodiment, $Y_1$ is NH.

In one embodiment, $Y_1$ is $NR_{12}$, $CH_2$—$NR_{12}$, $(CH_2)_2$—$NR_{12}$, $(CH_2)_3$—$NR_{12}$, $(CH_2)_4$—$NR_{12}$, $(CH_2)_5$—$NR_{12}$, or $(CH_2)_6$—$NR_{12}$. In one embodiment, $Y_1$ is $NR_{12}$, $CH_2$—$NR_{12}$, $(CH_2)_2$—$NR_{12}$, or $(CH_2)_3$—$NR_{12}$. In one embodiment, $Y_1$ is $NR_{12}$ or $CH_2$—$NR_{12}$. In one embodiment, $Y_1$ is $NR_{12}$.

In one embodiment, $R_{12}$ is selected from methyl, ethyl, propyl, butyl, i-butyl, t-butyl, pentyl, i-pentyl, and hexyl. In one embodiment, $R_{12}$ is $C_1$-$C_3$ alkyl selected from methyl, ethyl, and propyl.

In one embodiment, $R_{12}$ is selected from C(O)-methyl, C(O)-ethyl, C(O)-propyl, C(O)-butyl, C(O)-i-butyl, C(O)-t-butyl, C(O)-pentyl, C(O)-i-pentyl, and C(O)-hexyl. In one embodiment, $R_{12}$ is C(O)—$C_1$-$C_3$ alkyl selected from C(O)-methyl, C(O)-ethyl, and C(O)-propyl.

In one embodiment, $R_{13}$ is —$(CH_2)_n$—$(C_6$-$C_{10})$ aryl optionally substituted with one or more $R_{17}$. In another embodiment, $R_{13}$ is —$(CH_2)_3$—$(C_6$-$C_{10})$ aryl optionally substituted with one or more $R_{17}$. In another embodiment, $R_{13}$ is —$(CH_2)_2$—$(C_6$-$C_{10})$ aryl optionally substituted with one or more $R_{17}$. In another embodiment, $R_{13}$ is —$(CH_2)$—$(C_6$-$C_{10})$ aryl optionally substituted with one or more $R_{17}$. In another embodiment, $R_{13}$ is —$(C_6$-$C_{10})$ aryl optionally substituted with one or more $R_{17}$. In another embodiment, $R_{13}$ is —$(CH_2)_3$-phenyl optionally substituted with one or more $R_{17}$. In another embodiment, $R_{13}$ is —$(CH_2)_2$-phenyl optionally substituted with one or more $R_{17}$. In another embodiment, $R_{13}$ is —$(CH_2)$-phenyl optionally substituted with one or more $R_{17}$. In another embodiment, $R_{13}$ is -phenyl optionally substituted with one or more $R_{17}$. In another embodiment, $R_{13}$ is -phenyl.

In one embodiment, $R_{13}$ is —$(CH_2)_n$-heteroaryl optionally substituted with one or more $R_{17}$. In another embodiment, $R_{13}$ is —$(CH_2)_3$-heteroaryl optionally substituted with one or more $R_{17}$. In another embodiment, $R_{13}$ is —$(CH_2)_2$-heteroaryl optionally substituted with one or more $R_{17}$. In another embodiment, $R_{13}$ is —$(CH_2)$-heteroaryl optionally substituted with one or more $R_{17}$. In another embodiment, $R_{13}$ is -heteroaryl optionally substituted with one or more $R_{17}$. In one embodiment, the heteroaryl is a heteroaryl comprising one or two 5- or 6-membered rings and 1-4 heteroatoms selected from N, O, and S. In one embodiment, the heteroaryl is selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, benzoxazolyl, benzodioxazolyl, benzothiazolyl, benzoimidazolyl, benzothiophenyl, quinolinyl, isoquinolinyl, indolyl, and benzofuranyl. In one embodiment, the heteroaryl is a heteroaryl comprising one 5- or 6-membered ring and 1-3 heteroatoms selected from N, O, and S. In one embodiment, the heteroaryl is selected from pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, and pyrimidinyl.

In one embodiment, $R_{13}$ is —$(CH_2)_n$—$(C_3$-$C_7)$ cycloalkyl optionally substituted with one or more $R_{17}$. In one embodiment, $R_{13}$ is —$(CH_2)_3$—$(C_3$-$C_7)$ cycloalkyl optionally substituted with one or more $R_{17}$. In one embodiment, $R_{13}$ is —$(CH_2)_2$—$(C_3$-$C_7)$ cycloalkyl optionally substituted with one or more $R_{17}$. In one embodiment, $R_{13}$ is —$(CH_2)$—$(C_3$-$C_7)$ cycloalkyl optionally substituted with one or more $R_{17}$. In one embodiment, $R_{13}$ is —$(C_3$-$C_7)$ cycloalkyl optionally substituted with one or more $R_{17}$. In one embodiment, $R_{13}$ is —$(C_3$-$C_7)$ cycloalkyl optionally substituted with one or more $R_{17}$. In one embodiment, the $(C_3$-$C_7)$ cycloalkyl is selected from cyclopropyl, cyclobutyl, cyclopentyl, cyclohexyl, and cycloheptyl.

In one embodiment, $R_{13}$ is —$(CH_2)_n$-heterocycloalkyl optionally substituted with one or more $R_{17}$. In one embodiment, $R_{13}$ is —$(CH_2)_3$-heterocycloalkyl optionally substituted with one or more $R_{17}$. In one embodiment, $R_{13}$ is —$(CH_2)_2$-heterocycloalkyl optionally substituted with one or more $R_{17}$. In one embodiment, $R_{13}$ is —$(CH_2)$-heterocycloalkyl optionally substituted with one or more $R_{17}$. In one embodiment, $R_{13}$ is -heterocycloalkyl optionally substituted with one or more $R_{17}$. In one embodiment, the heterocycloalkyl is a heterocycloalkyl comprising one or two 5- or 6-membered rings and 1-4 heteroatoms selected from N, O, and S. In one embodiment, the heterocycloalkyl is selected from piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahydrofuranyl, morpholinyl, oxiranyl, azetidinyl, oxetanyl, thietanyl, 2-oxa-5-azabicyclo[2.2.1]heptanyl, 2,5-diazabicyclo[2.2.1]heptanyl, 2-oxa-6-azaspiro[3.3]heptanyl, and 2,6-diazaspiro[3.3]heptanyl. In one embodiment, the heterocycloalkyl is a heterocycloalkyl comprising one 5- or 6-membered ring and 1-3 heteroatoms selected from N, O, and S. In one embodiment, the heterocycloalkyl is selected from piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahydrofuranyl, morpholinyl, oxiranyl, azetidinyl, oxetanyl, and thietanyl.

In one embodiment, $R_{17}$ is $C_1$-$C_6$ alkyl, $C_1$-$C_6$ haloalkyl, $C_1$-$C_6$ alkoxy, $C_1$-$C_6$ haloalkoxy, or halogen. In another embodiment, $R_{17}$ is $NH_2$, CN, $NO_2$, OH, or C(O)OH. In yet another embodiment, $R_{17}$ is $C_1$-$C_6$ alkyl, $C_1$-$C_6$ alkoxy, or halogen. In another embodiment, $R_{17}$ is $C_1$-$C_6$ haloalkyl, $C_1$-$C_6$ haloalkoxy, or halogen. In yet another embodiment, $R_{17}$ is $NH_2$, CN, OH, or C(O)OH. In another embodiment, $R_{17}$ is halogen, $NH_2$, CN, OH, or C(O)OH. In yet another embodiment, $R_{17}$ is $C_1$-$C_6$ alkyl, halogen, $NH_2$, CN, OH, or C(O)OH. In yet another embodiment, $R_{17}$ is $C_1$-$C_6$ alkyl, $C_1$-$C_6$ haloalkyl, halogen, $NH_2$, CN, OH, or C(O)OH.

In one embodiment, $R_{18}$ is $C_1$-$C_3$ alkyl selected from methyl, ethyl, and propyl. In one embodiment, $R_{18}$ is methyl.

In another embodiment, $R_{18}$ is H.

In one embodiment, n is 0.
In one embodiment, n is 1.
In one embodiment, n is 2.
In one embodiment, n is 3.
In one embodiment, q is 0.
In one embodiment, q is 1.
In one embodiment, q is 2.

In one embodiment, each $R_{14}$ is independently $C_1$-$C_3$ alkyl selected from methyl, ethyl, and propyl.

In one embodiment, v is 0.
In one embodiment, v is 1.
In one embodiment, v is 2.
In one embodiment, v is 3.

In one embodiment, each $R_{16}$ is independently selected from halogen (e.g., F, Cl, Br, and I), OH, $C_1$-$C_6$ alkyl (e.g., methyl, ethyl, propyl, butyl, i-butyl, t-butyl, pentyl, i-pentyl, and hexyl), and $C_1$-$C_6$ alkoxy (e.g., methoxy, ethoxy, propoxy, butoxy, i-butoxy, t-butoxy, and pentoxy). In a further embodiment, each $R_{16}$ is independently selected from F, Cl, OH, methyl, ethyl, propyl, butyl, i-butyl, t-butyl, methoxy, and ethoxy.

In one embodiment, $R_{15}$ is H, deuterium, or $C_1$-$C_3$ alkyl. In another embodiment, $R_{15}$ is H or $C_1$-$C_3$ alkyl. In a further embodiment, $R_{15}$ is in the (S) or (R) configuration. In a further embodiment, $R_{15}$ is in the (S) configuration. In one embodiment, the compound comprises a racemic mixture of (S)—$R_{15}$ and (R)—$R_{15}$.

In one embodiment, $R_{15}$ is H.
In one embodiment, $R_{15}$ is deuterium.
In one embodiment, $R_{15}$ is $C_1$-$C_3$ alkyl selected from methyl, ethyl, and propyl. In one embodiment, $R_{15}$ is methyl.

In one embodiment, $R_{15}$ is F or Cl. In a further embodiment, $R_{15}$ is in the (S) or (R) configuration. In a further embodiment, $R_{15}$ is in the (R) configuration. In one embodiment, the compound comprises a racemic mixture of (S)—$R_{15}$ and (R)—$R_{15}$. In one embodiment, $R_{15}$ is F.

Any of the groups described herein for any of $Y_1$, Z, $R_{11}$, $R_{12}$, $R_{13}$, $R_{14}$, $R_{15}$, $R_{16}$, $R_{17}$, $R_{18}$, n, q and v can be combined with any of the groups described herein for one or more of the remainder of $Y_1$, Z, $R_{11}$, $R_{12}$, $R_{13}$, $R_{14}$, $R_{15}$, $R_{16}$, $R_{17}$, $R_{18}$, n, q and v, and may further be combined with any of the groups described herein for the Linker.

For a Degron of Formula D2:
(1) In one embodiment, Z is C(O) and $Y_1$ is a bond.
(2) In one embodiment, Z is C(O) and $Y_1$ is NH.
(3) In one embodiment, Z is C(O) and $Y_1$ is $(CH_2)_{0-6}$—O. In a further embodiment, Y is O.
(4) In one embodiment, Z is C(O); $Y_1$ is a bond; and q and v are each 0.
(5) In one embodiment, Z is C(O); $Y_1$ is NH; and q and v are each 0.
(6) In one embodiment, Z is C(O); $Y_1$ is $(CH_2)_{0-6}$—O; and q and v are each 0. In a further embodiment, $Y_1$ is O.
(7) In one embodiment, Z is C(O); $Y_1$ is a bond; and $R_{13}$ is —$(CH_2)_n$-phenyl optionally substituted with one or more $R_{17}$.
(8) In one embodiment, Z is C(O); $Y_1$ is a bond; and $R_{13}$ is —$(CH_2)$-phenyl optionally substituted with one or more $R_{17}$.
(9) In one embodiment, Z is C(O); $Y_1$ is a bond; and $R_{13}$ is —$(CH_2)$-phenyl.
(10) In one embodiment, Z is C(O); $Y_1$ is a bond; and $R_{15}$ is H.
(11) In one embodiment, Z is C(O); $Y_1$ is NH; and $R_{13}$ is —$(CH_2)_n$-phenyl optionally substituted with one or more $R_{17}$.
(12) In one embodiment, Z is C(O); $Y_1$ is NH; and $R_{13}$ is —$(CH_2)$-phenyl optionally substituted with one or more $R_{17}$.
(13) In one embodiment, Z is C(O); $Y_1$ is NH; and $R_{13}$ is —$(CH_2)$-phenyl.
(14) In one embodiment, Z is C(O); $Y_1$ is NH; and $R_{15}$ is H.
(15) In one embodiment, Z is C(O); $Y_1$ is NH; $R_{15}$ is H, and $R_{13}$ is —$(CH_2)_n$-phenyl optionally substituted with one or more $R_{17}$.
(16) In one embodiment, Z is C(O); $Y_1$ is NH; $R_{15}$ is H, and $R_{13}$ is —$(CH_2)$-phenyl optionally substituted with one or more $R_{17}$.
(17) In one embodiment, Z is C(O); $Y_1$ is NH; $R_{15}$ is H, and $R_{13}$ is —$(CH_2)$-phenyl.
(18) In one embodiment, Z is C(O); $Y_1$ is a bond; $R_{13}$ is —$(CH_2)_n$-phenyl optionally substituted with one or more $R_{17}$; and $R_{15}$ is H.
(19) In one embodiment, Z is C(O); $Y_1$ is a bond; $R_{13}$ is —$(CH_2)$-phenyl optionally substituted with one or more $R_{17}$; and $R_{15}$ is H.
(20) In one embodiment, Z is C(O); $Y_1$ is a bond; $R_{13}$ is —$(CH_2)$-phenyl; and $R_{15}$ is H.
(21) In one embodiment, Z is C(O); $Y_1$ is NH; $R_{13}$ is —$(CH_2)_n$-phenyl optionally substituted with one or more $R_{17}$; and $R_{15}$ is H.
(22) In one embodiment, Z is C(O); $Y_1$ is NH; $R_{13}$ is —$(CH_2)$-phenyl optionally substituted with one or more $R_{17}$; and $R_{15}$ is H.
(23) In one embodiment, Z is C(O); $Y_1$ is NH; $R_{13}$ is —$(CH_2)$-phenyl; and $R_{15}$ is H.
(24) In one embodiment, Z is C(O); $Y_1$ is $(CH_2)_{0-6}$—O; and $R_{13}$ is —$(CH_2)_n$-phenyl optionally substituted with one or more $R_{17}$. In a further embodiment, $Y_1$ is O.
(25) In one embodiment, Z is C(O); $Y_1$ is $(CH_2)_{0-6}$—O; and $R_{13}$ is —$(CH_2)$-phenyl optionally substituted with one or more $R_{17}$. In a further embodiment, $Y_1$ is O.
(26) In one embodiment, Z is C(O); $Y_1$ is $(CH_2)_{0-6}$—O; and $R_{13}$ is —$(CH_2)$-phenyl. In a
further embodiment, $Y_1$ is O.
(27) In one embodiment, Z is C(O); $Y_1$ is $(CH_2)_{0-6}$—O; and $R_{15}$ is H. In a further embodiment, $Y_1$ is O.
(28) In one embodiment, Z is C(O); $Y_1$ is $(CH_2)_{0-6}$—O; $R_{13}$ is —$(CH_2)_n$-phenyl optionally substituted with one or more $R_{17}$; and $R_{15}$ is H. In a further embodiment, $Y_1$ is O.
(29) In one embodiment, Z is C(O); $Y_1$ is $(CH_2)_{0-6}$—O; $R_{13}$ is —$(CH_2)$-phenyl optionally substituted with one or more $R_7$; and $R_{15}$ is H. In a further embodiment, $Y_1$ is O.
(30) In one embodiment, Z is C(O); $Y_1$ is $(CH_2)_{0-6}$—O; $R_{13}$ is —$(CH_2)$-phenyl; and $R_{15}$ is H. In a further embodiment, $Y_1$ is O.
(31) In one embodiment, q and v are each 0; and $Y_1$, Z, $R_{13}$, and $R_{15}$ are each as defined, where applicable, in any of (1)-(3) and (7)-(30).
(32) In one embodiment, n is 1; and $Y_1$, Z, $R_{13}$, $R_{15}$, and $R_{17}$, q, and v are each as defined, where applicable, in any of (1)-(30).

In one embodiment, the Degron is of Formula D2a, D2b, D2c, or D2d:

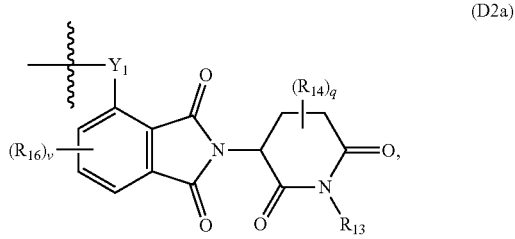

(D2a)

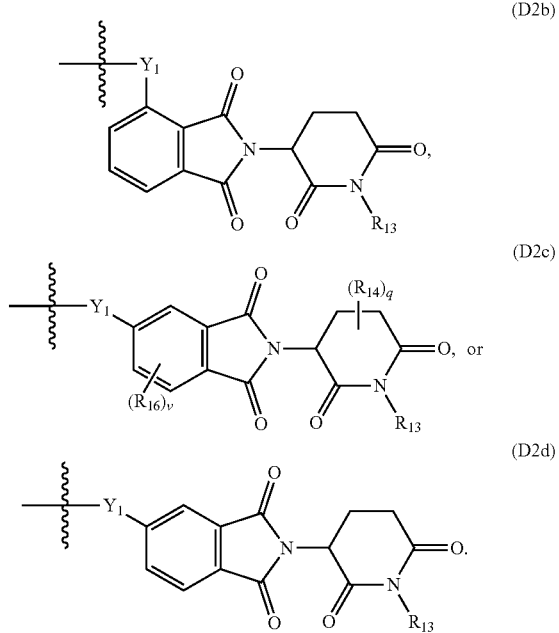

or an enantiomer, diastereomer, or stereoisomer thereof, wherein $Y_1$, $R_{13}$, $R_{14}$, $R_{16}$, q, and v are each as defined above in Formula D2, and can be selected from any moieties or combinations thereof described above.

For a Degron of Formula D2a, D2b, D2c, and D12d:
(1) In one embodiment, $Y_1$ is a bond, O, or NH. In one embodiment, $Y_1$ is a bond. In one embodiment, $Y_1$ is O. In one embodiment, $Y_1$ is NH
(2) In one embodiment, $Y_1$ is a bond and $R_{13}$ is —$(CH_2)_n$-phenyl optionally substituted with one or more $R_{17}$.
(3) In one embodiment, $Y_1$ is a bond and $R_{13}$ is —$(CH_2)$-phenyl optionally substituted with one or more $R_{17}$.
(4) In one embodiment, $Y_1$ is a bond and $R_{13}$ is —$(CH_2)$-phenyl.
(5) In one embodiment, $Y_1$ is NH and $R_{13}$ is —$(CH_2)_n$-phenyl optionally substituted with one or more $R_{17}$.
(6) In one embodiment, $Y_1$ is NH and $R_{13}$ is —$(CH_2)$-phenyl optionally substituted with one or more $R_{17}$.
(7) In one embodiment, $Y_1$ is NH and $R_{13}$ is —$(CH_2)$-phenyl.
(8) In one embodiment, $Y_1$ is $(CH_2)_{0-6}$—O and $R_{13}$ is —$(CH_2)_n$-phenyl optionally substituted with one or more $R_{17}$. In a further embodiment, $Y_1$ is O.
(9) In one embodiment, $Y_1$ is $(CH_2)_{0-6}$—O and $R_{13}$ is —$(CH_2)$-phenyl optionally substituted with one or more $R_{17}$. In a further embodiment, $Y_1$ is O.
(10) In one embodiment, $Y_1$ is $(CH_2)_{0-6}$—O and $R_{13}$ is —$(CH_2)$-phenyl. In a further embodiment, $Y_1$ is O.
(11) In one embodiment, v and q are each 0; and $Y_1$ and $R_{13}$ are each as defined, where applicable, in any of (1)-(10).

Linkers

The Linker is a bond or a carbon chain that serves to link a Targeting Ligand with a Degron. In one embodiment, the carbon chain optionally comprises one, two, three, or more heteroatoms selected from N, O, and S. In one embodiment, the carbon chain comprises only saturated chain carbon atoms. In one embodiment, the carbon chain optionally comprises two or more unsaturated chain carbon atoms (e.g., C=C or C≡C). In one embodiment, one or more chain carbon atoms in the carbon chain are optionally substituted with one or more substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl)$_2$, CN, $C_3$-$C_8$ cycloalkyl, heterocyclyl, phenyl, and heteroaryl).

In certain embodiments, the Linker comprises at least 5 chain atoms (e.g., C, O, N, and S). In one embodiment, the Linker comprises less than 25 chain atoms (e.g., C, O, N, and S). In one embodiment, the Linker comprises less than 20 chain atoms (e.g., C, O, N, and S). In one embodiment, the Linker comprises 4, 5, 6, 7, 8, 9, 10, 11, 12, 13, 14, 15, 16, 17, 18, 19, 20, 21, 22, 23, or 24 chain atoms (e.g., C, O, N, and S). In one embodiment, the Linker comprises 5, 6, 7, 8, 9, 10, 11, 12, 13, 14, 15, 16, 17, 18, 19, 20, 21, 22, 23, or 24 chain atoms (e.g., C, O, N, and S). In one embodiment, the Linker comprises 5, 7, 9, 11, 13, 15, 17, or 19 chain atoms (e.g., C, O, N, and S). In one embodiment, the Linker comprises 5, 7, 9, or 11 chain atoms (e.g., C, O, N, and S). In one embodiment, the Linker comprises 11, 13, 15, 17, or 19 chain atoms (e.g., C, O, N, and S). In one embodiment, the Linker comprises 11, 13, 15, 17, 19, 21, or 23 chain atoms (e.g., C, O, N, and S). In one embodiment, the Linker comprises 6, 8, 10, 12, 14, 16, 18, 20, 22, or 24 chain atoms (e.g., C, O, N, and S). In one embodiment, the Linker comprises 6, 8, 10, 12, 14, 16, 18, or 20 chain atoms (e.g., C, O, N, and S). In one embodiment, the Linker comprises 6, 8, 10, or 12 chain atoms (e.g., C, O, N, and S). In one embodiment, the Linker comprises 12, 14, 16, 18, or 20 chain atoms (e.g., C, O, N, and S).

In one embodiment, the Linker comprises from 11 to 19 chain atoms (e.g., C, O, N, and S).

In one embodiment, the Linker is a carbon chain optionally substituted with non-bulky substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl)$_2$, and CN). In one embodiment, the non-bulky substitution is located on the chain carbon atom proximal to the Degron (i.e., the carbon atom is separated from the carbon atom to which the Degron is bonded by at least 3, 4, or 5 chain atoms in the Linker). In one embodiment, the non-bulky substitution is located on the chain carbon atom proximal to the Targeting Ligand (i.e., the carbon atom is separated from the carbon atom to which the Degron is bonded by at least 3, 4, or 5 chain atoms in the Linker).

In one embodiment, the Linker is of Formula L0:

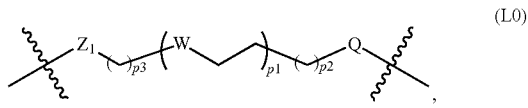

(L0)

or an enantiomer, diastereomer, or stereoisomer thereof, wherein
p is an integer selected from 0 to 12;
p2 is an integer selected from 0 to 12;
p3 is an integer selected from 1 to 6;
each W is independently absent, $CH_2$, O, S, NH, or $NR_{19}$;
$Z_1$ is absent, $CH_2C(O)NH$, $OCH_2C(O)NH$, $OCH_2C(O)NR_{19}$, $C(O)NH$, $C(O)NR_{19}$, $NHC(O)$, $NR_{19}C(O)$, $CH_2$, O, NH, or $NR_{19}$;
each $R_{19}$ is independently $C_1$-$C_3$ alkyl;
Q is absent or $NHC(O)CH_2$;
wherein the Linker is covalently bonded to a Degron via the

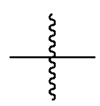

next to Q, and covalently bonded to a Targeting Ligand via the

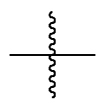

next to $Z_1$.

In one embodiment, the total number of chain atoms in the Linker is less than 30. In a further embodiment, the total number of chain atoms in the Linker is less than 20.

For a Linker of Formula L0:

(1) In one embodiment, p1 is an integer selected from 0 to 10.
(2) In one embodiment, p1 is an integer selected from 1 to 10.
(3) In one embodiment, p1 is selected from 1, 2, 3, 4, 5, and 6.
(4) In one embodiment, p1 is 0, 1, 2, 3, or 4.
(5) In one embodiment, p1 is 0.
(6) In one embodiment, p1 is 2.
(7) In one embodiment, p1 is 3.
(8) In one embodiment, p1 is 4.
(9) In one embodiment, p2 is an integer selected from 0 to 10.
(10) In one embodiment, p2 is selected from 0, 1, 2, 3, 4, 5, and 6.
(11) In one embodiment, p2 is 0, 1, 2, 3, or 4.
(12) In one embodiment, p2 is 0.
(13) In one embodiment, p2 is 1.
(14) In one embodiment, p2 is 2.
(15) In one embodiment, p3 is an integer selected from 1 to 6.
(16) In one embodiment, p3 is 0, 1, 2, or 3.
(17) In one embodiment, p3 is 0.
(18) In one embodiment, p3 is 1.
(19) In one embodiment, p3 is 2.
(20) In one embodiment, p3 is 3.
(21) In one embodiment, p3 is 6.
(22) In one embodiment, at least one W is $CH_2$.
(23) In one embodiment, at least one W is O.
(24) In one embodiment, at least one W is S.
(25) In one embodiment, at least one W is NH.
(26) In one embodiment, at least one W is $NR_{19}$; and each $R_{19}$ is independently $C_1$-$C_3$ alkyl selected from methyl, ethyl, and propyl. In one embodiment, at least one W is $NR_{19}$; and at least one $R_{19}$ is methyl.
(27) In one embodiment, each W is O.
(28) In one embodiment, Q is absent.
(29) In one embodiment, Q is $NHC(O)CH_2$.
(30) In one embodiment, $Z_1$ is absent.
(31) In one embodiment, Z is $CH_2C(O)NH$.
(32) In one embodiment, $Z_1$ is $CH_2$.
(33) In one embodiment, $Z_1$ is O.
(34) In one embodiment, $Z_1$ is NH.
(35) In one embodiment, $Z_1$ is $OCH_2C(O)NH$.
(36) In one embodiment, $Z_1$ is $OCH_2C(O)NR_{19}$.
(37) In one embodiment, $Z_1$ is $C(O)NH$.
(38) In one embodiment, $Z_1$ is $C(O)NR_{19}$.
(39) In one embodiment, $Z_1$ is NHC(O).
(40) In one embodiment, $Z_1$ is $NR_{19}C(O)$.
(41) In one embodiment, $Z_1$ is $NR_{19}$; and $R_{19}$ is $C_1$-$C_3$ alkyl selected from methyl, ethyl, and propyl.
(42) In one embodiment, W is $CH_2$ and p1 is 1.
(43) In one embodiment, W is $CH_2$, p1 is 1, and p3 is 3.
(44) In one embodiment, W is $CH_2$, p1 is 1, p3 is 3, and p2 is 0.
(45) In one embodiment, W is O and p1 is 1.
(46) In one embodiment, W is O, p1 is 1, and p3 is 1.
(47) In one embodiment, W is O, p1 is 1, p3 is 1, and p2 is 0.
(48) In one embodiment, W is $CH_2$ and p1 is 2.
(49) In one embodiment, W is $CH_2$, p1 is 2, and p3 is 1.
(50) In one embodiment, W is $CH_2$, p1 is 2, p3 is 1, and p2 is 1.
(51) In one embodiment, W is O and p1 is 2.
(52) In one embodiment, W is O, p1 is 2, and p3 is 1.
(53) In one embodiment, W is O, p1 is 2, p3 is 1, and p2 is 1.
(54) In one embodiment, W is $CH_2$, p1 is 2, and p3 is 2.
(55) In one embodiment, W is $CH_2$, p is 2, p3 is 2, and p2 is 0.
(56) In one embodiment, W is O, p1 is 2, and p3 is 2.
(57) In one embodiment, W is O, p1 is 2, p3 is 2, and p2 is 0.
(58) In one embodiment, W is $CH_2$ and p1 is 3.
(59) In one embodiment, W is $CH_2$, p1 is 3, and p3 is 1.
(60) In one embodiment, W is $CH_2$, p1 is 3, p3 is 1, and p2 is 0.
(61) In one embodiment, W is O and p1 is 3.
(62) In one embodiment, W is O, p1 is 3, and p3 is 3.
(63) In one embodiment, W is O, p1 is 3, p3 is 3, and p2 is 1.
(64) In one embodiment, W is $CH_2$, p1 is 3, and p3 is 2.
(65) In one embodiment, W is $CH_2$, p1 is 3, p3 is 2, and p2 is 0.
(66) In one embodiment, W is O, p1 is 3, and p3 is 2.
(67) In one embodiment, W is O, p1 is 3, p3 is 2, and p2 is 0.
(68) In one embodiment, W, p1, p2, and p3 are each as defined, where applicable, in any one of (1)-(27) and (42)-(67), and $Z_1$ is NH.
(69) In one embodiment. W, p1, p2, and p3 are each as defined, where applicable, in any one of (1)-(27) and (42)-(67), and $Z_1$ is $OCH_2C(O)NR_{19}$.
(70) In one embodiment, W, p1, p2, and p3 are each as defined, where applicable, in any one of (1)-(27) and (42)-(67), and $Z_1$ is C(O)NH.
(71) In one embodiment, W, p1, p2, and p3 are each as defined, where applicable, in any one of (1)-(27) and (42)-(67), and $Z_1$ is $C(O)NR_{19}$.
(72) In one embodiment, $Z_1$, W, p1, p2, and p3 are each as defined, where applicable, in any one of (1)-(27) and (30)-(71), and Q is absent.
(73) In one embodiment, $Z_1$, W, p1, p2, and p3 are each as defined, where applicable, in any one of (1)-(27) and (30)-(71), and Q is $NHC(O)CH_2$.
(74) In one embodiment, W, p1, p2, and p3 are each as defined, where applicable, in any one of (1)-(27) and (42)-(67), and Q is absent.
(75) In one embodiment, W, p1, p2, and p3 are each as defined, where applicable, in any one of (1)-(27) and (42)-(67), and Q is $NHC(O)CH_2$.
(76) In one embodiment, $Z_1$ is $CH_2C(O)NH$.

In a further embodiment, one W is NR$_{19}$ and three W are O. In one embodiment, R$_{19}$ is H or methyl. In a further embodiment, R$_{19}$ is methyl.

In certain embodiments, the Linker-Targeting Ligand (TL) has the structure selected from Table L:

TABLE L

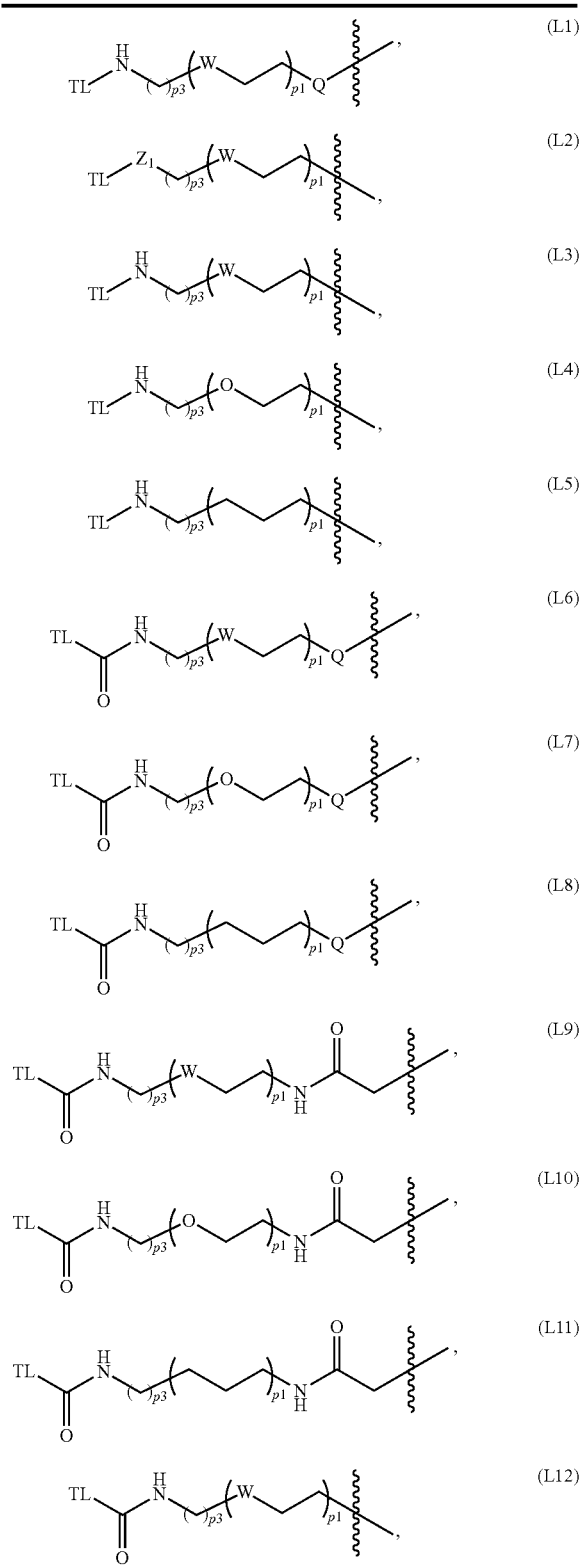

TABLE L-continued

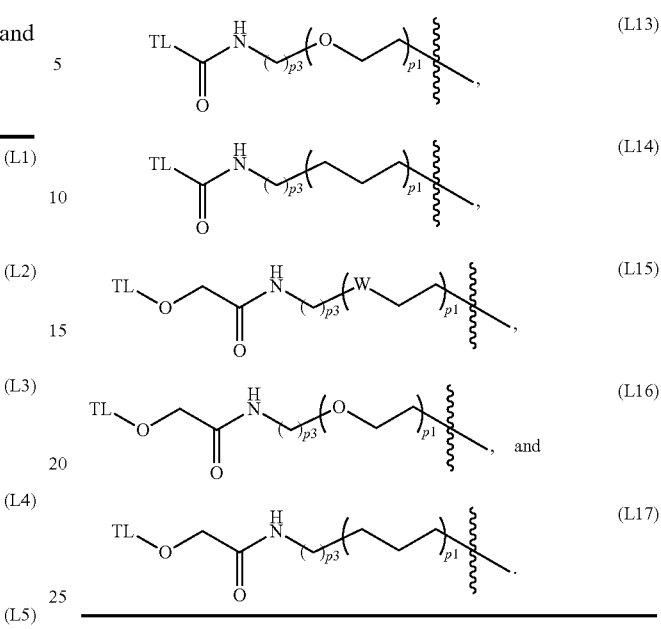

wherein TL, Z$_1$, Q, W, p1, and p3 are each as described herein.

Any one of the Degrons described herein can be covalently bound to any one of the Linkers described herein. Any one of the Targeting Ligands described herein can be covalently bound to any one of the Linkers described herein.

In certain embodiments, the present application relates to the Degron-Linker (DL), wherein the Degron is of Formula D1, and the Linker is selected from L1-L17. In one embodiment, the Degron is of Formula D1a or D1b, and the Linker is selected from L1-L17. In one embodiment, the Degron is of Formula D1a or D1b, and the Linker is L1 or L2. In one embodiment, the Degron is of Formula D1a or D1b, and the Linker is L1-L3. In one embodiment, the Degron is of Formula D1a or D1b, and the Linker is L3-L5. In one embodiment, the Degron is of Formula D1a or D1b, and the Linker is L1-L5. In one embodiment, the Degron is of Formula D1a or D1b, and the Linker is L6-L8. In one embodiment, the Degron is of Formula D1a or D1b, and the Linker is L9-L11. In one embodiment, the Degron is of Formula D1a or D1b, and the Linker is L12-L14. In one embodiment, the Degron is of Formula D1a or D1b, and the Linker is L15-L17. In one embodiment, the Degron is of Formula D1a or D1b, and the Linker is L4 or L5. In one embodiment, the Degron is of Formula D1a or D1b, and the Linker is L7 or L8. In one embodiment, the Degron is of Formula D a or D1b, and the Linker is L1, L2, L6, L9, L12, or L15. In one embodiment, the Degron is of Formula D1a or D1b, and the Linker is L10 or L11. In one embodiment, the Degron is of Formula D1a or D1b, and the Linker is L13 or L14. In one embodiment, the Degron is of Formula D1a or D1b, and the Linker is L16 or L17. In one embodiment, the Degron is of Formula D1a or D1b, and the Linker is L4, L5, L10, L10, L11, L13, L14, L16, or L17.

In certain embodiments, the present application relates to the Degron-Linker (DL), wherein the Degron is of Formula D2, and the Linker is selected from L1-L17. In one embodiment, the Degron is of Formula D2a, D2b, D2c, or D2d, and the Linker is selected from L1-L17. In one embodiment, the Degron is of Formula D2a, D2b, D2c, or D2d, and the Linker is L1 or L2. In one embodiment, the Degron is of Formula D2a, D2b, D2c, or D2d, and the Linker is L1-L3. In one embodiment, the Degron is of Formula D2a, D2b, D2c, or D2d, and the Linker is L1-L5. In one embodiment, the Degron is of Formula D2a, D2b, D2c, or D2d, and the Linker is L3-L5. In one embodiment, the Degron is of Formula D2a, D2b, D2c, or D2d, and the Linker is L6-L8. In one embodiment, the Degron is of Formula D2a, D2b, D2c, or D2d, and the Linker is L9-L11. In one embodiment, the Degron is of Formula D2a, D2b, D2c, or D2d, and the Linker is L12-L14. In one embodiment, the Degron is of Formula D2a, D2b, D2c, or D2d, and the Linker is L15-L17. In one embodiment, the Degron is of Formula D2a, D2b, D2c, or D2d, and the Linker is L4 or L5. In one embodiment, the Degron is of Formula D2a, D2b, D2c, or D2d, and the Linker is L7 or L8. In one embodiment, the Degron is of Formula D2a, D2b, D2c, or D2d, and the Linker is L1, L2, L6, L9, L12, or L15. In one embodiment, the Degron is of Formula D2a or D2b, and the Linker is L10 or L11. In one embodiment, the Degron is of Formula D2a or D2b, and the Linker is L1, L2, L3, L4, or L5. L1. In one embodiment, the Degron is of Formula D2a or D2b, and the Linker is L13 or L14. In one embodiment, the Degron is of Formula D2a or D2b, and the Linker is L16 or L17. In one embodiment, the Degron is of Formula D2a or D2b, and the Linker is L4, L5, L10, L10, L11, L13, L14, L16, or L17. In one embodiment, the Degron is of Formula D2c or D2d, and the Linker is L10 or L11. In one embodiment, the Degron is of Formula D2c or D2d, and the Linker is L1, L2, L3, L4, or L5. In one embodiment, the Degron is of Formula D2c or D2d, and the Linker is L13 or L14. In one embodiment, the Degron is of Formula D2c or D2d, and the Linker is L16 or L17. In one embodiment, the Degron is of Formula D2c or D2d, and the Linker is L4, L5, L10, L10, L11, L13, L14, L16, or L17.

In one embodiment, the Linker is designed and optimized based on SAR (structure-activity relationship) and X-ray crystallography of the Targeting Ligand with regard to the location of attachment for the Linker.

In one embodiment, the optimal Linker length and composition vary by the Targeting Ligand and can be estimated based upon X-ray structure of the Targeting Ligand bound to its target. Linker length and composition can be also modified to modulate metabolic stability and pharmacokinetic (PK) and pharmacodynamics (PD) parameters.

Targeting Ligands

Targeting Ligand (TL) (or target protein moiety or target protein ligand or ligand) is a small molecule which is capable of binding to a target protein of interest.

Some embodiments of the present application relate to TLs which include but are not limited to Hsp90 inhibitors, kinase inhibitors, MDM2 inhibitors, compounds targeting Human BET Bromodomain-containing proteins, compounds targeting cytosolic signaling protein FKBP12, HDAC inhibitors, human lysine methyltransferase inhibitors, angiogenesis inhibitors, immunosuppressive compounds, and compounds targeting the aryl hydrocarbon receptor (AHR).

In certain embodiments, the Targeting Ligand is a compound that is capable of binding to or binds to a kinase, a BET bromodomain-containing protein, a cytosolic signaling protein (e.g., FKBP12), a nuclear protein, a histone deacetylase, a lysine methyltransferase, a protein regulating angiogenesis, a protein regulating immune response, an aryl hydrocarbon receptor (AHR), an estrogen receptor, an androgen receptor, a glucocorticoid receptor, or a transcription factor (e.g., SMARCA4, SMARCA2, TRIM24).

In certain embodiments, a kinase to which the Targeting Ligand is capable of binding or binds includes, but is not limited to, a tyrosine kinase (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES1, or ZAP70), a serine/threonine kinase (e.g., casein kinase 2, protein kinase A, protein kinase B, protein kinase C, Rafkinases, CaM kinases, AKT1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PIM1, PIM2, PLK1, RIP2, RIP5, RSK1, RSK2, SGK2, SGK3, SIK1, STK33, TAO1, TAO2, TGF-beta, TLK2, TSSK1, TSSK2, ULK1, or ULK2), a cyclin dependent kinase (e.g., Cdk1-Cdk11), and a leucine-rich repeat kinase (e.g., LRRK2).

In certain embodiments, a nuclear protein to which the Targeting Ligand is capable of binding or binds includes, but is not limited to, BRD2, BRD3, BRD4, Antennapedia Homeodomain Protein, BRCA1, BRCA2, CCAAT-Enhanced-Binding Proteins, histones, Polycomb-group proteins, High Mobility Group Proteins, Telomere Binding Proteins, FANCA, FANCD2, FANCE, FANCF, hepatocyte nuclear factors. Mad2, NF-kappa B, Nuclear Receptor Coactivators, CREB-binding protein, p55, p107, p130, Rb proteins, p53, c-fos, c-jun, c-mdm2, c-myc, and c-rel.

In certain embodiments, a BET bromodomain-containing protein to which the Targeting Ligand is capable of binding or binds includes, but is not limited to, BRD1, BRD2, BRD3, BRD4, BRD5, BRD6, BRD7, BRD8, BRD9, BRD10, and BRDT. In certain embodiments, a BET bromodomain-containing protein is BRD4.

Non-limiting examples of TLs are shown in below and represent Targeting Ligands of certain types of proteins of interest.

In one embodiment the BRD Targeting Ligand is selected from

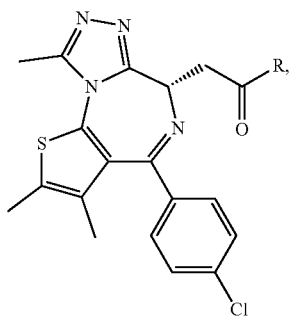

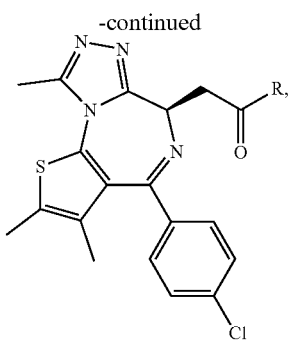

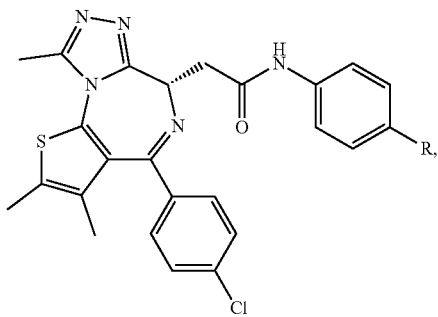

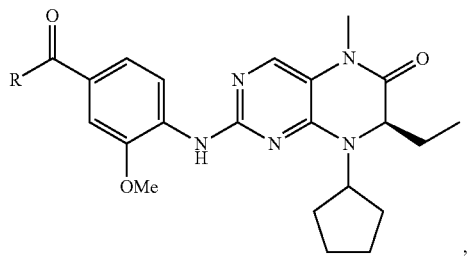

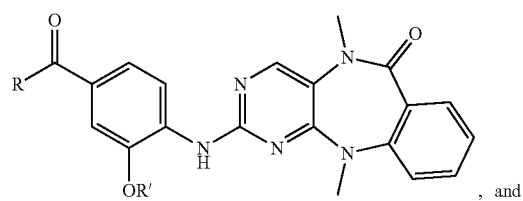

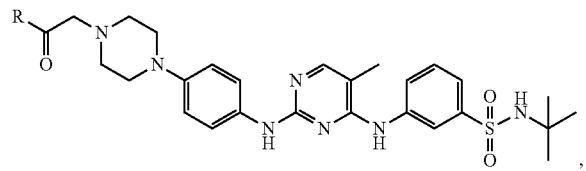

wherein:
R: Degron-Linker; R': methyl or ethyl

The present application further relates to the Targeting Ligands described herein, including a compound of Formula TL-I to TL-IV.

In certain embodiments, a Targeting Ligand is a compound of Formula TL-I:

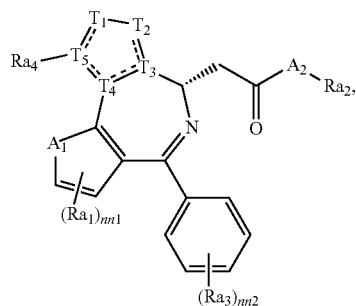

(TL-I)

or a pharmaceutically acceptable salt thereof, wherein:

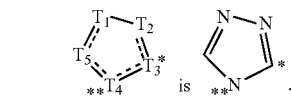

$A_1$ is S or C=C;
$A_2$ is $NRa_5$ or O;
nn1 is 0, 1, or 2;
each $Ra_1$ is independently $C_1$-$C_3$ alkyl, $(CH_2)_{0-3}$—CN, $(CH_2)_{0-3}$-halogen, $(CH_2)_{0-3}$—OH, $(CH_2)_{0-3}$—$C_1$-$C_3$ alkoxy, $C(O)NRa_5L$, OL, $NRa_5L$, or L;
$Ra_2$ is H, $C_1$-$C_6$ alkyl, $(CH_2)_{0-3}$-heterocyclyl, $(CH_2)_{0-3}$-phenyl, or L, wherein the heterocyclyl comprises one saturated 5- or 6-membered ring and 1-2 heteroatoms selected from N, O, and S and is optionally substituted with $C_1$-$C_3$ alkyl, L, or C(O)L, and wherein the phenyl is optionally substituted with $C_1$-$C_3$ alkyl, CN, halogen, OH, $C_1$-$C_3$ alkoxy, or L;
nn2 is 0, 1, 2, or 3;
each $Ra_3$ is independently $C_1$-$C_3$ alkyl, $(CH_2)_{0-3}$—CN, $(CH_2)_{0-3}$-halogen, L, or $C(O)NRa_5L$;
$Ra_4$ is $C_1$-$C_3$ alkyl;
in an alternative embodiment $Ra_4$ is hydrogen;
$Ra_5$ is H or $C_1$-$C_3$ alkyl; and
L is a Linker,
provided that the compound of Formula TL-I is substituted with only one L.

In certain embodiments,

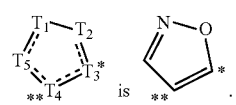

In certain embodiments,

In certain embodiments, $A_1$ is S.
In certain embodiments, $A_1$ is C=C.
In certain embodiments, $A_2$ is $NRa_5$. In further embodiments, $Ra_5$ is H. In other embodiments, $Ra_5$ is $C_1$-$C_3$ alkyl (e.g., methyl, ethyl, propyl, or i-propyl). In further embodiments, $Ra_5$ is methyl.

In certain embodiments, $A_2$ is O.
In certain embodiments, nn1 is 0.
In certain embodiments, nn1 is 1.
In certain embodiments, nn1 is 2.
In certain embodiments, at least one $Ra_1$ is $C_1$-$C_3$ alkyl (e.g., methyl, ethyl, propyl, or i-propyl). In further embodiments, at least one $Ra_1$ is methyl. In further embodiments, two $Ra_1$ are methyl.

In certain embodiments, at least one $Ra_1$ is CN, $(CH_2)$—CN, $(CH_2)_2$—CN, or $(CH_2)_3$—CN. In further embodiments, at least one $Ra_1$ is $(CH_2)$—CN.

In certain embodiments, at least one $Ra_1$ is halogen (e.g., F, Cl, or Br), $(CH_2)$-halogen, $(CH_2)_2$-halogen, or $(CH_2)_3$-halogen. In further embodiments, at least one $Ra_1$ is Cl, $(CH_2)$—Cl, $(CH_2)_2$—Cl, or $(CH_2)_3$—Cl.

In certain embodiments, at least one $Ra_1$ is OH, $(CH_2)$—OH, $(CH_2)_2$—OH, or $(CH_2)_3$—OH.

In certain embodiments, at least one $Ra_1$ is $C_1$-$C_3$ alkoxy (e.g., methoxy, ethoxy, or propoxy), $(CH_2)$—$C_1$-$C_3$ alkoxy, $(CH_2)_2$—$C_1$-$C_3$ alkoxy, or $(CH_2)_3$—$C_1$-$C_3$ alkoxy. In certain embodiments, at least one $Ra_1$ is methoxy.

In certain embodiments, one $Ra_1$ is $C(O)NRa_5L$. In further embodiments, $Ra_5$ is H. In other embodiments, $Ra_5$ is $C_1$-$C_3$ alkyl (e.g., methyl, ethyl, propyl, or i-propyl).

In certain embodiments, one $Ra_1$ is OL.
In certain embodiments, one $Ra_1$ is $NRa_5L$. In further embodiments, $Ra_5$ is H. In other embodiments, $Ra_5$ is $C_1$-$C_3$ alkyl (e.g., methyl, ethyl, propyl, or i-propyl). In other embodiments, $Ra_5$ is methyl.

In certain embodiments, one $Ra_1$ is L.
In certain embodiments, $Ra_2$ is H.
In certain embodiments, $Ra_2$ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra_2$ is methyl, ethyl, or t-butyl.

In certain embodiments, $Ra_2$ is heterocyclyl, $(CH_2)$-heterocyclyl, $(CH_2)_2$-heterocyclyl, or $(CH_2)_3$-heterocyclyl. In further embodiments, $Ra_2$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with $C_1$-$C_3$ alkyl (e.g., methyl, ethyl, propyl, or i-propyl).

In certain embodiments, the heterocyclyl is substituted with C(O)L.

In certain embodiments, the heterocyclyl is substituted with L.

In certain embodiments, $Ra_2$ is phenyl, $(CH_2)$-phenyl, $(CH_2)_2$-phenyl, or $(CH_2)_3$-phenyl. In further embodiments, $Ra_2$ is phenyl.

In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).

In certain embodiments, the phenyl is substituted with L.
In certain embodiments, $Ra_2$ is L.
In certain embodiments, nn2 is 0.
In certain embodiments, nn2 is 1.
In certain embodiments, nn2 is 2.
In certain embodiments, nn2 is 3.

In certain embodiments, at least one $Ra_3$ is $C_1$-$C_3$ alkyl (e.g., methyl, ethyl, propyl, or i-propyl). In further embodiments, at least one $Ra_3$ is methyl.

In certain embodiments, at least one $Ra_3$ is CN, $(CH_2)$—CN, $(CH_2)_2$—CN, or $(CH_2)_3$—CN. In further embodiments, at least one $Ra_3$ is CN.

In certain embodiments, at least one $Ra_3$ is halogen (e.g., F, Cl, or Br), $(CH_2)$-halogen, $(CH_2)_2$-halogen, or $(CH_2)_3$-halogen. In further embodiments, at least one $Ra_3$ is Cl, $(CH_2)$—Cl, $(CH_2)_2$—Cl, or $(CH_2)_3$—Cl. In further embodiments, at least one $Ra_3$ is Cl.

In certain embodiments, one $Ra_3$ is L.
In certain embodiments, one $Ra_3$ is $C(O)NRa_5L$. In further embodiments, $Ra_5$ is H. In other embodiments, $Ra_5$ is $C_1$-$C_3$ alkyl (e.g., methyl, ethyl, propyl, or i-propyl).

In certain embodiments, $Ra_4$ is $C_1$-$C_3$ alkyl (e.g., methyl, ethyl, propyl, or i-propyl). In further embodiments, $Ra_4$ is methyl.

In certain embodiments, $Ra_5$ is H.
In certain embodiments, $Ra_5$ is $C_1$-$C_3$ alkyl (e.g., methyl, ethyl, propyl, or i-propyl). In further embodiments, $Ra_5$ is methyl.

Each of the moieties defined for one of $T_1$, $T_2$, $T_3$, $T_4$, $T_5$, $A_1$, $A_2$, $Ra_1$, $Ra_2$, $Ra_3$, $Ra_4$, $Ra_5$, nn1, and nn2, can be combined with any of the moieties defined for the others of $T_1$, $T_2$, $T_3$, $T_4$, $T_5$, $A_1$, $A_2$, $Ra_1$, $Ra_2$, $Ra_3$, $Ra_4$, $Ra_5$, nn1, and nn2.

In certain embodiments,

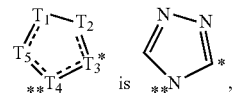

and $A_1$ is S.
In certain embodiments,

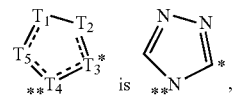

and $A_1$ is C=C.
In certain embodiments,

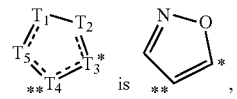

and $A_1$ is C=C.
In certain embodiments, $A_2$ is NH, and $Ra_2$ is $(CH_2)_{0-3}$-heterocyclyl. In further embodiments, $Ra_2$ is $(CH_2)_3$-heterocyclyl. In further embodiments, the heterocyclyl is piperazinyl. In further embodiments, the heterocyclyl is substituted with $C_1$-$C_3$ alkyl, L, or C(O)L.

In certain embodiments, $A_2$ is NH, and $Ra_2$ is $(CH_2)_{0-3}$-phenyl. In further embodiments, $Ra_2$ is phenyl. In further embodiments, the phenyl is substituted with OH or L.

In certain embodiments, $A_2$ is NH, and $Ra_2$ is L.
In certain embodiments, $A_2$ is NH, and $Ra_2$ is H or $C_1$-$C_6$ alkyl. In further embodiments, $Ra_2$ is $C_1$-$C_4$ alkyl.

In certain embodiments, $A_2$ is O, and $Ra_2$ is H or $C_1$-$C_6$ alkyl. In further embodiments, $Ra_2$ is $C_1$-$C_4$ alkyl.

In certain embodiments, a Targeting Ligand is a compound of Formula TL-I1:

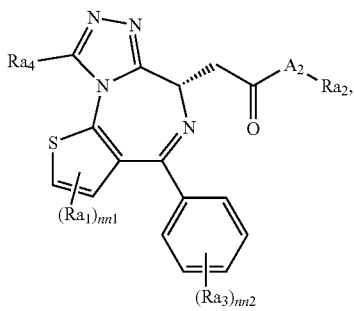

(TL-I1)

or a pharmaceutically acceptable salt thereof, wherein $A_2$, $Ra_1$, $Ra_2$, $Ra_3$, $Ra_4$, $Ra_5$, nn1, and nn2 are each as defined above in Formula TL-I.

Each of $A_2$, $Ra_1$, $Ra_2$, $Ra_3$, $Ra_4$, $Ra_5$, nn1, and nn2 may be selected from the moieties described above in Formula TL-I. Each of the moieties defined for one of $A_2$, $Ra_1$, $Ra_2$, $Ra_3$, $Ra_4$, $Ra_5$, nn1, and nn2, can be combined with any of the moieties defined for the others of $A_2$, $Ra_1$, $Ra_2$, $Ra_3$, $Ra_4$, $Ra_5$, nn1, and nn2, as described above in Formula TL-I.

In certain embodiments, a Targeting Ligand is a compound of Formula TL-I1a-TL-I1d:

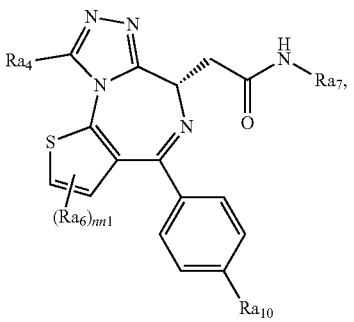

(TL-I1a)

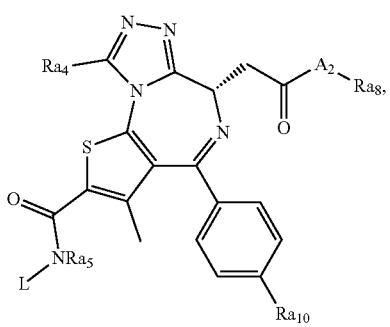

(TL-I1b)

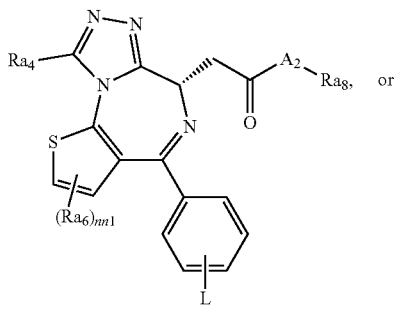

(TL-I1c)

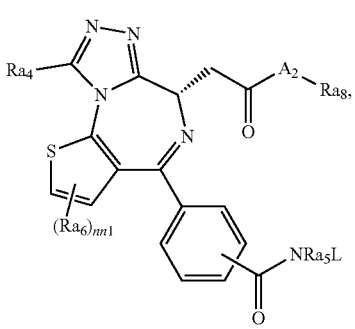

(TL-I1d)

or a pharmaceutically acceptable salt thereof, wherein:

each $Ra_6$ is independently $C_1$-$C_3$ alkyl, $(CH_2)_{0-3}$—CN, $(CH_2)_{0-3}$-halogen, $(CH_2)_{0-3}$—OH, or $(CH_2)_{0-3}$—$C_1$-$C_3$ alkoxy;

$Ra_7$ is $(CH_2)_{0-3}$-heterocyclyl, $(CH_2)_{0-3}$-phenyl, or L, wherein the heterocyclyl comprises one saturated 5- or 6-membered ring and 1-2 heteroatoms selected from N, O, and S and is substituted with L or C(O)L, and wherein the phenyl is substituted with L;

$Ra_8$ is H, $C_1$-$C_6$ alkyl, $(CH_2)_{0-3}$-heterocyclyl, or $(CH_2)_{0-3}$-phenyl, wherein the heterocyclyl comprises one saturated 5- or 6-membered ring and 1-2 heteroatoms selected from N, O, and S and is optionally substituted with $C_1$-$C_3$ alkyl, and wherein the phenyl is optionally substituted with $C_1$-$C_3$ alkyl, CN, halogen, OH, or $C_1$-$C_3$ alkoxy;

$Ra_{10}$ is $C_1$-$C_3$ alkyl, $(CH_2)_{0-3}$—CN, or $(CH_2)_{0-3}$-halogen; and $A_2$, $Ra_4$, $Ra_5$, nn1, and L are each as defined above in Formula TL-I.

In certain embodiments, nn1 is 0.
In certain embodiments, nn1 is 1.
In certain embodiments, nn1 is 2.
In certain embodiments, at least one $Ra_6$ is $C_1$-$C_3$ alkyl (e.g., methyl, ethyl, propyl, or i-propyl). In further embodiments, at least one $Ra_6$ is methyl. In further embodiments, two $Ra_6$ are methyl.

In certain embodiments, at least one $Ra_6$ is CN, $(CH_2)$—CN, $(CH_2)_2$—CN, or $(CH_2)_3$—CN. In further embodiments, at least one $Ra_6$ is $(CH_2)$—CN.

In certain embodiments, at least one $Ra_6$ is halogen (e.g., F, Cl, or Br), $(CH_2)$-halogen, $(CH_2)_2$-halogen, or $(CH_2)_3$-halogen. In further embodiments, at least one $Ra_6$ is Cl, $(CH_2)$—Cl, $(CH_2)_2$—Cl, or $(CH_2)_3$—Cl.

In certain embodiments, at least one $Ra_6$ is OH, $(CH_2)$—OH, $(CH_2)_2$—OH, or $(CH_2)_3$—OH.

In certain embodiments, at least one $Ra_6$ is $C_1$-$C_3$ alkoxy (e.g., methoxy, ethoxy, or propoxy), $(CH_2)$—$C_1$-$C_3$ alkoxy, $(CH_2)_2$—$C_1$-$C_3$ alkoxy, or $(CH_2)_3$—$C_1$-$C_3$ alkoxy. In certain embodiments, at least one $Ra_6$ is methoxy.

In certain embodiments, $Ra_7$ is heterocyclyl, $(CH_2)$-heterocyclyl, $(CH_2)_2$-heterocyclyl, or $(CH_2)_3$-heterocyclyl. In further embodiments, $Ra_7$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with C(O)L.

In certain embodiments, the heterocyclyl is substituted with L.

In certain embodiments, $Ra_7$ is phenyl, $(CH_2)$-phenyl, $(CH_2)_2$-phenyl, or $(CH_2)_3$-phenyl. In further embodiments, $Ra_7$ is phenyl.

In certain embodiments, $Ra_7$ is L.

In certain embodiments, $Ra_8$ is H.

In certain embodiments, $Ra_8$ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra_8$ is methyl, ethyl, or t-butyl.

In certain embodiments, $Ra_8$ is heterocyclyl, $(CH_2)$-heterocyclyl, $(CH_2)_2$-heterocyclyl, or $(CH_2)_3$-heterocyclyl. In further embodiments, $Ra_8$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with $C_1$-$C_3$ alkyl (e.g., methyl, ethyl, propyl, or i-propyl).

In certain embodiments, $Ra_8$ is phenyl, $(CH_2)$-phenyl, $(CH_2)_2$-phenyl, or $(CH_2)_3$-phenyl. In further embodiments, $Ra_8$ is phenyl.

In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).

In certain embodiments, $Ra_{10}$ is $C_1$-$C_3$ alkyl (e.g., methyl, ethyl, propyl, or i-propyl).

In certain embodiments, $Ra_{10}$ is CN, $(CH_2)$—CN, $(CH_2)_2$—CN, or $(CH_2)_3$—CN.

In certain embodiments, $Ra_{10}$ is halogen (e.g., F, Cl, or Br), $(CH_2)$-halogen, $(CH_2)_2$-halogen, or $(CH_2)_3$-halogen. In further embodiments, $Ra_{10}$ is Cl, $(CH_2)$—Cl, $(CH_2)_2$—Cl, or $(CH_2)_3$—Cl. In further embodiments, $Ra_{10}$ is Cl.

Each of $A_2$, $Ra_4$, $Ra_5$, and nn1 may be selected from the moieties described above in Formula TL-I. Each of the moieties defined for one of $A_2$, $Ra_4$, $Ra_5$, $Ra_6$, $Ra_7$, $Ra_8$, $Ra_{10}$, and nn1, can be combined with any of the moieties defined for the others of $A_2$, $Ra_4$, $Ra_5$, $Ra_6$, $Ra_7$, $Ra_8$, $Ra_{10}$, and nn1, as described above and in Formula TL-I.

In certain embodiments, a Targeting Ligand is a compound of Formula TL-I2:

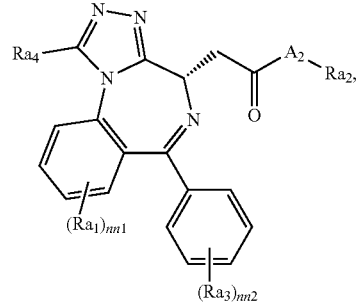
(TL-I2)

or a pharmaceutically acceptable salt thereof, wherein $A_2$, $Ra_1$, $Ra_2$, $Ra_3$, $Ra_4$, $Ra_5$, nn1, and nn2 are each as defined above in Formula TL-I.

Each of $A_2$, $Ra_1$, $Ra_2$, $Ra_3$, $Ra_4$, $Ra_5$, nn1, and nn2 may be selected from the moieties described above in Formula TL-I. Each of the moieties defined for one of $A_2$, $Ra_1$, $Ra_2$, $Ra_3$, $Ra_4$, $Ra_5$, nn1, and nn2, can be combined with any of the moieties defined for the others of $A_2$, $Ra_1$, $Ra_2$, $Ra_3$, $Ra_4$, $Ra_5$, nn1, and nn2, as described above in Formula TL-I.

In certain embodiments, a Targeting Ligand is a compound of Formula TL-I2a-TL-I2c:

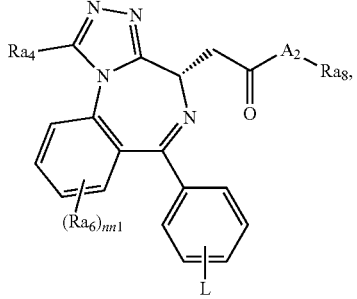
(TL-I2a)

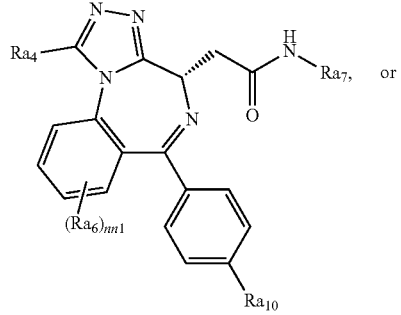
(TL-I2b)

or

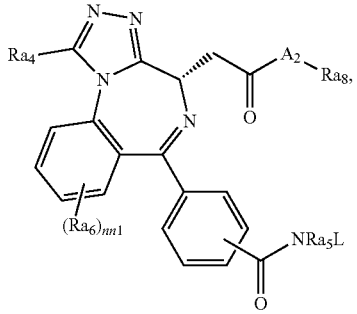
(TL-I2c)

or a pharmaceutically acceptable salt thereof, wherein $A_2$, $Ra_4$, $Ra_5$, nn1, and L are each as defined above in Formula TL-I, and $Ra_6$, $Ra_7$, $Ra_8$, and $Ra_{10}$ are each as defined above in Formula TL-I1a-TL-I1d.

Each of $A_2$, $Ra_4$, $Ra_5$, and nn1 may be selected from the moieties described above in Formula TL-I, and each of $Ra_6$, $Ra_7$, $Ra_8$, and $Ra_{10}$ may be selected from the moieties described above in Formula TL-I1a-TL-I1d. Each of the moieties defined for one of $A_2$, $Ra_4$, $Ra_5$, $Ra_6$, $Ra_7$, $Ra_8$, $Ra_{10}$, and nn1, can be combined with any of the moieties defined for the others of $A_2$, $Ra_4$, $Ra_5$, $Ra_6$, $Ra_7$, $Ra_8$, $Ra_{10}$, and nn1, as described above in Formula TL-I and TL-I1a-TL-I1d.

In certain embodiments, a Targeting Ligand is a compound of Formula TL-I3:

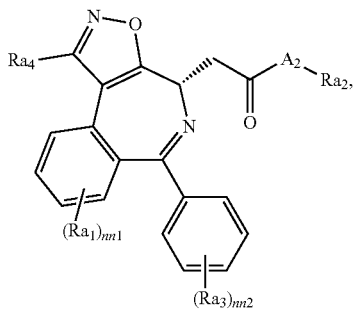

(TL-I3)

or a pharmaceutically acceptable salt thereof.

$A_2$, $Ra_1$, $Ra_2$, $Ra_3$, $Ra_4$, $Ra_5$, nn1, and nn2 are each as defined above in Formula TL-I. Each of $A_2$, $Ra_1$, $Ra_2$, $Ra_3$, $Ra_4$, $Ra_5$, nn1, and nn2 may be selected from the moieties described above in Formula TL-I. Each of the moieties defined for one of $A_2$, $Ra_1$, $Ra_2$, $Ra_3$, $Ra_4$, $Ra_5$, nn1, and nn2, can be combined with any of the moieties defined for the others of $A_2$, $Ra_1$, $Ra_2$, $Ra_3$, $Ra_4$, $Ra_5$, nn1, and nn2, as described above in Formula TL-I.

In certain embodiments, a Targeting Ligand is a compound of Formula TL-I3a-TL-I3c:

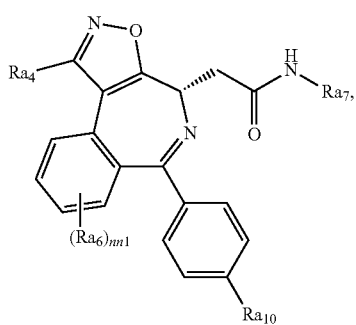

(TL-I3a)

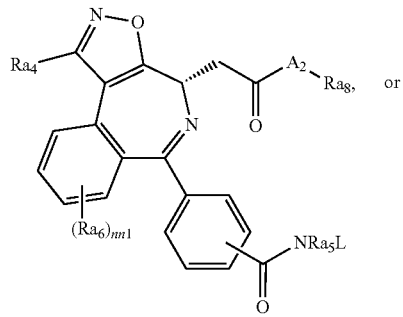

(TL-I3b)

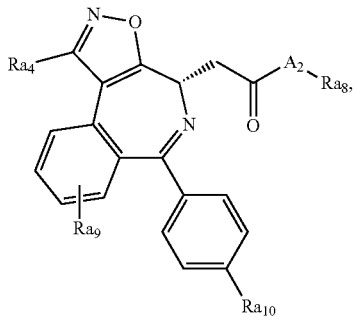

(TL-I3c)

or a pharmaceutically acceptable salt thereof, wherein:

$Ra_9$ is $C(O)NRa_5L$, OL, $NRa_5L$, or L;

$A_2$, $Ra_4$, $Ra_5$, nn1, and L are each as defined above in Formula TL-I; and $Ra_6$, $Ra_7$, $Ra_8$, and $Ra_{10}$ are each as defined above in Formula TL-I1a-TL-I1d.

In certain embodiments, $Ra_9$ is $C(O)NRa_5L$. In further embodiments, $Ra_5$ is H. In other embodiments, $Ra_5$ is $C_1$-$C_3$ alkyl (e.g., methyl, ethyl, propyl, or i-propyl).

In certain embodiments, $Ra_9$ is OL.

In certain embodiments, $Ra_9$ is $NRa_5L$. In further embodiments, $Ra_5$ is H. In other embodiments, $Ra_5$ is $C_1$-$C_3$ alkyl (e.g., methyl, ethyl, propyl, or i-propyl). In other embodiments, $Ra_5$ is methyl.

In certain embodiments, $Ra_9$ is L.

Each of $A_2$, $Ra_4$, $Ra_5$, and nn1 may be selected from the moieties described above in Formula TL-I, and each of $Ra_6$, $Ra_7$, $Ra_8$, and $Ra_{10}$ may be selected from the moieties described above in Formula TL-I1a-TL-I1d. Each of the moieties defined for one of $A_2$, $Ra_4$, $Ra_5$, $Ra_6$, $Ra_7$, $Ra_8$, $Ra_9$, $Ra_{10}$, and nn1, can be combined with any of the moieties defined for the others of $A_2$, $Ra_4$, $Ra_5$, $Ra_6$, $Ra_7$, $Ra_8$, $Ra_9$, $Ra_{10}$, and nn1, as described above and in Formula TL-I and TL-I1a-TL-I1d.

In certain embodiments, a Targeting Ligand is a compound of Formula TL-II:

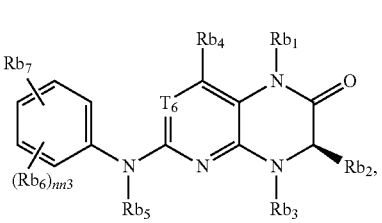

(TL-II)

or a pharmaceutically acceptable salt thereof, wherein:

$T_6$ is $CRb_4$ or N;

$Rb_1$, $Rb_2$, and $Rb_5$ are each independently H or $C_1$-$C_3$ alkyl;

$Rb_3$ is $C_3$-$C_6$ cycloalkyl;

each $Rb_4$ is independently H, $C_1$-$C_3$ alkyl, $C_1$-$C_3$ alkoxy, CN, or halogen;

nn3 is 0, 1, 2, or 3;

each $Rb_6$ is independently $C_1$-$C_3$ alkyl, $C_1$-$C_3$ alkoxy, CN, or halogen;

$Rb_7$ is $C(O)NRb_8L$, OL, $NRb_8L$, or L;

$Rb_8$ is H or $C_1$-$C_3$ alkyl; and

L is a Linker.

In certain embodiments, $T_6$ is $CRb_4$.

In certain embodiments, $T_6$ is N.

In certain embodiments, $Rb_1$ is H. In certain embodiments, $Rb_1$ is $C_1$-$C_3$ alkyl (e.g., methyl, ethyl, propyl, or i-propyl). In further embodiments, $Rb_1$ is methyl.

In certain embodiments, $Rb_2$ is H. In certain embodiments, $Rb_2$ is $C_1$-$C_3$ alkyl (e.g., methyl, ethyl, propyl, or i-propyl). In further embodiments, $Rb_2$ is methyl or ethyl.

In certain embodiments, $Rb_5$ is H. In certain embodiments, $Rb_5$ is $C_1$-$C_3$ alkyl (e.g., methyl, ethyl, propyl, or i-propyl).

In certain embodiments, $Rb_3$ is cyclopropyl, cyclobutyl, cyclopentyl, or cyclohexyl. In further embodiments, $Rb_3$ is cyclopentyl.

In certain embodiments, $Rb_4$ is H.

In certain embodiments, $Rb_4$ is $C_1$-$C_3$ alkyl (e.g., methyl, ethyl, propyl, or i-propyl).

In certain embodiments, $Rb_4$ is $C_1$-$C_3$ alkoxy (e.g., methoxy, ethoxy, or propoxy).

In certain embodiments, $Rb_4$ is CN.

In certain embodiments, $Rb_4$ is halogen (e.g., F, Cl, or Br).

In certain embodiments, nn3 is 0.

In certain embodiments, nn3 is 1.

In certain embodiments, nn3 is 2.

In certain embodiments, nn3 is 3.

In certain embodiments, at least one $Rb_6$ is $C_1$-$C_3$ alkyl (e.g., methyl, ethyl, propyl, or i-propyl). In further embodiments, at least one $Rb_6$ is methyl.

In certain embodiments, at least one $Rb_6$ is $C_1$-$C_3$ alkoxy (e.g., methoxy, ethoxy, or propoxy). In further embodiments, at least one $Rb_6$ is methoxy.

In certain embodiments, at least one $Rb_6$ is CN.

In certain embodiments, at least one $Rb_6$ is halogen (e.g., F, Cl, or Br).

In certain embodiments, $Rb_7$ is $C(O)NRb_8L$. In further embodiments, $Rb_8$ is H. In other embodiments, $Rb_8$ is $C_1$-$C_3$ alkyl (e.g., methyl, ethyl, propyl, or i-propyl).

In certain embodiments, $Rb_7$ is OL.

In certain embodiments, $Rb_7$ is $NRb_8L$. In further embodiments, $Rb_8$ is H. In other embodiments, $Rb_8$ is $C_1$-$C_3$ alkyl (e.g., methyl, ethyl, propyl, or i-propyl). In other embodiments, $Rb_8$ is methyl.

In certain embodiments, $Rb_7$ is L.

Each of the moieties defined for one of $T_6$, $Rb_1$, $Rb_2$, $Rb_3$, $Rb_4$, $Rb_5$, $Rb_6$, $Rb_7$, $Rb_8$, and nn3, can be combined with any of the moieties defined for the others of $T_6$, $Rb_1$, $Rb_2$, $Rb_3$, $Rb_4$, $Rb_5$, $Rb_6$, $Rb_7$, $Rb_8$, and nn3.

In certain embodiments, $Rb_3$ is cyclopentyl, and $Rb_7$ is $C(O)NRb_8L$.

In certain embodiments, a Targeting Ligand is a compound of Formula TL-III1:

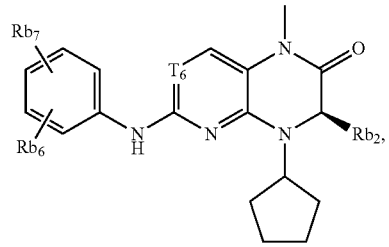

(TL-III1)

or a pharmaceutically acceptable salt thereof, wherein $T_6$, $Rb_2$, $Rb_4$, $Rb_6$, $Rb_7$, and $Rb_8$ are each as defined above in Formula TL-II.

Each of $T_6$, $Rb_2$, $Rb_4$, $Rb_6$, $Rb_7$, and $Rb_8$ may be selected from the moieties described above in Formula TL-II. Each of the moieties defined for one of $T_6$, $Rb_2$, $Rb_4$, $Rb_6$, $Rb_7$, and $Rb_8$, can be combined with any of the moieties defined for the others of $T_6$, $Rb_2$, $Rb_4$, $Rb_6$, $Rb_7$, and $Rb_8$, as described above in Formula TL-II.

In certain embodiments, a Targeting Ligand is a compound of Formula TL-III1a:

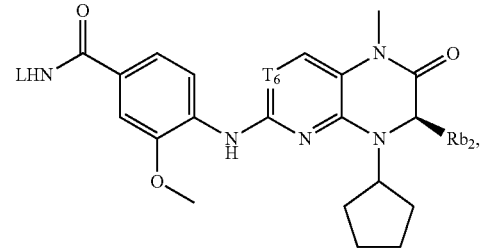

(TL-III1a)

or a pharmaceutically acceptable salt thereof, wherein $T_6$, $Rb_2$, and $Rb_4$ are each as defined above in Formula TL-II.

Each of $T_6$, $Rb_2$, and $Rb_4$ may be selected from the moieties described above in Formula TL-II. Each of the moieties defined for one of $T_6$, $Rb_2$, and $Rb_4$, can be combined with any of the moieties defined for the others of $T_6$, $Rb_2$, and $Rb_4$, as described above in Formula TL-II.

In certain embodiments, a Targeting Ligand is a compound of Formula TL-III:

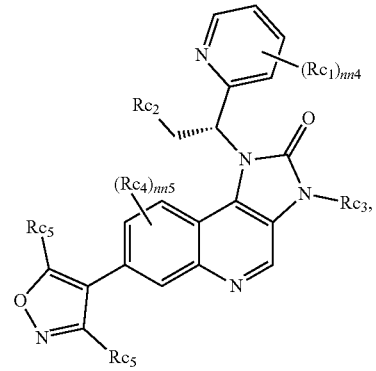

(TL-III)

or a pharmaceutically acceptable salt thereof, wherein:
nn4 is 0 or 1;
$Rc_1$ is $C(O)NRc_6L$, OL, $NRc_6L$, or L;
$Rc_2$ is H, $C_1$-$C_3$ alkyl, $C(O)NRc_6L$, OL, $NRc_6L$, or L;
$Rc_3$ is H, $C_1$-$C_3$ alkyl, C(O)L, or L;
nn5 is 0, 1, or 2;
each $Rc_4$ is independently $C_1$-$C_3$ alkyl or $C_1$-$C_3$ alkoxy;
each $Rc_5$ is independently H or $C_1$-$C_3$ alkyl;
$Rc_6$ is independently H or $C_1$-$C_3$ alkyl; and
L is a Linker,
provided that the compound of Formula TL-III is substituted with only one L.

In certain embodiments, nn4 is 0.
In certain embodiments, nn4 is 1.
In certain embodiments, $Rc_1$ is $C(O)NRc_6L$. In further embodiments, $Rc_6$ is H. In other embodiments, $Rc_6$ is $C_1$-$C_3$ alkyl (e.g., methyl, ethyl, propyl, or i-propyl).
In certain embodiments, $Rc_1$ is OL.
In certain embodiments, $Rc_1$ is $NRc_6L$. In further embodiments, $Rc_6$ is H. In other embodiments, $Rc_6$ is $C_1$-$C_3$ alkyl (e.g., methyl, ethyl, propyl, or i-propyl). In other embodiments, $Rc_6$ is methyl.
In certain embodiments, $Rc_1$ is L.
In certain embodiments, $Rc_2$ is H.
In certain embodiments, $Rc_2$ is $C_1$-$C_3$ alkyl (e.g., methyl, ethyl, propyl, or i-propyl). In further embodiments, $Rc_2$ is methyl.
In certain embodiments, $Rc_2$ is $C(O)NRc_6L$. In further embodiments, $Rc_6$ is H. In other embodiments, $Rc_6$ is $C_1$-$C_3$ alkyl (e.g., methyl, ethyl, propyl, or i-propyl).
In certain embodiments, $Rc_2$ is OL.
In certain embodiments, $Rc_2$ is $NRc_6L$. In further embodiments, $Rc_6$ is H. In other embodiments, $Rc_6$ is $C_1$-$C_3$ alkyl (e.g., methyl, ethyl, propyl, or i-propyl). In other embodiments, $Rc_6$ is methyl.
In certain embodiments, $Rc_2$ is L.
In certain embodiments, $Rc_3$ is H.
In certain embodiments, $Rc_3$ is $C_1$-$C_3$ alkyl (e.g., methyl, ethyl, propyl, or i-propyl).
In certain embodiments, $Rc_3$ is C(O)L.
In certain embodiments, $Rc_3$ is L.
In certain embodiments, nn5 is 0.
In certain embodiments, nn5 is 1.
In certain embodiments, nn5 is 2.
In certain embodiments, at least one $Rc_4$ is $C_1$-$C_3$ alkyl (e.g., methyl, ethyl, propyl, or i-propyl). In further embodiments, at least one $Rc_4$ is methyl.
In certain embodiments, at least one $Rc_4$ is $C_1$-$C_3$ alkoxy (e.g., methoxy, ethoxy, or propoxy). In further embodiments, at least one $Rc_4$ is methoxy.
In certain embodiments, at least one $Rc_5$ is H.
In certain embodiments, at least one $Rc_5$ is $C_1$-$C_3$ alkyl (e.g., methyl, ethyl, propyl, or i-propyl). In further embodiments, at least one $Rc_5$ is methyl. In further embodiments, two $Rc_5$ are methyl.

Each of the moieties defined for one of $Rc_1$, $Rc_2$, $Rc_3$, $Rc_4$, $Rc_5$, $Rc_6$, nn4, and nn5, can be combined with any of the moieties defined for the others of $Rc_1$, $Rc_2$, $Rc_3$, $Rc_4$, $Rc_5$, $Rc_6$, nn4, and nn5.

In certain embodiments, a Targeting Ligand is a compound of Formula TL-III1-TL-III3:

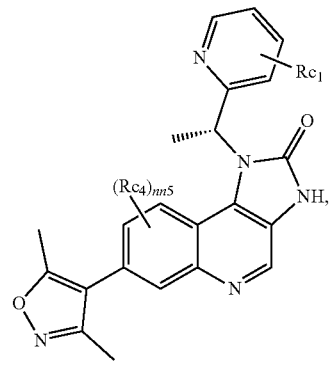

(TL-III1)

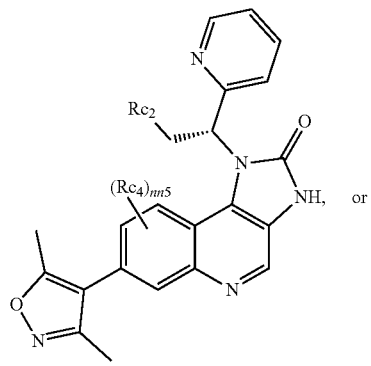

(TL-III2)

or

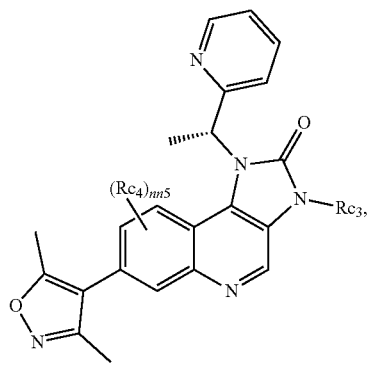

(TL-III3)

or a pharmaceutically acceptable salt thereof, wherein $Rc_1$, $Rc_2$, $Rc_3$, $Rc_4$, and nn5 are each as defined above in Formula TL-III.

Each of $Rc_1$, $Rc_2$, $Rc_3$, $Rc_4$, and nn5 may be selected from the moieties described above in Formula TL-III. Each of the moieties defined for one of $Rc_1$, $Rc_2$, $Rc_3$, $Rc_4$, and nn5, can be combined with any of the moieties defined for the others of $Rc_1$, $Rc_2$, $Rc_3$, $Rc_4$, and nn5, as described above in Formula TL-III.

In certain embodiments, a Targeting Ligand is a compound of Formula TL-IV:

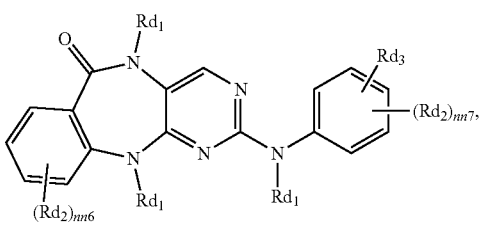

(TL-IV)

or a pharmaceutically acceptable salt thereof, wherein:
each $Rd_1$ is independently H or $C_1$-$C_3$ alkyl;
nn6 is 0, 1, 2, or 3;
nn7 is 0, 1, 2, or 3;
each $Rd_2$ is independently $C_1$-$C_3$ alkyl, $C_1$-$C_3$ alkoxy, CN, or halogen;
$Rd_3$ is C(O)$NRd_4$L, OL, $NRd_4$L, or L;
$Rd_4$ is H or $C_1$-$C_3$ alkyl; and
L is a Linker.

In certain embodiments, $Rd_1$ is H.
In certain embodiments, $Rd_1$ is $C_1$-$C_3$ alkyl (e.g., methyl, ethyl, propyl, or i-propyl). In further embodiments, $Rd_1$ is methyl.

In certain embodiments, nn6 is 0.
In certain embodiments, nn6 is 1.
In certain embodiments, nn6 is 2.
In certain embodiments, nn6 is 3.
In certain embodiments, nn7 is 0.
In certain embodiments, nn7 is 1.
In certain embodiments, nn7 is 2.
In certain embodiments, nn7 is 3.

In certain embodiments, at least one $Rd_2$ is $C_1$-$C_3$ alkyl (e.g., methyl, ethyl, propyl, or i-propyl). In further embodiments, at least one $Rd_2$ is methyl.

In certain embodiments, at least one $Rd_2$ is $C_1$-$C_3$ alkoxy (e.g., methoxy, ethoxy, or propoxy). In further embodiments, at least one $Rd_2$ is methoxy.

In certain embodiments, at least one $Rd_2$ is CN.
In certain embodiments, at least one $Rd_2$ is halogen (e.g., F, Cl, or Br).

In certain embodiments, $Rd_3$ is C(O)$NRd_4$L. In further embodiments, $Rd_4$ is H. In other embodiments, $Rd_4$ is $C_1$-$C_3$ alkyl (e.g., methyl, ethyl, propyl, or i-propyl).

In certain embodiments, $Rd_3$ is OL.
In certain embodiments, $Rd_3$ is $NRd_4$L. In further embodiments, $Rd_4$ is H. In other embodiments, $Rd_4$ is $C_1$-$C_3$ alkyl (e.g., methyl, ethyl, propyl, or i-propyl). In other embodiments, $Rd_4$ is methyl.

In certain embodiments, $Rd_3$ is L.

Each of the moieties defined for one of $Rd_1$, $Rd_2$, $Rd_3$, $Rd_4$, nn6, and nn7, can be combined with any of the moieties defined for the others of $Rd_1$, $Rd_2$, $Rd_3$, $Rd_4$, nn6, and nn7.

In certain embodiments, a Targeting Ligand is a compound of Formula TL-IV1:

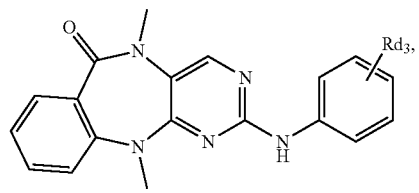

(TL-IV1)

or a pharmaceutically acceptable salt thereof, wherein $Rd_3$ is as defined above in Formula TL-IV. $Rd_3$ may be selected from the moieties described above in Formula TL-IV.

In certain embodiments, the Targeting Ligand is selected from the following in Table T, wherein R is a Linker:

TABLE T

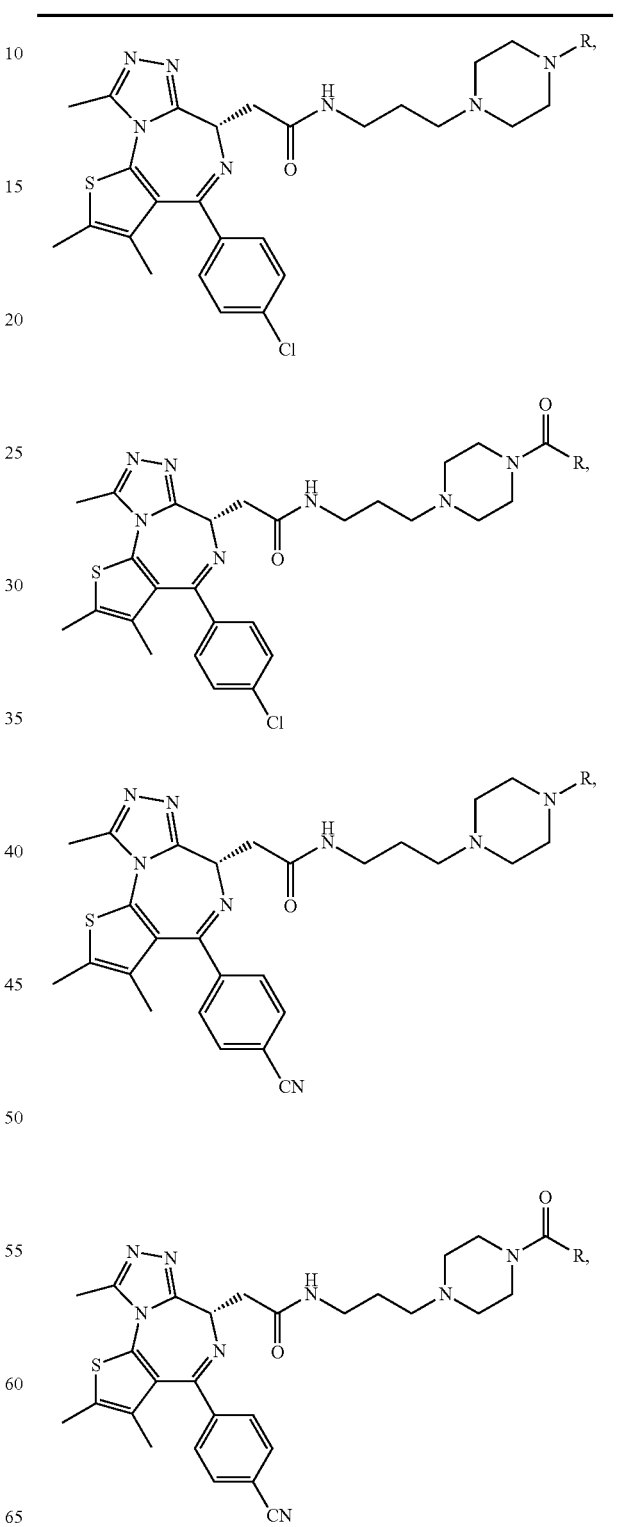

TABLE T-continued
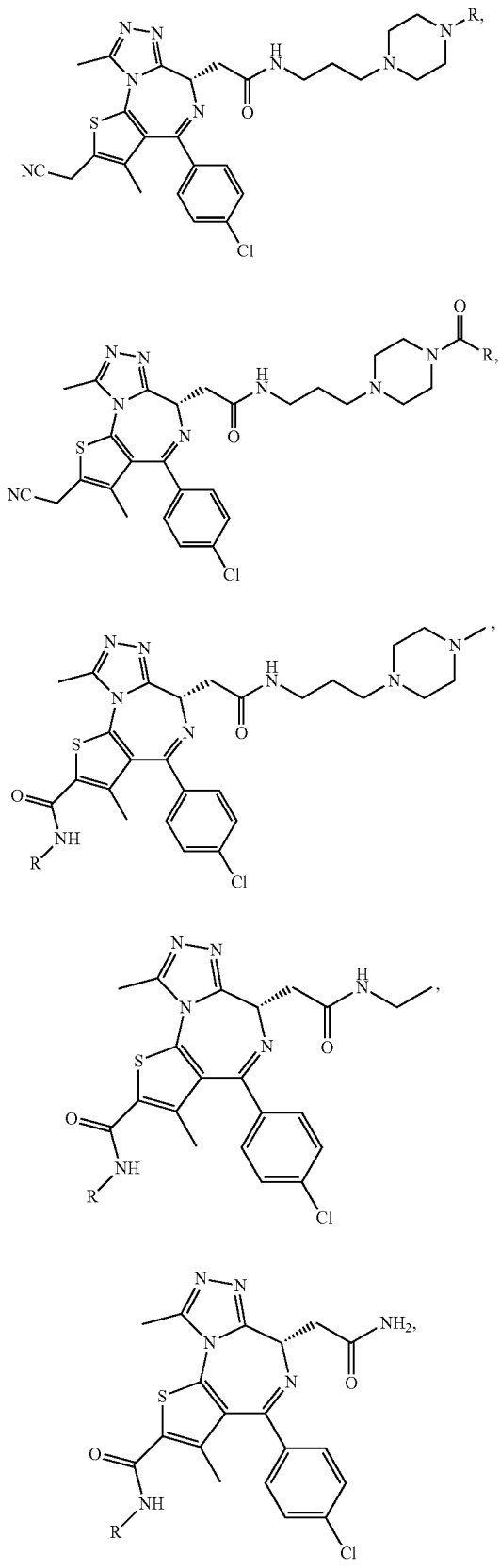
TABLE T-continued
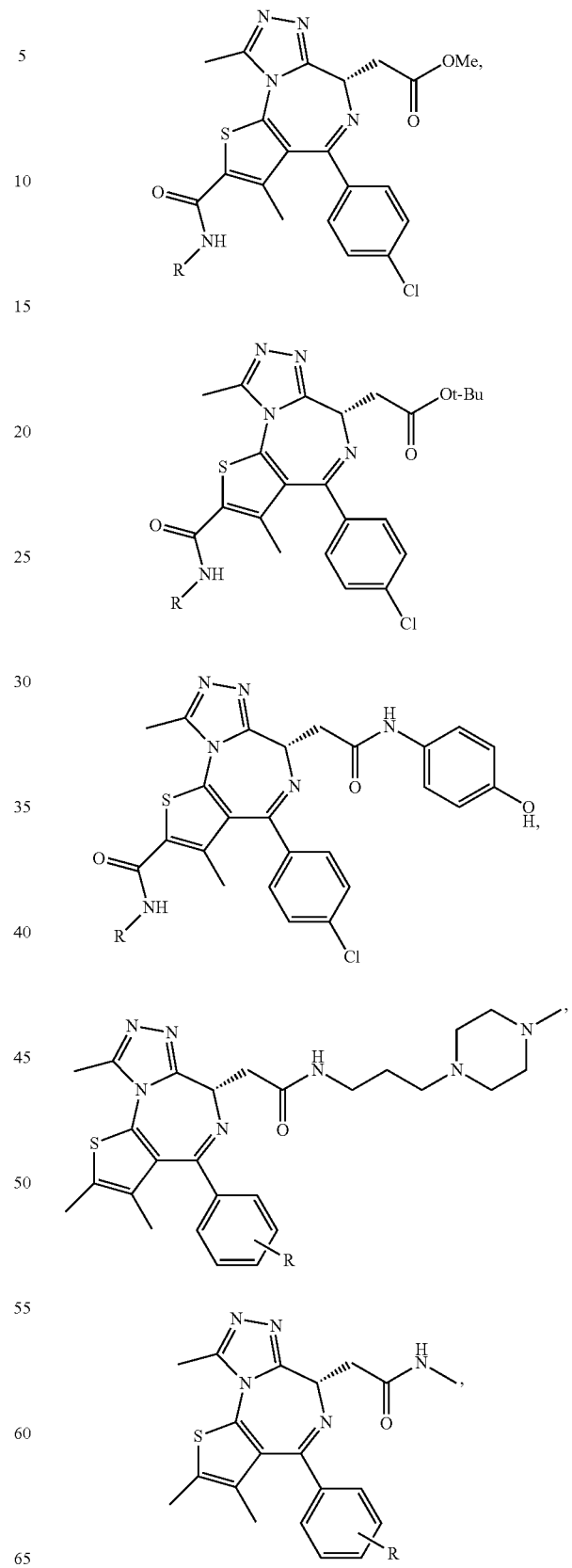

TABLE T-continued
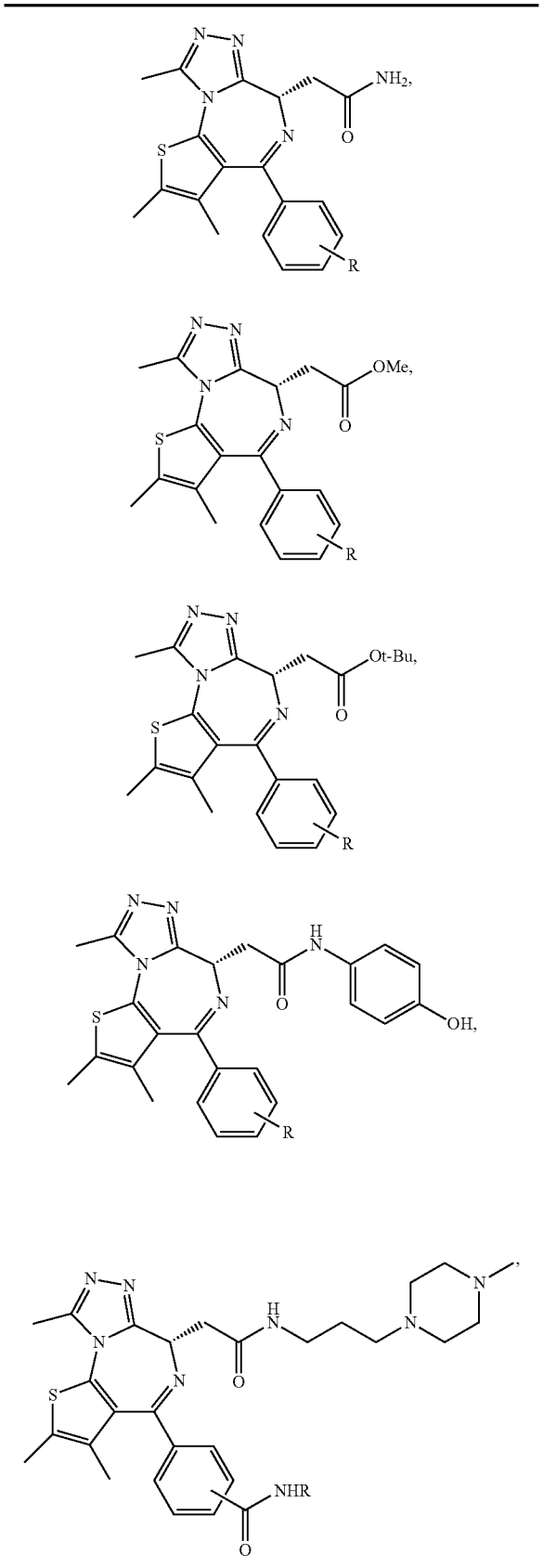
TABLE T-continued
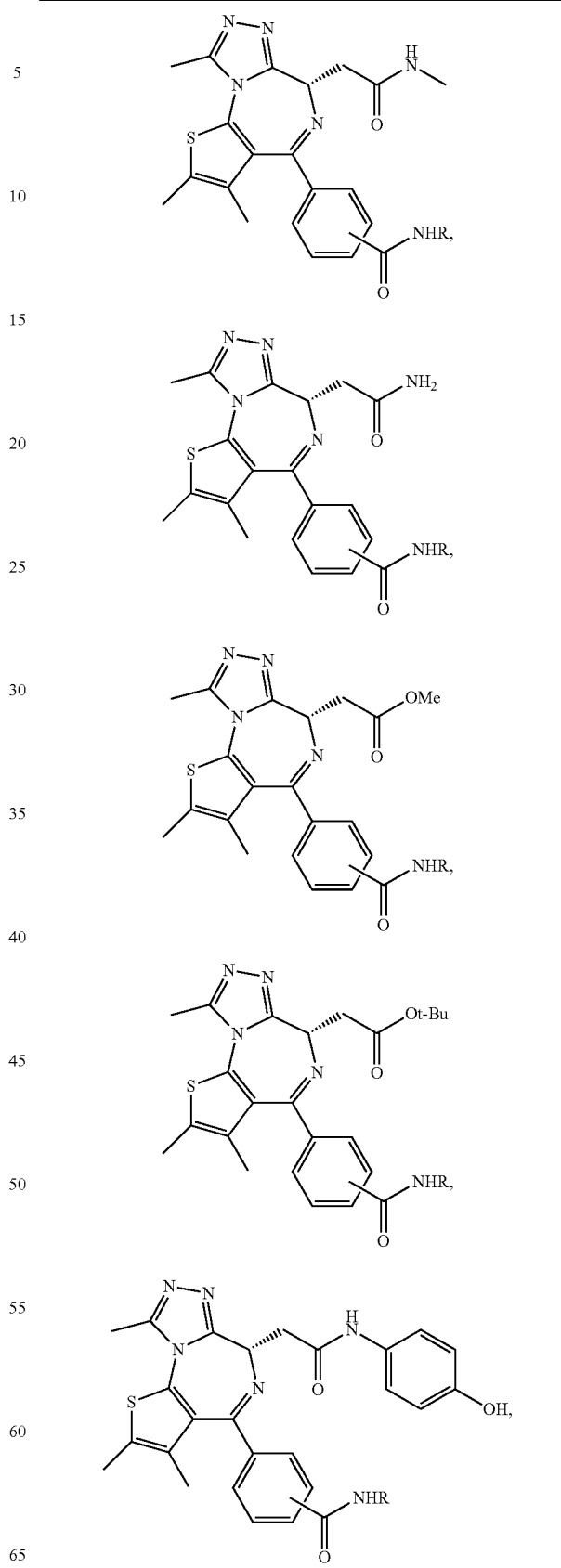

TABLE T-continued
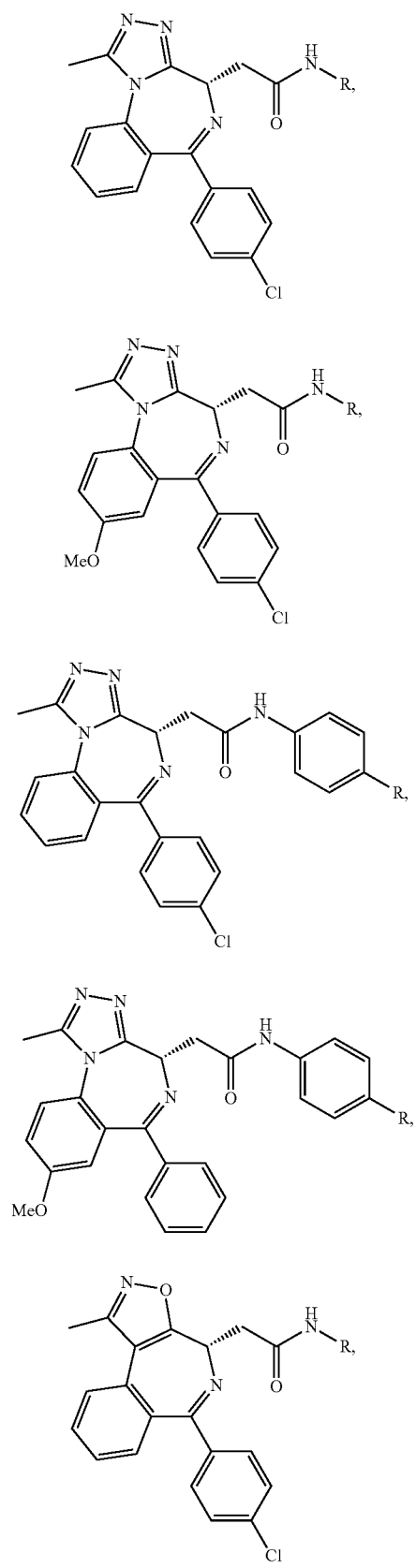
TABLE T-continued
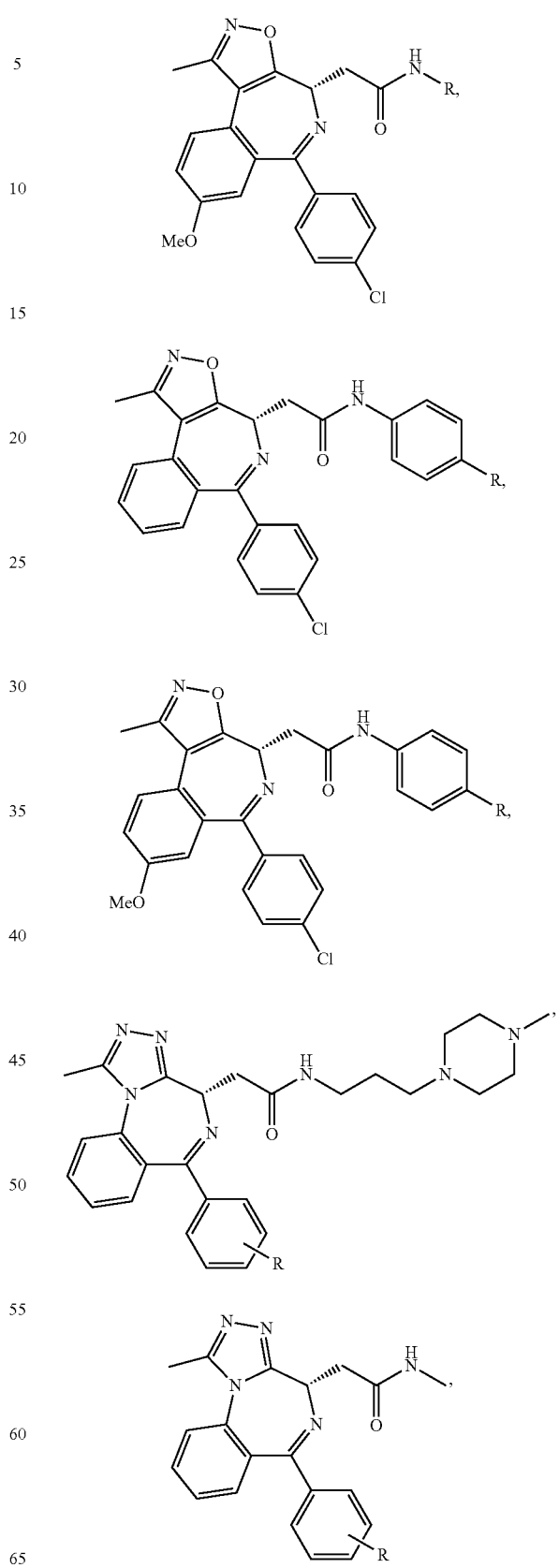

TABLE T-continued
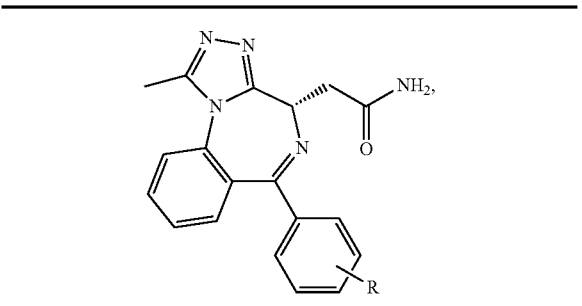
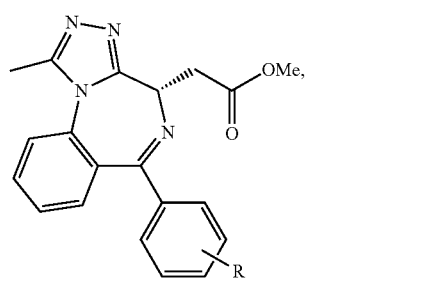
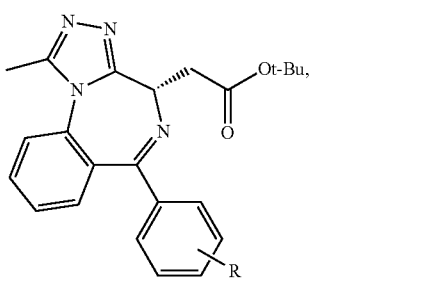
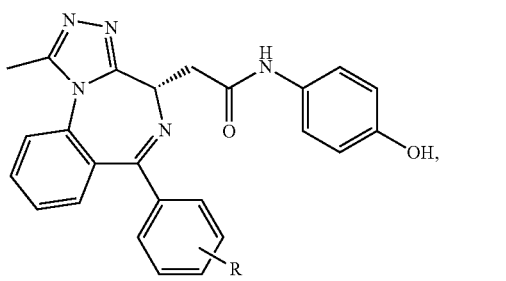
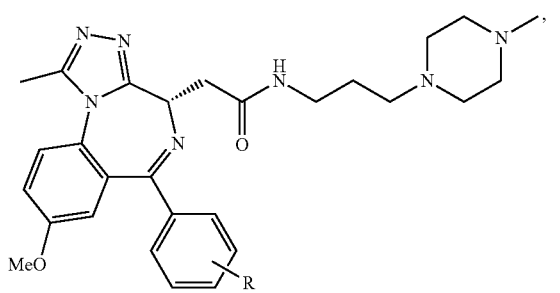
TABLE T-continued
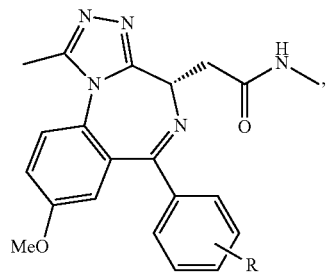
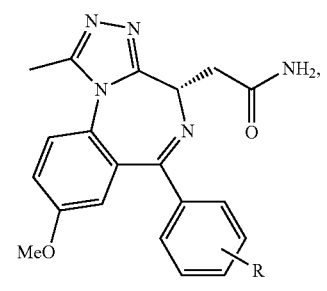
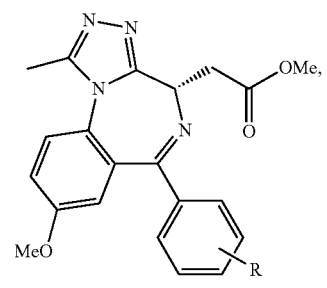
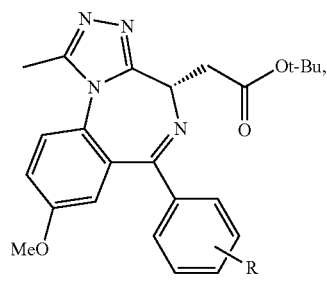
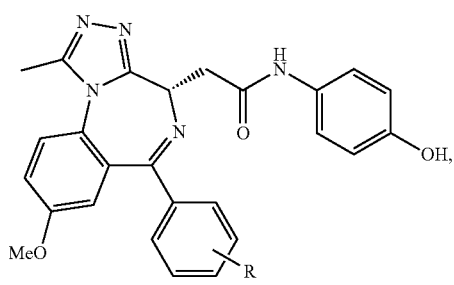

TABLE T-continued
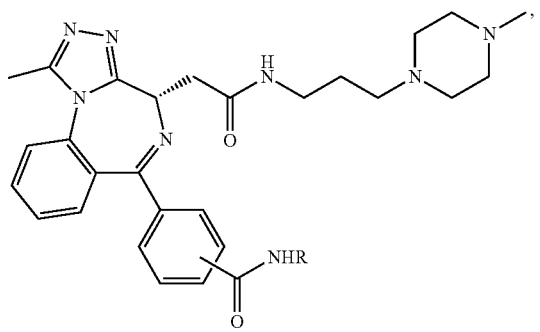
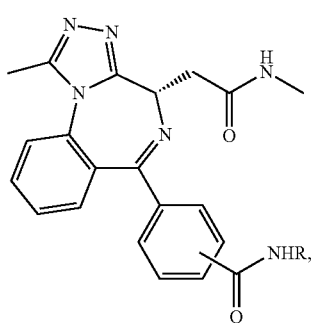
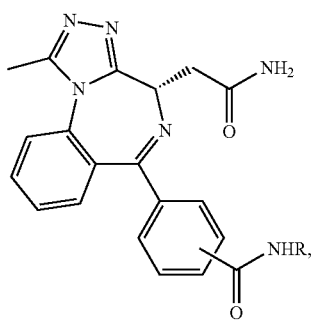
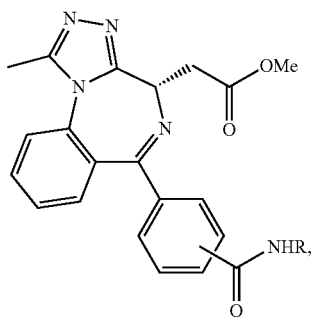
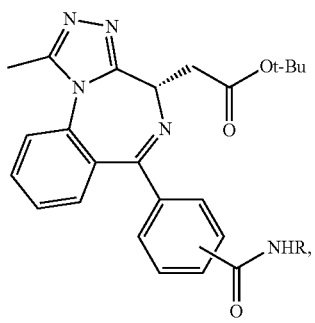
TABLE T-continued
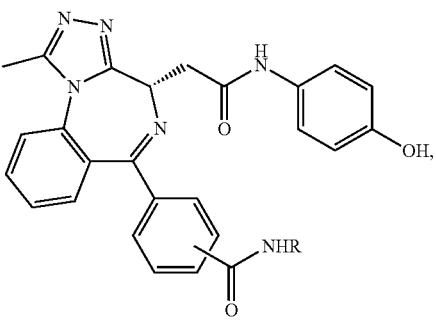
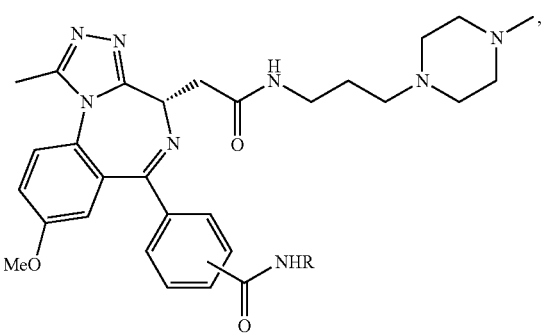
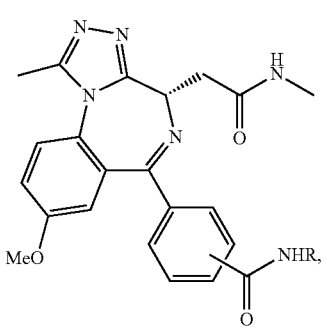
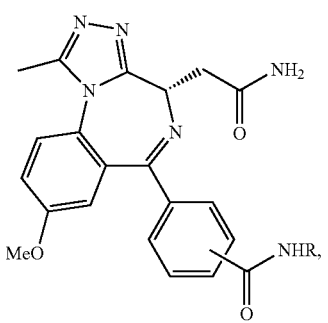
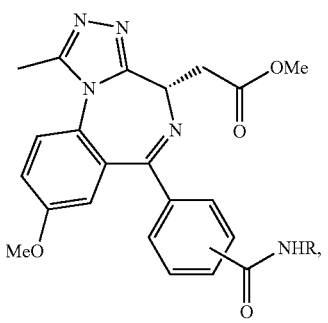

TABLE T-continued
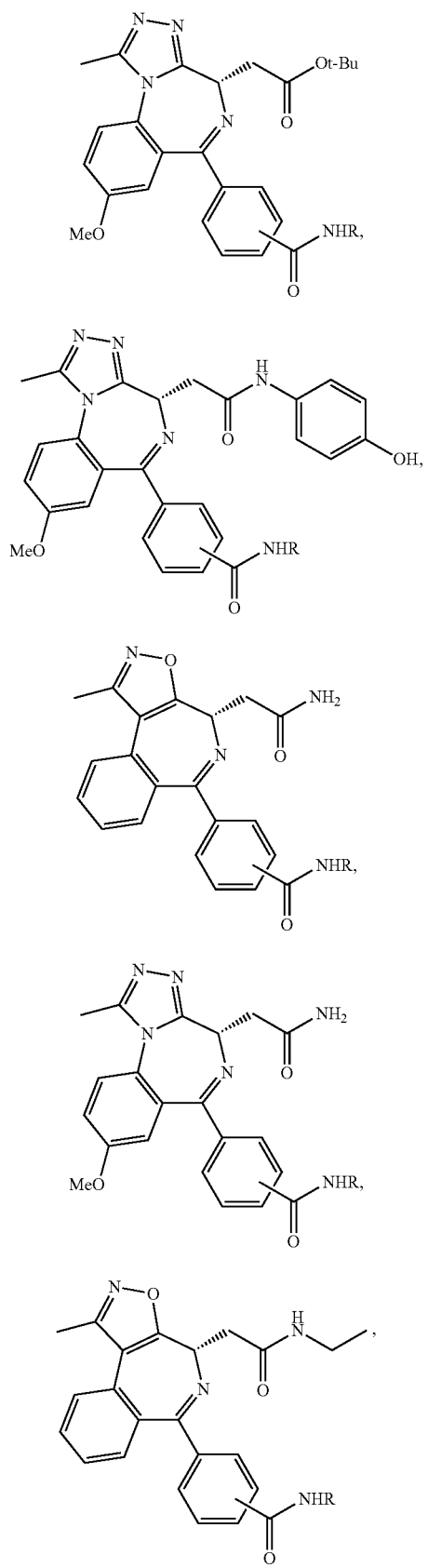
TABLE T-continued
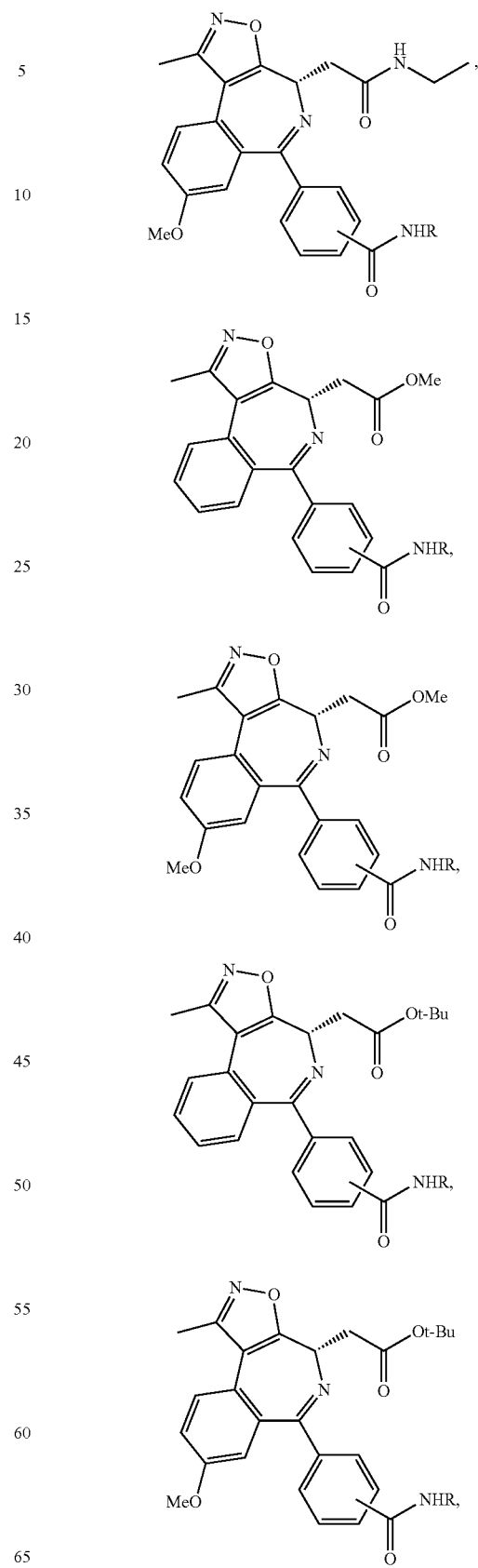

TABLE T-continued
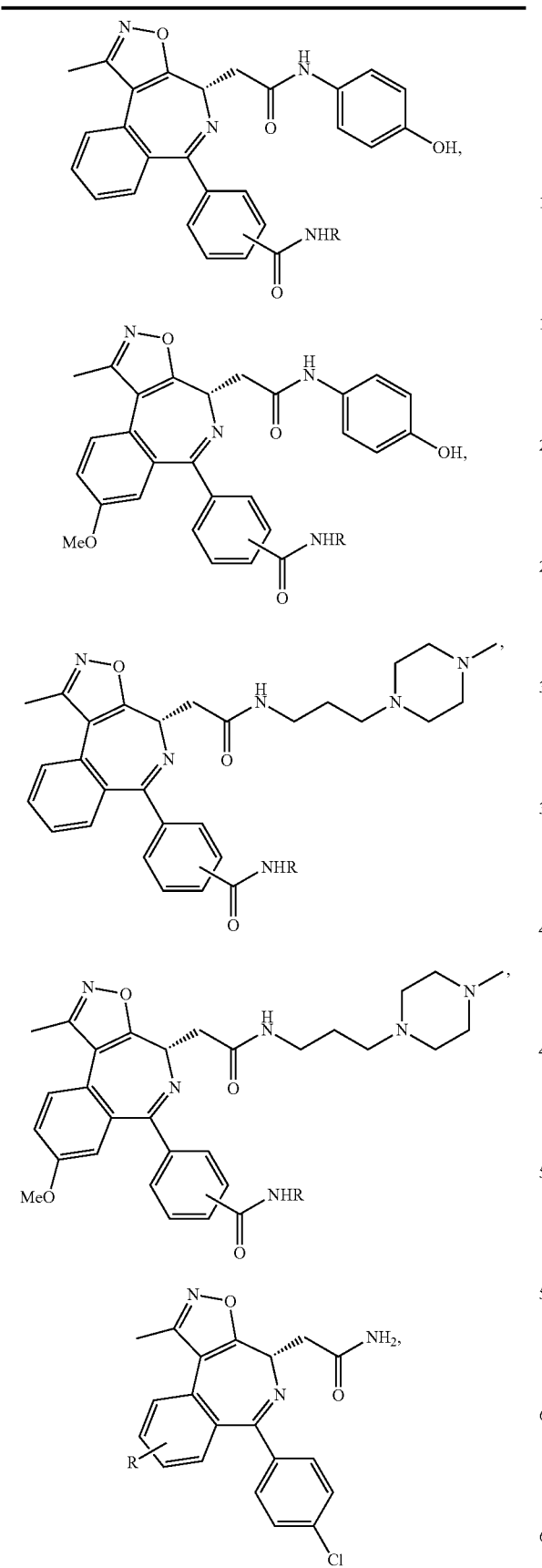
TABLE T-continued
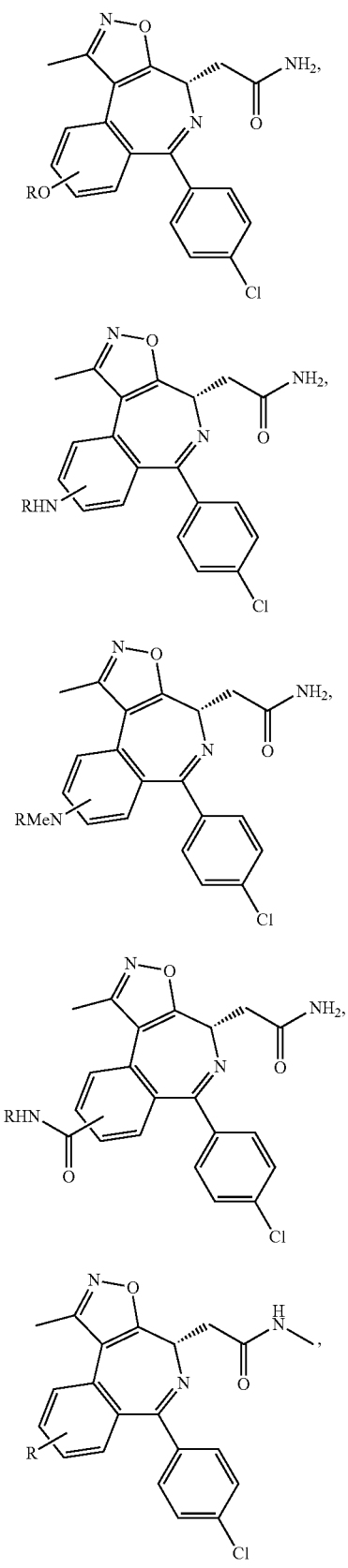

TABLE T-continued

TABLE T-continued
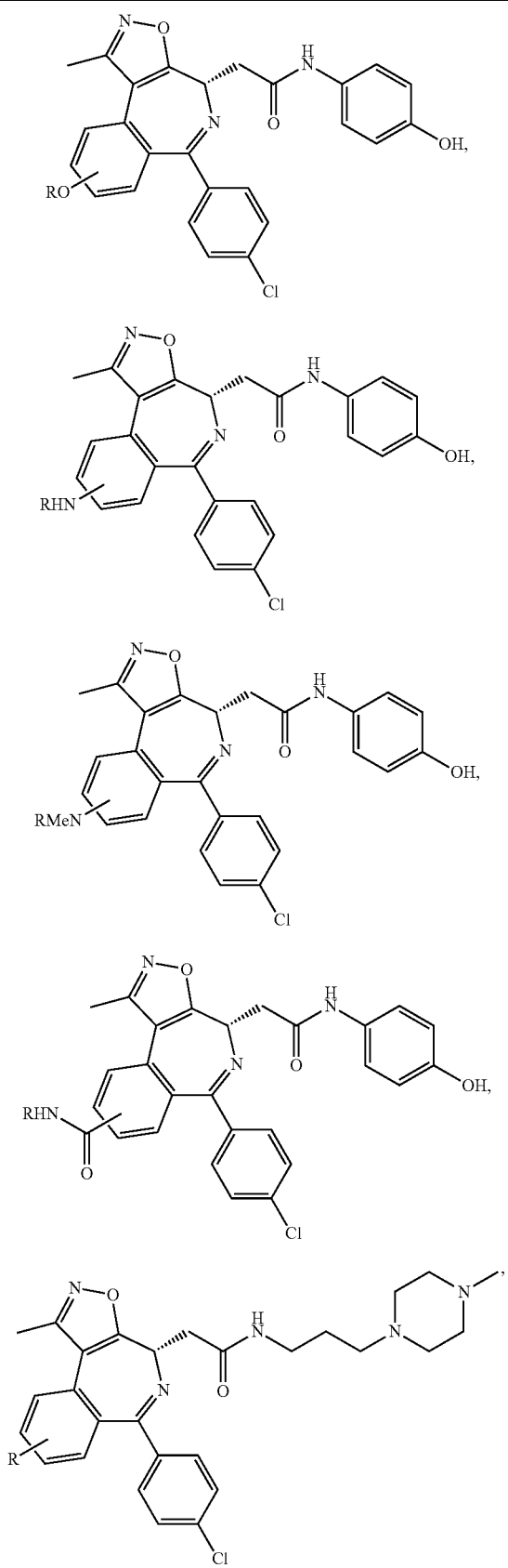
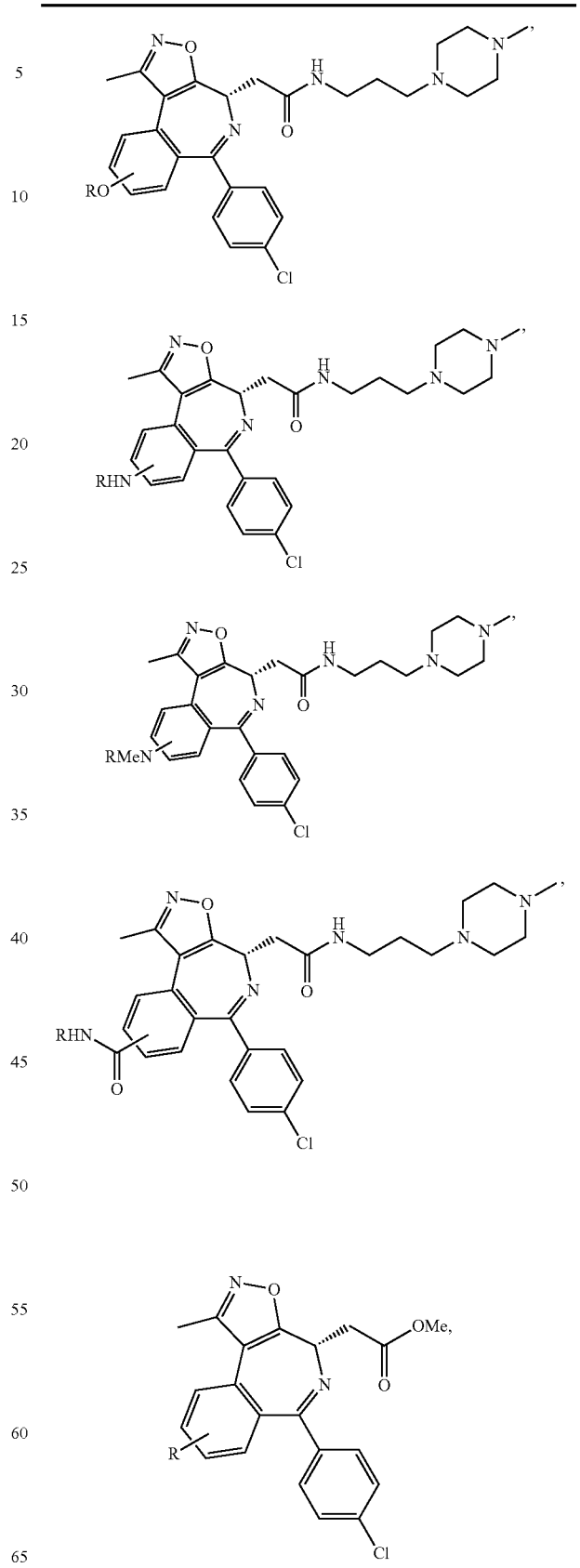

TABLE T-continued

TABLE T-continued
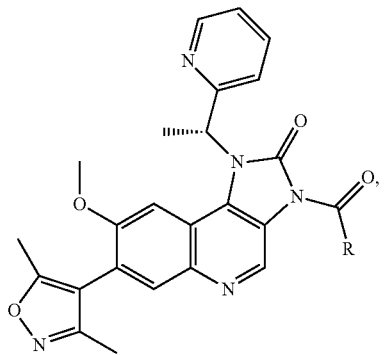
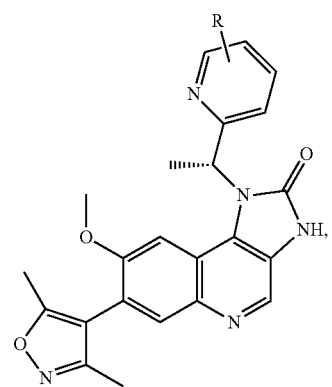
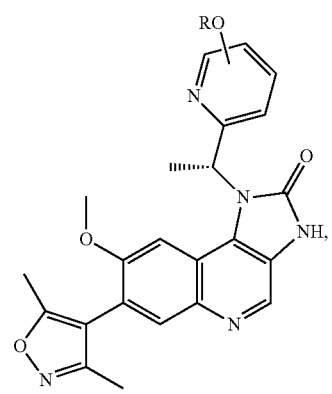
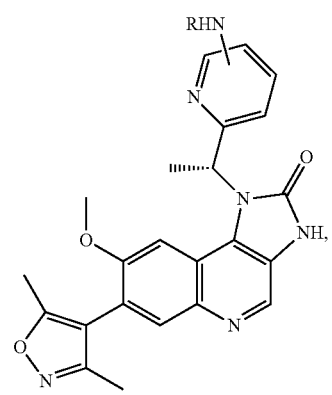
TABLE T-continued
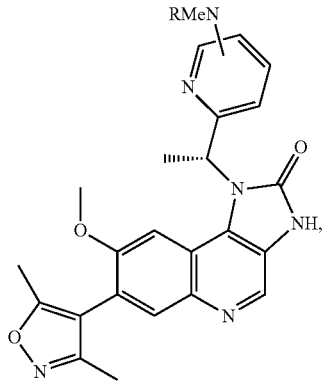
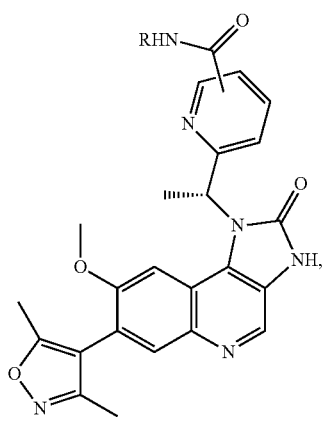
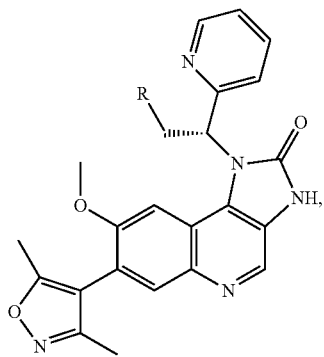
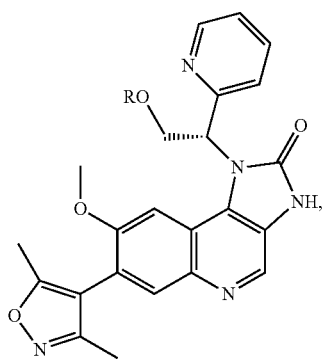

TABLE T-continued

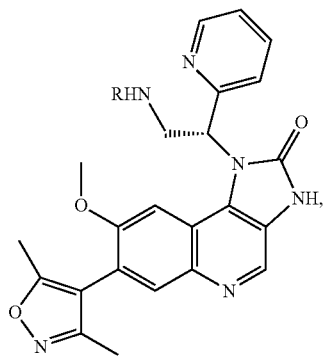

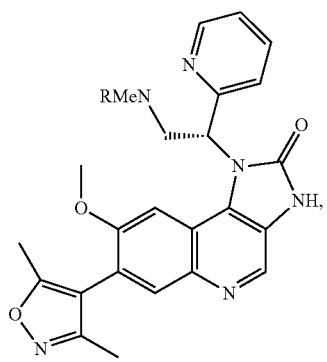

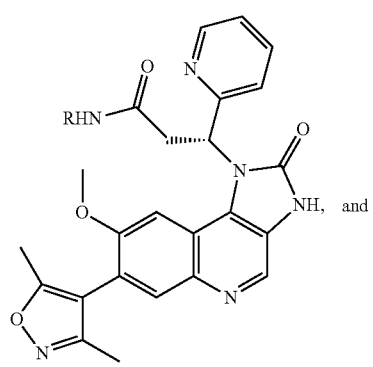

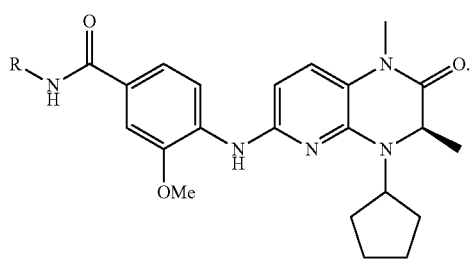

In certain embodiments, the present application relates to the compounds containing the TL moieties shown in Table 1.

TABLE 1

Targeting Ligands 1-4

| Compound | Structure |
|---|---|
| TL1 | 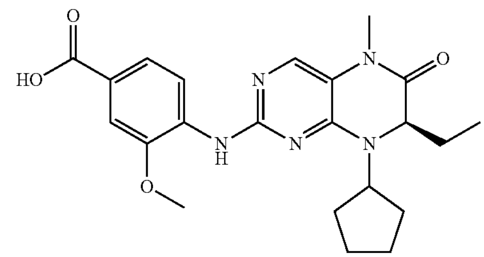 [SMILES: CC[C@@H]1C(=O)N(C)c2cnc(Nc3ccc(C(=O)O)cc3OC)nc2N1C1CCCC1] |
| TL2 | 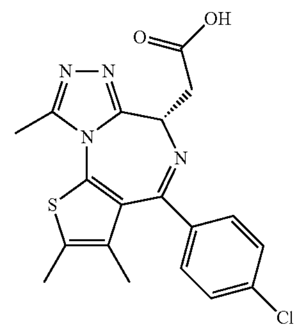 [SMILES: Cc1sc2c(c1C)C(c1ccc(Cl)cc1)=N[C@@H](CC(=O)O)c1nnc(C)n1-2] |
| TL3 | 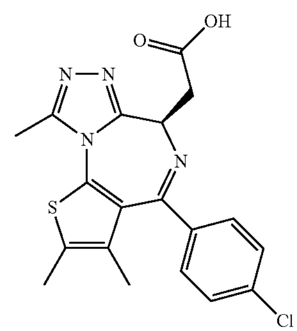 [SMILES: Cc1sc2c(c1C)C(c1ccc(Cl)cc1)=N[C@H](CC(=O)O)c1nnc(C)n1-2] |
| TL4 | 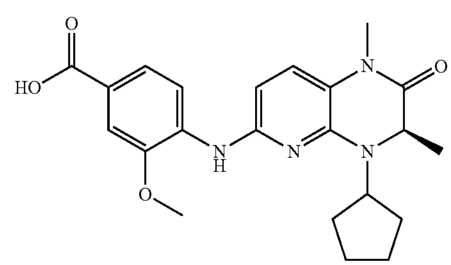 [SMILES: COc1cc(C(=O)O)ccc1Nc1ccc2c(n1)N(C1CCCC1)[C@H](C)C(=O)N2C] |

In certain embodiments, the TLs or targets are chosen based on existence (known target protein binding moieties) and ability to develop potent and selective ligands with functional positions that can accommodate a Linker. Some embodiments relate to targets with less selectivity, which may benefit from degradation coupled with proteomics as a measure of compound selectivity or target ID. Such cases include, but are not limited to a) targets that have multiple functionalities that are unable to be targeted by inhibition; b) targets that are resistant to inhibitors without altering their binding; c) targets that have ligands that do not alter the function of the target; and d) targets that would benefit from irreversible inhibition but lack reactive residues that can be targeted with covalent ligands.

ADDITIONAL EMBODIMENTS OF THE INVENTION

In certain embodiments, the present application relates to small molecule inducers of protein degradation, which have numerous advantages over inhibitors of protein function and can a) overcome resistance in certain cases; b) prolong the kinetics of drug effect by destroying the protein requiring resynthesis even after the small molecule has been metabolized; c) target all functions of a protein at once rather than a specific catalytic activity or binding event; d) expand the number of drug targets by including all proteins that a ligand can be developed for, rather than proteins whose activity can be affected by a small molecule inhibitor, antagonist or agonist; and e) have increased potency compared to inhibitors due to the possibility of the small molecule acting catalytically.

Some embodiments of the present application relate to degradation or loss of 30% to 100% of the target protein. Certain embodiments relate to the loss of 50-100% of the target protein. Other embodiments relate to the loss of 75-95% of the targeted protein.

Some embodiments of present application relate to the bifunctional compound having the following structure:

Some of the foregoing compounds can comprise one or more asymmetric centers, and thus can exist in various isomeric forms, e.g., stereoisomers and/or diastereomers. Accordingly, compounds of the application may be in the form of an individual enantiomer, diastereomer or geometric isomer, or may be in the form of a mixture of stereoisomers. In one embodiment, the compounds of the application are enantiopure compounds. In another embodiment, mixtures of stereoisomers or diastereomers are provided.

Furthermore, certain compounds, as described herein, may have one or more double bonds that can exist as either the Z or E isomer, unless otherwise indicated. The application additionally encompasses the compounds as individual Z/E isomers substantially free of other E/Z isomers and alternatively, as mixtures of various isomers.

In one embodiment, the present application relates to compounds that target proteins, which have numerous advantages over inhibitors of protein function (e.g., target protein or protein kinase activity) and can a) overcome resistance in certain cases; b) prolong the kinetics of drug effect by destroying the protein, thus requiring resynthesis of the protein even after the compound has been metabolized; c) target all functions of a protein at once rather than a specific catalytic activity or binding event; d) expand the

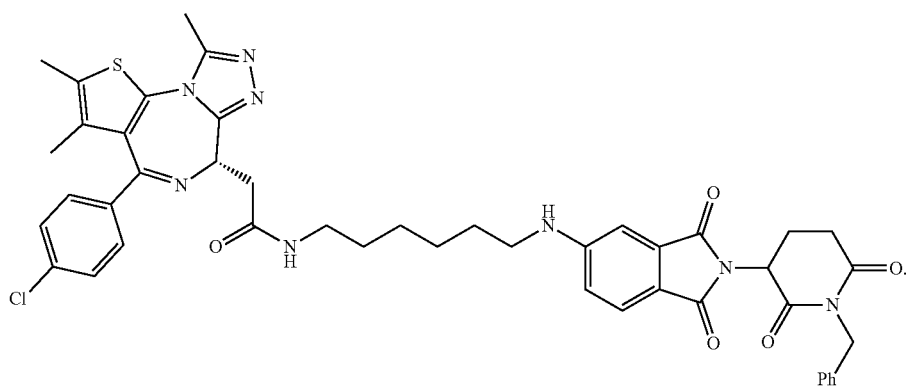 [SMILES: Cc1sc2c(c1C)C(c1ccc(Cl)cc1)=N[C@@H](CC(=O)NCCCCCCNc1ccc3c(c1)C(=O)N(C1CCC(=O)N(Cc4ccccc4)C1=O)C3=O)c1nnc(C)n1-2]

(I-1)

In and additional embodiment Compound I-1 binds endogenous human cereblon at least 5, 10, 20, 40, 100, 200, 300, 400, or 500 fold less than dBET6.

number of drug targets by including all proteins that a ligand can be developed for, rather than proteins whose activity (e.g., target protein or protein kinase activity) can be affected

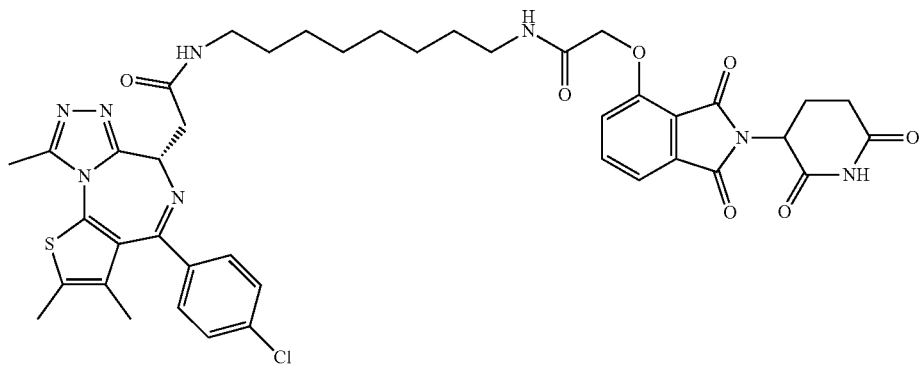

dBET6 by a small molecule inhibitor, antagonist or agonist; and e) have increased potency compared to inhibitors due to the possibility of the small molecule acting catalytically.

A bifunctional compound of the present application (e.g., a bifunctional compound of any of the formulae described herein, or selected from any bifunctional compounds described herein) is capable of modulating (e.g., decreasing) the amount of a targeted protein. A bifunctional compound of the present application (e.g., a bifunctional compound of any of the formulae described herein, or selected from any bifunctional compounds described herein) is also capable of degrading a targeted protein through the UPP pathway. Accordingly, a bifunctional compound of the present application (e.g., a bifunctional compound of any of the formulae described herein, or selected from any bifunctional compounds described herein) is capable of treating or preventing a disease or disorder in which the targeted protein plays a role. A bifunctional compound of the present application (e.g., a bifunctional compound of any of the formulae described herein, or selected from any bifunctional compounds described herein) is also capable of treating or preventing a disease or disorder in which the targeted protein plays a role or in which the targeted protein is deregulated (e.g., overexpressed).

Modulation of the targeted protein through mutant UPP-mediated degradation by a bifunctional compound of the application, such as those described herein, provides a new approach to the treatment, prevention, or amelioration of diseases or disorders in which the targeted protein plays a role, including but not limited to, cancer and metastasis. Further, modulation of the targeted protein through mutant UPP-mediated degradation by a bifunctional compound of the application, such as those described herein, also provides a new paradigm for treating, preventing, or ameliorating diseases or disorders in which the targeted protein is deregulated, for example toxic accumulation and overexpression.

In one embodiment, a bifunctional compound of the present application (e.g., a bifunctional compound of any of the formulae described herein, or selected from any bifunctional compounds described herein) is more efficacious in treating a disease or condition (e.g., cancer) than, or is capable of treating a disease or condition resistant to, the Targeting Ligand, when the Targeting Ligand is administered alone (i.e., not bonded to a Linker and a Degron). In one embodiment, a bifunctional compound of the present application (e.g., a bifunctional compound of any of the formulae described herein, or selected from any bifunctional compounds described herein) is capable of modulating (e.g., decreasing) the amount of the targeted protein, and thus is useful in treating a disease or condition (e.g., cancer) in which the targeted protein plays a role.

In certain embodiments, the bifunctional compound of the present application that is more efficacious in treating a disease or condition than, or is capable of treating a disease or condition resistant to, the Targeting Ligand (which is covalently bound to the Linker and Degron in the bifunctional compound), comprises the Targeting Ligand, a Linker as described herein, and a Degron of Formula D1, D2, D1a, D1b, D2a, D2b, D2c, or D2d. In further embodiments, the bifunctional compound comprises a Targeting Ligand and a Linker, as described herein, and a Degron of Formula D1. In further embodiments, the bifunctional compound comprises a Targeting Ligand and a Linker, as described herein, and a Degron of Formula D2. In further embodiments, the bifunctional compound comprises a Targeting Ligand and a Linker, as described herein, and a Degron of Formula D1a. In further embodiments, the bifunctional compound comprises a Targeting Ligand and a Linker, as described herein, and a Degron of Formula D1b. In further embodiments, the bifunctional compound comprises a Targeting Ligand and a Linker, as described herein, and a Degron of Formula D2a. In further embodiments, the bifunctional compound comprises a Targeting Ligand and a Linker, as described herein, and a Degron of Formula D2b. In further embodiments, the bifunctional compound comprises a Targeting Ligand and a Linker, as described herein, and a Degron of Formula D2c. In further embodiments, the bifunctional compound comprises a Targeting Ligand and a Linker, as described herein, and a Degron of Formula D2d.

In certain embodiments, the bifunctional compound of the present application that is more efficacious in treating a disease or condition than, or is capable of treating a disease or condition resistant to, the Targeting Ligand (which is covalently bound to the Linker and Degron in the bifunctional compound), comprises the Targeting Ligand, a Degron as described herein, and a Linker of Formula L0. In further embodiments, the Linker is selected from Table L.

In further embodiments, the bifunctional compound comprises a Targeting Ligand and a Linker, as described herein, and a Degron of Formula D2. In certain embodiments, the bifunctional compound of the present application that is more efficacious in treating a disease or condition than, or is capable of treating a disease or condition resistant to, the Targeting Ligand (which is covalently bound to the Linker and Degron in the bifunctional compound), comprises a Linker and a Degron, as described herein, and a Targeting Ligand selected from Hsp90 inhibitors, kinase inhibitors, MDM2 inhibitors, compounds targeting Human BET Bromodomain-containing proteins, compounds targeting cytosolic signaling protein FKBP12, HDAC inhibitors, human lysine methyltransferase inhibitors, angiogenesis inhibitors, immunosuppressive compounds, and compounds targeting the aryl hydrocarbon receptor (AHR). In further embodiments, the Targeting Ligand is a compound that is capable of binding to or binds to a kinase, a BET bromodomain-containing protein, a cytosolic signaling protein (e.g., FKBP12), a nuclear protein, a histone deacetylase, a lysine methyltransferase, a protein regulating angiogenesis, a protein regulating immune response, an aryl hydrocarbon receptor (AHR), an estrogen receptor, an androgen receptor, a glucocorticoid receptor, or a transcription factor (e.g., SMARCA4, SMARCA2, TRIM24). In further embodiments, the Targeting Ligand is a compound that is capable of binding to or binds to a BET bromodomain-containing protein or a cytosolic signaling protein. In further embodiments, the Targeting Ligand is of any one of Formulae TL-I, TL-II, TL-III, and TL-IV. In further embodiments, the Targeting Ligand is of any one of Formulae TL-I1, TL-I1a, TL-I1b, TL-I1c, TL-I1d, TL-I2, TL-I2a, TL-I2b, TL-I2c, TL-I3, TL-I3a, TL-I3b, TL-I3c, TL-II1, TL-II1a, TL-III1, TL-III2, TL-III3, and TL-IV1. In further embodiments, the Targeting Ligand is of any one of Formulae TL-I1, TL-I1a, TL-I1b, TL-I1c, TL-I1d, TL-I2, TL-I2a, TL-I2b, TL-I2c, TL-I3, TL-I3a, TL-I3b, and TL-I3c. In further embodiments, the Targeting Ligand is selected from any one of TL1, TL2, TL3, and TL4. In further embodiments, the Targeting Ligand is TL2. In certain embodiments, the Targeting Ligand is selected from Table T.

In certain embodiments, the bifunctional compound of the present application that is more efficacious in treating a disease or condition than, or is capable of treating a disease or condition resistant to, the Targeting Ligand (which is covalently bound to the Linker and Degron in the bifunctional compound), is Compound I-1.

In one embodiment, the bifunctional compound of the present application that is more efficacious in treating a disease or condition than, or is capable of treating a disease or condition resistant to, the Targeting Ligand, when the Targeting Ligand is administered alone (i.e., not bonded to a Linker and a Degron), is more potent in inhibiting the growth of cells (e.g., cancer cells) or decreasing the viability of cells (e.g., cancer cells), than the Targeting Ligand, when the Targeting Ligand is administered alone (i.e., not bonded to a Linker and a Degron). In one embodiment, the bifunctional compound inhibits the growth of cells (e.g., cancer cells) or decreases the viability of cells (e.g., cancer cells) at an $IC_{50}$ that is lower than the $IC_{50}$ of the Targeting Ligand (when the Targeting Ligand is administered alone (i.e., not bonded to a Linker and a Degron) for inhibiting the growth or decreasing the viability of the cells. In one embodiment, the $IC_{50}$ of the bifunctional compound is at most 90%, 80%, 70%, 60%, 50%, 40%, 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 50%, 40%, 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 30%, 20%, 10%, 8%, 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 10%, 8%, 5% 40/%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 5%, 4%, 3%, 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 2%, 1%, 0.8%, 0.5%, 0.4%, 0.3%, 0.2%, or 0.1% of the $IC_{50}$ of the Targeting Ligand. In one embodiment, the $IC_{50}$ of the bifunctional compound is at most 1%, 0.8%, 0.5%, 0.4%, 0.3%, 0.2%, or 0.1% of the $IC_{50}$ of the Targeting Ligand. In one embodiment, the bifunctional compound inhibits the growth of cells (e.g., cancer cells) or decreases the viability of cells (e.g., cancer cells) at an $E_{max}$ that is lower than the $E_{max}$ of the Targeting Ligand (when the Targeting Ligand is administered alone (i.e., not bonded to a Linker and a Degron)) for inhibiting the growth or decreasing the viability of the cells. In one embodiment, the $E_{max}$ of the bifunctional compound is at most 90%, 80%, 70%, 60%, 50%, 40%, 30%, 20%, 10%, 8%, 5%, 4%, 3%, 2%, or 1% of the $E_{max}$ of the Targeting Ligand. In one embodiment, the $E_{max}$ of the bifunctional compound is at most 50%, 40%, 30%, 20%, 10%, 8%, 5%, 4%, 3%, 2%, or 1% of the $E_{max}$ of the Targeting Ligand. In one embodiment, the $E_{max}$ of the bifunctional compound is at most 90%, 80%, 70%, 60%, 50%, 40%, 30%, 20%, or 10% of the $E_{max}$ of the Targeting Ligand.

Potency of the inhibitor can be determined by $EC_{50}$ value. A compound with a lower $EC_{50}$ value, as determined under substantially similar conditions, is a more potent inhibitor relative to a compound with a higher $EC_{50}$ value.

Potency of the inhibitor can also be determined by $IC_{50}$ value. A compound with a lower $IC_{50}$ value, as determined under substantially similar conditions, is a more potent inhibitor relative to a compound with a higher $IC_{50}$ value.

In certain embodiments, the bifunctional compounds of the present application are useful as anticancer agents, and thus may be useful in the treatment of cancer, by effecting tumor cell death or inhibiting the growth of tumor cells. In certain exemplary embodiments, the disclosed anticancer agents are useful in the treatment of cancers and other proliferative disorders, including, but not limited to breast cancer, cervical cancer, colon and rectal cancer, leukemia, lung cancer (e.g., non-small cell lung cancer), melanoma, multiple myeloma, non-Hodgkin's lymphoma, ovarian cancer, pancreatic cancer, prostate cancer, gastric cancer, leukemias (e.g., myeloid, lymphocytic, myelocytic and lymphoblastic leukemias), malignant melanomas, and T-cell lymphoma.

In certain embodiments, the bifunctional compound of the present application that is more efficacious in treating a disease or condition than, or is capable of treating a disease or condition resistant to, the Targeting Ligand (which is covalently bound to the Linker and Degron in the bifunctional compound), wherein the disease or condition is cancer (e.g., cancer described herein). In further embodiments, the cancer is selected from bladder cancer, brain cancer, breast cancer, colon cancer, gastric cancer, kidney cancer, liver cancer, lung cancer, ovarian cancer, pancreatic cancer, prostate cancer, astrocytoma, glioblastoma, leukemia, lymphoma, melanoma, and neuroblastoma. In further embodiments, the cancer is selected from breast cancer, gastric cancer, lung cancer, pancreatic cancer, astrocytoma, lymphoma, melanoma, and neuroblastoma.

In some embodiments, the bifunctional compounds of the present disclosure are capable of binding to a mutant E3 ubiquitin ligase containing one or more mutations. In some embodiments, the bifunctional compounds are capable of binding to mutant cereblon containing one or more mutations. In some embodiments, the mutant cereblon contains one or more mutations selected from N350C, H352C, W379A, and F401A. In other embodiments, the mutant cereblon contains a combination of mutations, wherein the combination is selected from N350C/H352C, N350C/W379A, N350C/F401A, H352C/W379A, H352C/F401A, and W379A/F401A.

In some embodiments, the compounds of the present disclosure are capable of binding to a mutant E3 ubiquitin ligase containing one or more mutations, but do not affect the activity of a wild-type E3 ubiquitin ligase. In some embodiments, the compounds are capable of binding to a mutant cereblon containing one or more mutations, but do not affect the activity of a wild-type cereblon.

Binding of a E3 ubiquitin ligase containing one or more mutations, such as those described herein, but not a wild-type E3 ubiquitin ligase, provides a new approach to the treatment, prevention, or amelioration of diseases including, but not limited to, cancer and metastasis, inflammation, arthritis, systemic lupus erythematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy.

In some embodiments, the bifunctional compounds of the disclosure exhibit greater binding of a mutant E3 ubiquitin ligase containing one or more mutations as described herein relative to a wild-type E3 ubiquitin ligase. In some embodiments, the bifunctional compounds exhibit greater binding of CRBN containing one or more mutations as described herein relative to a wild-type CRBN. In certain embodiments, the compounds of the disclosure exhibit at least 2-fold, 3-fold, 5-fold, 10-fold, 25-fold, 50-fold or 100-fold greater binding of CRBN containing one or more mutations as described herein relative to a wild-type CRBN. In various embodiments, the compounds of the disclosure exhibit up to 1000-fold greater binding of CRBN containing one or more mutations as described herein relative to a wild-type CRBN. In various embodiments, the compounds of the disclosure exhibit up to 10000-fold greater binding of CRBN having a combination of mutations described herein (e.g., N350C/H352C, N350C/W379A, N350C/F401A, H352C/W379A, H352C/F401A, and W379A/F401A) relative to a wild-type CRBN.

In some embodiments, the bifunctional compounds of the disclosure exhibit from about 2-fold to about 10-fold greater binding of CRBN containing one or more mutations as described herein relative to a wild-type CRBN. In various embodiments, the compounds of the disclosure exhibit from about 10-fold to about 100-fold greater binding of CRBN containing one or more mutations as described herein relative to a wild-type CRBN. In various embodiments, the compounds of the disclosure exhibit from about 100-fold to about 1000-fold greater binding of CRBN containing one or more mutations as described herein relative to a wild-type CRBN. In various embodiments, the compounds of the disclosure exhibit from about 1000-fold to about 10000-fold greater binding of CRBN containing one or more mutations as described herein relative to a wild-type CRBN.

Another aspect of the present application relates to a method for treating a disease or condition which is modulated by a targeted protein. The method comprises administering to a subject in need thereof an effective amount of a pharmaceutical composition comprising a bifunctional compound of Formula (II), or an enantiomer, diastereomer, or stereoisomer, or a pharmaceutically acceptable salt thereof, and a pharmaceutically acceptable carrier.

Another aspect of the present application relates to use of a compound of Formula (II), or an enantiomer, diastereomer, or stereoisomer, or a pharmaceutically acceptable salt thereof, for treating a disease or condition which is modulated by a targeted protein.

Another aspect of the present application relates to use of a pharmaceutical composition comprising a compound of Formula (II), or an enantiomer, diastereomer, or stereoisomer, or a pharmaceutically acceptable salt thereof, and a pharmaceutically acceptable carrier, for treating a disease or condition which is modulated by a targeted protein.

The present application also relates to use of a compound of Formula (II), or an enantiomer, diastereomer, or stereoisomer, or a pharmaceutically acceptable salt thereof, in the manufacture of a medicament for treating a disease or condition which is modulated by a targeted protein.

In another aspect, the present application relates to use of a pharmaceutical composition comprising a compound of Formula (II), or an enantiomer, diastereomer, or stereoisomer, or a pharmaceutically acceptable salt thereof, and a pharmaceutically acceptable carrier, in the manufacture of a medicament for treating a disease or condition which is modulated by a targeted protein.

Another aspect of the present application relates to a method for treating cancer (e.g., a cancer modulated by a targeted protein), comprising administering a therapeutically effective amount of a compound of Formula (II), or an enantiomer, diastereomer, or stereoisomer, or a pharmaceutically acceptable salt thereof, to a subject in need thereof.

Another aspect of the present application relates to a method for treating cancer (e.g., a cancer modulated by a targeted protein), comprising administering a therapeutically effective amount of a pharmaceutical composition comprising a compound of Formula (II), or an enantiomer, diastereomer, or stereoisomer, or a pharmaceutically acceptable salt thereof, and a pharmaceutically acceptable carrier, to a subject in need thereof.

The present application also relates to use of a compound of Formula (II), or an enantiomer, diastereomer, or stereoisomer, or a pharmaceutically acceptable salt thereof, for treating cancer (e.g., a cancer modulated by a targeted protein).

Another aspect of the present application relates to use of a pharmaceutical composition comprising a compound of Formula (II), or an enantiomer, diastereomer, or stereoisomer, or a pharmaceutically acceptable salt thereof, and a pharmaceutically acceptable carrier, for treating cancer (e.g., a cancer modulated by a targeted protein).

In another aspect, the present application relates to use of a compound of Formula (II), or an enantiomer, diastereomer, or stereoisomer, or a pharmaceutically acceptable salt thereof, in the manufacture of a medicament for treating cancer (e.g., a cancer modulated by a targeted protein).

Another aspect of the present application relates to use of a pharmaceutical composition comprising a compound of Formula (II), or an enantiomer, diastereomer, or stereoisomer, or a pharmaceutically acceptable salt thereof, and a pharmaceutically acceptable carrier, in the manufacture of a medicament for treating cancer (e.g., a cancer modulated by a targeted protein).

In certain embodiments, the disease or condition (e.g., cancer) is resistant to treatment with the Targeting Ligand.

In certain embodiments, a bifunctional compound of Formula (II) is a bifunctional compound of Formula (I).

Another aspect of the present application relates to a polynucleotide comprising a nucleotide sequence encoding an amino acid sequence that is substantially similar to the amino acid sequence of an E3 ubiquitin ligase. In certain embodiments, the E3 ubiquitin ligase is a cereblon. In certain embodiments, the cereblon is a wild-type cereblon. In certain embodiments, the cereblon is a cereblon that contains one or more mutations.

Another aspect of the present application relates to a polypeptide comprising an amino acid sequence that is substantially similar to the amino acid sequence of an E3 ubiquitin ligase. In certain embodiments, the E3 ubiquitin ligase is a cereblon. In certain embodiments, the cereblon is a wild-type cereblon. In certain embodiments, the cereblon is a cereblon that contains one or more mutations.

Method of Synthesizing the Compounds

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts. P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application. The processes generally provide the desired final compound at or near the end of the overall process, although it may be desirable in certain instances to further convert the compound to a pharmaceutically acceptable salt, ester or prodrug thereof. Suitable synthetic routes are depicted in the schemes below.

Those skilled in the art will recognize if a stereocenter exists in the compounds disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below.

Compounds of the present application can be synthesized by following the steps outlined in General Scheme 1 which comprise different sequences of assembling intermediates 1a, 1b, 1c, 1d, 1e, 1f, 1g, and 1h. Starting materials are either commercially available or made by known procedures in the reported literature or as illustrated.

General Scheme 1:

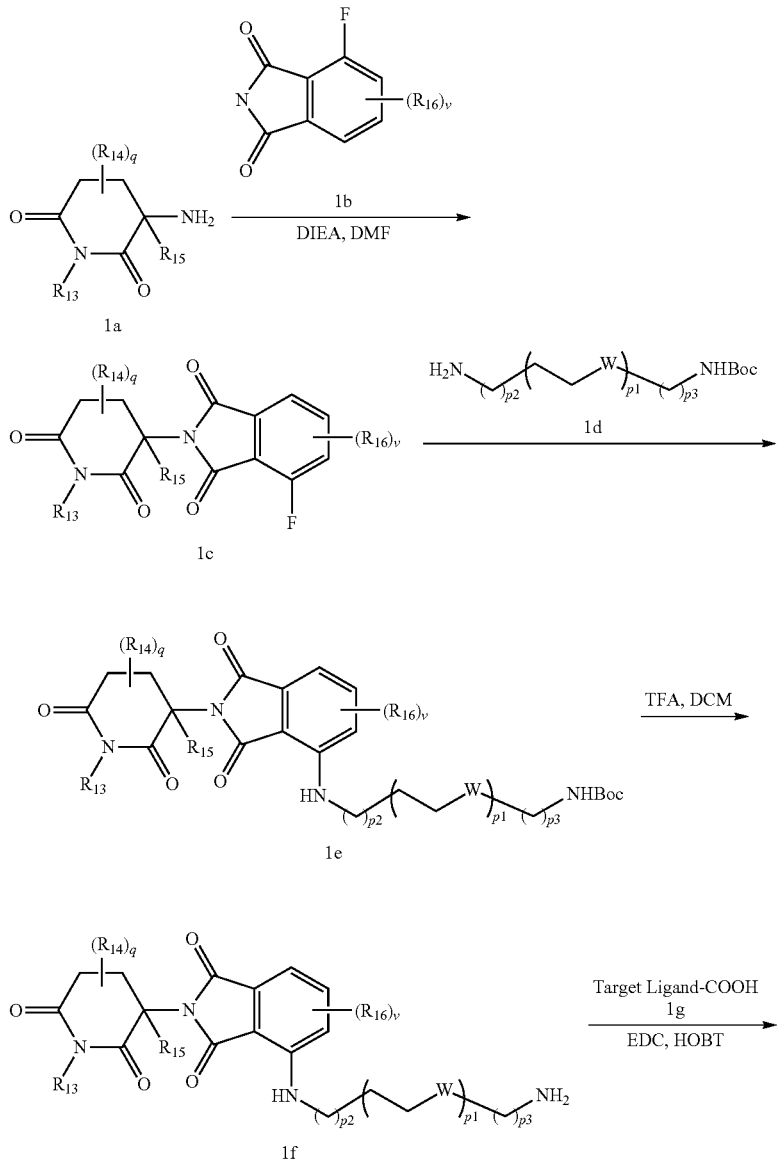

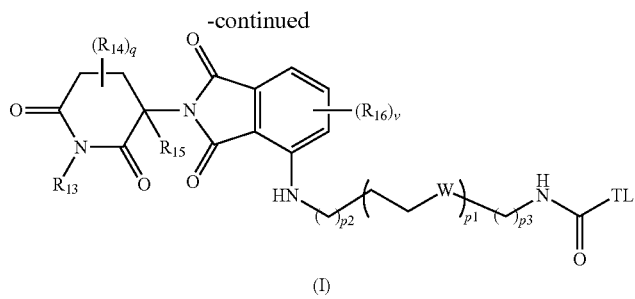

(I)

wherein TL (Target Ligand), $R_{13}$, $R_{14}$, $R_{15}$, $R_{16}$, W, p1, p2, p3, q, and v are as defined herein above.

The general way of preparing representative compounds of the present application (i.e., Compounds of Formula (I) shown above) using intermediates 1a, 1b, 1c, 1d, 1e, 1f, and 1g is outlined in General Scheme 1. Reaction of 1a with 1b in the presence of a base, i.e., diisopropylethylamine (DI-PEA), and in a solvent, i.e., dimethylformamide (DMF), provides intermediate 1c. Reaction of 1d with fluoride Ic provides intermediate 1e. Deprotection of the 1e in the presence of TFA in a solvent, i.e., dichloromethane (DCM) or methanol (MeOH), provides 1f. Coupling of 1f and Target Ligand 1g under standard coupling conditions using a coupling reagent, i.e., 1-ethyl-3-(3-dimethylaminopropyl) carbodiimide (EDC) and hydroxybenzotriazole or bis(dimethylamino)methylene]-1H-1,2,3-triazolo[4,5-b]pyridinium 3-oxide hexafluorophosphate (HATU), in a solvent, i.e., DCM or DMF, provides bifunctional compound of Formula (I).

General Scheme 2:

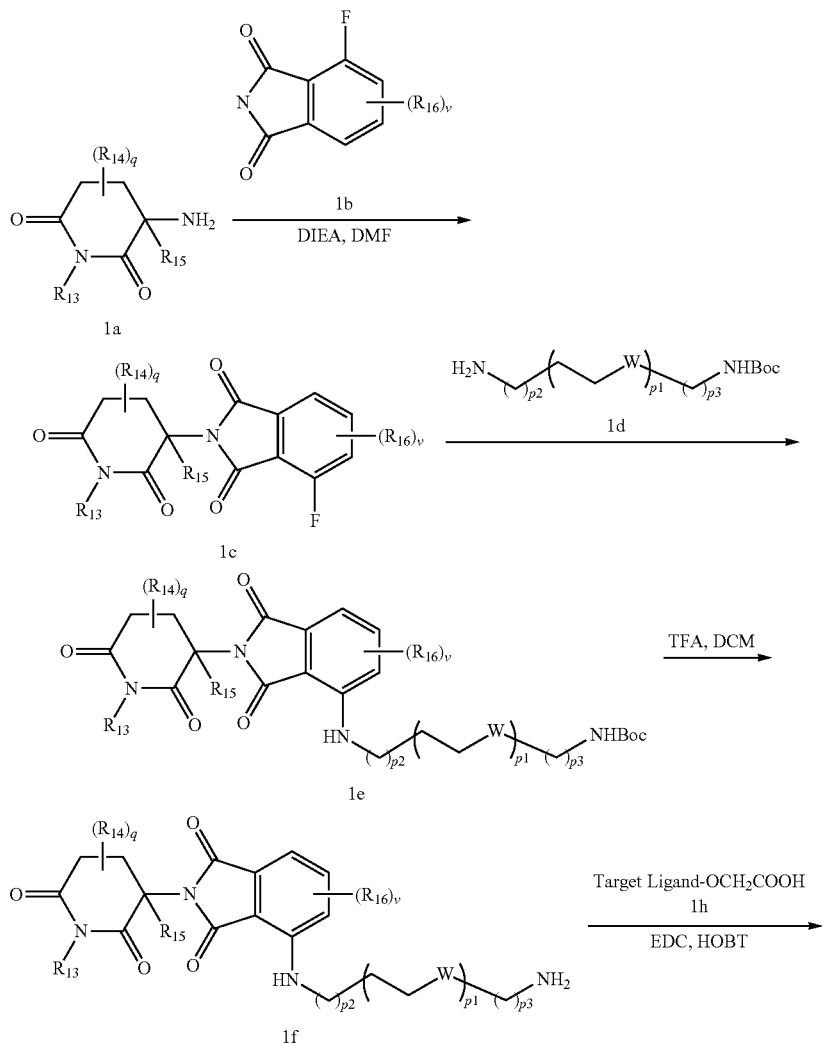

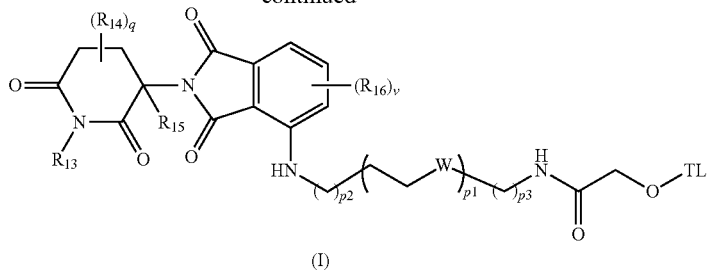

(I)

wherein TL (Target Ligand), $R_{13}$, $R_{14}$, $R_{15}$, $R_{16}$, W, p1, p2, p3, q, and v are as defined herein above.

The general way of preparing representative compounds of the present application (i.e., Compound of Formula (I) shown above) using intermediates 1a, 1b, 1c, 1d, 1e, 1f, and 1h is outlined in General Scheme 2. Reaction of 1a with 1b in the presence of a base, i.e., diisopropylethylamine (DIPEA), and in a solvent, i.e., dimethylformamide (DMF), provides intermediate 1c. Reaction of 1d with fluoride 1c provides intermediate 1e. Deprotection of the 1e in the presence of TFA in a solvent, i.e., dichloromethane (DCM) or methanol (MeOH), provides 1f. Coupling of 1f and Target Ligand 1h under standard coupling conditions using a coupling reagent, i.e., EDC and hydroxybenzotriazole or HATU, in a solvent, i.e., DCM or DMF, provides bifunctional compound of Formula (I).

In certain embodiments, the methods described above are carried out in solution phase. In certain other embodiments, the methods described above are carried out on a solid phase. In certain embodiments, the synthetic method is amenable to high-throughput techniques or to techniques commonly used in combinatorial chemistry.

A mixture of enantiomers, diastereomers, cis/trans isomers resulting from the process described above can be separated into their single components by chiral salt technique, chromatography using normal phase, reverse phase or chiral column, depending on the nature of the separation. It should be understood that in the description and formula shown above, the various groups TL (Target Ligand), $R_{13}$, $R_{14}$, $R_{15}$, $R_{16}$, W, p1, p2, p3, q, and v and other variables are as defined above, except where otherwise indicated. Furthermore, for synthetic purposes, the compounds of General Schemes 1 and 2 are merely representative with elected radicals to illustrate the general synthetic methodology of the compounds of Formula (I) as defined herein.

Biological Assays

Expression of Mutant and Wildtype CRBN in Cells

Cells are treated with PBS or doxycycline. CRBN signal is normalized to Vinculin signal, and the fold induction for each condition over the PBS-treated condition is measured. CRBN levels are detected by immunoblotting at various time points.

Measurement of Degradation of BRD4 by Bifunctional Compounds

Mutant and wild-type cells are treated with doxycycline, followed by treatment with DMSO or bifunctional compound disclosed herein at various concentrations. BRD4 levels are measured and detected by immunoblotting.

Methods of Treatment

In general, methods of using the bifunctional compounds of the present application comprise administering to a subject in need thereof a therapeutically effective amount of a bifunctional compound of the present application. The bifunctional compounds of the application are generally inducers of target protein degradation.

Another aspect of the application relates to a method of treating, preventing, or alleviating a disease or condition, comprising administering to a subject in need thereof a therapeutically effective amount of a bifunctional compound disclosed herein. In some embodiments, the bifunctional compound is capable of binding to a mutant E3 ubiquitin ligase. In further embodiments, the bifunctional compound is capable of binding to a mutant cereblon.

In certain embodiments, the present application related to a method of treating, preventing, or alleviating a disease or condition, comprising administering to a subject in need thereof a therapeutically effective amount of a bifunctional compound of Formula (II), or a pharmaceutically acceptable salt, hydrate, solvate, prodrug, stereoisomer, or tautomer thereof. In some embodiments, the bifunctional compound is capable of binding to a mutant E3 ubiquitin ligase. In further embodiments, the bifunctional compound is capable of binding to a mutant cereblon.

In certain embodiments, the present application related to a method of treating, preventing, or alleviating a disease or condition, comprising administering to a subject in need thereof a therapeutically effective amount of a pharmaceutical composition comprising a bifunctional compound of Formula (II), or a pharmaceutically acceptable salt, hydrate, solvate, prodrug, stereoisomer, or tautomer thereof and a pharmaceutically acceptable excipient. In some embodiments, the bifunctional compound is capable of binding to a mutant E3 ubiquitin ligase. In further embodiments, the bifunctional compound is capable of binding to a mutant cereblon.

Another aspect of the present application relates to the use of a bifunctional compound of Formula (II), or a pharmaceutically acceptable salt, hydrate, solvate, prodrug, stereoisomer, or tautomer thereof, in the manufacture of a medicament for treating, preventing, or alleviating a disease or condition. In some embodiments, the bifunctional compound is capable of binding to a mutant E3 ubiquitin ligase. In further embodiments, the bifunctional compound is capable of binding to a mutant cereblon.

In another aspect, the present application relates to the use of a pharmaceutical composition comprising a bifunctional compound of Formula (II), or a pharmaceutically acceptable salt, hydrate, solvate, prodrug, stereoisomer, or tautomer thereof, and a pharmaceutically acceptable excipient in the manufacture of a medicament for treating, preventing, or alleviating a disease or condition. In some embodiments, the bifunctional compound is capable of binding to a mutant E3 ubiquitin ligase. In further embodiments, the bifunctional compound is capable of binding to a mutant cereblon.

Another aspect of the present application relates to a bifunctional compound of Formula (II), or a pharmaceutically acceptable salt, hydrate, solvate, prodrug, stereoisomer, or tautomer thereof, for use in treating, preventing, or alleviating a disease or condition. In some embodiments, the bifunctional compound is capable of binding to a mutant E3 ubiquitin ligase. In further embodiments, the bifunctional compound is capable of binding to a mutant cereblon.

In another aspect, the present application relates to a pharmaceutical composition comprising a bifunctional compound of Formula (II), or a pharmaceutically acceptable salt, hydrate, solvate, prodrug, stereoisomer, or tautomer thereof, and a pharmaceutically acceptable excipient for use in treating a disease or condition. In some embodiments, the bifunctional compound is capable of binding to a mutant E3 ubiquitin ligase. In further embodiments, the bifunctional compound is capable of binding to a mutant cereblon.

In certain embodiments, the present application relates to a method of treating, preventing, or alleviating a disease or condition, comprising administering to a patient in need thereof a bifunctional compound of Formula (II) or a pharmaceutically acceptable salt, hydrate, solvate, prodrug, stereoisomer, or tautomer thereof, and an immune effector cell, for example a T cell, that expresses a mutant E3 ubiquitin ligase and further expresses a chimeric antigen receptor (CAR) or engineered T-cell receptor (TCR).

In certain embodiments, the present application related to a method of treating, preventing, or alleviating a disease or condition, comprising administering to a subject in need thereof a therapeutically effective amount of a bifunctional compound of Formula (III), or a pharmaceutically acceptable salt, hydrate, solvate, prodrug, stereoisomer, or tautomer thereof. In some embodiments, the bifunctional compound is capable of binding to a mutant E3 ubiquitin ligase. In further embodiments, the bifunctional compound is capable of binding to a mutant cereblon.

In certain embodiments, the present application related to a method of treating, preventing, or alleviating a disease or condition, comprising administering to a subject in need thereof a therapeutically effective amount of a pharmaceutical composition comprising a bifunctional compound of Formula (III), or a pharmaceutically acceptable salt, hydrate, solvate, prodrug, stereoisomer, or tautomer thereof and a pharmaceutically acceptable excipient. In some embodiments, the bifunctional compound is capable of binding to a mutant E3 ubiquitin ligase. In further embodiments, the bifunctional compound is capable of binding to a mutant cereblon.

Another aspect of the present application relates to the use of a bifunctional compound of Formula (III), or a pharmaceutically acceptable salt, hydrate, solvate, prodrug, stereoisomer, or tautomer thereof, in the manufacture of a medicament for treating, preventing, or alleviating a disease or condition. In some embodiments, the bifunctional compound is capable of binding to a mutant E3 ubiquitin ligase. In further embodiments, the bifunctional compound is capable of binding to a mutant cereblon.

In another aspect, the present application relates to the use of a pharmaceutical composition comprising a bifunctional compound of Formula (III), or a pharmaceutically acceptable salt, hydrate, solvate, prodrug, stereoisomer, or tautomer thereof, and a pharmaceutically acceptable excipient in the manufacture of a medicament for treating, preventing, or alleviating a disease or condition. In some embodiments, the bifunctional compound is capable of binding to a mutant E3 ubiquitin ligase. In further embodiments, the bifunctional compound is capable of binding to a mutant cereblon.

Another aspect of the present application relates to a bifunctional compound of Formula (III), or a pharmaceutically acceptable salt, hydrate, solvate, prodrug, stereoisomer, or tautomer thereof, for use in treating, preventing, or alleviating a disease or condition. In some embodiments, the bifunctional compound is capable of binding to a mutant E3 ubiquitin ligase. In further embodiments, the bifunctional compound is capable of binding to a mutant cereblon.

In another aspect, the present application relates to a pharmaceutical composition comprising a bifunctional compound of Formula (III), or a pharmaceutically acceptable salt, hydrate, solvate, prodrug, stereoisomer, or tautomer thereof, and a pharmaceutically acceptable excipient for use in treating a disease or condition. In some embodiments, the bifunctional compound is capable of binding to a mutant E3 ubiquitin ligase. In further embodiments, the bifunctional compound is capable of binding to a mutant cereblon.

In certain embodiments, the present application relates to a method of treating, preventing, or alleviating a disease or condition, comprising administering to a patient in need thereof a bifunctional compound of Formula (III) or a pharmaceutically acceptable salt, hydrate, solvate, prodrug, stereoisomer, or tautomer thereof, and an immune effector cell, for example a T cell, that expresses a mutant E3 ubiquitin ligase and further expresses a chimeric antigen receptor (CAR) or engineered T-cell receptor (TCR).

In certain embodiments, the disease or disorder is cancer or a proliferation disease.

In further embodiments, the disease or disorder is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In another embodiment, the disease or disorder is NUT midline carcinoma.

In certain embodiments, bifunctional compounds of the application are useful in the treatment of proliferative diseases (e.g., cancer, benign neoplasms, inflammatory disease, and autoimmune diseases). In certain embodiments, according to the methods of treatment of the present application, levels of cell proteins of interest, e.g., pathogenic and oncogenic proteins are modulated, or their growth is inhibited by contacting said cells with a bifunctional compound, or a pharmaceutically acceptable salt, hydrate, solvate, prodrug, stereoisomer, or tautomer thereof, as described herein, to a subject in need thereof. In certain embodiments, a method for the treatment of cancer is provided comprising administering a therapeutically effective amount of a bifunctional compound, or a pharmaceutically acceptable salt, hydrate, solvate, prodrug, stereoisomer, or tautomer thereof, or a pharmaceutical composition comprising a bifunctional compound, or a pharmaceutically acceptable salt, hydrate, solvate, prodrug, stereoisomer, or tautomer thereof, to a subject in need thereof, in such amounts and for such time as is necessary to achieve the desired result. Preferably, the compounds of present application are administered orally or intravenously. In certain embodiments of the present application a "therapeutically effective amount" of the bifunctional compound or pharmaceutical composition comprising the bifunctional compound is that amount effective for killing or inhibiting the growth of tumor cells. The compounds and compositions, according to the method of the present application, may be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like. In certain embodiments of the present application a "therapeutically effective amount" of the bifunctional compound or pharmaceutical composition comprising a bifunctional compound is that amount effective for reducing the levels of target proteins. In certain embodiments of the present application a "therapeutically effective amount" of the compound or pharmaceutical composition is that amount effective to kill or inhibit the growth of skin cells.

In certain embodiments, the method involves the administration of a therapeutically effective amount of the bifunctional compound, or a pharmaceutically acceptable derivative thereof to a subject (including, but not limited to a human or animal) in need of it. In certain embodiments, the bifunctional compounds as useful for the treatment of cancer (including, but not limited to, glioblastoma, retinoblastoma, breast cancer, cervical cancer, colon and rectal cancer, leukemia, lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer.

In certain embodiments, the bifunctional compound described herein are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer. In certain embodiments, the bifunctional compound anticancer agents are active against solid tumors.

The bifunctional compounds and compositions of this application are particularly useful for treating or lessening the severity of a disease, condition, or disorder where a target protein is implicated in the disease, condition, or disorder. In one aspect, the present application provides a method for treating or lessening the severity of a disease, condition, or disorder where a target protein is implicated in the disease state. In another aspect, the present application provides a method for treating or lessening the severity of a disease, condition, or disorder mediated by a target protein where inhibition of enzymatic activity is implicated in the treatment of the disease. In another aspect, this application provides a method for treating or lessening the severity of a disease, condition, or disorder with bifunctional compounds that inhibit enzymatic activity by binding to the target protein. Another aspect provides a method for treating or lessening the severity of a disease, condition, or disorder mediated by target protein by inhibiting enzymatic activity of the target protein with a target protein inhibitor.

One aspect of this application provides bifunctional compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast; ovary; cervix; prostate; colorectal; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject bifunctional compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the bifunctional compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more bifunctional compounds of the application in the manufacture of a medicament for the treatment of cancer, including without limitation the various types of cancer disclosed herein.

In some embodiments, the bifunctional compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the bifunctional compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject bifunctional compounds may be administered for the purpose of preventing said hyperplasias, dysplasias or pre-cancerous lesions from continuing to expand or from becoming cancerous. Examples of precancerous lesions may occur in skin, esophageal tissue, breast and cervical intra-epithelial tissue.

Another aspect of this application provides a method for the treatment or lessening the severity of a disease selected from a proliferative or hyperproliferative disease, comprising administering a therapeutically effective amount of a bifunctional compound, or a pharmaceutically acceptable composition comprising a bifunctional compound, to a subject in need thereof.

The compounds and compositions of this application are also useful in biological samples. One aspect of the application relates to inhibiting the target protein activity in a biological sample, which method comprises contacting said biological sample with a bifunctional compound of the application or a composition comprising said bifunctional compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of target protein activity in a biological sample is useful for a variety of purposes that are known to one of skill in the art. Examples of such purposes include, but are not limited to, blood transfusion, organtransplantation, and biological specimen storage.

Another aspect of this application relates to the study of proteins in biological and pathological phenomena; the study of intracellular signal transduction pathways mediated by such target protein or protein kinases; and the comparative evaluation of new target protein or protein kinase inhibitors. Examples of such uses include, but are not limited to, biological assays such as enzyme assays and cell-based assays.

The activity of the compounds and compositions of the present application may be assayed in vitro, in vivo, or in a cell line. In vitro assays include assays that determine inhibition of either the target protein activity or ATPase activity of the activated target protein. Alternate in vitro assays quantitate the ability of the inhibitor to bind to the target protein and may be measured either by radio labelling the inhibitor prior to binding, isolating the inhibitor/protein kinase or inhibitor/target protein complex and determining the amount of radio label bound, or by running a competition experiment where new inhibitors are incubated with the target protein or protein kinase bound to known radioligands. Detailed conditions for assaying a compound utilized in this application as an inhibitor of various target proteins or protein kinases are set forth in the Examples below.

In accordance with the foregoing, the present application further provides a method for preventing or treating any of the diseases or disorders described above in a subject in need of such treatment, which method comprises administering to said subject a therapeutically effective amount of a bifunctional compound of the application, or a pharmaceutically acceptable salt, hydrate, solvate, prodrug, stereoisomer, or tautomer thereof. For any of the above uses, the required dosage will vary depending on the mode of administration, the particular condition to be treated and the effect desired.

Pharmaceutical Compositions

In another aspect, the application provides a pharmaceutical composition comprising a therapeutically effective amount of a bifunctional compound of the present application or a pharmaceutically acceptable salt, hydrate, solvate, prodrug, stereoisomer, or tautomer thereof, and a pharmaceutically acceptable carrier. In certain embodiments, these compositions optionally further comprise one or more additional therapeutic agents. Alternatively, a compound of this application may be administered to a patient in need thereof in combination with the administration of one or more other therapeutic agents. For example, additional therapeutic agents for conjoint administration or inclusion in a pharmaceutical composition with a compound of this application may be, for example, an approved chemotherapeutic agent, or it may be any one of a number of agents undergoing approval in the Food and Drug Administration that ultimately obtain approval for the treatment of any disorder associated with cellular hyperproliferation. In certain other embodiments, the additional therapeutic agent is an anticancer agent, as discussed in more detail herein.

Bifunctional compounds of the application can be administered as pharmaceutical compositions by any conventional route, in particular enterally, e.g., orally, e.g., in the form of tablets or capsules, or parenterally, e.g., in the form of injectable solutions or suspensions, or topically, e.g., in the form of lotions, gels, ointments or creams, or in a nasal or suppository form. Pharmaceutical compositions comprising a compound of the present application in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include a therapeutically effective amount of a compound of the present application with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type refers to those salts which are, within the scope of sound medical judgment, suitable for use in contact with the tissues of humans and lower animals without undue toxicity, irritation, allergic response and the like, and are commensurate with a reasonable benefit/risk ratio. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols such a propylene glycol or polyethylene glycol; esters such as ethyl oleate and ethyl laurate, agar; buffering agents such as magnesium hydroxide and aluminum hydroxide; alginic acid, pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds and compositions of the application can be administered in therapeutically effective amounts in a combinational therapy with one or more therapeutic agents (pharmaceutical combinations) or modalities, e.g., an anti-proliferative, anti-cancer, immunomodulatory or anti-inflammatory agent. Where the compounds of the application are administered in conjunction with other therapies, dosages of the co-administered compounds will of course vary depending on the type of co-drug employed, on the specific drug employed, on the condition being treated and so forth. Compounds and compositions of the application can be administered in therapeutically effective amounts in a combinational therapy with one or more therapeutic agents (pharmaceutical combinations) or modalities, e.g., anti-proliferative, anti-cancer, immunomodulatory or anti-inflammatory agent, and/or non-drug therapies, etc. For example, synergistic effects can occur with anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

It will also be appreciated that the bifunctional compounds and pharmaceutical compositions of the present application can be formulated and employed in combination therapies, that is, the compounds and pharmaceutical compositions can be formulated with or administered concurrently with, prior to, or subsequent to, one or more other desired therapeutics or medical procedures. The bifunctional compounds may be administered in combination with one or more separate pharmaceutical agents, i.e., a chemotherapeutic agent, an immunotherapeutic agent, or an adjunctive therapeutic agent. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a bifunctional compound of the present application may be administered concurrently with another immunomodulatory agent or anticancer agent, or they may achieve different effects (e.g., control of any adverse effects).

Additionally, the present application provides pharmaceutically acceptable derivatives of the bifunctional compounds, and methods of treating a subject using these bifunctional compounds, or pharmaceutical compositions thereof, or either of these in combination with one or more additional therapeutic agents. For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

For example, other therapies or anticancer agents that may be used in combination with the bifunctional compounds of the present application include surgery, radiotherapy, endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs.

In certain embodiments, the pharmaceutical compositions of the present application further comprise one or more additional therapeutically active ingredients (e.g., chemotherapeutic and/or palliative). For purposes of the application, the term "palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

Additionally, the present application provides pharmaceutically acceptable derivatives of the bifunctional compounds, and methods of treating a subject using these bifunctional compounds or pharmaceutical compositions thereof, or either of these in combination with one or more additional therapeutic agents.

It will also be appreciated that certain of the bifunctional compounds of present application can exist in free form for treatment, or where appropriate, as a pharmaceutically acceptable derivative thereof. According to the present application, a pharmaceutically acceptable derivative includes, but is not limited to, pharmaceutically acceptable salts, esters, salts of such esters, or a prodrug or other adduct or derivative of a bifunctional compound of this disclosure which upon administration to a patient in need is capable of providing, directly or indirectly, a compound as otherwise described herein, or a metabolite or residue thereof.

Polypeptides, Polynucleotides, and Cells of the Application and Methods of Use Thereof The present application also relates to a polynucleotide comprising a nucleotide sequence encoding an amino acid sequence that is substantially similar to the amino acid sequence of an E3 ubiquitin ligase, and a polypeptide comprising an amino acid sequence that is substantially similar to the amino acid sequence of a E3 ubiquitin ligase. In some embodiments, the polynucleotide comprises a nucleotide sequence encoding an amino acid sequence that is substantially similar to the amin acid sequence of a cereblon. In some embodiments, the polypeptide comprises an amino acid sequence that is substantially similar to the amino acid sequence of a cereblon. Two polynucleotide sequences or two polypeptide sequences are "substantially similar" if they exhibit a degree of identity of at least 80%, 85%, 87%, 90%, 95%, 98%, or 99%. In certain embodiments, two polynucleotide sequences or two polypeptide sequences are "substantially similar" if they exhibit a degree of identity of between 80% and 99%, between 85% and 99%, between 87% and 99%, between 90% and 99%, between 92% and 99%, between 95% and 99%, between 97% and 99%, and between 98% and 99%.

The term "sequence identity" or, "identity" when used in the context of comparing polynucleotide sequences or polypeptide sequences, refers to the degree to which two or more polynucleotide sequences or two or more polypeptide sequences are identical on a base-by-base or residue-by-residue basis over a particular region of comparison (e.g., the protein coding region). The percentage of sequence identity is calculated by comparing two optimally aligned sequences over the region of comparison, determining the number of positions at which the identical nucleic acid bases (e.g., A, T, C, G, U, or I, in the case of polynucleotides) or amino acid residues (e.g., Ala, Ile, Arg, Phe, etc., in the case of polypeptides) occur in both sequences to yield the number of matched positions, dividing the number of matched positions by the total number of positions in the region of comparison (i.e., the window size), and multiplying the result by 100 to yield the percentage of sequence identity. Whether two or more polynucleotide sequences or two or more polypeptide sequences are substantially similar can be determined by methods well-known in the art. For example, the percentage of sequence identity of two or more polynucleotide sequences or two or more polypeptide sequences can be assessed by using online tools, such as BLAST® and GenePAST™.

A "cereblon" as used herein, refers to a cereblon in any organism. In certain embodiments, a "cereblon" as used herein, refers to a cereblon in a mammal, such as a human, a monkey, a dog, a cat, a horse, a cow, a pig, a guinea pig, a rat, a mouse, a zebra fish, and the like. In certain embodiments, a cereblon as used herein, refers to a cereblon in an experimental animal, such as a monkey, a rat, a mouse, and a zebra fish. In certain embodiments, a cereblon as used herein, refers to a cereblon in a human. In certain embodiments, a cereblon as used herein, refers to a cereblon selected from the following:

(1) a human cereblon:

```
                                                                    SEQ ID NO: 1
  1    magegdqqda  ahnmgnhlpl  lpaeseeede  mevedqdske  akkpniinfd  tslptshtyl
 61    gadmeefhgr  tlhdddscqv  ipvlpqvmmi  lipgqtlplq  lfhpaevsmv  rnliqkdrtf
121    avlaysnvqe  reaqfgttae  iyayreeqdf  gieivkvkai  grqrfkvlel  rtqsdgiqqa
181    kvqilpecvl  pstmsavqle  slnkcqifps  kpvsredqcs  ykwwqkyqkr  kfhcanltsw
241    prwlyslyda  etlmdrikkq  lrewdenlkd  dslpsnpidf  syrvaaclpi  ddvlriqllk
301    igsaiqrlrc  eldimnkcts  lcckqcqete  ittkneifsl  slcgpmaayv  nphgyvhetl
361    tvykacnlnl  igrpstehsw  fpayawtvaq  ckicashigw  kftatkkdms  pqkfwgltrs
421    allptipdtc  dcispdkvil  cl
```

```
                                                                    SEQ ID NO: 2
  1    magegdqqda  ahnmgnhlpl  lpeseeedem  evedqdskea  kkpniinfdt  slptshtylg
 61    admeefhgrt  lhdddscqvi  pvlpqvmmil  ipgqtlplql  fhpqevsmvr  nliqkdrtfa
121    vlaysnvqer  eaqfgttaei  yayreeqdfg  ieivkvkaig  rqrfkvlelr  tqsdgiqqak
181    vqilpecvlp  stmsavqles  lnkcqifpsk  pvsredqcsy  kwwqkyqkrk  fhcanltswp
241    rwlyslydae  tlmdrikkql  rewdenlkdd  slpsnpidfs  yrvaaclpid  dvlriqllki
301    gsaiqrlrce  ldimnkctsl  cckqcqetei  ttkneifsls  lcgpmaayvn  phgyvhetlt
361    vykacnlnli  grpstehswf  pgyawtvaqc  kicashigwk  ftatkkdmsp  qkfwgltrsa
421    llptipdted  eispdkvilc  l
```

-continued (2) a mouse cereblon:

SEQ ID NO: 3

```
  1  magegdqqda ahnmgnhlpl lpdsededde iemevedqds kearkpniin fdtslptsht
 61  ylgadmeefh grtlhdddsc qvipvlpevl milipgqtlp lqlshpqevs mvrnliqkdr
121  tfavlaysnv qereaqfgtt aeiyayreeq efgievvkvk aigrqrfkvl elrtqsdgiq
181  qakvqilpec vlpstmsavq leslnkcqvf pskpiswedq ysckwwqkyq krkfhcanlt
241  swprwlysly daetlmdrik kqlrewdenl kddslpenpi dfsyrvaacl piddvlriql
301  lkigsaiqrl rceldimnkc tslcckqcqe teittkneif slslcgpmaa yvnphgyvhe
361  tltvykasnl nligrpstvh swfpgyawti aqckicashi gwkftatkkd mspqkfwglt
421  rsallptipe tedeispdkv ilcl
```

SEQ ID NO: 4

```
  1  magegdqqda ahnmgnhlpl lpadsededd eiemevedqd skearkpnii nfdtslptsh
 61  tylgadmeef hgrtlhddds cqvipvlpev lmilipgqtl plqlshpqev smvrnliqkd
121  rtfavlaysn vqereaqfgt taeiyayree qefgievvkv kaigrqrfkv lelrtqsdgi
181  qqakvqilpe cvlpstmsav qleslnkcqv fpskpiswed qysckwwqky qkrkfhcanl
241  tswprwlysl ydaetlmdri kkqlrewden lkddslpenp idfsyrvaac lpiddvlriq
301  llkigsaiqr lrceldimnk ctslcckqcq eteittknei fslslcgpma ayvnphgyvh
361  etltvykasn lnligrpstv hswfpgyawt iaqckicash igwkftatkk dmspqkfwgl
421  trsallptip etedeispdk vilcl
```

(3) a rat cereblon:

SEQ ID NO: 5

```
  1  magegdhqda ahnmgnhlpl lpadsededd eiemevedqd skearkpnii nfdtslptsh
 61  tylgadmeef hgrtlhddds cqvipvlpev mmilipgqtl plqlshpqev smvrnliqkd
121  rtfavlaysn vqereaqfgt taeiyayree qefgievvkv kaigrqrfkv lelrtqsdgi
181  qqakvqilpe cvlpstmsav qleslnkcqi fpskpiswed qysckwwqky qkrkfhcanl
241  tswprwlysl ydaetlmdri kkqlrewden lkedslpanp idfsyrvaac lpiddviriq
301  likigsaiar lrceldimnk ctsicckgcq eteittknei fslsicgpma ayvnphgyvh
361  etitvykasn lnligrpstv hswfpgyawt iagckicash igwkftatkk dmspqkfwgl
421  trsallptip etedeispdk vilcl
```

(4) a cow cereblon:

SEQ ID NO: 6

```
  1  magegdpeda ahnmgnhlpl lpaeeeeede iemevedqdn kepkkpniin fdtslptsht
 61  ylgsdmeefh grtlhdddsc pvipvlpqvv mtlipgqtlp lglfspqevs mvrnliqkdr
121  tfavlaysnv qereaqfgtt aeiyayreeq dfgievvkvk aigrqrfkvl eirtqsdgiq
181  qakvqilpec vlpstmsavq leslnkcrif pskpvswedq csykwwqkyq krkfhcanlt
241  swprwlysly daetlmdrik kqlrewdenl kedslpsnpi dfsyrvaacl piddvlriql
301  lkigsaiqrl rceldimnkc tslcckqcqe teittkneif slslcgpmaa yvnphgyvhe
361  tltvykasnl nligrpstdh swfpgyawti aqcricashi gwkftatkkd mspqkfwglt
421  rsallptipd teddispdkv ilcl
```

(5) a zebra fish cereblon:

SEQ ID NO: 7

```
  1  mqnqlqllpe neeeeeddme tedrdgedve kpsiinfdts lptshaylgs dmeefhgrtl
 61  hdedsvqnlp vlphvalili pgqtlplqlf rpqevsmfrn lvsqdrtfav lahspdpsgt
121  etkaefgtta eiyafreeqe ygietvkika vgrqrfrvhd irtqadgirq akvqilperi
181  lpdplcalaf lprlhthspq tkhtqttppq krcsqnyrqk klhcasmtsw ppwvyslyds
```

```
-continued 241    ktlmsrvkkq lhewdenlkd eslptnptdf syrvaaclpi ddalrlqllk igsaiqrlrc 301    eldimdrcts lcckqcqdte itskneifsl slygpmaayv nphgyvhetl tvykasnlnl 361    igrpstlhsw fpgyawtiaq crtcsshmgw kfsavkkdls pprfwgltrs allptipqge 421    egvegsrllc l
```

The above amino acid sequences of cereblons from different species are for illustration only and are not intended to limit the scope of the present application. Other sequences of cereblons can be identified through routine methods known in the art, such as BLAST® and GenePAST™.

In certain embodiments, the present application relates to a wild-type E3 ubiquitin ligase. In other embodiments, the present application relates to an E3 ubiquitin ligase containing one or more mutations. In certain embodiments, the wild-type E3 ubiquitin ligase is a cereblon, such as a cereblon described above (e.g., SEQ ID NOs: 1-7). In other embodiments, the E3 ubiquitin ligase is a cereblon containing one or more mutations. In certain embodiments, the present application relates to a cereblon containing one or more mutations at amino acid residues selected from N350, H352, W379, and F401 in SEQ ID NO: 2, or at amino acid residues in other cereblons which correspond to N350, H352, W379, and F401 in SEQ ID NO: 2. For example, a mutant cereblon may contain one or more mutations at amino acid residues selected from N351, H353, W380, and F402 in SEQ ID NO: 1, or at amino acid residues selected from N353, H355, W382, and F404 in SEQ ID NO: 3, or at amino acid residues selected from N354, H356, W383, and F405 in SEQ ID NO: 4, or at amino acid residues selected from N354, H356, W383, and F405 in SEQ ID NO: 5, or at amino acid residues selected from N353, H355, W382, and F404 in SEQ ID NO: 6, or at amino acid residues selected from N341, H343, W370, and F392 in SEQ ID NO: 7. In certain embodiments, the present application relates to a mutant cereblon of SEQ ID NO:2 having one or more mutations selected from N350C, H352C, W379A, and F401A, or a mutant cereblon having one or more of the same mutations (e.g., N→C, H→C, W→A, and F→A) at amino acid residues in other cereblons which correspond to N350, H352, W379, and F401. For example, a mutant cereblon of the present application is selected from a mutant cereblon of SEQ ID NO: 1 having one or more mutations selected from N351C, H353C, W380A, and F402A, a mutant cereblon of SEQ ID NO: 3 having one or more mutations selected from N353C, H355C, W382A, and F404A, a mutant cereblon of SEQ ID NO: 4 having one or more mutations selected from N354C, H356C, W383A, and F405A, a mutant cereblon of SEQ ID NO: 5 having one or more mutations selected from N354C, H356C, W383A, and F405A, a mutant cereblon of SEQ ID NO: 6 having one or more mutations selected from N353C, H355C, W382A, and F404A, and a mutant cereblon of SEQ ID NO: 7 having one or more mutations selected from N341C, H343C, W370A, and F392A. In one embodiment, the polynucleotide encoding mutant cereblon further includes a tissue-specific promoter sequence operably linked to the nucleic acid sequence encoding mutant cereblon.

The nucleic acids encoding a mutant E3 ubiquitin ligase of the present invention can be linked to another nucleic acid so as to be expressed under control of a suitable promoter. Examples of the promoter include a promoter that constitutively promotes the expression of a gene, a promoter that induces the expression of a gene by the action of a drug or the like (e.g. tetracycline or doxorubicin). The nucleic acid of the present invention can be also linked to, in order to attain efficient transcription of the nucleic acid, other regulatory elements that cooperate with a promoter or a transcription initiation site, for example, a nucleic acid comprising an enhancer sequence or a terminator sequence. In addition to the nucleic acid of the present invention, a gene that can be a marker for confirming expression of the nucleic acid (e.g. a drug resistance gene, a gene encoding a reporter enzyme, or a gene encoding a fluorescent protein) may be incorporated.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the nucleic acids encoding a mutant E3 ubiquitin ligase are operably linked to a tissue specific promoter in order to get expression of the mutant E3 ubiquitin ligase in a particular tissue. In mammalian cells, each gene has its own promoter, and some promoters can only be activated in a specific cell type (see Zhang et al., Evaluation of promoters for use in tissue-specific gene delivery, Methods Mol Biol. 2008; 434: 205-219, incorporated herein by reference). In one embodiment, the nucleic acids encoding a mutant cereblon are operably linked to a tissue specific promoter. Tissue-specific promoters are well known in the art. For example, tissue specific promoters include, but are not limited to, B29 promoter (B cells), CD14 promoter (Monocytic cells), CD43 promoter (Leukocytes & platelets), CD45 promoter (Haematopoietic cells), CD68 promoter (Macrophages), Desmin promoter (Muscle), Elastase-1 promoter (Pancreatic acinar cells), Endoglin promoter (Endothelial cells), Fibronectin promoter (Differentiating cells, healing tissues), Flt-1 promoter (Endothelial cells), GFAP promoter (Astrocytes), GPIIb promoter (Megakaryocytes), ICAM-2 promoter (Endothelial cells), Mouse INF-β promoter (Hematopoietic cells), Mb promoter (Muscle), NphsI promoter (Podocytes), OG-2 promoter (Osteoblasts, Odonblasts), SP-B promoter (Lung), SYN1 promoter (Neurons), WASP promoter (Hematopoietic cells), bAlb promoter (Liver), hAlb promoter (Liver), RU5' promoter (Mature neurons), APOA2 (hepatocytes), SERPINA1 (hepatocytes), CYP3A4 (hepatocytes), MIR122 (hepatocytes), INS (pancreatic cells), IRS2 (pancreatic cells), PDX1 (pancreatic cells), ALX3 (pancreatic cells), PPY (pancreatic cells), MYH6 (myocytes), MYL2 (myocytes), TNNI3 (myocytes), NPPA (myocytes), Slc8a1 (myocytes), SYN1 (neurons), GFAP (astrocytes), INA (neuroprogenitors), NES (nestin), MOBP (oligodendrocytes), MBP (oligodendrocytes), TH (dopaminergic neurons), FOXA2 (dopaminergic neurons), FLG (keratinocytes), K14 (keratinocytes), TGM3 (keratinocytes), ITGAM (monocytes, macrophages, granulocytes, NK cells), PBSN (prostratic epithelium), UPK2 (bladder), Sbp (prostate), FER1L4 (bladder), ENG (endothelial cells), CD8 (T-cells), and CD4 (T-cells). In some embodiments, the tissue specific promoter is a tumor specific promoter. Examples of tumor specific promoters include, but are not limited to, AFP promoter (Hepatocellular carcinoma), CCKAR promoter (pancreatic cancer), CEA promoter (epithelial cancers), c-erbB2 promoter (breast and pancreatic cancers), COX-2 promoter (tumor), CXCR4 promoter(tumor), E2F-1 (tumor), HE4 promoter (tumor), LP promoter (tumor), midkine promoter (tumor), MUC1 promoter (carcinoma cells), PSA promoter (prostate cancers), Survivin promoter (tumor), TRP1 promoter (melanoma), and Tyr promoter (melanoma).

The present invention contemplates a composition comprising the nucleic acid of the present invention as an active ingredient, together with a pharmaceutically acceptable excipient. Suitable pharmaceutically acceptable excipients are well known to a person skilled in the art. Examples of the pharmaceutically acceptable excipients include phosphate buffered saline (e.g. 0.01 M phosphate, 0.138 M NaCl, 0.0027 M KCl, pH 7.4), an aqueous solution containing a mineral acid salt such as a hydrochloride, a hydrobromide, a phosphate, or a sulfate, saline, a solution of glycol or ethanol, and a salt of an organic acid such as an acetate, a propionate, a malonate or a benzoate. An adjuvant such as a wetting agent or an emulsifier, and a pH buffering agent can also be used. As the pharmaceutically acceptable excipients, excipients described in Remington's Pharmaceutical Sciences (Mack Pub. Co., N.J. (1991)) (which is incorporated herein by reference) can be appropriately used. The composition of the present invention can be formulated into a known form suitable for parenteral administration, for example, injection or infusion. Further, the composition of the present invention may comprise formulation additives such as a suspending agent, a preservative, a stabilizer and/or a dispersant, and a preservation agent for extending a validity term during storage. The composition may be in a dry form for reconstitution with an appropriate sterile liquid prior to use. For fine particle-mediated administration, a particle such as a gold particle of a microscopic size can be coated with a DNA.

The present application also relates to a method of introducing a mutant E3 ubiquitin ligase into a subject. In some embodiments, the mutant E3 ubiquitin ligase is a cereblon. In certain embodiments, the method comprises introducing one or more mutations (e.g., the mutations described herein) into the endogenous cereblon of the subject. In certain embodiments, the method comprises replacing the endogenous cereblon in the subject with a mutant cereblon comprising one or more mutations (e.g., the mutations described herein). In certain embodiments, the entire endogenous cereblon sequence is replaced with a mutant cereblon comprising one or more mutations. In certain embodiments, only a portion of the endogenous cereblon (e.g., the 100 amino acid residues at the C-terminal of the endogenous cereblon) is replaced with a corresponding portion of a mutant cereblon comprising one or more mutations. In certain embodiments, the method comprises expressing a mutant cereblon comprising one or more mutations (e.g., the mutations described herein) in the subject. In certain embodiments, the method comprises introducing a mutant cereblon into a cell (e.g., a T cell), and introducing the cell containing the mutant cereblon into the subject.

Methods of introducing a mutation into an endogenous gene or replacing an endogenous gene or a portion thereof with a mutant gene are well known in the art. In certain embodiments, a variety of DNA nucleases may be utilized to introduce mutations into an endogenous gene. In certain embodiments, the DNA nuclease is deficient in its nuclease activity. In certain embodiments, the enzyme is a Zinc-finger nuclease. In further embodiments, the Zinc-finger nuclease is selected from ZF-FokI and ZF-Tn3. In certain embodiments, the enzyme is a transcription activator-like effector nuclease (TALEN). In further embodiments, the TALEN is TAL-FokI. In certain embodiments, the enzyme is a homing endonuclease. In further embodiments, the homing endonuclease is selected from LAGLIDADG, GIY-YIG, His-Cys, H—N—H, PD-(D/E)xK, and Vsr-like. In certain embodiments, the enzyme is a Clustered Regularly Interspaced Short Palindromic Repeats (CRISPR) enzyme. In further embodiments, the CRISPR enzyme is a type II CRISPR enzyme. In further embodiments, the type II CRISPR enzyme is Cas9. In certain embodiments, the CRISPR enzyme is deficient in its nuclease activity. In certain embodiments, various DNA integrases may be utilized to introduce mutations into an endogenous gene or replace an endogenous gene with a mutant gene. In certain embodiments, the DNA integrase is selected from λ-int and φC31. In certain embodiments, a DNA recombinase may be utilized to introduce mutations into an endogenous gene or replace an endogenous gene with a mutant gene. In certain embodiments, the DNA recombinase is selected from Cre, Flp, and RMCE.

When the nucleic acid of the present invention is introduced into a cell ex vivo, the nucleic acid of the present invention may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid of the present invention is also useful as described later. Particularly, a composition in a form suitable for administration to a living body which contains the nucleic acid of present invention carried by a suitable vector is suitable for in vivo gene therapy.

As described above, some embodiments of the present invention are based on the genomic insertion of a gene encoding a functional, mutant E3 ubiquitin ligase or introducing a genetic mutation into an endogenous E3 ubiquitin ligase gene into a cell, wherein upon expression a mutant E3 ubiquitin ligase that can be recognized by and bound to a bifunctional compound is produced. In some embodiments, the mutant E3 ubiquitin ligase is a mutant cereblon. In one embodiment, the nucleic acid sequence encoding a mutant cereblon is operably linked to a nucleic acid sequence comprising a tissue specific promoter sequence which, upon expression, expresses the mutant cereblon in a tissue specific manner. In another embodiment, the cell has inserted into its genome a nucleotide encoding a mutant cereblon in-frame with a tissue specific promoter nucleotide sequence which, upon expression, expresses the mutant cereblon in a tissue specific manner.

Insertion of the nucleic acid sequence encoding the mutant E3 ubiquitin ligase can be performed or achieved by any known and effective genomic editing processes. The nucleic acid encoding the mutant E3 ubiquitin ligase of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. Preferably, a virus vector lacking the replicating ability so as not to self-replicate in an infected cell is preferably used.

In addition, a non-virus vector can also be used in the present invention in combination with a liposome and a condensing agent such as a cationic lipid as described in WO 96/10038, WO 97/18185, WO 97/25329, WO 97/30170, and WO 97/31934 (which are incorporated herein by reference). The nucleic acid of the present invention can be also introduced into a cell by calcium phosphate transduction, DEAE-dextran, electroporation, or particle bombardment.

For example, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+envAm-12 (U.S. Pat. No. 5,278,056), and Psi-Crip (PNAS 85 (1988):6460-6464). A retrovirus particle can also be prepared using a 293 cell or a 293T-cell having high transfection efficiency. Many kinds of retrovirus vectors produced based on retroviruses and packaging cells that can be used for packaging of the retrovirus vectors are widely commercially available from many companies.

In the step of introducing a nucleic acid into a cell, a functional substance for improving the introduction efficiency can also be used (e.g. WO 95/26200 and WO 00/01836 (which are incorporated herein by reference)). Examples of the substance for improving the introduction efficiency include a substance having ability to bind to a virus vector, for example, fibronectin and a fibronectin fragment. Preferably, a fibronectin fragment having a heparin binding site, for example, a fragment commercially available as RetroNetcin (registered trademark, CH-296, manufactured by TAKARA BIC INC.) can be used. Also, polybrene which is a synthetic polycation having an effect of improving the efficiency of infection of a retrovirus into a cell, a fibroblast growth factor, V type collagen, polylysine or DEAE-dextran can be used.

In one aspect of the present invention, the functional substance can be used in a state of being immobilized on a suitable solid phase, for example, a container used for cell culture (plate, petri dish, flask or bag) or a carrier (microbeads etc.).

In order to assess the expression of a mutant E3 ubiquitin ligase polypeptide or portion thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

The cell expressing the mutant E3 ubiquitin ligase of the present invention is a cell in which the nucleic acid encoding a mutant E3 ubiquitin ligase described above is introduced and expressed by the cell. In one embodiment, the cell expressing the mutant E3 ubiquitin ligase expresses a mutant cereblon.

In one aspect, the present invention utilizes the CRISPR-Cas9 system to produce a mutant E3 ubiquitin ligase by insertion of a mutant E3 ubiquitin ligase gene or from the mutation of an endogenous E3 ubiquitin ligase gene. In some embodiments, the present invention utilizes the CRISP-Cas9system to produce a mutant cereblon. In certain embodiments, the CRISPR-Cas9 system is employed in order to insert an expression cassette for mutant cereblon present in a homologous recombination (HR) "donor" sequence with the mutant cereblon nucleic acid sequence serving as a "donor" sequence inserted into the genome during homologous recombination following CRISPR-Cas endonucleation. The HR targeting vector contains homology arms at the 5' and 3'end of the expression cassette homologous to the genomic DNA surrounding the targeting locus.

The present invention provides for insertion of a mutant E3 ubiquitin ligase sequence (also called a "donor sequence" or "donor" or "transgene") with the target gene of interest. It will be readily apparent that the donor sequence need not be identical to the genomic sequence where it is placed. A donor sequence can contain a non-homologous sequence flanked by two regions of homology to allow for efficient HR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, for example, the mutant cereblon of the present invention, said sequences can be present in a donor nucleic acid molecule and flanked by regions of homology to sequence in the region of interest. Alternatively, a donor molecule may be integrated into a cleaved target locus via non-homologous end joining (NHEJ) mechanisms. See, e.g., U.S. 2011/0207221 and U.S.

2013/0326645, incorporated herein by reference. In certain embodiments, the donor sequence encodes for a mutant cereblon.

The donor mutant E3 ubiquitin ligase encoding sequence for insertion can be DNA or RNA, single-stranded and/or double-stranded and can be introduced into a cell in linear or circular form. See, e.g., U.S. 2010/0047805, U.S. 2011/0281361, and 2011/0207221, incorporated herein by reference. The donor sequence may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3'-terminus of a linear molecule and/or self-complementary oligonucleotides are ligated to one or both ends. See, for example, Chang et al. *Proc. Natl. Acad. Sci.* 84, (1987):4959-4963 and Nehls et al. *Science,* 272, (1996):886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

The donor polynucleotide encoding a mutant E3 ubiquitin ligase can be introduced into a cell as part of a vector molecule having additional sequences such as, for example, CRISPR-Cas sequences, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The present invention takes advantage of well-characterized insertion strategies, for example the CRISPR-Cas9 system. In general, the "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus. (See, e.g., Ruan, J. et al. "Highly efficient CRISPR/Cas9-mediated transgene knockin at the H11 locus in pigs." *Sci. Rep.* 5, (2015): 14253; and Park A, Won S T, Pentecost M, Bartkowski W, and Lee B "CRISPR/Cas9 Allows Efficient and Complete Knock-In of a Destabilization Domain-Tagged Essential Protein in a Human Cell Line, Allowing Rapid Knockdown of Protein Function." PLoS ONE 9(4), (2014): e95101, both incorporated herein by reference).

The Cas nuclease is a well-known molecule. The protein sequence encoded by the Cas-9 nuclease gene may be found in the SwissProt database under accession number Q99ZW2—(SEQ. ID. NO.: 8):

```
MDKKYSIGLDIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP
VENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE
DNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQ
SITGLYETRIDLSQLGGD.
```

In some embodiments, the CRISPR/Cas nuclease or CRISPR/Cas nuclease system includes a non-coding RNA molecule (guide) RNA, which sequence-specifically binds to DNA, and a Cas protein (e.g., Cas9), with nuclease functionality (e.g., two nuclease domains).

In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*.

In some embodiments, a Cas nuclease and gRNA (including a fusion of crRNA specific for the target sequence and fixed tracrRNA), and a donor sequence encoding a mutant E3 ubiquitin ligase are introduced into the cell. In general, target sites at the 5' end of the gRNA target the Cas nuclease to the target site, e.g., the gene, using complementary base pairing. In some embodiments, the target site is selected based on its location immediately 5' of a protospacer adjacent motif (PAM) sequence, such as typically NGG, or NAG. In this respect, the gRNA is targeted to the desired sequence by modifying the first 20 nucleotides of the guide RNA to correspond to the target DNA sequence.

In some embodiments, the CRISPR system induces DSBs at the target site, followed by homologous recombination of the donor sequence encoding a mutant E3 ubiquitin ligase into the genomic locus of interest, as discussed herein. In other embodiments, Cas9 variants, deemed "nickases" are used to nick a single strand at the target site. In some aspects, paired nickases are used, e.g., to improve specificity, each directed by a pair of different gRNAs targeting sequences such that upon introduction of the nicks simultaneously, a 5' overhang is introduced.

In general, a CRISPR system is characterized by elements that promote the formation of a CRISPR complex at the site of a target sequence. Typically, in the context of formation of a CRISPR complex, "target sequence" generally refers to a sequence to which a guide sequence is designed to have complementarity, where hybridization between the target sequence and a guide sequence promotes the formation of a CRISPR complex, and wherein insertion of the donor sequence encoding a mutant cereblon is to take place. Full complementarity is not necessarily required, provided there is sufficient complementarity to cause hybridization and promote formation of a CRISPR complex.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of the CRISPR complex.

As with the target sequence, in some embodiments, complete complementarity is not necessarily needed. In some embodiments, the tracr sequence has at least 50%, 60%, 70%, 80%, 90%, 95% or 99% of sequence complementarity along the length of the tracr mate sequence when optimally aligned. In some embodiments, one or more vectors driving expression of one or more elements of the CRISPR system are introduced into the cell such that expression of the elements of the CRISPR system direct formation of the CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. In some embodiments, CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises a regulatory element operably linked to an enzyme-coding sequence encoding the CRISPR enzyme, such as a Cas protein. Non-limiting examples of Cas proteins include Cas1, Cas IB, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. These enzymes are known; for example, the amino acid sequence of *S. pyogenes* Cas9 protein may be found in the SwissProt database under accession number Q99ZW2 (incorporated herein by reference).

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of the CRISPR complex to a target sequence may be assessed by any suitable assay. For example, the components of the CRISPR system sufficient to form the CRISPR complex, including the guide sequence to be tested, may be provided to the cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of the CRISPR complex, including the guide sequence to be tested and a control guide sequence different from the test guide sequence, and comparing binding or rate of cleavage at the target sequence between the test and control guide sequence reactions.

A guide sequence may be selected to target any target sequence. In some embodiments, the target sequence is a sequence within a genome of a cell. Exemplary target sequences include those that are unique in the target genome which provide for insertion of the mutant E3 ubiquitin ligase donor nucleic acid in an in-frame orientation. In some embodiments, a guide sequence is selected to reduce the degree of secondary structure within the guide sequence. Secondary structure may be determined by any suitable polynucleotide folding algorithm.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences.

As contemplated herein, the CRISPR-Cas system is used to insert a nucleic acid sequence encoding a mutant E3 ubiquitin ligase with the genomic sequence of interest in a eukaryotic, for example, human cell, for example a T-cell. In certain embodiments, the CRISPR-Cas system is used to insert a nucleic acid sequence encoding a mutant cereblon with the genomic sequence of interest in a eukaryotic cell. In some embodiments, the method comprises allowing the CRISPR complex to bind to the genomic sequence of interest to effect cleavage of the genomic sequence, wherein the CRISPR complex comprises the CRISPR enzyme complexed with a guide sequence hybridized to a target sequence within said target polynucleotide, wherein said guide sequence is linked to a tracr mate sequence which in turn hybridizes to a tracr sequence.

In some aspects, the polypeptides of the CRISPR-Cas system and donor sequence are administered or introduced to the cell. The nucleic acids typically are administered in the form of an expression vector, such as a viral expression vector. In some aspects, the expression vector is a retroviral expression vector, an adenoviral expression vector, a DNA plasmid expression vector, or an AAV expression vector. In some aspects, one or more polynucleotides encoding CRISPR-Cas system and donor sequence delivered to the cell. In some aspects, the delivery is by delivery of more than one vectors.

Methods of delivering nucleic acid sequences to cells as described herein are described, for example, in U.S. Pat. Nos. 8,586,526; 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

The various polynucleotides as described herein may also be delivered using vectors containing sequences encoding one or more of compositions described herein. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties.

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 1991/17424 and WO 1991/16024. Delivery can be to cells (e.g. in vitro or ex vivo administration) or target tissues (e.g. in vivo administration).

In some embodiments, delivery is via the use of RNA or DNA viral based systems for the delivery of nucleic acids. Viral vectors in some aspects may be administered directly to patients (in vivo) or they can be used to treat cells in vitro or ex vivo, and then administered to patients. Viral-based systems in some embodiments include retroviral, lentivirus, adenoviral, adeno-associated and herpes simplex virus vectors for gene transfer. The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66, (1992):2731-2739; Johann et al., *J. Virol.* 66, (1992):1635-1640; Sommerfelt et al., *J. Virol.* 176, (1990):58-69; Wilson et al., *J. Virol.* 63, (1989):2374-2378; Miller et al., *J. Virol.* 65, (1991):2220-2224; and PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160, (1987):38-47; U.S. Pat. No. 4,797,368; WO 1993/24641; Kotin, *Human Gene Therapy* 5, (1994):793-801; Muzyczka, *J. Clin. Invest.* 94, (1994):1351. Construction of recombinant AAV vectors is described in a number of publications, including U.S. Pat. No. 5,173,414; Tratschin et al., *Mol. Cell. Biol.* 5, (1985):3251-3260; Tratschin, et al., *Mol. Cell. Biol.* 4, (1984):2072-2081; Hermonat & Muzyczka, *PNAS* 81, (1984):6466-6470; and Samulski et al., *J. Virol.* 63, (1989):3822-3828.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85, (1995):3048-305; Kohn et al., *Nat. Med* 1, (1995):1017-1023; Malech et al., *PNAS* 94(22), (1997):12133-12138). PA317/pLASN was the first therapeutic vector used in a gene therapy trial. (Blaese et al., *Science* 270, (1995):475-480). Transduction efficiencies of 50% or greater have been observed for MFG-S packaged vectors. (Ellem et al., *Immunol Immunother.* 44(1), (1997): 10-20; and Dranoff et al., *Hum. Gene Ther.* 1, (1997):111-112).

Vectors suitable for introduction of polynucleotides described herein also include non-integrating lentivirus vectors (IDLV). See, for example, Naldini et al. *Proc. Natl. Acad. Sci.* 93, (1996):11382-11388; Dull et al. *J. Virol.* 72, (1998):8463-8471; Zuffery et al. *J. Virol.* 72, (1998):9873-9880; Follenzi et al. *Nature Genetics* 25, (2000):217-222; and U.S. 2009/0117617.

Recombinant adeno-associated virus vectors (rAAV) may also be used to deliver the compositions described herein. All vectors are derived from a plasmid that retains only the AAV inverted terminal repeats flanking the transgene expression cassette. Efficient gene transfer and stable transgene delivery are key features for this vector system. (Wagner et al., *Lancet* 351, (1998):9117 1702-3, and Kearns et al., *Gene Ther.* 9, (1996):748-55). Other AAV serotypes, including AAV1, AAV3, AAV4, AAV5, AAV6, AAV8, AAV9 and AAVrh10, pseudotyped AAV such as AAV2/8, AAV2/5 and AAV2/6 and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7, (1998): 1083-1089). Additional examples of the use of adenovirus vectors for gene transfer in clinical trials include Rosenecker et al., *Infection* 24(1), (1996):5-10; Sterman et al., *Hum. Gene Ther.* 9(7), (1998):1083-1089; Welsh et al., *Hum. Gene Ther.* 2, (1995):205-218; Alvarez et al., *Hum. Gene Ther.* 5, (1997):597-613; Topf et al., *Gene Ther.* 5, (1998):507-513; Sterman et al., *Hum. Gene Ther.* 7, (1998): 1083-1089.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

The vector can be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci.* 92, (1995):9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Vectors can be delivered in vivo by administration to an individual subject, typically by systemic administration (e.g., intravenous, intraperitoneal, intramuscular, intrathecal, intratracheal, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

In some embodiments, the polypeptides of the CRISPR-Cas system are synthesized in situ in the cell as a result of the introduction of polynucleotides encoding the polypeptides into the cell. In some aspects, the polypeptides of the CRISP-Cas system could be produced outside the cell and then introduced thereto. Methods for introducing a CRISPR-Cas polynucleotide construct into animal cells are known and include, as non-limiting examples stable transformation methods wherein the polynucleotide construct is integrated into the genome of the cell, transient transformation methods wherein the polynucleotide construct is not integrated into the genome of the cell, and virus mediated methods, as described herein. Preferably, the CRISPR-Cas polynucleotide is transiently expressed and not integrated into the genome of the cell. In some embodiments, the CRISPR-Cas polynucleotides may be introduced into the cell by for example, recombinant viral vectors (e.g. retroviruses, adenoviruses), liposome and the like. For example, in some aspects, transient transformation methods include microinjection, electroporation, or particle bombardment. In some embodiments, the CRISPR-Cas polynucleotides may be included in vectors, more particularly plasmids or virus, in view of being expressed in the cells.

In some embodiments, non-CRISPR-CAS viral and non-viral based gene transfer methods can be used to insert nucleic acids encoding a mutant cereblon in frame in the genomic locus of interest in mammalian cells or target tissues. Such methods can be used to administer nucleic acids encoding components of a ZFP, ZFN, TALE, and/or TALEN system to cells in culture, or in a host organism including a donor sequence encoding a mutant cereblon for in-frame insertion into the genomic locus of interest.

Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, *Science* 256, (1992):808-813; Nabel & Feigner, *TIBTECH* 11, (1993): 211-217; Mitani & Caskey, *TIBTECH* 11, (1993): 162-166; Dillon. *TIBTECH* 11, (1993): 167-173; Miller, *Nature* 357, (1992):455-460; Van Brunt, Biotechnology 6(10), (1988): 1149-1154; Vigne, *Restorative Neurology and Neuroscience* 8, (1995):35-36; Kremer & Perricaudet, *British Medical Bulletin* 51(1), (1995):31-44; and Yu et al., *Gene Therapy* 1, (1994): 13-26.

The preparation of lipid:nucleic acid complexes, including targeted liposomes such as immunolipid complexes, is well known to one of skill in the art (see, e.g., Crystal, *Science* 270, (1995):404-410; Blaese et al., *Cancer Gene Ther.* 2, (1995):291-297; Behr et al., *Bioconjugate Chem.* 5, (1994):382-389; Remy et al., *Bioconjugate Chem.* 5, (1994): 647-654; Gao et al., *Gene Therapy* 2, (1995):710-722; Ahmad et al., *Cancer Res.* 52, (1992):4817-4820; and U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al *Nature Biotechnology* 27(7), (2009):643).

Engineered Immune Effector Cells

In one aspect of the invention, provided herein is an immune effector cell, for example a T-cell, expresses a mutant E3 ubiquitin ligase as described above and further comprises a chimeric antigen receptor (CAR) or engineered T-cell receptor (TCR). The CAR or TCR of the T-cell can be bound by a bifunctional compound comprising a mutant E3 ubiquitin ligase-binding moiety and a moiety capable of binding to an intracellular signaling domain of a CAR or TCR. In certain embodiments, the E3 ubiquitin ligase is a mutant cereblon. CARs and TCR are known in the art. In general, a CAR and TCR both comprise an intracellular signaling domain that can be bound by the bifunctional compound in order to bring the CAR or TCR cytoplasmic domain into proximity of the mutant cereblon, such that the CAR or TCR, or a portion thereof, is ubiquitinated, and then degraded by a proteasome. By degrading at least a portion of the intracellular signaling domain of the CAR or TCR, the ability of the CAR or TCR to stimulate the T-cell is reduced without killing the T-cell, allowing for the control of T-cell activation and a reduction in the potential deleterious side effects associated with adoptive T-cell therapies.

The structures of CARs and TCRs are well known and are generally designed to target a tumor antigen of interest by way of engineering a desired antigen binding moiety that specifically binds to an antigen on a tumor cell. In the context of the present invention, tumor antigen refers to antigens that are common to specific types of cancer. Tumor antigens are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, mesothelin, α-Folate receptor, CAIX, EGP-2, EGP-40, IL13R-a2, KDR, kappa-light chain, LeY, L1 cell adhesion molecule, murine CMV, NKG2D ligands, GD2, GD3, VEGF-R2, MART-1, tyrosinase, GP 100, Erb-B3, Erb-B4, CD19, CD20, CD37, TRP-1, TRP-2, MAGE-1, MAGE-3, BAGE, GAGE-1, GAGE-2, p15; p53, Ras, BCR-ABL, E2A-PRL, H4-RET, IGH-IGK, MYL-RAR; Epstein Barr virus antigens EBVA and the human papillomavirus (HPV) antigens E6 and E7, TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS. In an embodiment, the antigen binding moiety portion of the CAR targets an antigen that includes but is not limited to CD19, CD20, CD30, CD44, CD22, ROR1, Mesothelin, CD33/IL3Ra, c-Met, PSMA, Glycolipid F77, EGFRvIII, GD-2, MY-ESO-1 TCR, MAGE A3 TCR, and the like.

In one embodiment, the antigen binding moiety portion of the CAR targets a particular cell surface molecule on a cell, wherein the cell surface molecule is associated with a particular type of cell, for example a cluster of differentiation molecule.

Depending on the desired antigen to be targeted, the CAR or TCR of the invention can be engineered to include the appropriate antigen bind moiety that is specific to the desired antigen target. For example, if CD19 is the desired antigen that is to be targeted, an antibody or antibody fragment, for example a scFv for CD19 can be used as the antigen bind moiety for incorporation into the CAR of the invention. In one embodiment, the antigen binding domain is comprised of a scFv. Single chain antibodies refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad.

Sci. USA 85:5879-5883; Ward et al. (1989) Nature 341:544-546; Skerra et al. (1988) Science 240:1038-1041.

The engineered T-cells of the present invention can be designed to include a transmembrane domain that is fused to the extracellular domain. In one embodiment, the transmembrane domain that naturally is associated with one of the domains is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or GITR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain. A glycine-serine doublet provides a particularly suitable linker.

In one embodiment, the transmembrane domain in the engineered T-cell of the invention is derived from the CD8 transmembrane domain. In some instances, the transmembrane domain comprises the CD8a hinge domain.

Further, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR or TCR of the present invention.

The intracellular signaling domain, or cytoplasmic signaling domain, used interchangeably herein, of the engineered T-cell is responsible for activation of at least one of the normal effector functions of the immune cell in which the CAR or TCR has been placed, and is the target of the bifunctional compounds. The term "effector function" refers to a specialized function of a cell. Effector function of a T-cell, for example, may be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal and is capable of being bound by the bifunctional compound. The term intracellular signaling domain is thus meant to include any truncated portion of the intracellular signaling domain sufficient to transduce the effector function signal.

Examples of intracellular signaling domains for use in the engineered T-cells of the invention include the cytoplasmic sequences of the native T-cell receptor and co-receptors that act in concert to initiate signal transduction following antigen receptor engagement, as well as any derivative or variant of these sequences and any synthetic sequence that has the same functional capability.

It is known that signals generated through the TCR alone may not be sufficient for full activation of the T-cell and that a secondary or co-stimulatory signal may also be required. Thus, T-cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. In one embodiment, the cytoplasmic signaling molecule in the CAR of the invention comprises a cytoplasmic signaling sequence derived from CD3 zeta.

The cytoplasmic domain of the CAR can be designed to comprise the CD3-zeta signaling domain by itself or combined with any other desired cytoplasmic domain(s) useful in the context of the engineered T-cell. For example, the cytoplasmic domain of the engineered T-cell can comprise a CD3 zeta chain portion and a costimulatory signaling region. The costimulatory signaling region refers to a portion of the engineered T-cell comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, any of the costimulatory elements known in the art as useful in the construction of engineered T-cells are within the scope of the invention and can be a target of the bifunctional compound.

Immune effector cells, for example T-cells, expressing a CAR or TCR can be engineered by introducing the nucleic acid encoding a CAR or TCR described above into a cell. In one embodiment, the step is carried out ex vivo. For example, a cell can be transformed ex vivo with a virus vector or a non-virus vector carrying the nucleic acid of the present invention to produce a cell expressing the, for example, CAR or TCR of the present invention.

The nucleic acid encoding the CAR or TCR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. Preferably, a virus vector lacking the replicating ability so as not to self-replicate in an infected cell is preferably used.

In addition, a non-virus vector can also be used in the present invention in combination with a liposome and a condensing agent such as a cationic lipid as described in WO 96/10038, WO 97/18185, WO 97/25329, WO 97/30170, and WO 97/31934 (which are incorporated herein by reference). The nucleic acid of the present invention can be also introduced into a cell by calcium phosphate transduction, DEAE-dextran, electroporation, or particle bombardment.

For example, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+envAm-12 (U.S. Pat. No. 5,278,056), and Psi-Crip (PNAS 85 (1988):6460-6464). A retrovirus particle can also be prepared using a 293 cell or a 293T-cell having high transfection efficiency. Many kinds of retrovirus vectors produced based on retroviruses and packaging cells that can be used for packaging of the retrovirus vectors are widely commercially available from many companies.

In the step of introducing a nucleic acid into a cell, a functional substance for improving the introduction efficiency can also be used (e.g. WO 95/26200 and WO 00/01836 (which are incorporated herein by reference)). Examples of the substance for improving the introduction efficiency include a substance having ability to bind to a virus vector, for example, fibronectin and a fibronectin fragment. Preferably, a fibronectin fragment having a heparin binding site, for example, a fragment commercially available as RetroNetcin (registered trademark, CH-296, manufactured by TAKARA BIC INC.) can be used. Also, polybrene which is a synthetic polycation having an effect of improving the efficiency of infection of a retrovirus into a cell, a fibroblast growth factor, V type collagen, polylysine or DEAE-dextran can be used.

In one aspect of the present invention, the functional substance can be used in a state of being immobilized on a suitable solid phase, for example, a container used for cell culture (plate, petri dish, flask or bag) or a carrier (microbeads etc.).

In order to assess the expression of a CAR or TCR polypeptide or portion thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the hosT-cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

The cell expressing the CAR or TCR of the present invention is a cell in which the nucleic acid encoding a CAR or TCR described above is introduced and expressed by the cell. The cell of the present invention binds to a specific antigen via the CAR or TCR, and then a signal is transmitted into the cell, and as a result, the cell is activated. The activation of the cell expressing the CAR or TCR is varied depending on the kind of a host cell and an intracellular domain of the CAR or TCR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and a macrophage. In order to confirm the presence of the recombinant DNA sequence in the cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

An immune effector cell such as lymphocytes including but not limited to cytotoxic lymphocytes, T-cells, cytotoxic T-cells, T helper cells, Th17 T-cells, natural killer (NK) cells, natural killer T (NKT) cells, mast cells, dendritic cells, killer dendritic cells, or B cells derived from a mammal, for example, a human cell, or a cell derived from a non-human mammal such as a monkey, a mouse, a rat, a pig, a horse, or a dog can be used. For example, a cell collected, isolated, purified or induced from a body fluid, a tissue or an organ such as blood (peripheral blood, umbilical cord blood etc.) or bone marrow can be used. A peripheral blood mononuclear cell (PBMC), an immune cell (a dendritic cell, a B cell, a hematopoietic stem cell, a macrophage, a monocyte, a NK cell or a hematopoietic cell (a neutrophil, a basophil)), an umbilical cord blood mononuclear cell, a fibroblast, a precursor adipocyte, a hepatocyte, a skin keratinocyte, a mesenchymal stem cell, an adipose stem cell, various cancer cell strains, or a neural stem cell can be used. In the present invention, particularly, use of a T-cell, a precursor cell of a T-cell (a hematopoietic stem cell, a lymphocyte precursor cell etc.) or a cell population containing them is preferable. Examples of the T-cell include a CD8-positive T-cell, a CD4-positive T-cell, a regulatory T-cell, a cytotoxic T-cell, and a tumor infiltrating lymphocyte. The cell population containing a T-cell and a precursor cell of a T-cell includes a PBMC. The aforementioned cells may be collected from a living body, obtained by expansion culture of a cell collected from a living body, or established as a cell strain. When transplantation of the produced CAR-expressing cell or a cell differentiated from the produced CAR-expressing cell into a living body is desired, it is preferable to introduce the nucleic acid into a cell collected from the living body itself or a conspecific living body thereof.

In one embodiment, the CAR or TCR expressing cell is a T-cell isolated from a subject for autologous therapy. Typically, prior to expansion and genetic modification of the T-cells of the invention, a source of T-cells is obtained from a subject. T-cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T-cell lines available in the art, may be used. In certain embodiments of the present invention, T-cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T-cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium may lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca2+-free, Mg2+-free PBS, PlasmaLyte A, or other saline solution with or without buffer. Alternatively, the undesirable components of the apheresis sample may be removed and the cells directly resuspended in culture media.

In another embodiment, T-cells are isolated from peripheral blood lymphocytes by lysing the red blood cells and depleting the monocytes, for example, by centrifugation through a PERCOLL™ gradient or by counterflow centrifugal elutriation. A specific subpopulation of T-cells, such as CD3+, CD28+, CD4+, CD8+, CD45RA+, and CD45RO+ T-cells, can be further isolated by positive or negative selection techniques. For example, in one embodiment, T-cells are isolated by incubation with anti-CD3/anti-CD28 (i.e., 3×28)-conjugated beads, such as DYNABEADS® M-450 CD3/CD28 T, for a time period sufficient for positive selection of the desired T-cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T-cells from patients with leukemia, use of longer incubation times, such as 24 hours, can increase cell yield. Longer incubation times may be used to isolate T-cells in any situation where there are few T-cells as compared to other cell types, such as in isolating tumor infiltrating lymphocytes (TIL) from tumor tissue or from immune-compromised individuals. Further, use of longer incubation times can increase the efficiency of capture of CD8+ T-cells. Thus, by simply shortening or lengthening the time T-cells are allowed to bind to the CD3/CD28 beads and/or by increasing or decreasing the ratio of beads to T-cells (as described further herein), subpopulations of T-cells can be preferentially selected for or against at culture initiation or at other time points during the process. Additionally, by increasing or decreasing the ratio of anti-CD3 and/or anti-CD28 antibodies on the beads or other surface, subpopulations of T-cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T-cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T-cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T-cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T-cells that normally have weaker CD28 expression.

In a related embodiment, it may be desirable to use lower concentrations of cells. By significantly diluting the mixture of T-cells and surface (e.g., particles such as beads), interactions between the particles and cells is minimized. This selects for cells that express high amounts of desired antigens to be bound to the particles. For example, CD4+ T-cells express higher levels of CD28 and are more efficiently captured than CD8+ T-cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T-cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T-cells, isolated and frozen for later use in T-cell therapy for any number of diseases or conditions that would benefit from T-cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T-cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids. FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66 (1991):807-815; Henderson et al., *Immun* 73 (1991):316-321; Bierer et al., *Curr. Opin. Immun* 5 (1993):763-773). In a further embodiment, the cells are isolated for a patient and frozen for later use in conjunction with (e.g., before, simultaneously or following) bone marrow or stem cell transplantation, T-cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T-cells are obtained from a patient directly following treatment. In this regard, it has been observed that following certain cancer treatments, in particular treatments with drugs that damage the immune system, shortly after treatment during the period when patients would normally be recovering from the treatment, the quality of T-cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T-cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T-cells, B cells, dendritic cells, and other cells of the immune system.

Whether prior to or after genetic modification of the T-cells to express a desirable CAR or TCR, the T-cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T-cells of the invention are expanded by contact with a surface having attached thereto an agent that stimulates a CD3/TCR complex associated signal and a ligand that stimulates a co-stimulatory molecule on the surface of the T-cells. In particular, T-cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a population of T-cells can be contacted with an anti-CD3 antibody and an anti-CD28 antibody, under conditions appropriate for stimulating proliferation of the T-cells. To stimulate proliferation of either CD4+ T-cells or CD8+ T-cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berge et al., *Transplant Proc.* 30(8) (1998):3975-3977; Haanen et al., *J. Exp. Med.* 190(9) (1999):1319-1328, 1999; and Garland et al., *J. Immunol Meth.* 227(1-2) (1999):53-63).

In certain embodiments, the primary stimulatory signal and the co-stimulatory signal for the T-cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T-cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4+ T-cell expansion and T-cell growth is used. In certain aspects of the present invention, a ratio of anti CD3:CD28 antibodies bound to the beads is used such that an increase in T-cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T-cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T-cells. The ratio of anti-CD3- and anti-CD28-coupled particles to T-cells that result in T-cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T-cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T-cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T-cells. In one embodiment the cells (for example, 104 to 109 T-cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T-cells. Such populations of cells may have therapeutic value and would be desirable to obtain in certain embodiments. For example, using high concentration of cells allows more efficient selection of CD8+ T-cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T-cells are cultured together for about eight days. In another embodiment, the beads and T-cells are cultured together for 2-3 days. Several cycles of stimulation may also be desired such that culture time of T-cells can be 60 days or more. Conditions appropriate for T-cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T-cells. Antibiotics, e.g., penicillin and streptomycin, are included only in experimental cultures, not in cultures of cells that are to be infused into a subject. The targeT-cells are maintained under conditions necessary to support growth, for example, an appropriate temperature (e.g., 37° C.) and atmosphere (e.g., air plus 5% CO2).

T-cells that have been exposed to varied stimulation times may exhibit different characteristics. For example, typical blood or apheresed peripheral blood mononuclear cell products have a helper T-cell population (TH, CD4+) that is greater than the cytotoxic or suppressor T-cell population (TC, CD8+). Ex vivo expansion of T-cells by stimulating CD3 and CD28 receptors produces a population of T-cells that prior to about days 8-9 consists predominately of TH cells, while after about days 8-9, the population of T-cells comprises an increasingly greater population of TC cells. Depending on the purpose of treatment, infusing a subject with a T-cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T-cell product for specific purposes.

The cell expressing the mutant E3 ubiquitin ligase, for example a mutant cereblon, and CAR or TCR can be used as a therapeutic agent for a disease. The therapeutic agent can be the cell expressing the mutant E3 ubiquitin ligase and CAR or TCR as an active ingredient, and may further include a suitable excipient. Examples of the excipient include the aforementioned pharmaceutically acceptable excipients for the composition includes the nucleic acid of the present invention as an active ingredient, various cell culture media, and isotonic sodium chloride. The disease against which the cell expressing the mutant E3 ubiquitin ligase and CAR or TCR is administered is not limited as long as the disease shows sensitivity to the cell. Examples of the disease include a cancer (blood cancer (leukemia), solid tumor etc.), an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis. The cell expressing the mutant E3 ubiquitin ligase and CAR or TCR of the present invention that binds to an antigen possessed by a cell that is desired to be decreased or eliminated for treatment of the aforementioned diseases, that is, a tumor antigen, a viral antigen, a bacterial antigen or the like is administered for treatment of these diseases. The cell of the present invention can also be utilized for prevention of an infectious disease after bone marrow transplantation or exposure to radiation, donor lymphocyte transfusion for the purpose of remission of recurrent leukemia, and the like. The therapeutic agent comprising the cell expressing the mutant E3 ubiquitin ligase and CAR or TCR as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

In a particular embodiment, the mutant E3 ubiquitin ligase and CAR or TCR expressing cell is an autologous T-cell from a subject with cancer. Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Other hematological cancers include T-cell or NK-cell lymphoma, for example, but not limited to: peripheral T-cell lymphoma; anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sezary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In one embodiment, the mutant E3 ubiquitin ligase and CAR or TCR expressing cells can be used in an effective amount to treat a host, for example a human, with a lymphoma or lymphocytic or myelocytic proliferation disorder or abnormality. For example, the CAR expressing cells as described herein can be administered to a host suffering from a Hodgkin Lymphoma or a Non-Hodgkin Lymphoma. For example, the host can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, mutant E3 ubiquitin ligase and CAR or TCR expressing cells disclosed herein can be used in an effective amount to treat a host, for example a human, with a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

Alternatively, mutant E3 ubiquitin ligase and CAR or TCR expressing cells disclosed herein can be used in an effective amount to treat a host, for example a human with a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mediastinal large B cell lymphoma; Nodal marginal zone B cell lymphoma (NMZL): Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T-cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In one embodiment, mutant E3 ubiquitin ligase and CAR or TCR expressing cells disclosed herein can be used in an effective amount to treat a host, for example a human with leukemia. For example, the host may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); large granular lymphocytic leukemia; or Adult T-cell chronic leukemia. In one embodiment, the patient suffers from an acute myelogenous leukemia, for example an undifferentiated AML (MO); myeloblastic leukemia (M1: with/without minimal cell maturation); myeloblastic leukemia (M2; with cell maturation), promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

In one embodiment, a mutant E3 ubiquitin ligase and CAR or TCR expressing cell disclosed herein can be used in an effective amount to treat a host, for example a human with a solid tumor. Examples include, but are not limited to, but are not limited to: estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, adenocarcinoma of the colon, adenocarcinoma of the rectum, central nervous system germ cell tumors, teratomas, estrogen receptor-negative breast cancer, estrogen receptor-positive breast cancer, familial testicular germ cell tumors, HER2-negative breast cancer, HER2-positive breast cancer, male breast cancer, ovarian immature teratomas, ovarian mature teratoma, ovarian monodermal and highly specialized teratomas, progesterone receptor-negative breast cancer, progesterone receptor-positive breast cancer, recurrent breast cancer, recurrent colon cancer, recurrent extragonadal germ cell tumors, recurrent extragonadal non-seminomatous germ cell tumor, recurrent extragonadal seminomas, recurrent malignant testicular germ cell tumors, recurrent melanomas, recurrent ovarian germ cell tumors, recurrent rectal cancer, stage III extragonadal non-seminomatous germ cell tumors, stage III extragonadal seminomas, stage III malignant testicular germ cell tumors, stage III ovarian germ cell tumors, stage IV breast cancers, stage IV colon cancers, stage IV extragonadal non-seminomatous germ cell tumors, stage IV extragonadal seminoma, stage IV melanomas, stage IV ovarian germ cell tumors, stage IV rectal cancers, testicular immature teratomas, testicular mature teratomas, estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, metastatic colorectal cancer, metastatic melanoma, or cisplatin-refractory, unresectable germ cell tumors, carcinoma, sarcoma, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, fibrosarcoma, myxosarcoma, chondrosarcoma, osteosarcoma, chordoma, malignant fibrous histiocytoma, hemangiosarcoma, angiosarcoma, lymphangiosarcoma. Mesothelioma, leiomyosarcoma, rhabdomyosarcoma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, IsleT-cell carcinoma, malignant carcinoid, malignant paraganglioma, melanoma, Merkel cell neoplasm, cystosarcoma phylloide, salivary cancers, thymic carcinomas, bladder cancer, and Wilms tumor, a blood disorder or a hematologic malignancy, including, but not limited to, myeloid disorder, lymphoid disorder, leukemia, lymphoma, myelodysplastic syndrome (MDS), myeloproliferative disease (MPD), masT-cell disorder, and myeloma (e.g., multiple myeloma).

In another embodiment, a mutant E3 ubiquitin ligase and CAR or TCR expressing cell disclosed herein can be used in an effective amount to treat a host, for example a human with an autoimmune disorder. Examples include, but are not limited to: Acute disseminated encephalomyelitis (ADEM); Addison's disease; Agammaglobulinemia; Alopecia areata; Amyotrophic lateral sclerosis (Also Lou Gehrig's disease; Motor Neuron Disease); Ankylosing Spondylitis; Antiphospholipid syndrome; Antisynthetase syndrome; Atopic allergy; Atopic dermatitis; Autoimmune aplastic anemia; Autoimmune arthritis; Autoimmune cardiomyopathy; Autoimmune enteropathy; Autoimmune granulocytopenia; Autoimmune hemolytic anemia; Autoimmune hepatitis; Autoimmune hypoparathyroidism; Autoimmune inner ear disease; Autoimmune lymphoproliferative syndrome; Autoimmune myocarditis; Autoimmune pancreatitis; Autoimmune peripheral neuropathy; Autoimmune ovarian failure; Autoimmune polyendocrine syndrome; Autoimmune progesterone dermatitis; Autoimmune thrombocytopenic purpura; Autoimmune thyroid disorders; Autoimmune urticarial; Autoimmune uveitis; Autoimmune vasculitis; Balo disease/Balo concentric sclerosis; Behcet's disease; Berger's disease; Bickerstaffs encephalitis; Blau syndrome; Bullous pemphigoid; Cancer; Castleman's disease; Celiac disease; Chagas disease; Chronic inflammatory demyelinating polyneuropathy; Chronic inflammatory demyelinating polyneuropathy; Chronic obstructive pulmonary disease; Chronic recurrent multifocal osteomyelitis; Churg-Strauss syndrome; Cicatricial pemphigoid; Cogan syndrome; Cold agglutinin disease; Complement component 2 deficiency; Contact dermatitis; Cranial arteritis; CREST syndrome; Crohn's disease; Cushing's Syndrome; Cutaneous leukocytoclastic angiitis; Dego's disease; Dercum's disease; Dermatitis herpetiformis; Dermatomyositis; Diabetes mellitus type 1; Diffuse cutaneous systemic sclerosis; Discoid lupus erythematosus; Dressler's syndrome; Drug-induced lupus; Eczema; Endometriosis; Enthesitis-related arthritis; Eosinophilic fasciitis; Eosinophilic gastroenteritis; Eosinophilic pneumonia; Epidermolysis bullosa acquisita; Erythema nodosum; Erythroblastosis fetalis; Essential mixed cryoglobulinemia; Evan's syndrome; Extrinsic and intrinsic reactive airways disease (asthma); Fibrodysplasia ossificans progressive; Fibrosing alveolitis (or Idiopathic pulmonary fibrosis); Gastritis; Gastrointestinal pemphigoid; Glomerulonephritis; Goodpasture's syndrome; Graves' disease; Guillain-Barré syndrome (GBS); Hashimoto's encephalopathy; Hashimoto's thyroiditis; Hemolytic anemia; Henoch-Schonlein purpura; Herpes gestationis (Gestational Pemphigoid); Hidradenitis suppurativa; Hughes-Stovin syndrome; Hypogammaglobulinemia; Idiopathic inflammatory demyelinating diseases; Idiopathic pulmonary fibrosis; Idiopathic thrombocytopenic purpura; IgA nephropathy; Immune glomerulonephritis; Immune nephritis; Immune pneumonitis; Inclusion body myositis; inflammatory bowel disease; Interstitial cystitis; Juvenile idiopathic arthritis aka Juvenile rheumatoid arthritis; Kawasaki's disease; Lambert-Eaton myasthenic syndrome; Leukocytoclastic vasculitis; Lichen planus; Lichen sclerosus; Linear IgA disease (LAD); Lupoid hepatitis aka Autoimmune hepatitis; Lupus erythematosus; Majeed syndrome; microscopic polyangiitis; Miller-Fisher syndrome; mixed connective tissue disease; Morphea; Mucha-Habermann disease aka *Pityriasis lichenoides* et *varioliformis acuta*; Multiple sclerosis; Myasthenia gravis; Myositis; Ménière's disease; Narcolepsy; Neuromyelitis optica (also Devic's disease); Neuromyotonia; Occular cicatricial pemphigoid; Opsoclonus myoclonus syndrome; Ord's thyroiditis; Palindromic rheumatism; PANDAS (pediatric autoimmune neuropsychiatric disorders associated with *streptococcus*); Paraneoplastic cerebellar degeneration; Paroxysmal nocturnal hemoglobinuria (PNH); Parry Romberg syndrome; Pars planitis; Parsonage-Turner syndrome; Pemphigus vulgaris; Perivenous encephalomyelitis; Pernicious anaemia; POEMS syndrome; Polyarteritis *nodosa*; Polymyalgia rheumatic; Polymyositis; Primary biliary cirrhosis; Primary sclerosing cholangitis; Progressive inflammatory neuropathy; Psoriasis; Psoriatic arthritis; pure red cell aplasia; Pyoderma gangrenosum; Rasmussen's encephalitis; Raynaud phenomenon; Reiter's syndrome; relapsing polychondritis; restless leg syndrome; retroperitoneal fibrosis; rheumatic fever; rheumatoid arthritis; Sarcoidosis; Schizophrenia; Schmidt syndrome; Schnitzler syndrome; Scleritis; Scleroderma; Sclerosing cholangitis; serum sickness; Sjögren's syndrome; Spondyloarthropathy; Stiff person syndrome; Still's disease; Subacute bacterial endocarditis (SBE); Susac's syndrome; Sweet's syndrome; Sydenham chorea; sympathetic ophthalmia; systemic lupus erythematosus; Takayasu's arteritis; temporal arteritis (also known as "gianT-cell arteritis"); thrombocytopenia; Tolosa-Hunt syndrome; transverse myelitis; ulcerative colitis; undifferentiated connective tissue disease; undifferentiated spondyloarthropathy; urticarial vasculitis; vasculitis; vitiligo; viral diseases such as Epstein Barr Virus (EBV), Hepatitis B, Hepatitis C, HIV, HTLV 1, Varicella-Zoster Virus (VZV) and Human Papilloma Virus (HPV); or Wegener's granulomatosis. In some embodiments, the autoimmune disease is an allergic condition, including those from asthma, food allergies, atopic dermatitis, and rhinitis.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In one embodiment, the antigen binding moiety portion of the CAR or TCR of the invention is designed to treat a particular cancer. For example, a CAR or TCR designed to target CD19 can be used to treat cancers and disorders including but are not limited to pre-B ALL (pediatric indication), adult ALL, mantle cell lymphoma, diffuse large B-cell lymphoma, salvage post allogenic bone marrow transplantation, and the like.

In another embodiment, the CAR or TCR can be designed to target CD22 to treat diffuse large B-cell lymphoma.

In one embodiment, cancers and disorders include but are not limited to pre-B ALL (pediatric indication), adult ALL, mantle cell lymphoma, diffuse large B-cell lymphoma, salvage post allogenic bone marrow transplantation, and the like can be treated using a combination of CARs that target CD19, CD20, CD22, and ROR1.

In one embodiment, the CAR or TCR can be designed to target mesothelin to treat mesothelioma, pancreatic cancer, ovarian cancer, and the like.

In one embodiment, the CAR or TCR can be designed to target CD33/IL3Ra to treat acute myelogenous leukemia and the like.

In one embodiment, the CAR or TCR can be designed to target CD30 to treat lymphoma, for example Hodgkin lymphoma, and the like.

In one embodiment, the CAR or TCR can be designed to target c-Met to treat triple negative breast cancer, non-small cell lung cancer, and the like.

In one embodiment, the CAR or TCR can be designed to target PSMA to treat prostate cancer and the like.

In one embodiment, the CAR or TCR can be designed to target Glycolipid F77 to treat prostate cancer and the like.

In one embodiment, the CAR or TCR can be designed to target EGFRvIII to treat gliobastoma and the like.

In one embodiment, the CAR or TCR can be designed to target GD-2 to treat neuroblastoma, melanoma, and the like.

In one embodiment, the CAR or TCR can be designed to target NY-ESO-1 TCR to treat myeloma, sarcoma, melanoma, and the like.

In one embodiment, the CAR or TCR can be designed to target MAGE A3 TCR to treat myeloma, sarcoma, melanoma, and the like.

In one embodiment, the CAR or TCR can be designed to target CEA to treatcolorectal cancer and the like.

In one embodiment, the CAR or TCR can be designed to target erb-B2, erb-B3, and/or erb-B4 to treat breast cancer, and the like.

In one embodiment, the CAR or TCR can be designed to target IL-13R-a2 to treat glioma, glioblastoma, or medulloblastoma, and the like.

However, the invention should not be construed to be limited to solely to the antigen targets and diseases disclosed herein. Rather, the invention should be construed to include any antigenic or ligand target that is associated with a disease where a CAR or TCR having a cytoplasmic binding domain can be used to treat the disease.

Pharmaceutical compositions of mutant E3 ubiquitin ligase and CAR or TCR expressing cells of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "a tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T-cells described herein may be administered at a dosage of $10^4$ to $10^9$ cells/kg body weight, preferably $10^5$ to $10^6$ cells/kg body weight, including all integer values within those ranges. T-cell compositions may also be administered multiple times at these dosages. The cells can be administered by using infusion techniques that are commonly known in immunotherapy (see, e.g., Rosenberg et al., *New Eng. J. of Med.* 319 (1988):1676). The optimal dosage and treatment regime for a particular patient can readily be determined by one skilled in the art of medicine by monitoring the patient for signs of disease and adjusting the treatment accordingly.

The administration of the mutant E3 ubiquitin ligase and CAR or TCR expressing cells may be carried out in any convenient manner, including by aerosol inhalation, injection, ingestion, transfusion, implantation or transplantation. The mutant E3 ubiquitin ligase and CAR or TCR expressing cells described herein may be administered to a patient subcutaneously, intradermally, intratumorally, intranodally, intramedullary, intramuscularly, by intravenous (i.v.) injection, or intraperitoneally. In one embodiment, the mutant E3 ubiquitin ligase and CAR or TCR expressing cells of the present invention are administered to a patient by intradermal or subcutaneous injection. In another embodiment, the mutant E3 ubiquitin ligase and CAR or TCR expressing cells of the present invention are preferably administered by i.v. injection. The mutant E3 ubiquitin ligase and CAR or TCR expressing cells may be injected directly into a tumor, lymph node, or site of infection.

The dosage of the above treatments to be administered to a patient will vary with the precise nature of the condition being treated and the recipient of the treatment. The scaling of dosages for human administration can be performed according to art-accepted practices.

in one embodiment, a method is provided that includes:

(i) removing immune effector cells, for example T-cells, from a patient with a disorder of diseased cells that can be treated by increasing the ability of the patient's T-cells to recognize and bind to the diseased cells;

(ii) transforming the T-cells ex vivo by inserting a gene encoding a CAR or TCR having at least a sequence targeting a diseased cell surface antigen and an intracellular signaling domain amino acid sequence that can be recognized by and bound to a bifunctional compound to form a CAR or TCR T-cell;

(iii) transforming the T-cells ex vivo by inserting a gene encoding a functional, mutant E3 ubiquitin ligase or introducing a genetic mutation into an endogenous cE3 ubiquitin ligase gene, wherein, upon expression, produces a mutant E3 ubiquitin ligase that can be recognized by and bound to a bifunctional compound;

(iii) administering to the patient the CAR or TCR T-cells; and then (iv) administering to the patient, as needed, a bifunctional compound which binds to a) the intracellular signaling domain of the CAR or TCR and b) the mutant E3 ubiquitin ligase in a manner that brings the CAR or TCR into proximity of the mutant E3 ubiquitin ligase, such that the CAR or TCR, or a portion thereof, is ubiquitinated, and then degraded by a proteasome.

By degrading at least a portion of the intracellular signaling domain of the CAR or TCR, the ability of the CAR or TCR to activate the immune effector cell, for example a CAR T-cell, is diminished. As contemplated herein, sufficient degradation of the CAR or TCR occurs wherein the CAR's or TCR's signaling functionality is disrupted.

In certain embodiments, a mutant E3 ubiquitin ligase (e.g., a mutant cereblon described herein) is introduced into the T cell as described herein. In certain embodiments, a mutant E3 ubiquitin ligase (e.g., a mutant cereblon described herein) is introduced into the T cell by introducing one or more mutations (e.g., the mutations described herein) into the endogenous E3 ubiquitin ligase gene of the T cell. In certain embodiments, a mutant E3 ubiquitin ligase (e.g., a mutant cereblon described herein) is introduced into the T cell by replacing the endogenous E3 ubiquitin ligase with the mutant E3 ubiquitin ligase comprising one or more mutations (e.g., the mutations described herein). In certain embodiments, the entire endogenous E3 ubiquitin ligase sequence is replaced with a mutant E3 ubiquitin ligase sequence comprising one or more mutations. In certain embodiments, only a portion of the endogenous E3 ubiquitin ligase (e.g., the 100 amino acid residues at the C-terminal of an endogenous cereblon) is replaced with a corresponding portion of a mutant E3 ubiquitin ligase comprising one or more mutations. In certain embodiments, a mutant E3 ubiquitin ligase (e.g., a mutant cereblon described herein) is introduced into the T cell by expressing (e.g., overexpressing) the mutant E3 ubiquitin ligase comprising one or more mutations (e.g., the mutations described herein) in the T cell.

In certain embodiments, a mutant cereblon (e.g., a mutant cereblon described herein) is introduced into the T cell as described herein. In certain embodiments, a mutant cereblon (e.g., a mutant cereblon described herein) is introduced into the T cell by introducing one or more mutations (e.g., the mutations described herein) into the endogenous cereblon of the T cell. In certain embodiments, a mutant cereblon (e.g., a mutant cereblon described herein) is introduced into the T cell by replacing the endogenous cereblon with the mutant cereblon comprising one or more mutations (e.g., the mutations described herein). In certain embodiments, the entire endogenous cereblon sequence is replaced with a mutant cereblon comprising one or more mutations. In certain embodiments, only a portion of the endogenous cereblon (e.g., the 100 amino acid residues at the C-terminal of the endogenous cereblon) is replaced with a corresponding portion of a mutant cereblon comprising one or more mutations. In certain embodiments, a mutant cereblon (e.g., a mutant cereblon described herein) is introduced into the T cell by expressing (e.g., overexpressing) the mutant cereblon comprising one or more mutations (e.g., the mutations described herein) in the T cell.

In certain embodiments, the antigen receptor of the T cell is a chimeric antigen receptor ("CAR"). CARs (also known as chimeric T cell receptors, artificial T cell receptors, and chimeric immunoreceptors) are proteins that are engineered to allow the T cells to recognize an antigen on a target cell (e.g., a cancer cell). Methods of designing and making CARs are well described in the art. In certain embodiments, the CAR comprises a polypeptide of an antigen receptor fused with a target protein of the present application.

The present application also relates to a method of modulating the number of T cells in a subject in need thereof, comprising:

(a) obtaining a T cell from the subject;

(b) introducing a mutant cereblon into the T cell;

(c) introducing the T cell from step (b) into the subject; and (d) administering to the subject a bifunctional compound of the present application, wherein the bifunctional compound comprises a Targeting Ligand that is capable of binding to an antigen receptor of the T cell.

In certain embodiments, the antigen receptor of the T cell is a CAR. In certain embodiments, the CAR comprises a polypeptide of an antigen receptor fused with a target protein of the present application.

In certain embodiments, the T cell is introduced to the subject parenterally (e.g., intravenously, intraarterially, intraosseously, intracerebrally, intracerebroventricularly, or intrathecally). In certain embodiments, the T cell is introduced to the subject intravenously or intraarterially.

In certain embodiments, after a mutant cereblon is introduced to the T cell, the T cell is propagated (i.e., multiplied in number) before being introduced to the subject. Methods of propagating T cells are known in the art.

Regulating Proteins of Interest

In one aspect, provided herein is a method of treating a subject suffering from a disorder associated with the overexpression, toxic accumulation, or gain of function of a protein of interest comprising:

(i) transforming an affected cell by inserting a nucleic acid encoding a functional, mutant E3 ubiquitin ligase, for example a mutant cereblon, or introducing a genetic mutation into an endogenous E3 ubiquitin ligase gene, wherein upon expression a mutant E3 ubiquitin ligase that can be recognized by and bound to a bifunctional compound is produced; and (ii) administering to the subject, as needed, a bifunctional compound, wherein the bifunctional compound binds to a) the protein of interest and b) the mutant E3 ubiquitin ligase in a manner that brings the protein of interest into proximity of the mutant E3 ubiquitin ligase, such that the protein of interest is ubiquitinated, and then degraded by a proteasome. The protein of interest targeted for degradation can be one implicated in a genetic disorder. By way of a non-limiting example, a protein encoded by a mutated gene, for example, alpha-1 antitrypsin (A1AT), may be targeted for degradation by a bifunctional compound. By targeting A1AT, the function of the mutated A1AT can be regulated or modulated through bifunctional compound administration, allowing the cell to maintain some function of the A1AT endogenous protein while reducing the effects of A1AT over-expression. In one embodiment, the protein of interest to be targeted for degradation includes, but is not limited to, alpha-1 antitrypsin (A1AT), β-catenin (CTNNB1), apolipoprotein B (APOB), angiopoietin-like protein 3 (ANGPTL3), proprotein convertase subtilisin/kexin type 9 (PCSK9), apolipoprotein C3 (APOC3), low density lipoprotein receptor (LDLR), C-reactive protein (CRP), apolipoprotein a (Apo (a)), Factor VII, Factor XI, antithrombin III (SERPINC1), phosphatidylinositol glycan class A (PIG-A), C5, alpha-1 antitrypsin (SERPINA1), hepcidin regulation (TMPRSS6), (delta-aminolevulinate synthase 1 (ALAS-1), acylCaA:diacylglycerol acyltransferase (DGAT), miR-122, miR-21, miR-155, miR-34a, prekallikrein (KLKB1), connective tissue growth factor (CCN2), intercellular adhesion molecule 1 (ICAM-1), glucagon receptor (GCGR), glucorticoid receptor (GCCR), protein tyrosine phosphatase (PTP-1B), c-Raf kinase (RAF1), fibroblast growth factor receptor 4 (FGFR4), vascular adhesion molecule-1 (VCAM-1), very late antigen-4 (VLA-4), transthyretin (TTR), survival motor neuron 2 (SMN2), growth hormone receptor (GHR), dystophia myotonic protein kinase (DMPK), cellular nucleic acid-binding protein (CNBP or ZNF9), clusterin (CLU), eukaryotic translation initiation factor 4E (eIF-4e), MDM2, MDM4, heat shock protein 27 (HSP 27), signal transduction and activator of transcription 3 protein (STAT3), vascular endothelial growth factor (VEGF), kinesin spindle protein (KIF11), hepatitis B genome, the androgen receptor (AR), Atonal homolog 1 (ATOH1), vascular endothelial growth factor receptor 1 (FLT1), retinoschism 1 (RS1), retinal pigment epithelium-specific 65 kDa protein (RPE65), Rab escort protein 1 (CHM), and the sodium channel, voltage gated, type X, alpha subunit (PN3 or SCN10A). Non-limiting examples of particular genes involved in disorders that may be targeted for dTAG insertion include by way of non-limiting example, alpha-1 antitrypsin (A1AT), apolipoprotein B (APOB), angiopoietin-like protein 3 (ANGPTL3), proprotein convertase subtilisin/kexin type 9 (PCSK9), apolipoprotein C3 (APOC3), catenin (CTNNB1), low density lipoprotein receptor (LDLR), C-reactive protein (CRP), apolipoprotein a (Apo(a)), Factor VII, Factor XI, antithrombin III (SERPINC1), phosphatidylinositol glycan class A (PIG-A), C5, alpha-1 antitrypsin (SERPINA1), hepcidin regulation (TMPRSS6), (delta-aminolevulinate synthase 1 (ALAS-1), acylCaA:diacylglycerol acyltransferase (DGAT), miR-122, miR-21, miR-155, miR-34a, prekallikrein (KLKB1), connective tissue growth factor (CCN2), intercellular adhesion molecule 1 (ICAM-1), glucagon receptor (GCGR), glucorticoid receptor (GCCR), protein tyrosine phosphatase (PTP-1B), c-Raf kinase (RAF1), fibroblast growth factor receptor 4 (FGFR4), vascular adhesion molecule-1 (VCAM-1), very late antigen-4 (VLA-4), transthyretin (TTR), survival motor neuron 2 (SMN2), growth hormone receptor (GHR), dystophia myotonic protein kinase (DMPK), cellular nucleic acid-binding protein (CNBP or ZNF9), clusterin (CLU), eukaryotic translation initiation factor 4E (eIF-4e), MDM2, MDM4, heat shock protein 27 (HSP 27), signal transduction and activator of transcription 3 protein (STAT3), vascular endothelial growth factor (VEGF), kinesin spindle protein (KIF11), hepatitis B genome, the androgen receptor (AR), Atonal homolog 1 (ATOH1), vascular endothelial growth factor receptor 1 (FLT1), retinoschism 1 (RS1), retinal pigment epithelium-specific 65 kDa protein (RPE65), Rab escort protein 1 (CHM), and the sodium channel, voltage gated, type X, alpha subunit (PN3 or SCN10A). Additional proteins of interest that may be targeted include proteins associated with gain of function mutations, for example, cancer causing proteins.

In particular embodiments, the protein of interest for targeting is apoB-100, ANGPTL3, PCSK9, APOC3, CRP, ApoA, Factor XI, Factor VII, antithrombin III, phosphatidylinositol glycan class A (PIG-A), the C5 component of complement, Alpha-1-antitrypsin (A1AT), TMPRSS6, ALAS-1, DGAT-2, KLB1, CCN2, ICAM, glucagon receptor, glucocorticoid receptor, PTP-1B, FGFR4, VCAM-1, VLA-4, GCCR, TTR, SMN1, GHR, DMPK, or NAV1.8.

In one embodiment, the protein of interest is associated with Alzheimer's disease (Amyloid β peptide (Aβ); Tau protein), Cerebral β-amyloid angiopathy (Amyloid β peptide (Aβ)), Retinal ganglion cell degeneration in glaucoma (Amyloid β peptide (Aβ)), Prion diseases (Prion protein), Parkinson's disease and other synucleinopathies (α-Synuclein), Tauopathies (Microtubule-associated protein tau (Tau protein)), Frontotemporal lobar degeneration (FTLD) (Ubi+, Tau−) (TDP-43), FTLD-FUS (Fused in sarcoma (FUS) protein), Amyotrophic lateral sclerosis (ALS) (Superoxide dismutase. TDP-43, FUS), Huntington's disease and other triplet repeat disorders (Proteins with tandem glutamine expansions), Familial British dementia (ABri), Familial Danish dementia (Adan), Hereditary cerebral hemorrhage with amyloidosis (Icelandic) (HCHWA-I) (Cystatin C), CADASIL (Notch3), Alexander disease (Glial fibrillary acidic protein (GFAP)), Seipinopathies (Seipin), Familial amyloidotic neuropathy, Senile systemic amyloidosis (Transthyretin), Serpinopathies (Serpins), AL (light chain) amyloidosis (primary systemic amyloidosis) (Monoclonal immunoglobulin light chains), AH (heavy chain) amyloidosis (Immunoglobulin heavy chains), AA (secondary) amyloidosis (Amyloid A protein), Type II diabetes (Islet amyloid polypeptide (IAPP; amylin)), Aortic medial amyloidosis (Medin (lactadherin)), ApoAI amyloidosis (Apolipoprotein AI), ApoAII amyloidosis (Apolipoprotein AII), ApoAIV amyloidosis (Apolipoprotein AIV), Familial amyloidosis of the Finnish type (FAF) (Gelsolin), Lysozyme amyloidosis (Lysozyme), Fibrinogen amyloidosis (Fibrinogen), Dialysis amyloidosis (Beta-2 microglobulin), Inclusion body myositis/myopathy (Amyloid β peptide (Aβ)), Cataracts (Crystallins), Retinitis pigmentosa with rhodopsin mutations (rhodopsin), Medullary thyroid carcinoma (Calcitonin), Cardiac atrial amyloidosis (Atrial natriuretic factor), Pituitary prolactinoma (Prolactin), Hereditary lattice corneal dystrophy (Keratoepithelin), Cutaneous lichen amyloidosis (Keratins), Mallory bodies (Keratin intermediate filament proteins), Corneal lactoferrin amyloidosis (Lactoferrin), Pulmonary alveolar proteinosis (Surfactant protein C (SP-C)), Odontogenic (Pindborg) tumor amyloid (Odontogenic ameloblast-associated protein), Seminal vesicle amyloid (Semenogelin I), Cystic Fibrosis (cystic fibrosis transmembrane conductance regulator (CFTR) protein), Sickle cell disease (Hemoglobin), and Critical illness myopathy (CIM) (Hyperproteolytic state of myosin ubiquitination).

In one aspect of the invention, provided herein is a transgenic animal, for example, a mouse, that expresses a mutant E3 ubiquitin ligase as described above. In certain embodiments, the transgenic animal expresses a mutant cereblon. The mutant E3 ubiquitin ligase is incorporated into a transgenic animal by transfection of a transgene containing the genetic sequence of the mutant E3 ubiquitin ligase into a fertilized egg or embryonic stem cell of the target organism. The mutant E3 ubiquitin ligase may be expressed in specific tissues within the animal by inclusion of a tissue specific promoter within the transgene used during the transgenesis. Exposure of the transgenic animal with tissue specific expression expression of the mutant E3 ubiquitin ligase to a bifunctional compound of the present invention would lead to tissue-specific degradation of the protein of interest within the transgenic animal. Creation of transgenic animals is known in the art. In some embodiments, the transgenic animal expressing the mutant E3 ubiquitin ligase is created by a microinjection method. The transgenic animal is created using a microinjection method by superovulating a female animal; collecting the eggs from the female and fertilizing them in vitro; injecting a transgene containing solution into the male pronucleus of the fertilized eggs using a micropipette; incubating the eggs containing the transgenes until the eggs reach a two-cell stage; and implanting the eggs into the uterus of a pseudo-pregnant female animal. In one embodiment, the transgenic animal expressing a mutant cereblon is created using a microinjection method. In some embodiments, the transgenic animal expressing the mutant E3 ubiquitin ligase is created by manipulation of embryonic stem cells. The transgene containing the genetic sequence for the mutant E3 ubiquitin ligase can be incorporated into embryonic stem cells by a number of methods including, but not limited to, microinjection, electroporation, or by using a retrovirus. The transgenic animal is created by a method involving the manipulation of embryonic stem cells by obtaining embryonic stem cells from the inner cell mass of a blastocyst; incorporation the transgene into the embryonic stem cells by microinjection, electroporation, or by using a retrovirus; growing the embryonic stem cells in vitro; and inserting the embryonic stems cells into a blastocyst and implanting the blastocyst into a host's uterus. In one embodiment, the transgenic animal expressing a mutant cereblon is created by a methods involving microinjection of the transgene into embryonic stem cells. In another embodiment, the transgenic animal expressing a mutant cereblon is created by a method using electroporation of embryonic stem cells. In another embodiment, the transgenic animal expressing a mutant cereblon is created by using a method where embryonic stem cells are infected with a retrovirus.

EXAMPLES

Analytical Methods, Materials, and Instrumentation

Reactions were monitored using a Waters Acquity UPLC/MS system (Waters PDA eλ Detector, QDa Detector, Sample manager—FL, Binary Solvent Manager) using an Acquity UPLC® BEH C18 column (2.1×50 mm, 1.7 μm particle size): solvent gradient=90% A at 0 min, 1% A at 1.8 min; solvent A=0.1% formic acid in Water; solvent B=0.1% formic acid in Acetonitrile; flow rate: 0.6 mL/min. Reaction products were purified by flash column chromatography using CombiFlash®Rf with Teledyne Isco RediSep® Rf High Performance Gold or Silicycle SiliaSep™ High Performance columns (4 g, 12 g, 24 g, 40 g or 80 g), a Waters HPLC system using SunFire™ Prep C18 column (19×100 mm, 5 μm particle size): solvent gradient=80% A at 0 min, 5% A at 25 min; solvent A=0.035% TFA in Water; solvent B=0.035% TFA in MeOH; flow rate: 25 mL/min (Method A), and a Waters Acquity UPLC/MS system (Waters PDA eλ Detector, QDa Detector, Sample manager—FL, Binary Solvent Manager) using Acquity UPLC® BEH C18 column (2.1×50 mm, 1.7 μm particle size): solvent gradient=80% A at 0 min, 5% A at 2 min; solvent A=0.1% formic acid in Water; solvent B=0.1% formic acid in Acetonitrile; flow rate: 0.6 mL/min (method B). The purity of all compounds was over 95% and was analyzed with a Waters LC/MS system. $^1$H NMR was obtained using a 300, 400 or 500 MHz Bruker Avance III nuclear magnetic resonance spectrometer. Chemical shifts are reported relative to dimethyl sulfoxide (δ=2.50) for $^1$H NMR. Splitting is reported as (br=broad, s=singlet, d=doublet, t=triplet, q=quartet, m=multiplet).

Abbreviations used in the following examples and elsewhere herein are:
atm atmosphere
DIPEA N,N-diisopropylethylamine
DMF N,N-dimethylformamide
ESI electrospray ionization
EtOAc ethyl acetate
HCl hydrochloric acid
HATU 1-[bis(dimethylamino)methylene]-1H-1,2,3-triazolo[4,5-b]pyridinium 3-oxide hexafluorophosphate
HPLC high-performance liquid chromatography
LCMS liquid chromatography-mass spectrometry
MeOH methanol
MHz megahertz
MS mass spectrometry
NMP N-methyl-2-pyrrolidone
NMR nuclear magnetic resonance
ppm parts per million Example 1: Synthesis of Intermediate (2-1)

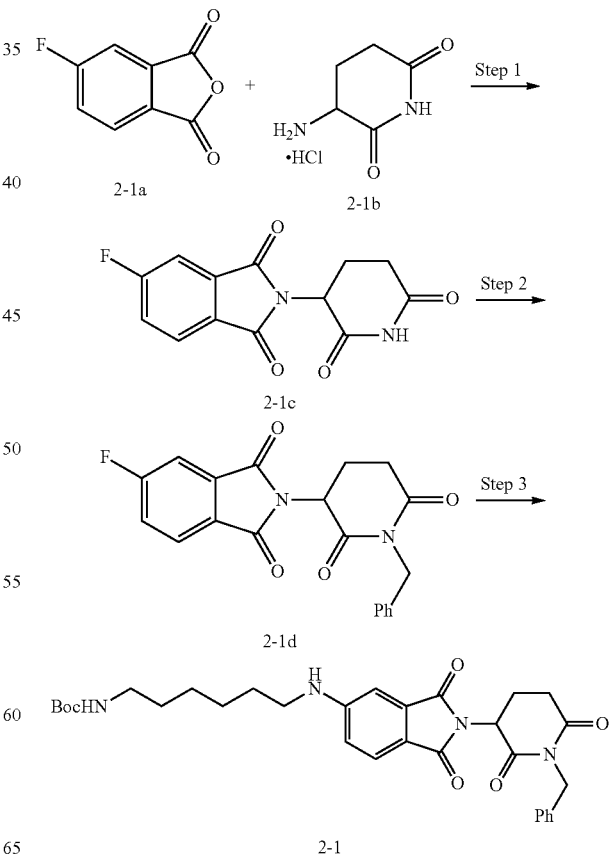

Step 1. 2-(2,6-Dioxopiperidin-3-yl)-5-fluoroisoindoline-1,3-dione (2-1c)

In a 100 mL round-bottomed flask, a mixture of 4-fluorophthalic anhydride (2-1a, 2.0 g, 12.0 mmol, 1 equiv), potassium acetate (3.66 g, 37.3 mmol, 3.1 equiv) and 3-aminopiperidine-2,6-dione hydrochloride (2-1b, 2.2 g, 33.2 mmol, 1.1 equiv) in acetic acid (30 mL, 0.4 M) was heated to 90° C. overnight. The reaction mixture was cooled to room temperature, diluted to a volume of 100 mL with water, and subsequently cooled on ice for 30 minutes. The resulting slurry was transferred to 50 mL Falcon tubes and centrifuged at 3500 rpm for 5 minutes. The supernatant was discarded and the black solid was transferred to a 250 mL round-bottomed flask with methanol and concentrated in vacuo. The crude product was purified by flash column chromatography on silica gel (eluting with 15:1 $CH_2Cl_2$: MeOH) to afford the title compound 2-1c as a white solid (2.93 g, 88%). $^1$H NMR (500 MHz, DMSO-$d_6$) δ 11.14 (s, 1H), 8.02 (dd, J=8.3, 4.5 Hz, 1H), 7.86 (dd, J=7.4, 2.3 Hz, 1H), 7.77-7.68 (m, 1H), 5.17 (dd, J=13.0, 5.4 Hz, 1H), 2.90 (ddd, J=17.2, 13.9, 5.5 Hz, 1H), 2.66-2.52 (m, 2H), 2.14-2.03 (m, 1H); MS (ESI) calcd for $C_{13}H_{10}FN_2O_4$ [M+H]$^+$ 277.06, found 277.24.

Step 2. 2-(1-Benzyl-2,6-dioxopiperidin-3-yl)-5-fluoroisoindoline-1,3-dione (2-1d)

To a stirred solution of 2-(2,6-dioxopiperidin-3-yl)-5-fluoroisoindoline-1,3-dione (2-1c, 200 mg, 0.724 mmol, 1 equiv) in DMF (3.6 mL, 0.2 M) was added potassium iodide (132 mg, 0.796 mmol, 1.1 equiv), potassium carbonate (110 mg, 0.796 mmol, 1.1 equiv) and benzyl bromide (146 µL, 1.23 mmol, 1.7 equiv), and the resulting mixture was heated to 50° C. for two days. The reaction mixture was then cooled to room temperature and taken up in ethyl acetate (30 mL). The organic layer was washed with water (2×25 mL) and brine (3×20 mL), dried over sodium sulfate, filtered, and concentrated in vacuo. The crude product was purified by flash column chromatography on silica gel (eluting with 0→5% MeOH in $CH_2Cl_2$) to give the title compound 2-1d as a white solid (128 mg, 48%). $^1$H NMR (500 MHz, CDCl$_3$) δ 7.85 (dd, J=8.2, 4.4 Hz, 1H), 7.52 (dd, J=7.0, 2.3 Hz, 1H), 7.43-7.36 (m, 1H), 7.36-7.31 (m, 2H), 7.29-7.24 (m, 2H), 7.23-7.18 (m, 1H), 5.04 (d, J=14.0 Hz, 1H), 4.99 (dd, J=12.6, 5.3 Hz, 1H), 4.88 (d, J=14.0 Hz, 1H), 3.01-2.89 (m, 1H), 2.85-2.68 (m, 2H), 2.11-2.04 (m, 1H). MS (ESI) [M+H]$^+$: 367.34.

Step 3. tert-Butyl (6-((2-(1-benzyl-2,6-dioxopiperidin-3-yl)-1,3-dioxoisoindolin-5-yl)amino) hexyl)-carbamate (2-1)

To stirred solution of 2-(1-benzyl-2,6-dioxopiperidin-3-yl)-5-fluoroisoindoline-1,3-dione (2-1d, 128 mg, 0.349 mmol, 1 equiv) in NMP (1.75 mL, 0.2 M) was added DIPEA (122 µL, 0.700 mmol, 2 equiv) and N-boc-1,6-hexanediamine (79 µL, 0.349 mmol, 1 equiv), and the resulting mixture was heated to 90° C. overnight. The reaction mixture was then cooled to room temperature and taken up in ethyl acetate (20 mL) and water (20 mL). The organic layer was washed with brine (3×15 mL), dried over sodium sulfate, filtered, and concentrated in vacuo. The crude product was purified by flash column chromatography on silica gel (eluting with 0-10% MeOH in $CH_2Cl_2$) to give the title compound 2-1 as a yellow film (72 mg, 37%). MS (ESI) [M+H]$^+$: 563.49.

Example 2: N-(6-((2-(1-Benzyl-2,6-dioxopiperidin-3-yl)-1,3-dioxoisoindolin-5-yl)amino) hexyl)-2-((S)-4-(4-chlorophenyl)-2,3,9-trimethyl-6H-thieno[3,2-f] [1,2,4]triazolo[4,3-a][1,4]diazepin-6-yl)acetamide (I-1)

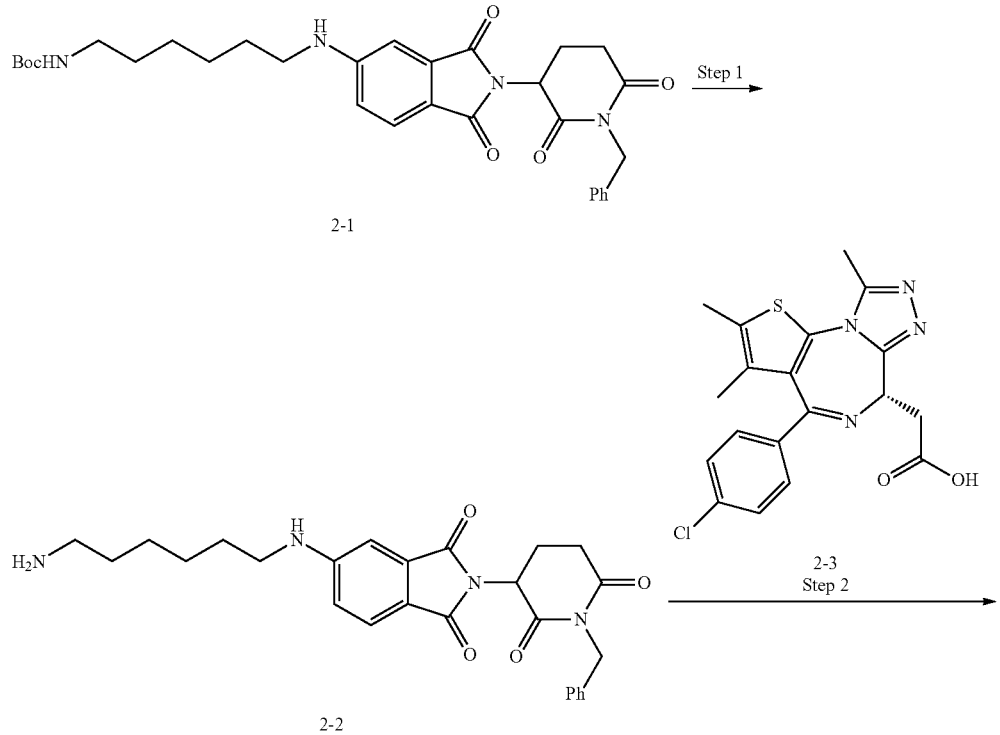

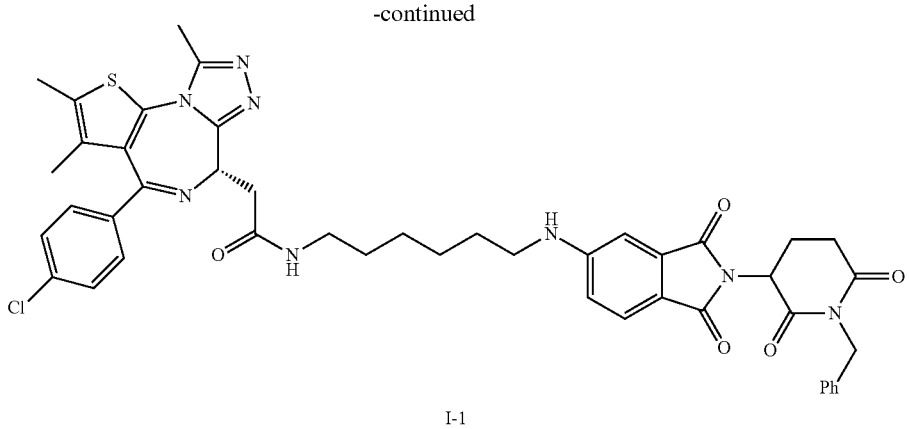

I-1

Step 1. 5-((6-Aminohexyl)amino)-2-(1-benzyl-2,6-dioxopiperidin-3-yl)isoindoline-1,3-dione (2-2)

To a 4 mL vial containing tert-butyl (6-((2-(1-benzyl-2,6-dioxopiperidin-3-yl)-1,3-dioxoisoindolin-5-yl)amino)hexyl)-carbamate (2-1, 76 mg, 0.133 mmol, 1 equiv) was added hydrochloric acid (4 M in dioxane, 300 µL), and the resulting mixture was stirred at room temperature for 1 hour. Upon completion, the volatiles were removed in vacuo, and the crude product was carried onto the next step without further purification.

Step 2. N-(6-((2-(1-Benzyl-2,6-dioxopiperidin-3-yl)-1,3-dioxoisoindolin-5-yl)amino) hexyl)-2-((S)-4-(4-chlorophenyl)-2,3,9-trimethyl-6H-thieno[3,2-f][1,2,4]triazolo[4,3-a][1,4]diazepin-6-yl)acetamide (I-1)

To 5-((6-aminohexyl)amino)-2-(1-benzyl-2,6-dioxopiperidin-3-yl)isoindoline-1,3-dione (2-2) in DMF (666 µL, 0.2 M) was added (S)-2-(4-(4-chlorophenyl)-2,3,9-trimethyl-6H-thieno[3,2-f][1,2,4]triazolo[4,3-a][1,4]diazepin-6-yl)acetic acid (2-3, 54 mg, 0.133 mmol, 1 equiv), HATU (51 mg, 0.133 mmol, 1 equiv) and DIPEA (116 µL, 0.666 mmol, 5 equiv), and the resulting mixture was stirred at room temperature overnight. The reaction mixture was taken up in ethyl acetate (25 mL), and the organic layer was washed with saturated aqueous sodium bicarbonate (15 mL), water (15 mL), and brine (3×15 mL), dried over sodium sulfate, filtered, and concentrated in vacuo. The crude residue was purified by flash column chromatography on silica gel (eluting with 0→5% MeOH in $CH_2Cl_2$) to give the title bifunctional compound I-1 as a bright yellow solid (27 mg, 24%). $^1$H NMR (500 MHz, $CDCl_3$) δ 7.56 (d, J=8.3 Hz, 1H), 7.41 (d, J=8.2 Hz, 2H), 7.38-7.31 (m, 5H), 7.31-7.20 (m, 3H), 6.96 (d, J=2.1 Hz, 1H), 6.79 (t, J=5.7 Hz, 1H), 6.75 (dd, J=8.3, 2.2 Hz, 1H), 5.07 (dd, J=14.1, 1.5 Hz, 1H), 4.99-4.85 (m, 2H), 4.70-4.61 (m, 1H), 3.62 (dd, J=14.4, 8.5 Hz, 1H), 3.36 (ddd, J=13.8, 8.5, 6.0 Hz, 2H), 3.27 (d, J=13.2, 6.3 Hz, 1H), 3.21-3.12 (m, 2H), 3.02-2.91 (m, 1H), 2.88-2.73 (m, 2H), 2.69 (s, 3H), 2.39 (d, J=6.1 Hz, 3H), 2.14-2.05 (m, 1H), 1.67 (s, 3H), 1.61 (q, J=7.0 Hz, 2H), 1.55 (q, J=6.7 Hz, 2H), 1.40 (ddd, J=22.4, 12.7, 6.9 Hz, 4H). MS (ESI) [M+H]$^+$: 845.53.

Example 3: Synthesis of Intermediate (2-1)

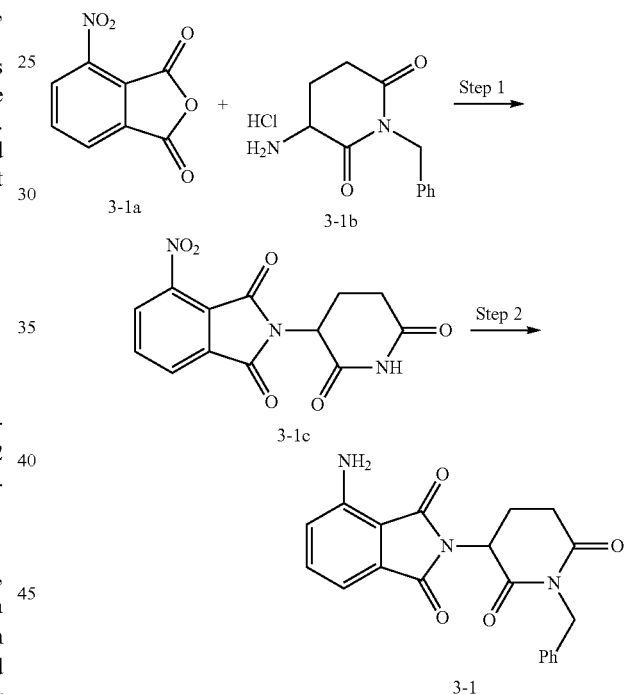

Step 1. 2-(1-Benzyl-2,6-dioxopiperidin-3-yl)-4-nitroisoindoline-1,3-dione (3-1c)

In a 20 mL glass vial, a mixture of 3-nitrophthalic anhydride (3-1a, 105 mg, 0.544 mmol, 1 equiv), potassium acetate (165 mg, 1.69 mmol, 3.1 equiv) and 3-amino-1-benzylpiperidine-2,6-dione hydrochloride (3-1b, 152 mg, 0.598 mmol, 1.1 equiv) in acetic acid (1.8 mL, 0.3 M) was stirred at room temperature overnight. The resulting purple reaction mixture was diluted to 20 mL with water, and subsequently cooled on ice for 30 minutes. The resulting slurry was transferred to 50 mL Falcon tubes and centrifuged at 3500 rpm for 5 minutes. The supernatant was discarded and the black solid was transferred to a 250 mL round-bottomed flask with methanol and concentrated in vacuo. The residue was purified by flash column chromatography on silica gel (eluting with 9:1 CH$_2$Cl$_2$:MeOH) to afford the title compound 3-1c as a purple solid (48 mg, 22%). $^1$H NMR (500 MHz, Methanol-d$_4$) δ 8.23-8.13 (m, 2H), 7.60 (1, J=7.9 Hz, 1H), 7.28-7.14 (m, 5H), 5.06-4.95 (m, 1H), 4.82 (s, 2H), 2.88-2.76 (m, 2H), 2.52-2.40 (m, 1H), 1.96-1.88 (m, 1H); MS (ESI) calcd for C$_{20}$H$_{16}$N$_3$O$_6$. MS (ESI) [M+H]$^+$: 394.29.

Step 2. 4-Amino-2-(l-benzyl-2,6-dioxopiperidin-3-yl)isoindoline-1,3-dione (3-1)

A solution of 2-(1-benzyl-2,6-dioxopiperidin-3-yl)-4-nitroisoindoline-1,3-dione (3-1c, 48 mg, 0.122 mmol), palladium(II) acetate (2.7 mg, 0.0122 mmol, 10 mol %), and potassium fluoride (15 mg, 0.244 mmol, 2 equiv) in THF: water (8:1) (1.2 mL, 0.1 M) was stirred at room temperature. Triethylsilane (78 μL, 0.488 mmol, 4 equiv) was then added slowly, and the resulting black solution was stirred at room temperature for 1 hour. The reaction mixture was filtered through a pad of celite, which was washed excessively with ethyl acetate. The filtrate was concentrated in vacuo and the residue was purified by flash column chromatography on silica gel (eluting with 0→100% EtOAc in hexanes) to afford the title compound as a yellow powder (7 mg, 66%). $^1$H NMR (500 MHz, DMSO-d$_6$) δ 7.47 (dd, J=8.4, 7.0 Hz, 1H), 7.35-7.28 (m, 2H), 7.27-7.21 (m, 3H), 7.01 (dd, J=7.7, 5.6 Hz, 2H), 6.53 (s, 2H), 5.26 (dd, J=13.0, 5.4 Hz, 1H), 4.92 (d, J=14.8 Hz, 1H), 4.79 (d, J=14.9 Hz, 1H), 3.08 (ddd, J=17.2, 14.0, 5.4 Hz, 1H), 2.80 (ddd, J=17.2, 4.4, 2.5 Hz, 1H), 2.68-2.55 (m, 1H), 2.13-2.03 (m, 1H); MS (ESI) calcd for C$_{20}$H$_{18}$N$_3$O$_4$. MS (ESI) [M+H]$^+$: 364.34.

Biological Studies
Materials and Methods

Mutagenesis was performed on CRBN cDNA contained in pENTR223 (Harvard Plasmid Repository HsCD00288047) using the Q5 Site-Directed Mutagenesis Kit (New England Biolabs). The mutant and wildtype CRBN cDNA was transferred to the tetracycline-inducible pLXI401 vector using LR Clonase II (New England Biolabs). For lentiviral packaging, HEK293T cells were transfected with this vector, along with pMD2.G (Addgene #12259) and psPAX2 (Addgene #12260) in Lipofectamine-2000 and Opti-MEM (Thermo Fisher Scientific) for 8 hours. The media was replaced with DMEM (Thermo Fisher Scientific) and harvested after 48 and 72 hours. The virus-containing media was filtered through 0.45 μm Steriflip units (Millipore) and concentrated using Lenti-X Concentrator solution (Clontech). 3 million CRBN null HEK293T cells were transduced with 300 μL of this virus with 8 μg/mL polybrene (Millipore) in a 12-well plate, spinning at 2000 rpm for 1 hour. Successfully transduced cells were selected by adding 4 μg/mL puromycin (Thermo Fisher Scientific) for 3 days.

Figure 1B:
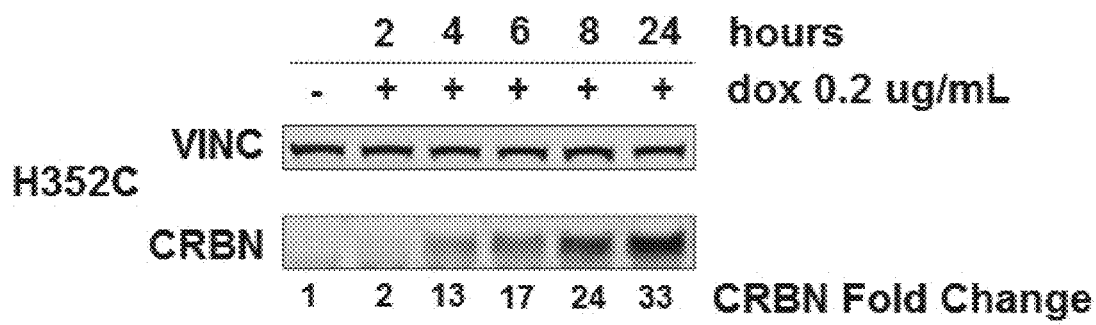
Figure 1C:
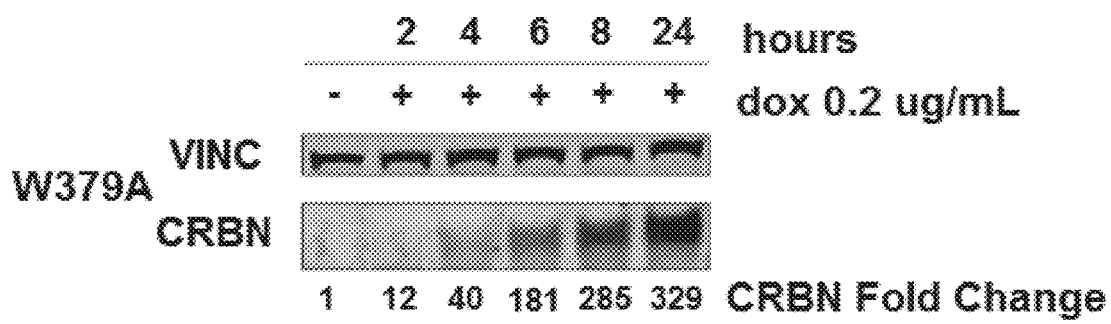
Figure 1D:
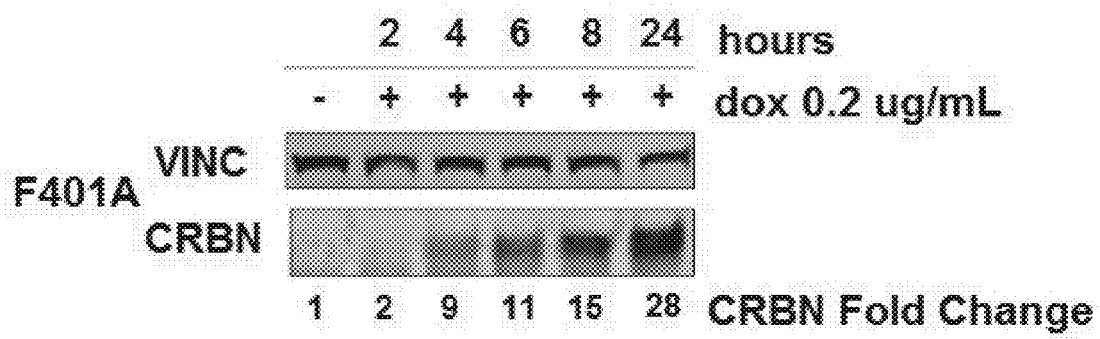
Figure 1E:
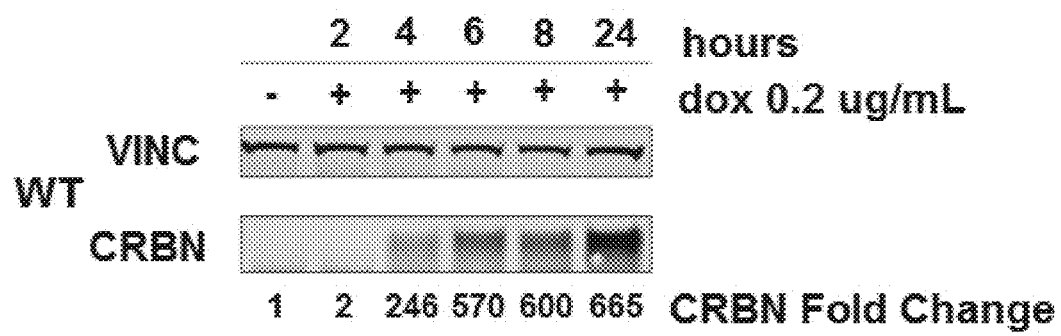

Example 4. Expression of Mutant and Wildtype CRBN in Cells Treated with Doxycycline 250,000-500,000 cells/well in a 6-well plate were treated with PBS or 0.2 μg/mL doxycycline. CRBN signal was normalized to Vinculin signal, and the fold induction for each condition over the PBS-treated condition was determined. For 24 hours, N350C CRBN, H352C CRBN, W379A CRBN, F401A CRBN, and WT CRBN levels were detected by immunoblotting at various time points. The results are shown in FIGS. 1A-1E.

Example 5. Degradation of BRD4 by Bifunctional Compound I-1

Figure 2A:
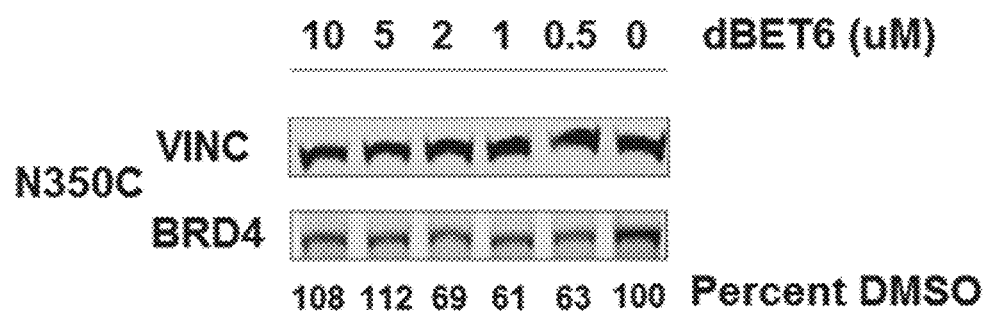
FIG. 2A-2E are immunoblots displaying levels of BRD4 in cells harboring mutant or WT CRBN after treatment with 0.2 µg/mL doxycycline for 16 hours, followed by treatment for four hours with DMSO or dBET6 at the concentrations shown.
Figure 2B:
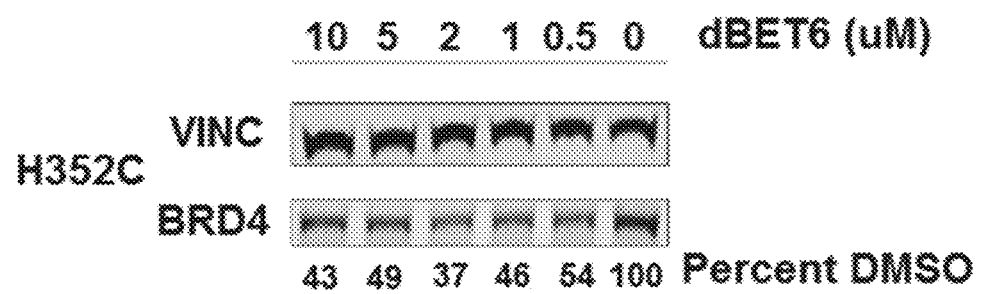
Figure 2C:
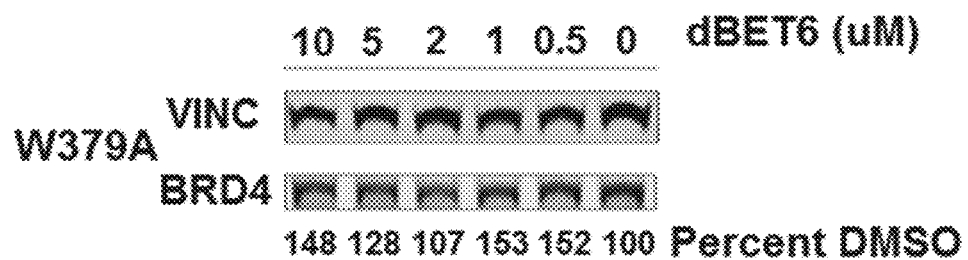
Figure 2D:
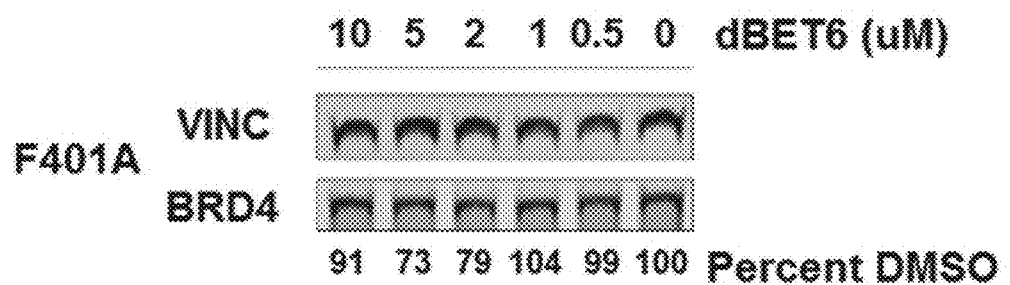
Figure 2E:
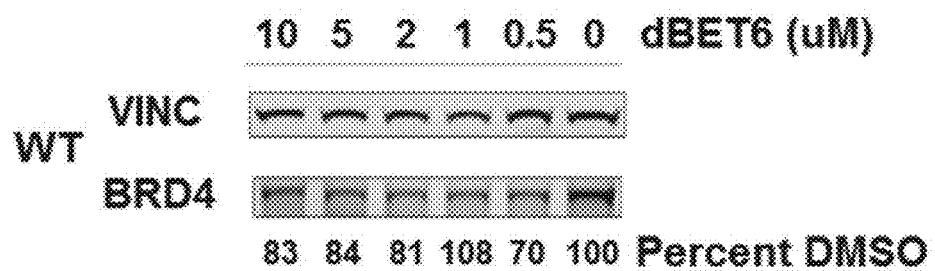
Figure 3:
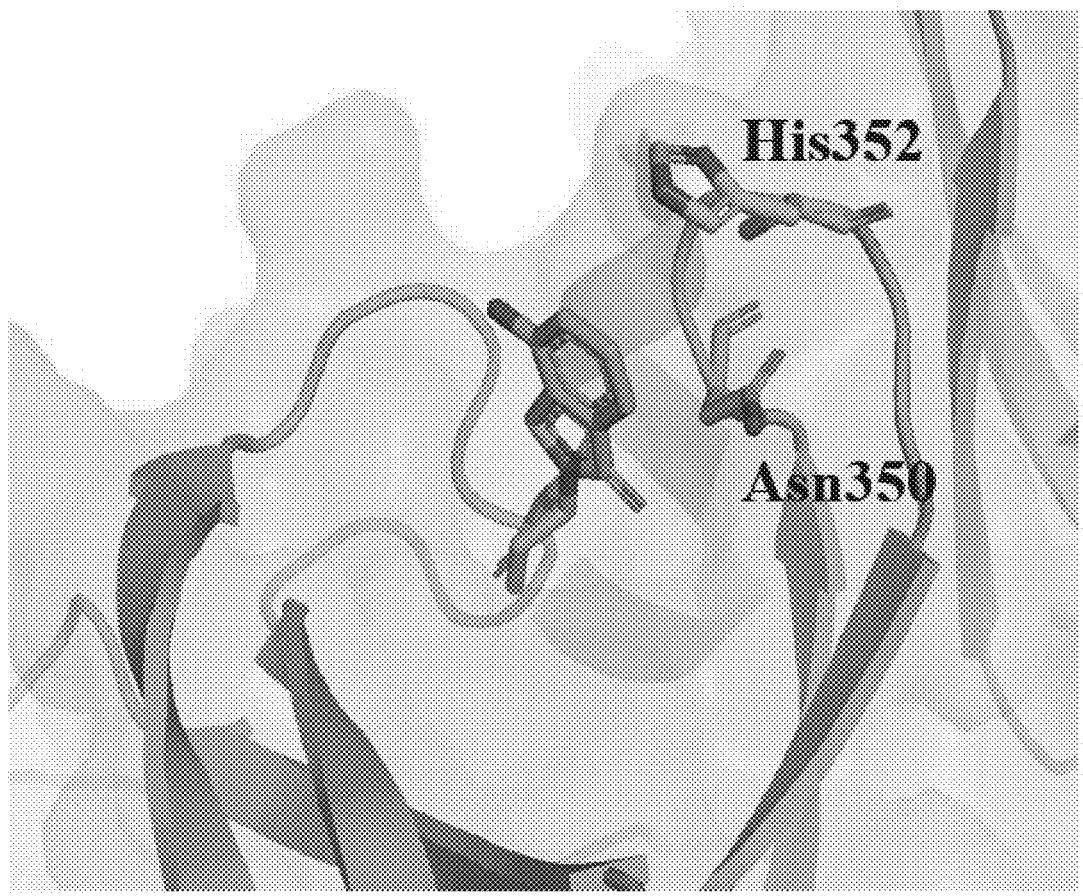
FIG. 3 is a crystal structure of the lenalidomide binding pocket of cereblon. The protein is rendered in a ribbon format and transparent solvent accessible surface. The position of His352 and Asn350 is displayed where mutation of either or both of these residues to cysteine allow for the design of covalent ligands.
Figure 4:
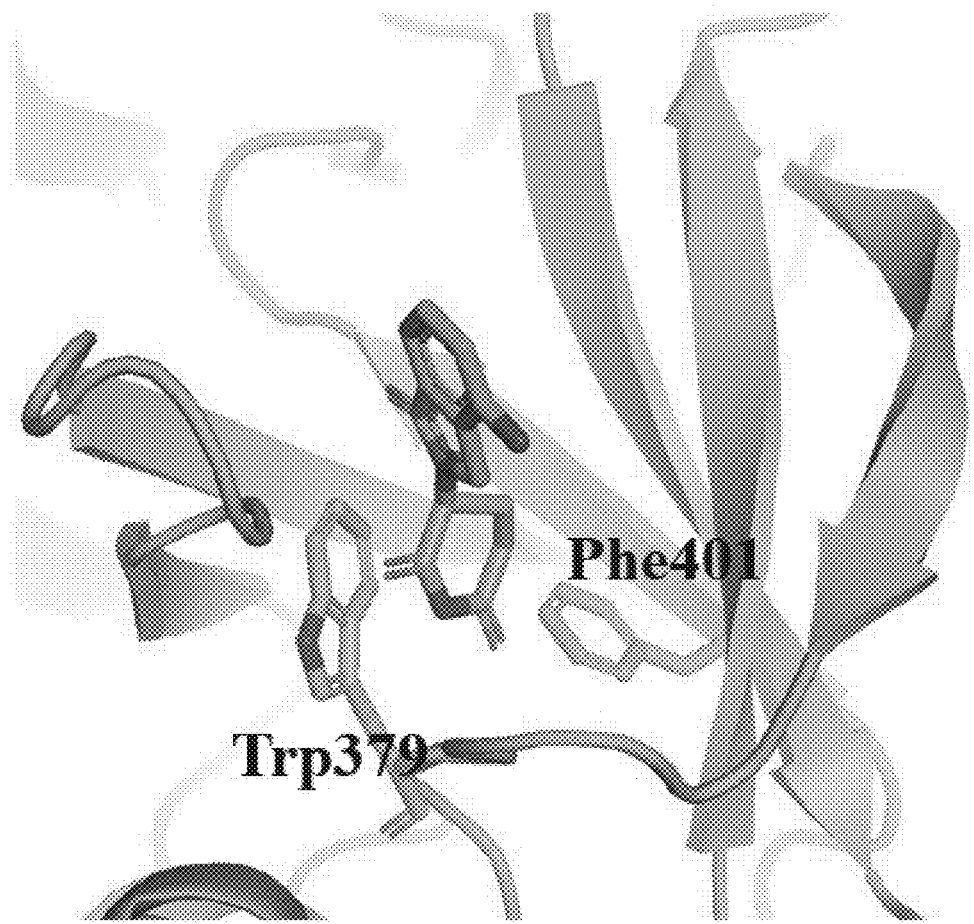
FIG. 4 is a crystal structure of the lenalidomide binding pocket of cereblon. The protein is rendered in a ribbon format and transparent solvent accessible surface. The position of Trp379 and Phe401 is displayed where mutation of either or both of these residues to alanine allow for the design of "bumped" ligands.
Figure 5:
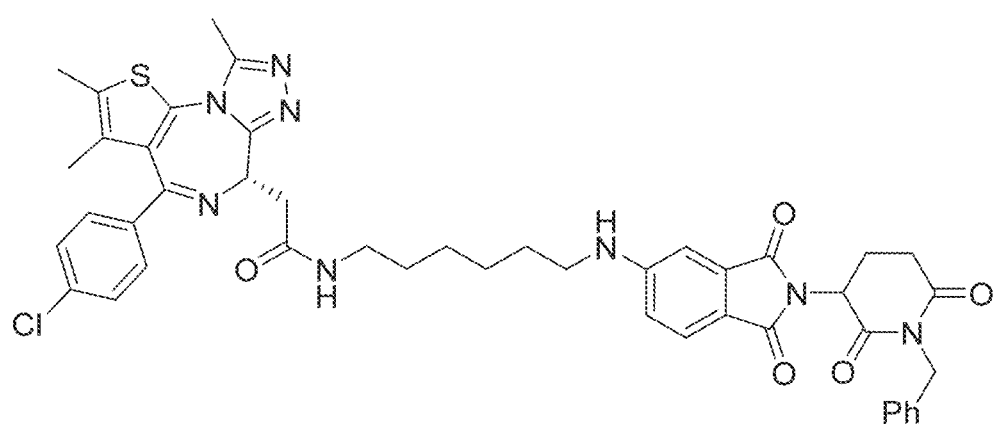
FIG. 5 is the chemical structure of Compound I-1.

250,000-500,000 cells/well (Mutant and WT) in a 6-well plate were treated with 0.2 μg/mL doxycycline for 16 hours, followed by a 4 hour treatment with DMSO or bifunctional Compound I-1 at the concentrations shown in FIGS. 2A-2E. BRD4 signal was normalized to Vinculin signal, and the percent remaining for each condition compared to the DMSO-treated condition was determined. BRD4 levels in WT cells and in mutant cells (N350C CRBN, H352C CRBN, W379A CRBN, F401A CRBN) when treated with DMSO or Compound 1-1 were detected by immunoblotting (See FIGS. 2A-2E).

Example 6. Endogenous F401A Mutation of Human CRBN

To engineer the endogenous CRBN protein containing a F401A point mutation, a homologous donor construct (SEQ. ID NO. 9) is cloned. To initiate homologous recombination, a CRISPR sgRNA (SEQ. ID NO. 10) is used to allow for gene editing of the endogenous CRBN locus. CAS9 expression induces a double strand break which is repaired by homologous recombination repair using the donor construct as template. The end result is a gene locus encoding a CRBN protein with a F401A point mutation.

SEQ. ID NO. 9
TACAGAAATGTTTCCTTAGCTGATATCTTTCCTTAATTTCTTAGGTATGC

CTGGACTGTTGCCCAGTGTAAGATCTGTGCAAGCCATATTGGATGGAAGG

CTACTGCCACCAAAAAAGACATGTGACCTCAAAAATTTTGGGGCTTAACG

CGATCTGCTCTGTTGCCCACGATCCCAGACACTGAAGATGAAATAAGTCC

SEQ. ID NO. 10
CCATATTGGATGGAAGTTTA

EQUIVALENTS

Those skilled in the art will recognize, or be able to ascertain using no more than routine experimentation, many equivalents to the specific embodiments and methods described herein. Such equivalents are intended to be encompassed by the scope of the present application.

All patents, patent applications, and literature references cited herein are hereby expressly incorporated by reference.

We claim:
1. A compound of structure:
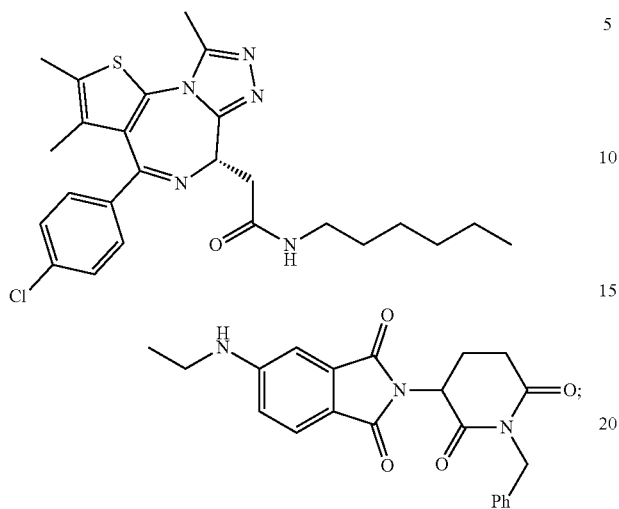
or a pharmaceutically acceptable salt thereof.
2. A pharmaceutical composition comprising a compound of structure:
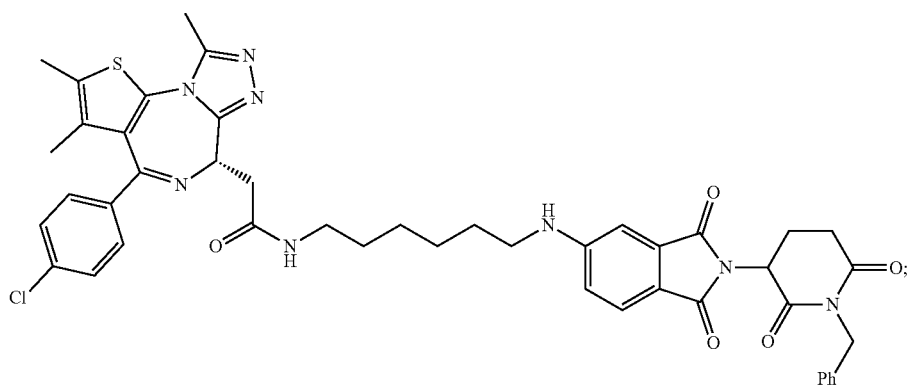
or a pharmaceutically acceptable salt thereof, and a pharmaceutically acceptable excipient.
* * * * *